US005088810A

United States Patent [19]

Galanter et al.

[11] Patent Number: 5,088,810

[45] Date of Patent: Feb. 18, 1992

[54] VISION TRAINING METHOD AND APPARATUS

[76] Inventors: Stephen M. Galanter, 1732 Riverview Rd., Gladwyne, Pa. 19035; Barry G. Millis, 352 Gribbel Rd., Wyncote, Pa. 19095

[21] Appl. No.: 299,680

[22] Filed: Jan. 23, 1989

[51] Int. Cl.[5] ................ A61B 3/02

[52] U.S. Cl. ................ 351/203; 351/243; 351/246

[58] Field of Search ................ 351/203, 224, 225, 226, 351/237, 243, 246

[56] References Cited

U.S. PATENT DOCUMENTS

| | | | |
|---|---|---|---|
| 4,294,522 | 10/1981 | Jacobs . | |
| 4,325,697 | 4/1982 | Regan et al. . | |
| 4,408,846 | 10/1983 | Balliet | 351/203 |
| 4,523,821 | 6/1985 | Lang et al. | 351/214 |
| 4,533,221 | 8/1985 | Trachtman | 351/203 |
| 4,611,583 | 9/1986 | Wasserman | 128/76.5 |
| 4,660,945 | 4/1987 | Trachtman | 351/203 |
| 4,869,589 | 9/1989 | Blair | 351/243 |

*Primary Examiner*—Rodney B. Bovernick
*Attorney, Agent, or Firm*—Woodcock Washburn Kurtz Mackiewicz & Norris

[57] ABSTRACT

A vision training system according to the present invention is computer based and is self-advancing and self-directed. The system is operable in two modes, a diagnostic mode and a therapeutic exercise mode. Therapeutic exercises are automatically tailored for a subject based upon the subject's test results in the diagnostic mode. The system has particular application for subjects who suffer from near point visual stress, but is not limited thereto.

16 Claims, 136 Drawing Sheets

```
Personal Information:
Name.....................................00000000000000000000
Home Address.............................
Company..................................
Social Security Number...................
Date of Birth............................
Work Practices:
1. Average number of hours per day of computer operation.........
2. Does your work at the VDT involve:  (Y or N)
   Data entry only......     Text composition.......
   Data interpretation......
3. Is it an effort to maintain your concentration while reading..
4. Do you tend to skip words or lines of print while reading.....
5. After reading, do you look up and notice that distant objects
   are momentarily blurred.......................................
6. Does print tend to appear blurry after reading more than 10
   minutes.......................................................
7. Do words apear to float while reading.........................
8. Do you experience headaches at the computer or shortly after..
9. Are you aware of any tendency to move your head closer to, or
   away from what you are reading................................
10. Do you have bodily discomfort while working, such as
    Neck( ), Shoulder ( ), or wrist ( ) pain.
```

Fig. 4

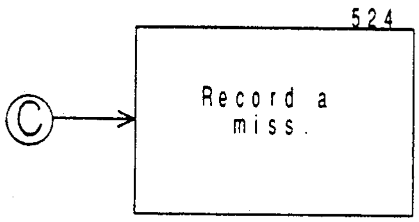
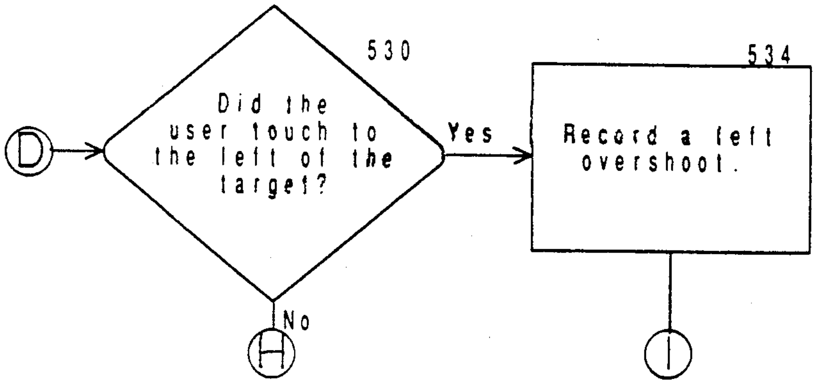
Fig. 6d

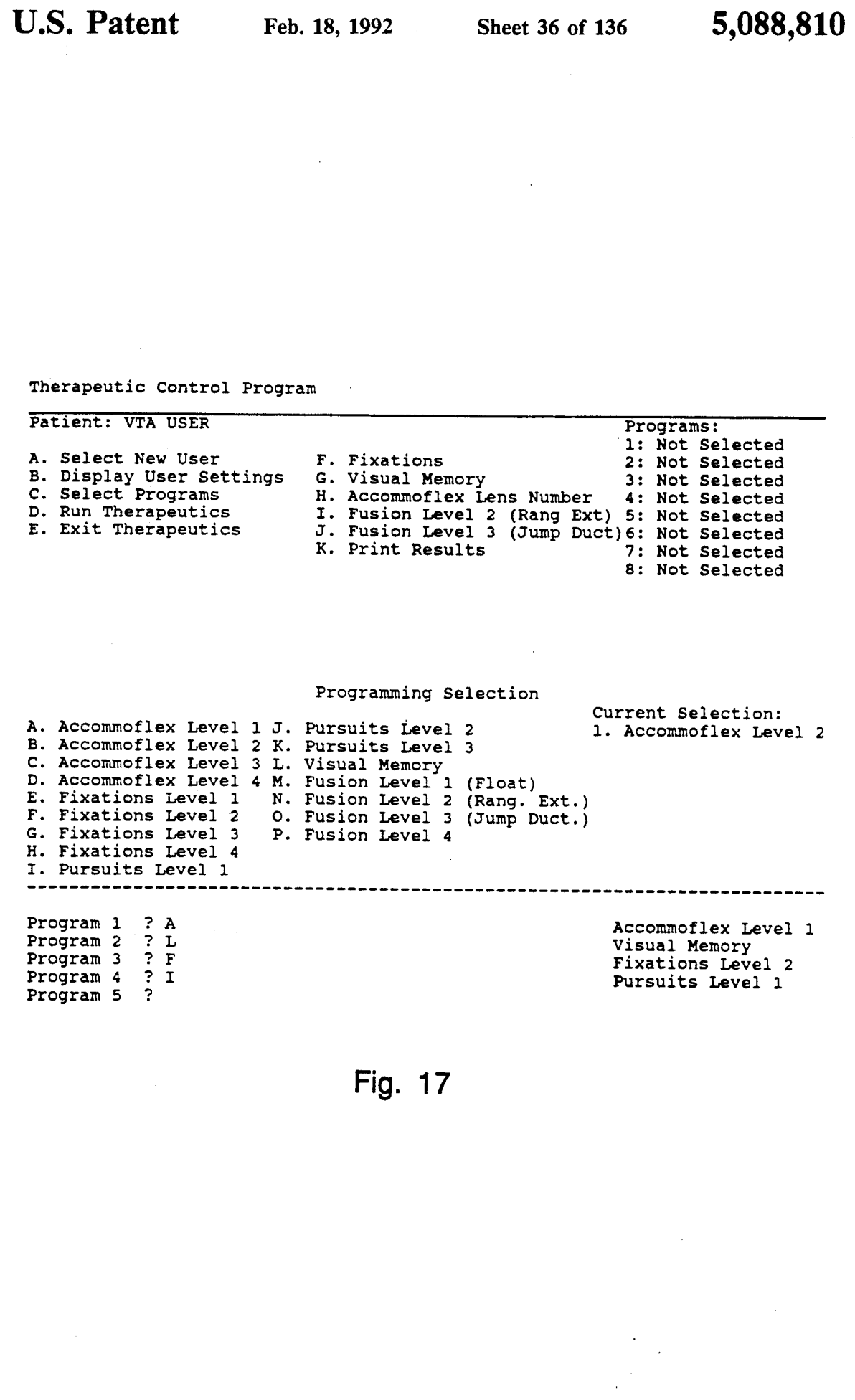

```
Therapeutic Control Program
______________________________________________________________________________
Patient: VTA USER                                                  Programs:
                                                                   1: Not Selected
A. Select New User          F. Fixations                           2: Not Selected
B. Display User Settings    G. Visual Memory                       3: Not Selected
C. Select Programs          H. Accommoflex Lens Number             4: Not Selected
D. Run Therapeutics         I. Fusion Level 2 (Rang Ext)           5: Not Selected
E. Exit Therapeutics        J. Fusion Level 3 (Jump Duct)          6: Not Selected
                            K. Print Results                       7: Not Selected
                                                                   8: Not Selected
```

```
                          Programming Selection
                                                     Current Selection:
A. Accommoflex Level 1 J. Pursuits Level 2           1. Accommoflex Level 2
B. Accommoflex Level 2 K. Pursuits Level 3
C. Accommoflex Level 3 L. Visual Memory
D. Accommoflex Level 4 M. Fusion Level 1 (Float)
E. Fixations Level 1   N. Fusion Level 2 (Rang. Ext.)
F. Fixations Level 2   O. Fusion Level 3 (Jump Duct.)
G. Fixations Level 3   P. Fusion Level 4
H. Fixations Level 4
I. Pursuits Level 1
------------------------------------------------------------------------------

Program 1  ? A                                          Accommoflex Level 1
Program 2  ? L                                          Visual Memory
Program 3  ? F                                          Fixations Level 2
Program 4  ? I                                          Pursuits Level 1
Program 5  ?
```

Fig. 17

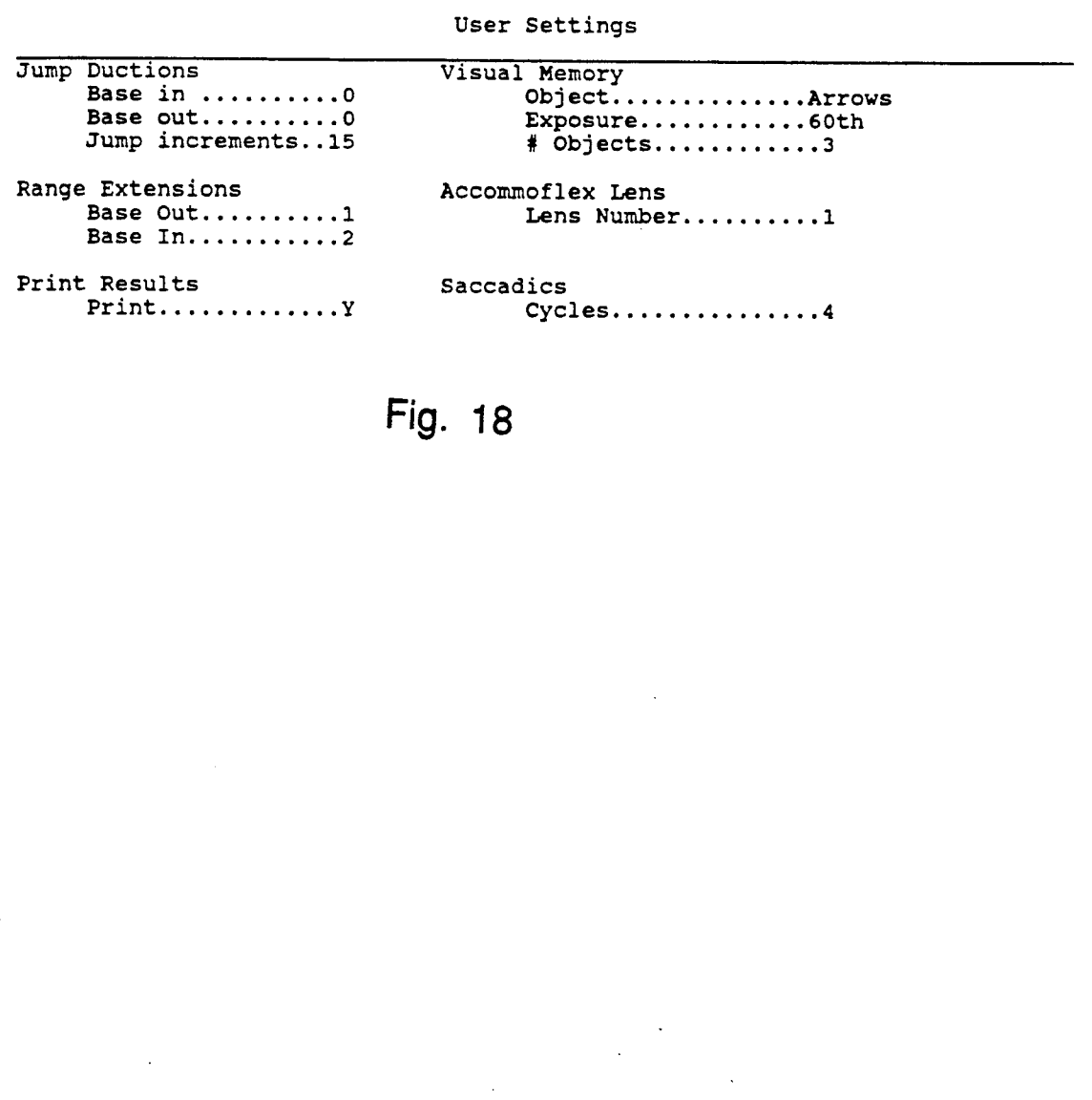

User Settings

```
Jump Ductions                   Visual Memory
     Base in ..........0              Object..............Arrows
     Base out..........0              Exposure............60th
     Jump increments..15              # Objects............3

Range Extensions                Accommoflex Lens
     Base Out..........1              Lens Number..........1
     Base In...........2

Print Results                   Saccadics
     Print.............Y              Cycles...............4
```

Fig. 18

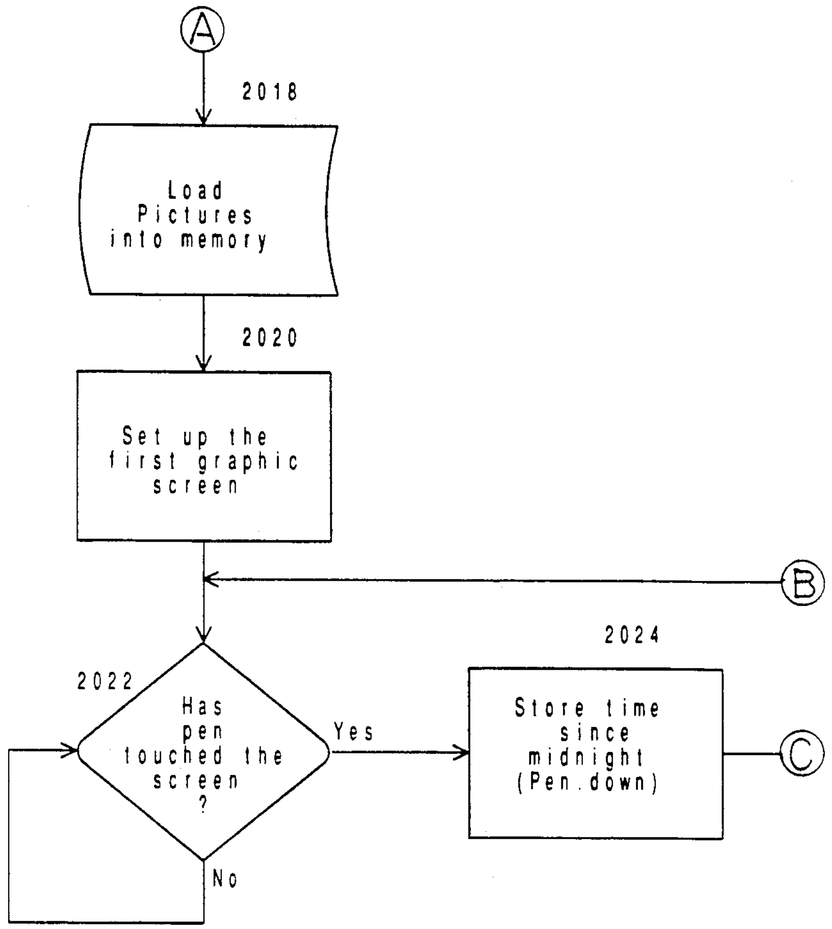
Fig. 24b
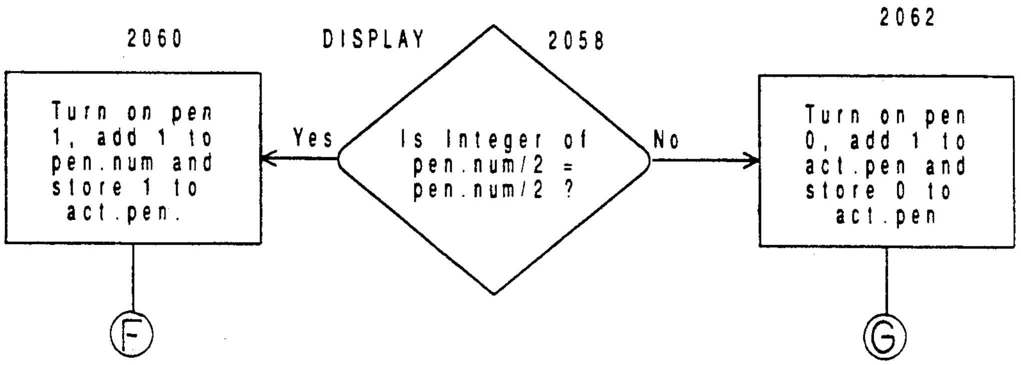

Every 2 seconds, the program will run the following routine regardless what the main program is doing. This routine updates the display prompts.

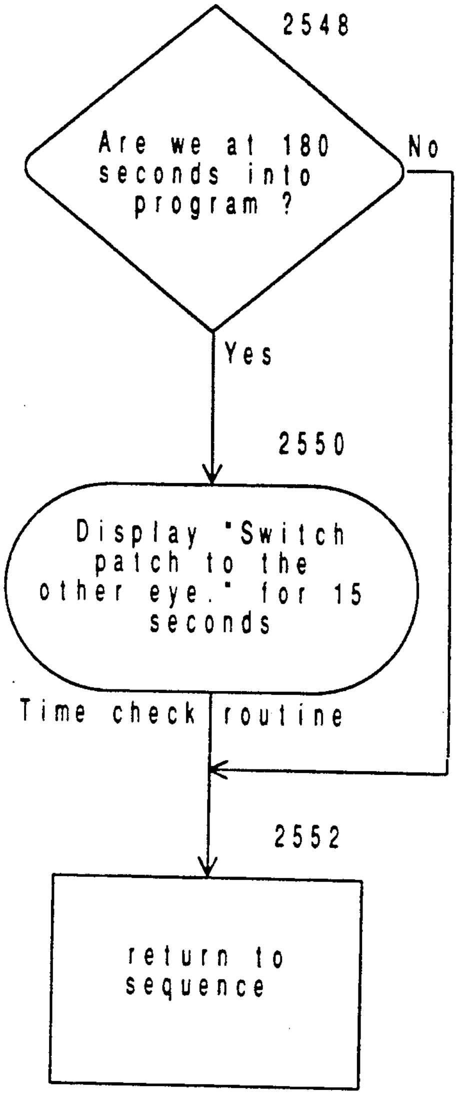
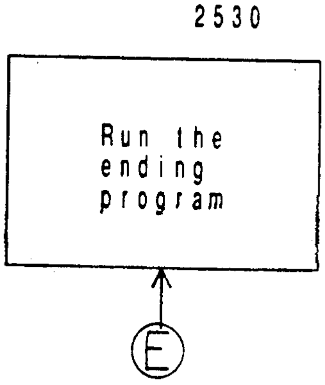
Fig. 31c

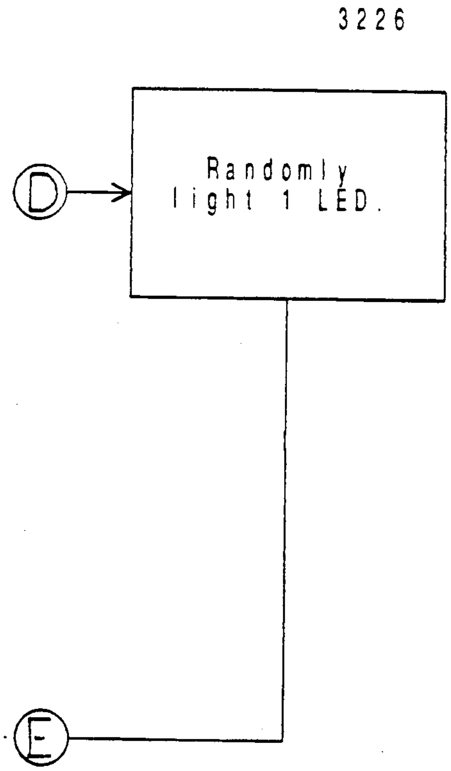
3226
Randomly light 1 LED.
D
E

VISION TRAINING METHOD AND APPARATUS

BACKGROUND OF THE INVENTION

The present invention relates generally to the field of vision training. More particularly, the present invention is directed to a fully automated, self-advancing, computer-based vision training method and apparatus including self-directed diagnostic and therapeutic routines.

Training methods for improving visual function have developed over the past forty years. It is generally recognized that the most effective approach to vision training includes, but is not limited to, a variety of activities that develop accommodation, convergence, pursuit and saccadic eye movement, visualization, visual memory and binocular integration, all of which terms are well known in the art. Although symptoms might suggest a problem in one area, for example accommodation, it would generally be agreed that effective treatment should include attention to all the major visual abilities.

Vision training has been found to be an excellent way to restore efficient stable vision for most people exhibiting visual stress response. However, to be most effective, vision training has, in the past, been carried out in an optometrist's office under direct professional supervision. Traditional vision training procedures utilize devices such as stereoscopes, vectograms, cheiroscopes, Marsden balls, overhead and slide projectors, and a variety of other simple devices. While these procedures have been effective, there is a need for careful observation by the professional staff to ascertain whether or not the goal of each activity has been achieved. In general, data collection and analysis is cumbersome, inefficient, time consuming and unreliable.

The present invention addresses the need for a vision training system and method that is compact, efficient, and cost-effective. It achieves these goals and also provides consistent user feedback, and renders collection and analysis of data simple. The vision training system of the present invention represents a departure from the prior art in that the entire vision training method is computerized, self-directed, self-advancing and requires minimal or no professional supervision. Additionally, the vision training system of the present invention is particularly suited for treatment of conditions arising from near point visual stress.

SUMMARY OF THE INVENTION

The vision training system of the present invention is designed to develop and enhance visual abilities and to reduce visual and other stress related symptoms associated with intense close work, e.g., near point visual stress. According to the present invention, a specially programmed personal computer and related input and output devices provide a means for achieving these criteria. A training method of the type described and claimed herein is programmed in the computer and the system can easily be taken to the work place, school or home, and training can be supervised by one's self or by non-technical personnel. The program preferably includes data collection and analysis routines, as described herein. According to the invention, as optimal performance levels are reached on a therapeutic exercise activity, the subject's performance is compared with preset performance values stored in memory, and either the next higher level of difficulty within a particular exercise, or the next exercise in a particular sequence of exercises is presented to the subject at the next training session. The program automatically increases the level of difficulty much as a clinician would do manually.

According to the method of the present invention, a diagnostic battery of tests is first presented to a subject to create a performance profile and to document complaints, both of which are stored in the system. Diagnostic tests include, but are not limited to, saccadics, visual memory, accommodative flexibility,. fusion ranges and phorias. See FIGS. 1a and 1b. A performance profile is compiled and printed. The subject and his performance data are added to a data base of the program and the subject is assigned a user number. If the subject does not meet stored, pre-established acceptable performance criteria, a therapeutic exercise routine is tailored and presented to the subject. See FIGS. 2a, b and c. The therapeutic exercise routine comprises the following eye exercises:

(a) four levels of accommodative ability;
(b) three levels of eye tracking, or pursuits, ability;
(c) three levels of saccadics ability;
(d) four levels of binocular integration, or fusion, ability;
(e) two levels of visual memory ability; and,
(f) z-axis binocularity ability.

The presentation of the therapeutic exercises may be configured in a therapeutic control program so that the exercise routines are optimally designed for a particular subject. In a configuration routine, configuration values representing the particular exercise configuration for each subject are retained and correlated to each user number to provide continuity between training sessions by each subject. Default configuration values are used if the configuration routine is bypassed. The therapeutic control program can:

(1) use the default values to select the exercise routine; or,
(2) select an exercise routine that is based on performance in previous therapy sessions; or,
(3) operate in a self-directing mode, where configuration and exercise level values are triggered by the performance of the subject.

The basic presentation of the program is preferably the same for all subjects; approximately 24 one-half hour bi-weekly training sessions are suggested. Each exercise preferably lasts about six minutes with approximately four activities per session. Each subject starts at the lowest level of each exercise (a) through (e) above and proceeds through succeeding levels of difficulty at his own pace. Exercise (f) is a single level activity with variable configurations.

BRIEF DESCRIPTION OF THE DRAWINGS

FIG. 4 is a questionnaire provided to a subject by the vision training system according to the practice of the present invention.

FIGS. 6a-6e are a flowchart illustrating Saccadics Level I and II diagnostic routines.

FIG. 17 are displays provided by the vision training system of the present invention in connection with a therapeutic exercise portion of the method of the present invention.

FIG. 18 is a display provided by the vision training system of the present invention in connection with a therapeutic exercise configuration program.

FIGS. 24a-24g are a flowchart illustrating Fixations Level I, II, and III exercise routines.

FIGS. 31a-31d are a flowchart illustrating Pursuits Level II and III therapeutic exercise routines.

FIGS. 36a-36m are a flowchart illustrating Depth of Fusion Level I and II therapeutic exercise routines.

FIGS. 39a-39m are a flowchart illustrating a Depth of Fusion Level III therapeutic exercise routine.

FIG. 41a is a top plan view of a binocular shaft according to the present invention; FIG. 41b is side plan view of a binocular shaft according to the present invention.

FIGS. 42a-42f are a flowchart illustrating a binocular shaft, or z axis binocularity, therapeutic exercise routine.

DETAILED DESCRIPTION OF THE PREFERRED EMBODIMENT

Figure 3A:
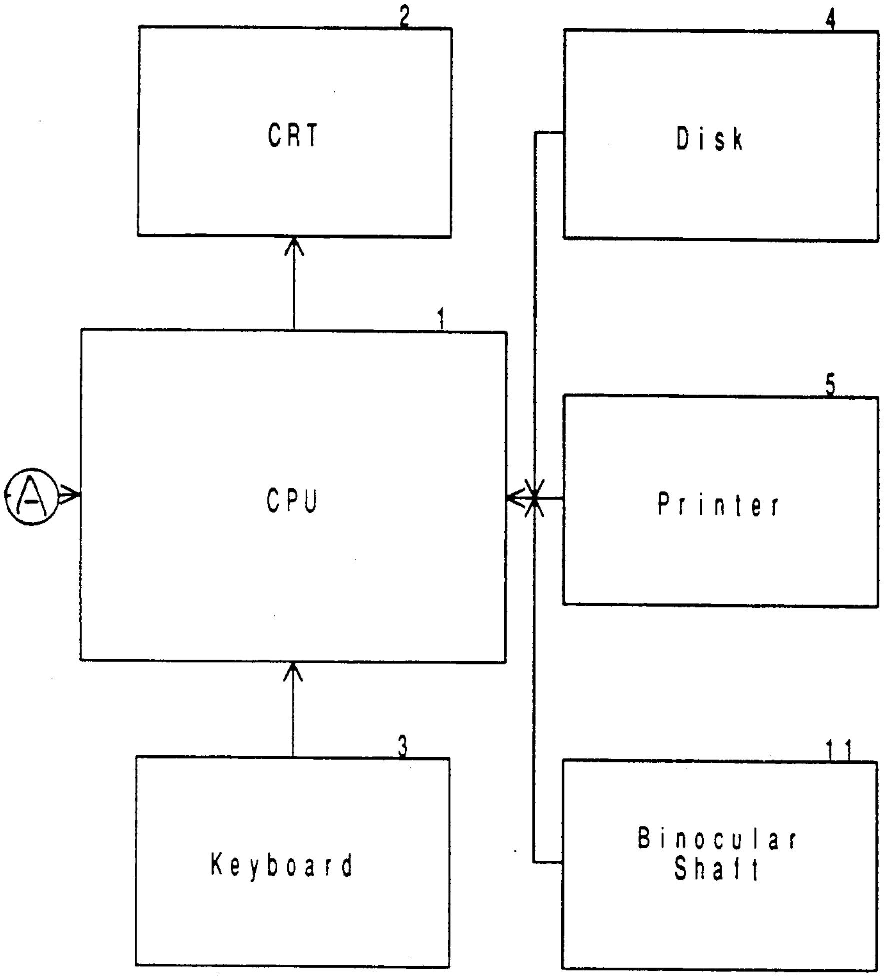
FIGS. 3a, 3b are a block diagram of a vision training system according to the present invention.
Figure 3B:
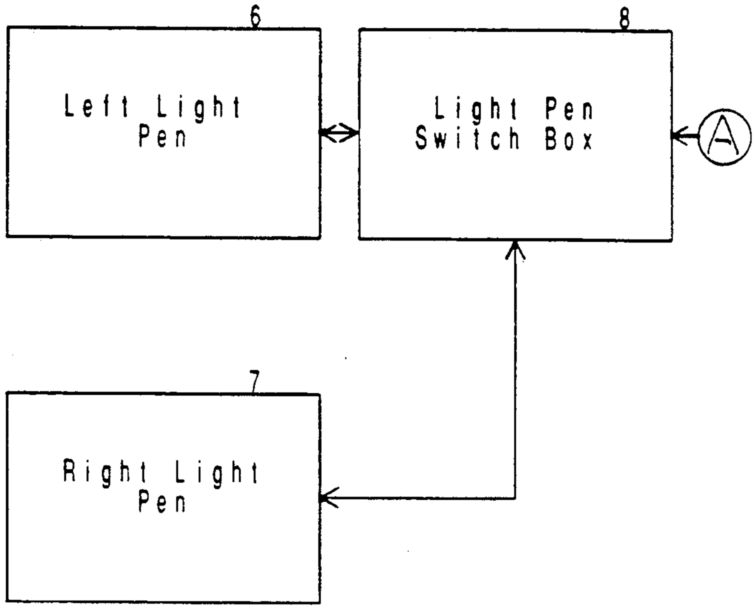

Referring now to the drawings wherein like numerals represent like elements, there is illustrated in FIGS. 3a and 3b hardware of a vision training system according to the present invention. The preferred embodiment of the vision training system comprises a computer, 1, interconnected with a high resolution color monitor (CRT), 2, a keyboard 3, a high capacity disk unit 4, a printer 5, and two light pens, 6 (pen #1) and 7 (pen #2), for inputting responses to the computer based on visual stimuli presented on the CRT. A computer controlled switch box 8 selects only one of the light pens 6 or 7 at any given time. A so called "binocular shaft", 11, discussed in more detail hereinafter, is also coupled to and driven by the computer.

The system is also capable of expansion to include means for providing auditory output, such as digitally stored voice recordings, and for receiving and processing voice responses from the subject, both by well known means. The computer is programmed by well known programming techniques to perform the functions described below.

A. Diagnostic Routines

Figure 1A:
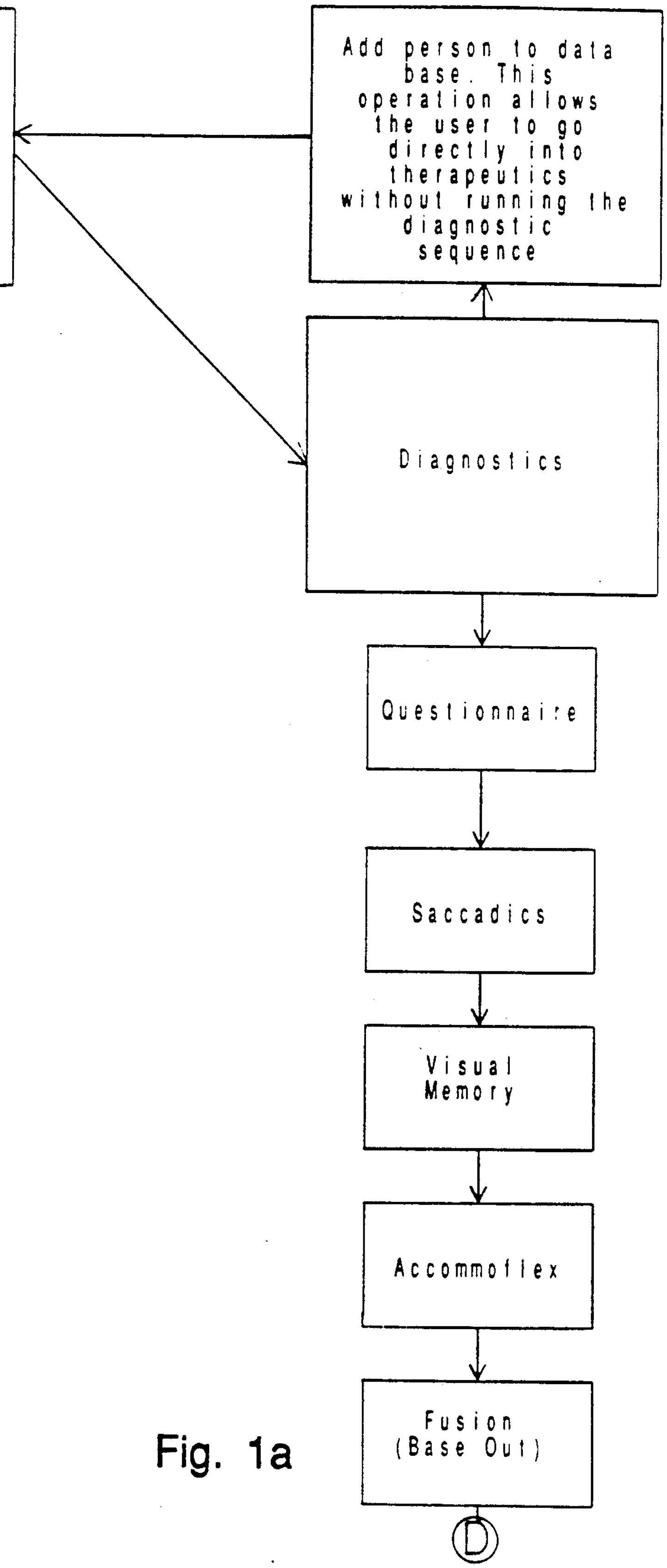
FIGS. 1a, 1b are a block diagram illustrating the various diagnostic routines that a vision training system programmed according to the present invention may present to a subject.
Figure 2C:
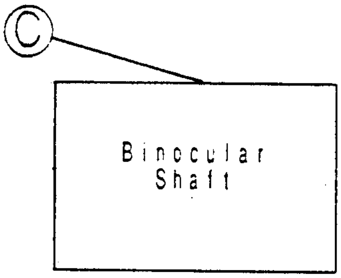
FIGS. 2a–2c is a block diagram illustrating the various therapeutic exercise routines that a vision training system programmed according to the present invention may present to a subject.
Figure 1B:
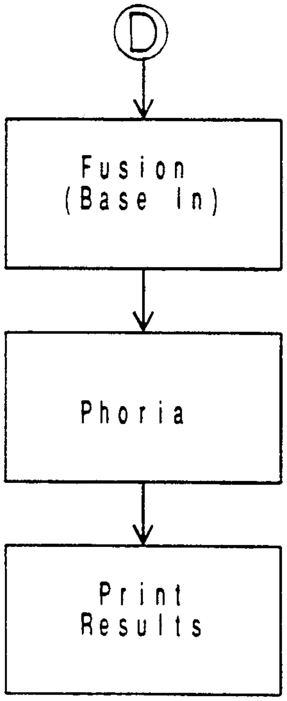

From a main menu (e.g., FIGS. 1a and 1b), a diagnostic routine is selected. The first part of the diagnostic battery is a questionnaire with answers entered through the keyboard. See FIG. 4. Subsequently, the information is processed and a printout including vital information and symptoms is provided. The programs described below are linked by the software so that the diagnostic routines automatically follow the questionnaire.

Diagnostic testing includes five areas: saccadics, Visual Memory, accommodation, fusion, and phoria, in that order. These will now be described.

1.) Saccadics

The purpose of the Saccadics diagnostic routine is to test the accuracy of the subject's saccadic eye movements and hand/eye coordination. The test consists of three levels, I, II, and III.

(a) Description of Level I

Figure 5:
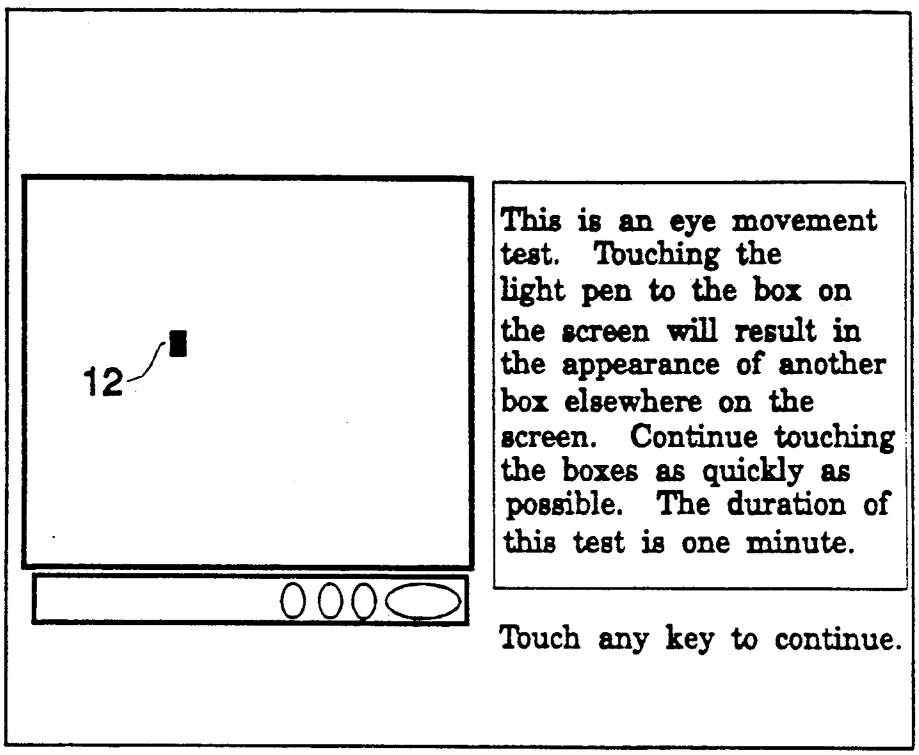
FIG. 5 is a display provided by the vision training of the present invention in connection with a Saccadics Level I diagnostic routine.

The subject reads instructions (not shown) and touches the CRT screen with the active light pen to continue. Except as noted herein, the "active" light pen is always the same pen, e.g., pen #1. In other routines, the active pen alternates between pen #1 and pen #2, as discussed below). The subject is instructed to view a small green box 12 (see FIG. 5) on the CRT screen and to touch the light pen to the box as quickly as possible; this triggers the appearance of a second box (not shown) which appears at a random distance and position relative to the first. The subject touches the second box and then a third box (not shown) appears and so on for one minute. Each box remains on the CRT screen until the light pen touches the CRT screen. An auditory tone preferably accompanies each light pen touch.

The computer output from the foregoing includes (i) the mean response time, (ii) the total number of trials, and (iii) the accuracy, as a function of undershooting or overshooting; that is, if the first target appears in the top left corner of the screen and the second target appears in the bottom right corner, the subject must make a down/right eye movement to go from the first target to the second target. If the subject's touch is to the left and below the second target, the computer records a response as a horizontal undershoot and a vertical overshoot. Undershooting or overshooting is always recorded relative to the position of the previous target.

The following is a detailed description of the flowchart, shown in FIGS. 6*a* through 6*e*, for the Saccadics Level I Diagnostic routine. First an instruction screen (not shown) is displayed, block 510. Next, the program waits for the subject to touch the screen with the active light pen, block 512, before continuing on to block 514 where the target is displayed for 3 seconds. Next, the program randomly chooses X and Y coordinates and what target to display, block 515. The target is displayed at the coordinates X, Y on the screen (CRT), block 517, and the program waits for the subject to touch the screen with the active light pen, block 519. After the subject touches the screen with the active light pen, the X and Y coordinates of the pen location are stored, block 521. Next, the program checks to determine whether the active pen touched the right target, block 522. If not, the miss is recorded, block 524, and the program loops back to block 515. If the active pen did touch the right target, the program compares the position of the target to the position of the previous target, block 528. If the position of the target was to the left of the previous target, the program executes the loop beginning at block 530. If the position of the target was to the right of the previous target, the loop beginning at block 536 is executed. At block 530, the program checks to determine whether the subject touched to the left of the target. If so, this is recorded as a left overshoot, block 534, and the program jumps to block 542. If the subject did not touch to the left of the target, this is recorded as a left undershoot, block 532, and the program jumps to block 542. If the target was placed to the right of the previous target, the loop beginning at block 536 is executed. At block 536, the program checks to determine whether the subject touched to the right of the target. If so, this is recorded as a right overshoot, block 538, and the program jumps to block 542. If the subject did not touch to the right of the target, this is recorded as a right undershoot, block 540, and the program continues on to block 542. At block 542, the target is erased. At block 544, a check is made to determine whether 3 minutes have passed since the first target was shown. If so, the results are printed and stored and the next routine in the battery is run. If not, the program loops back to block 515.

(b) Description of Level II

Figure 7:
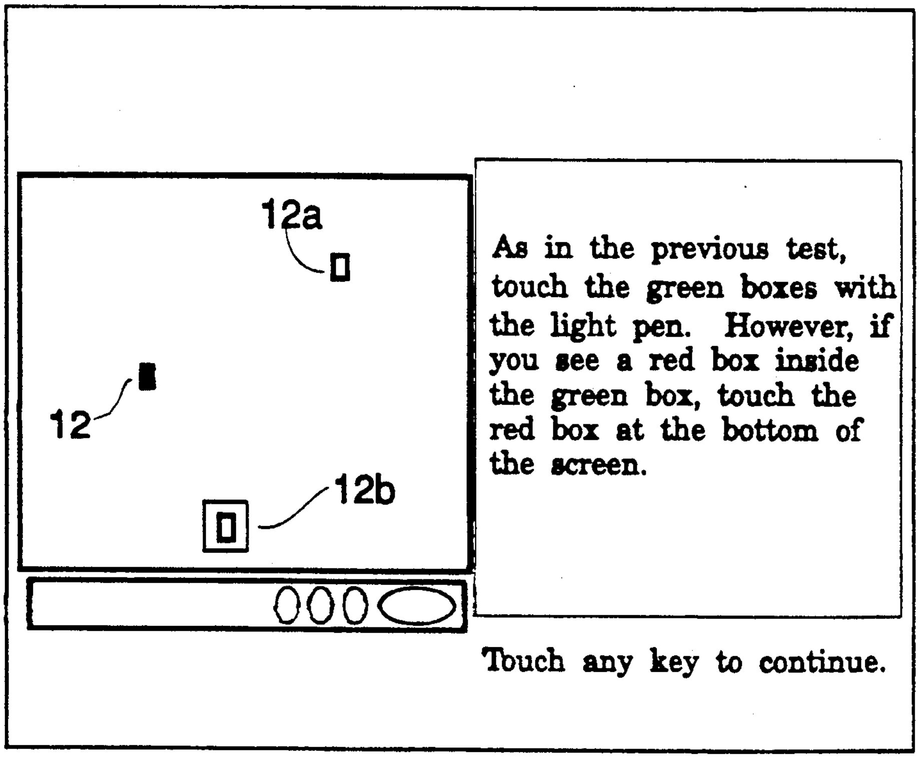
FIG. 7 is a display provided by the vision training system of the present invention in connection with a Saccadics Level II diagnostic routine.
Figure 6A:
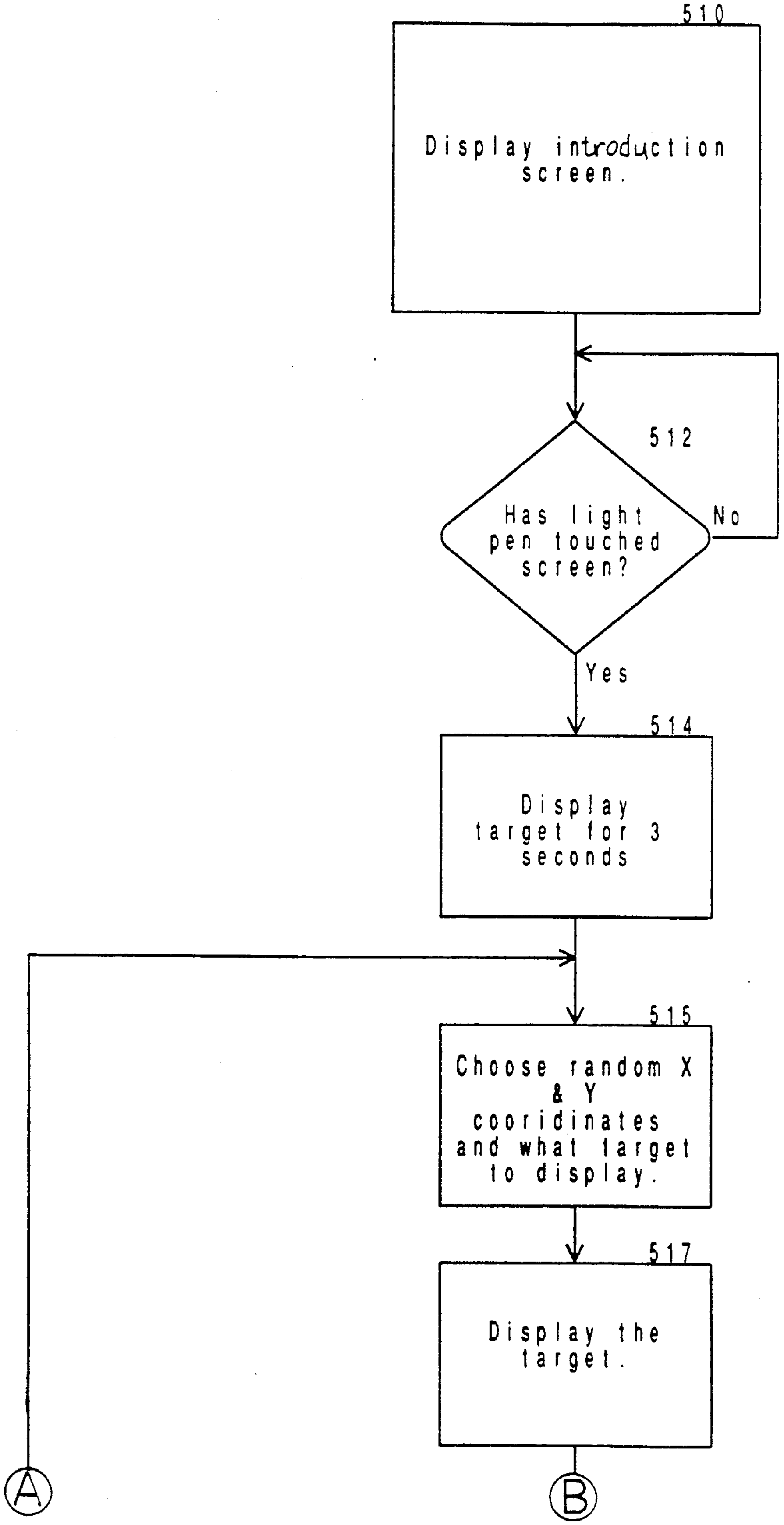
Figure 6B:
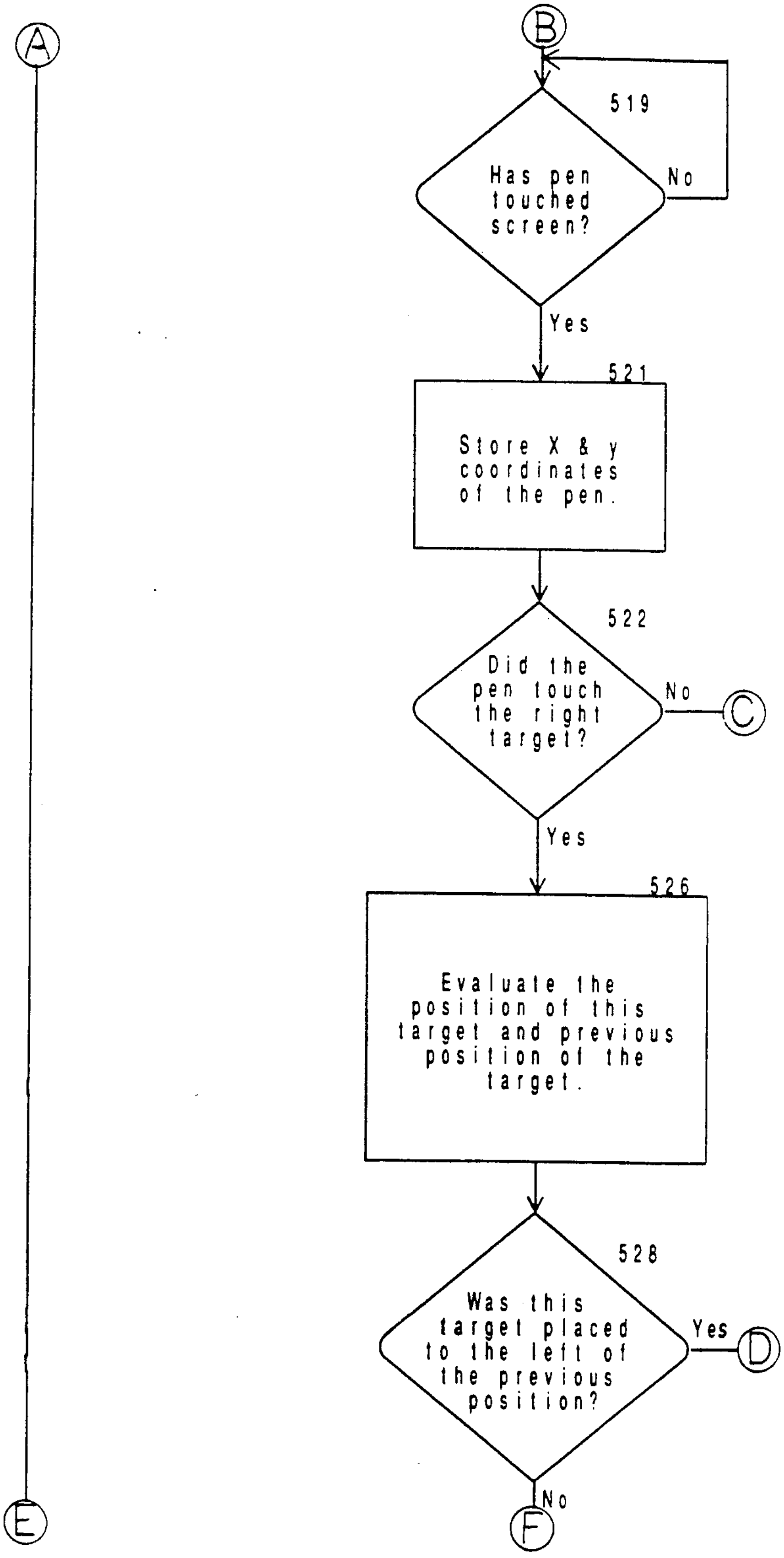
Figure 6C:
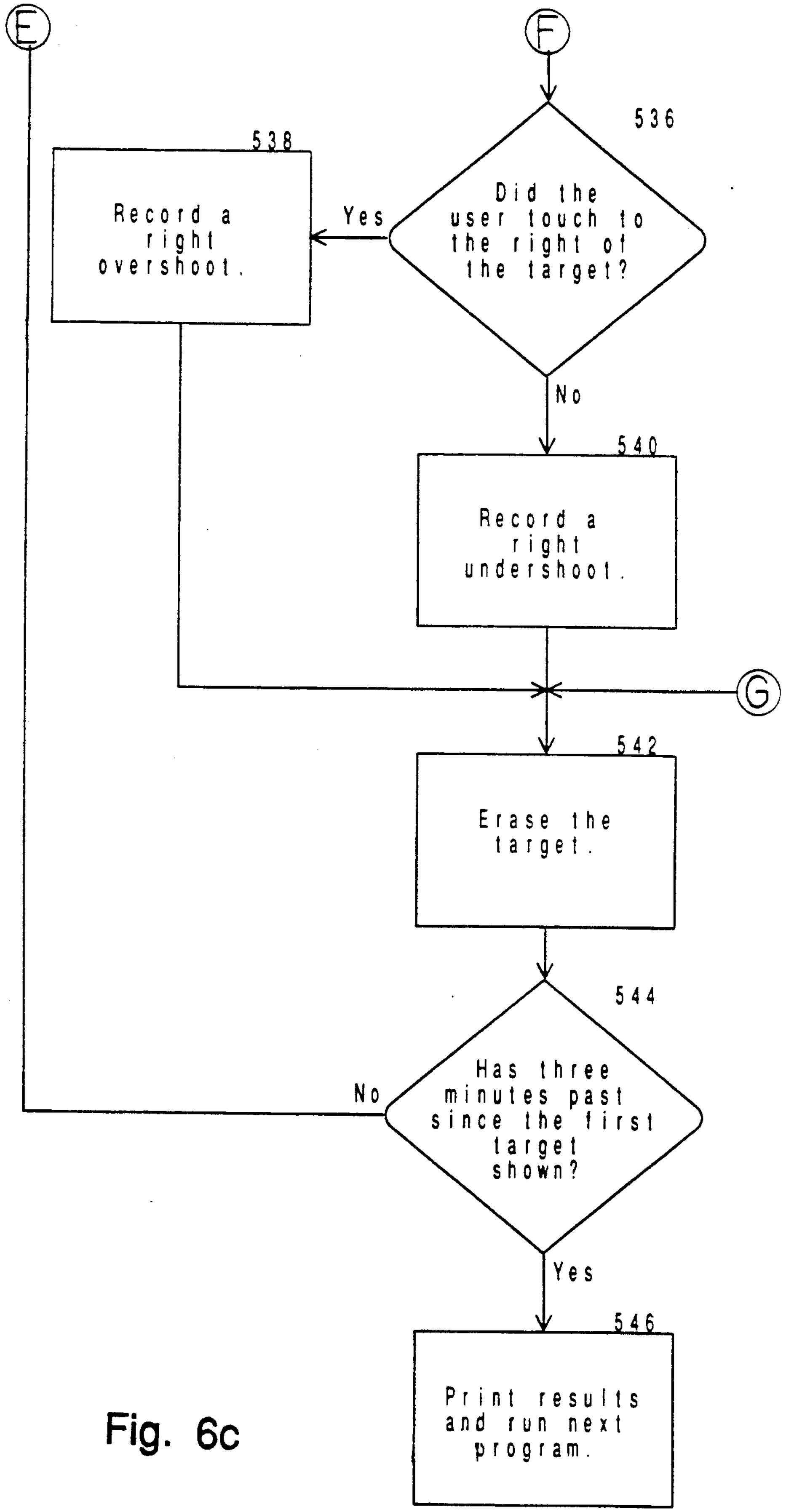
Figure 6E:
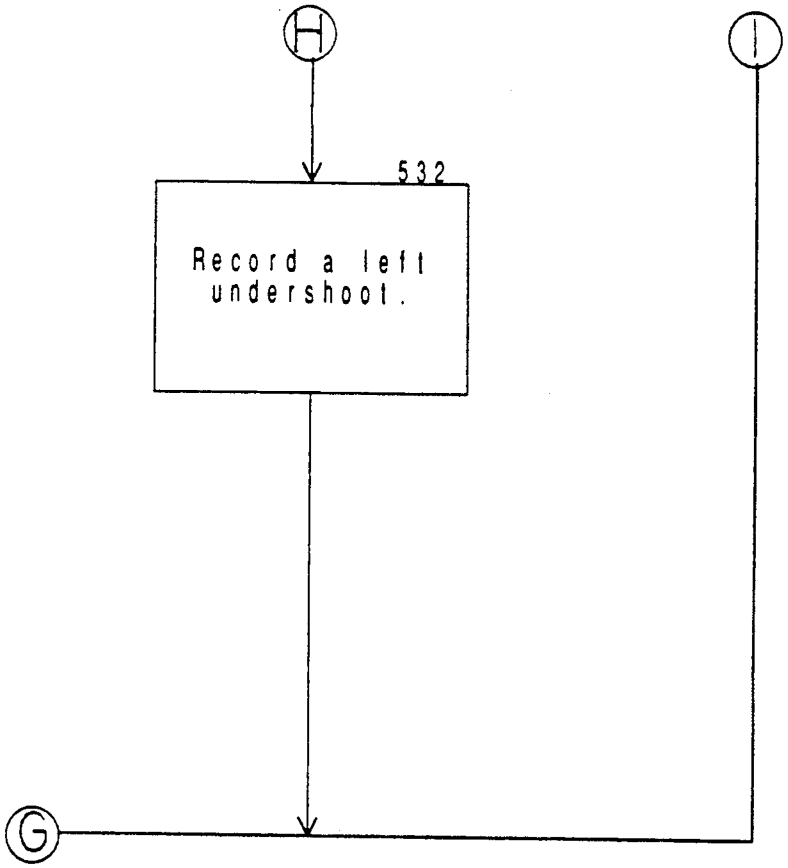

The target is a solid green box 12 on a white background or a box 12*a* with a green border and red interior in the center on a white background (see FIG. 7). At all times, a box 12*b* with a green border and red interior is visible at the bottom of screen. The solid green box 12 is touched with the light pen as in Level I. If a box with a red interior appears, the box 12*b* at the bottom of the screen is to be touched. The targets are presented on a random basis so that the subject cannot anticipate whether the next target will be a solid green box or one with red in it. The test runs for one minute and a new target appears as soon as the screen is touched with the active light pen.

The computer output includes the (i) mean response time, (ii) total number of trials, and (iii) accuracy (overshooting or under-shooting), as in Level I, and also the number of times a red box was touched incorrectly and correctly.

The program for the Saccadics Level II diagnostic is nearly identical to the program for the Saccadics Level I diagnostic (FIGS. 6*a* through 6*e*) with the following two exceptions. At block 522 a check is made to determine whether the active pen touched the target. At block 524 a correct response is recorded.

(c) Description of Level III

The purpose of Level III is to test the speed and accuracy of Saccadic eye movement without the eye-hand component.

Figure 8:
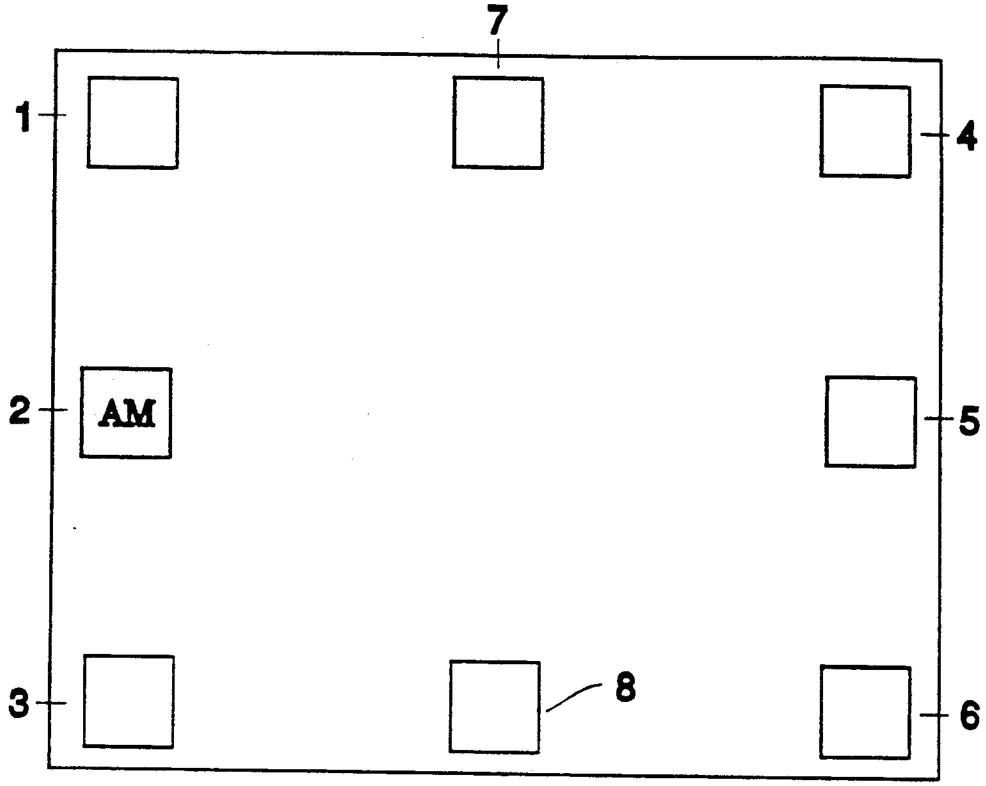
FIG. 8 is a display provided by the vision training system of the present invention in connection with a Saccadics Level III diagnostic routine.

The targets are eight one inch square boxes numbered 1-8 and are displayed along the perimeter of the screen. Letters flash inside one box at a time in configured parameters (see FIG. 8). The subject is instructed to read the instruction screen (not shown) and to touch the screen with the light pen to continue. Saccadics are first tested horizontally, then vertically, and finally diagonally. Prior to its trial, the target box is flashed three times to inform the subject which box to watch. With each direction, the presentation of letters starts with a duration of one second, e.g., two letters appear in box number 2 for one second, and then two new letters (randomly chosen) appear in box number 5 for one second. This continues for three to eight cycles. The subject is instructed to input on the keyboard the last set of letters presented in the series. When the last set of letters disappears, there is a tone and the box turns red. If the entered letters are correct, another horizontal presentation begins with a duration of 0.5 seconds. If the entered answer had previously been incorrect, the presentation is repeated with a duration of one second. If the entered letters are again incorrect, the test is terminated. However, if the entered letters are correct, the test is continued by reducing the duration by 0.1 second until two incorrect answers are entered. The sequence is repeated for box numbers 7 and 8, then box numbers 3 and 4, then box numbers 1 and 6.

The computer output includes, for each direction of presentation, the shortest duration with which the subject accurately entered the letters.

The following is a detailed description of the flowchart, shown in FIGS. 9*a* through 9*f* for the Saccadics Level III diagnostic routine. First, an instruction screen (not shown) is displayed, block 3250. Next, the program waits for the active pen to touch the screen, block 3252 before it loads the displays the main working screen. Next, the program stores the values of 2 and 5 to variables BOX-1 and BOX-2 respectively, block 3256. Next the program stores 1 to the variable THIS-SEQUENCE and 0 to ERROR-COUNT, block 3258. Next, the program stores the value of 1 to the variable FLASH-DURATION signifying seconds to wait between boxes, block 3260. Next, boxes BOX-1 and BOX-2 are flashed to identify which boxes the letters will be appearing, block 3262. Next, a sequence duration is randomly selected to identify how many times this set of boxes will flash, block 3264. Next, two letters are randomly selected and displayed in BOX-1, block 3266. Next, there is a wait for the FLASH-DURATION period (seconds) to expire, block 3268. Two letters are randomly selected and displayed in BOX-2 and the letters in BOX-1 are erased, block 3270. Next, there is a wait for the FLASH-DURATION period to expire. After completion of FLASH-DURATION, the letters in BOX-2 are erased. Next, one is added to the variable THIS-SEQUENCE, block 3274. Next, the value of THIS-SEQUENCE is checked against the value of SEQUENCE-DURATION, block 3276. If the two variable are equal, flow proceeds to block 3278, otherwise flow proceeds to block 3278. At block 3266, the program instructs the user, "Please enter the last two letters displayed". The subject inputs the two letters via the keyboard. The program checks the letters the user entered against the two letters in BOX-2, block 3280. If the user entered the two correct letters, flow continues to block 3282, otherwise flow continues to block 3284. In block 3282, the program decreases the value of FLASH-DURATION by 0.1 and continues at block 3264. In block 3284, one is added to the value of ERROR-COUNT. Next, the value of ERROR-COUNT is checked, block 3286. If ERROR-COUNT equals 2, the user has reached maximum speed and the value of FLASH-DURATION is stored, block 3286. If the maximum speed has been reached, the values 7 and 8, then 3 and 4, then 1 and 6 are stored to BOX-1 and BOX-2 respectively, block 3290. After box 1 and box 6 have been displayed the program prints the results and continues to the next diagnostic program. If the maximum speed has not been reached, the program continues at block 3264.

2.) Visual Memory and Perceptual Span

Figure 10:
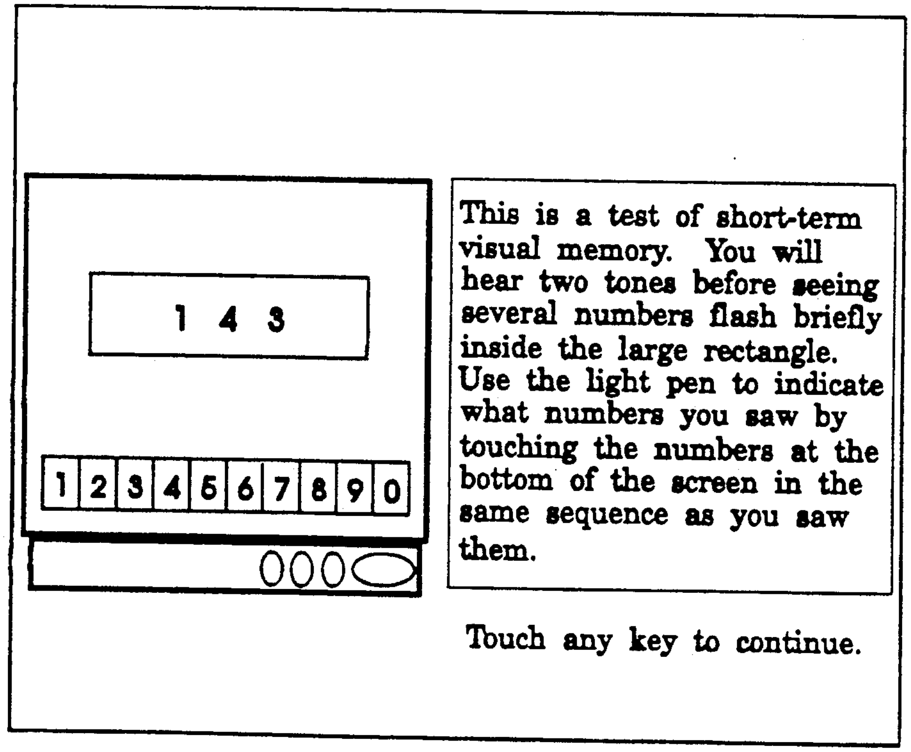
FIG. 10 is a display provided by the vision training system of the present invention in connection with a Visual Memory diagnostic routine.
Figure 9A:
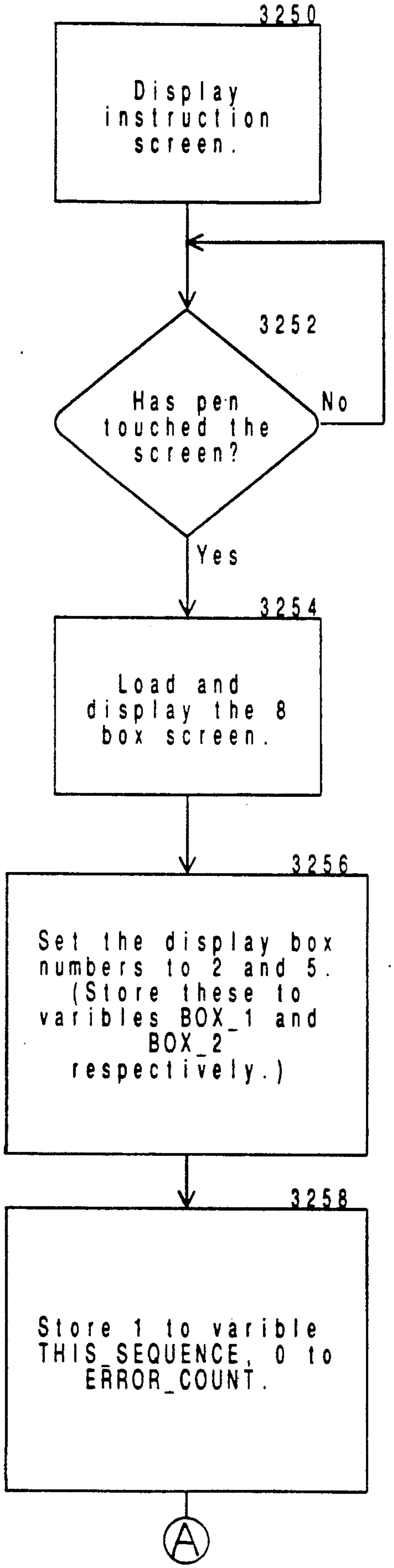
FIGS. 9a-9f are a flowchart illustrating a Saccadics Level III diagnostic routine.
Figure 9B:
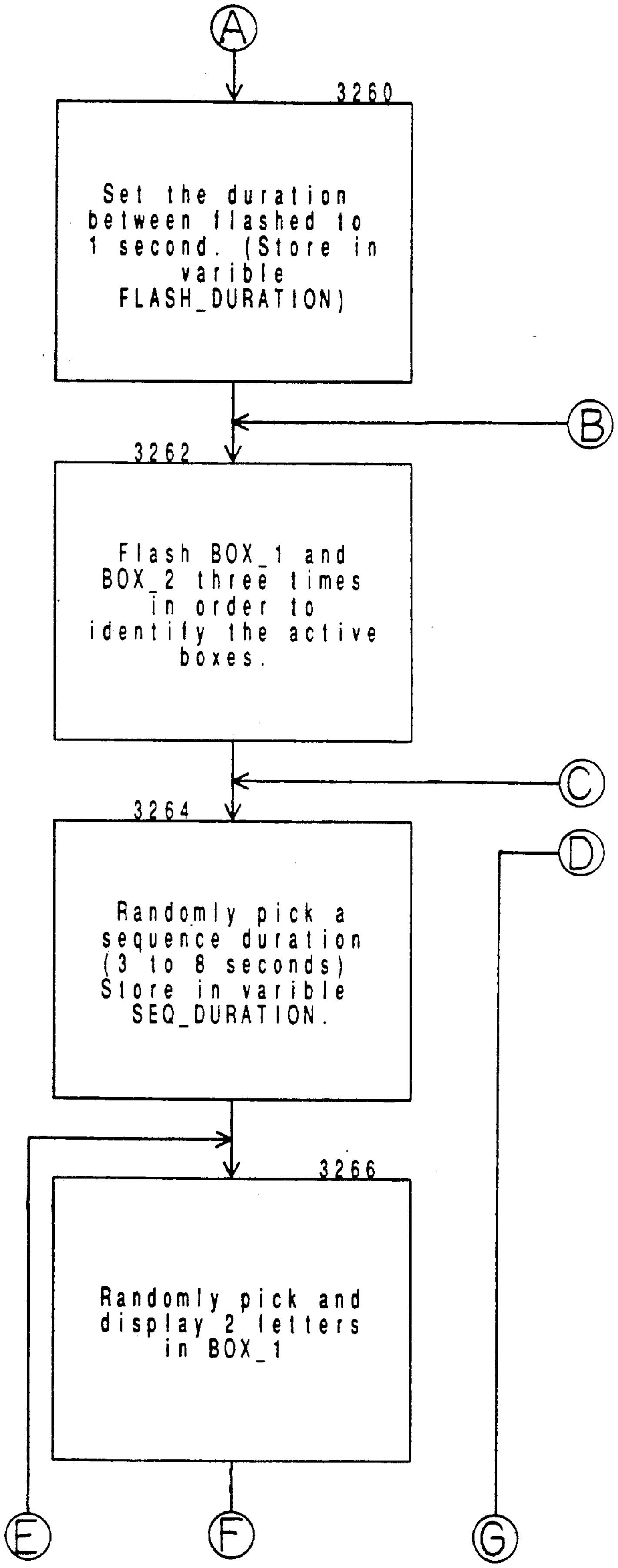
Figure 9C:
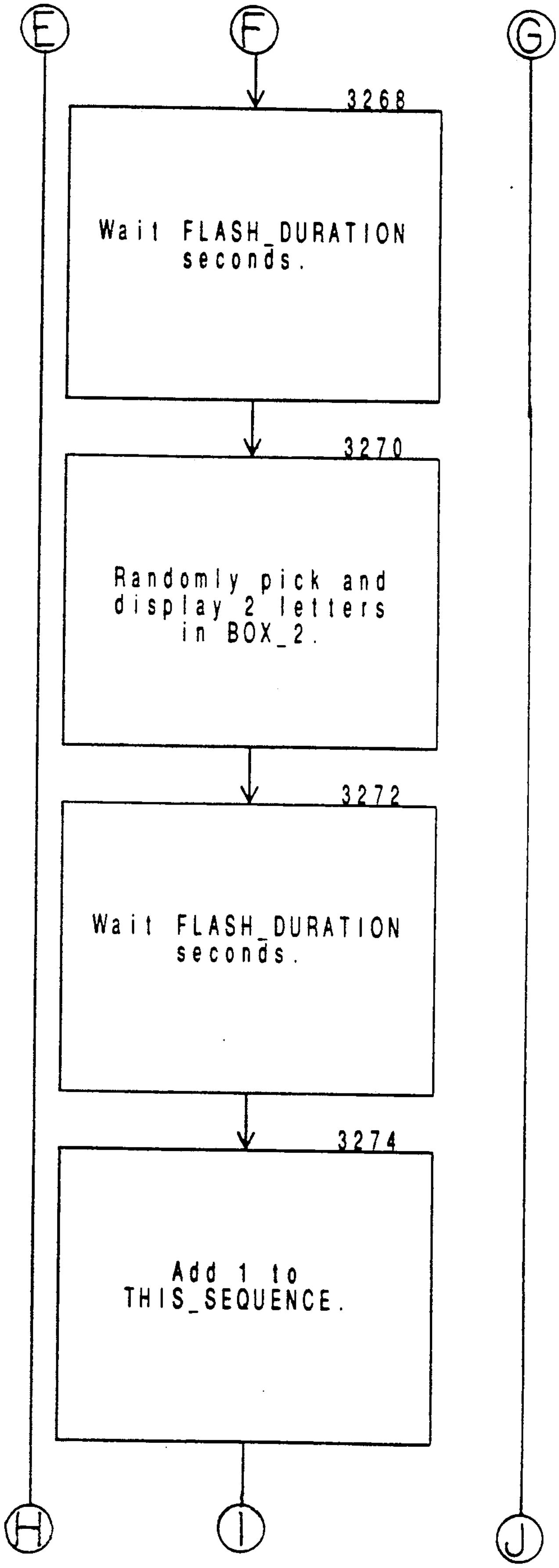
Figure 9D:
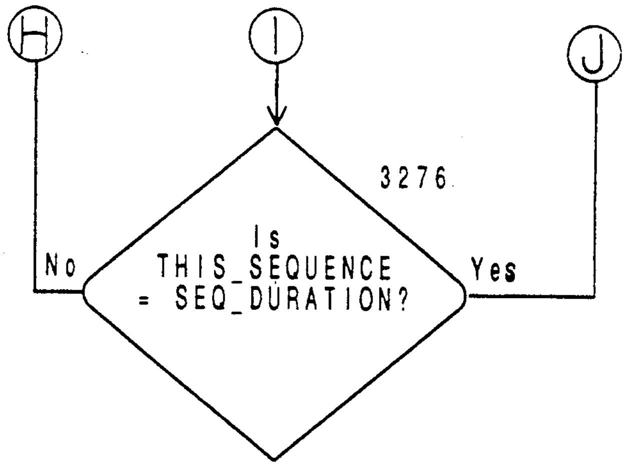
Figure 9E:
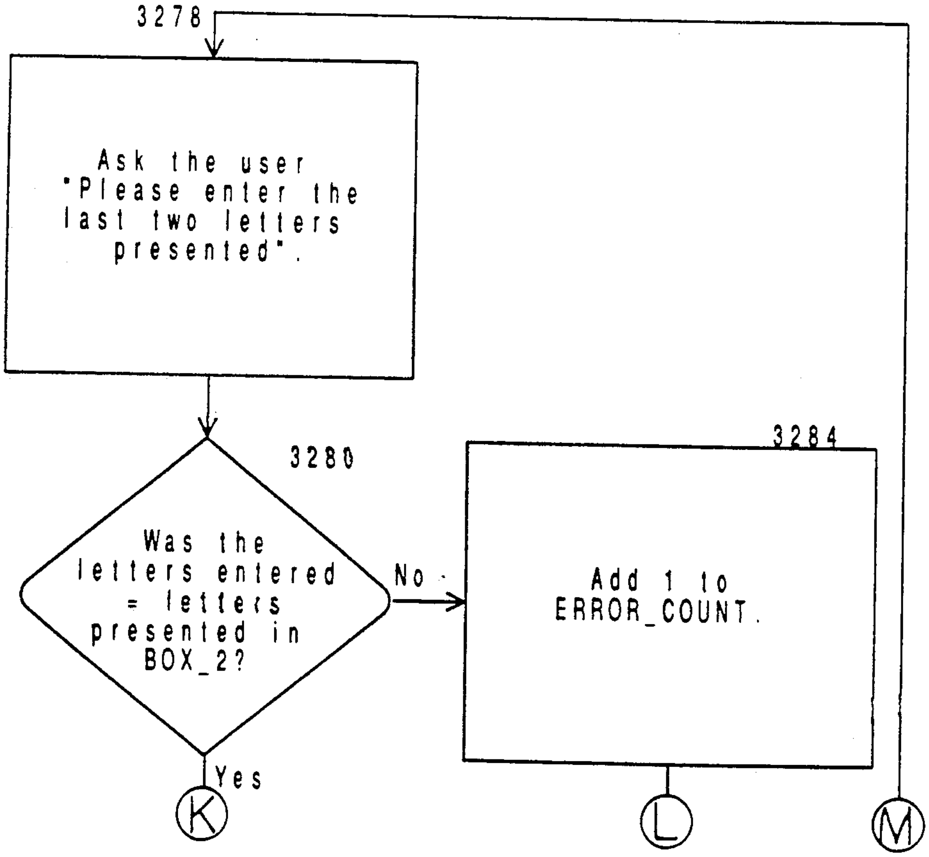
Figure 9F:
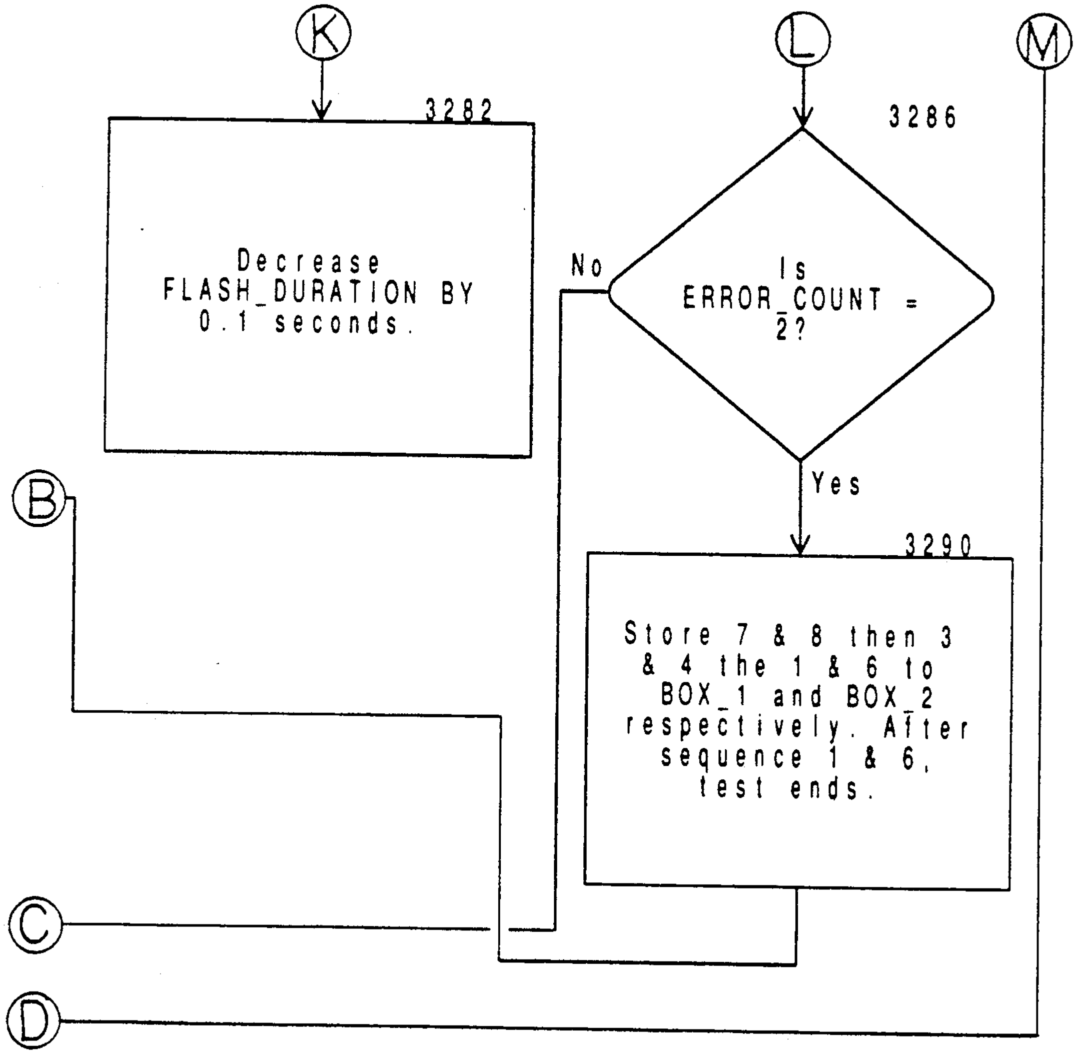

The purpose of the Visual Memory and Perceptual Span diagnostic routine is to test short-term Visual Memory and perceptual span. The target is a horizontal row of numbers flashed for 1/60th of a second. The subject reads instructions (not shown) and touches the screen with the active light pen to continue. The subject then watches a rectangular frame on the screen. See FIG. 10. The flashed numbers are preferably proceeded by two tones separated by one second. The subject, using the active light pen, is instructed to indicate the number seen by touching corresponding numbers displayed at the bottom of the screen. The length of the flashed sequence starts at three digits and, following a correct response, increases by one number at a time. Errors in three consecutive trials terminates the test.

The output includes (i) the longest sequence presented and (ii) the longest sequence correctly identified.

Figure 11A:
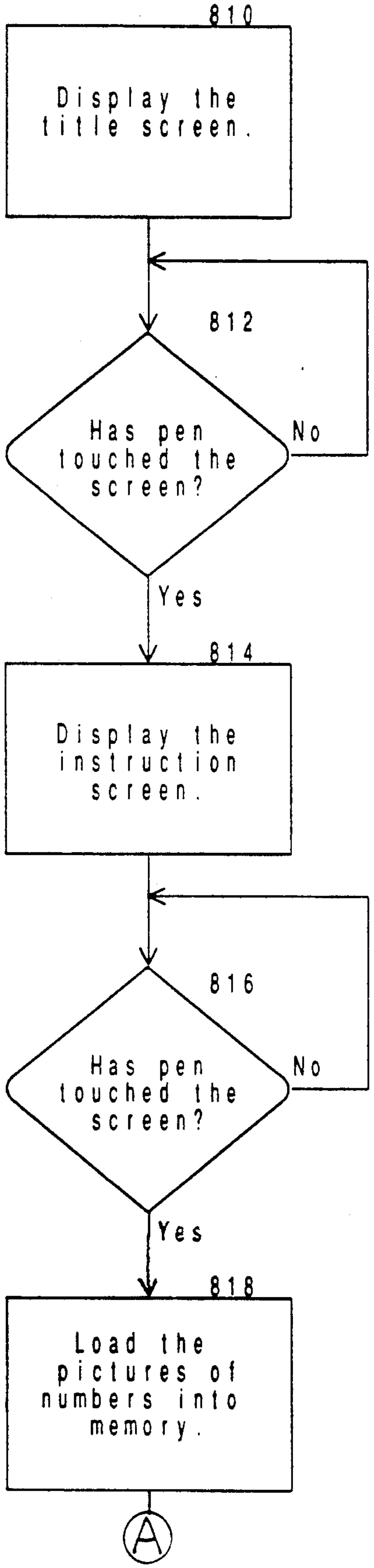
FIGS. 11a-11c are a flowchart illustrating a Visual Memory diagnostic routine.
Figure 11B:
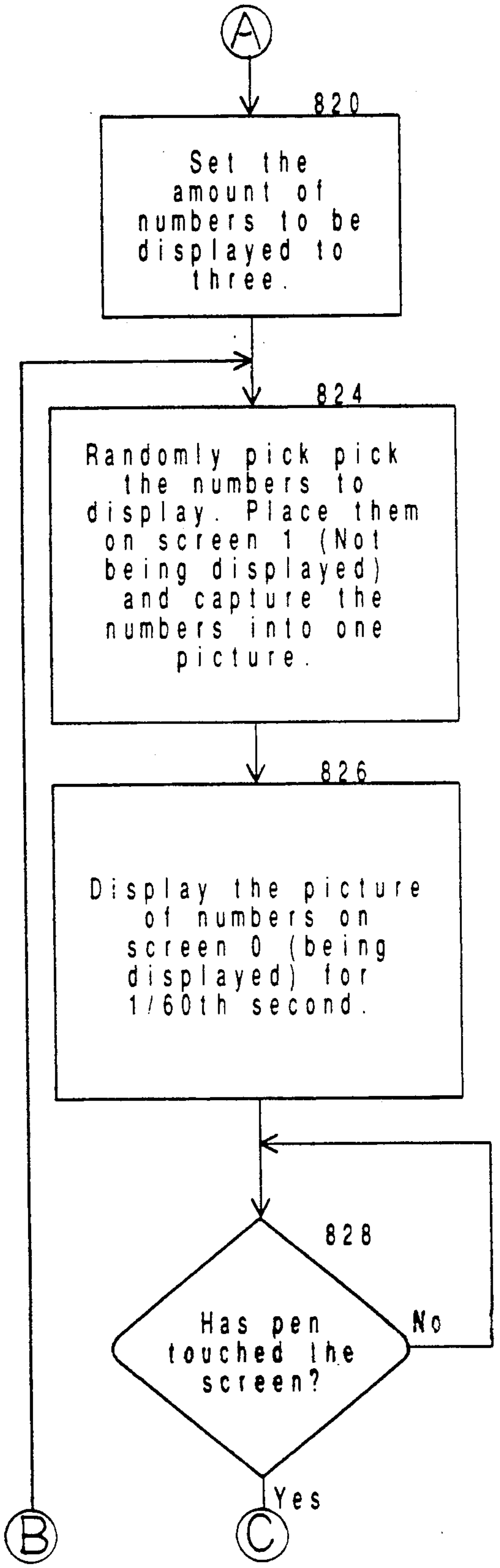
Figure 11C:
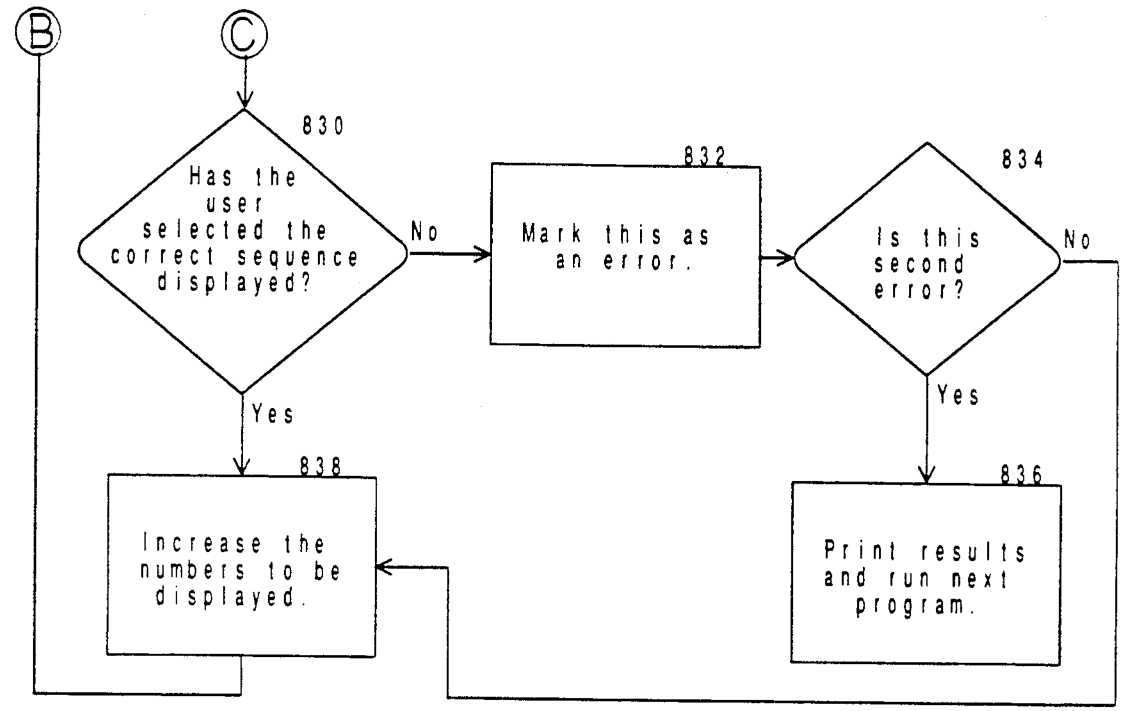

The following is a detailed description of the flowchart, shown in FIGS. 11*a*, *b* and *c*, for the Visual Memory and Perceptual Span Diagnostic routine. At block 810 of FIG. 11*a* a title screen (not shown) is displayed. Next, the program checks to determine whether the subject has touched the screen with the active light pen, block 812, before displaying an instruction screen (not shown), block 814. Next, the program waits for the subject to touch the screen with the active light pen, block 816, before continuing on to block 818 where pictures of numbers are loaded into memory. Next, the number of numbers to be displayed is set to three, block 820. Next, the program randomly picks the numbers to display, places them on Screen 1, which is not being displayed, and captures the numbers into one picture, block 824. These numbers are then displayed on Screen 0, i.e. the CRT, for 1/60th of a second, block 826. The program then waits for the active pen to touch the screen, block 828, before checking to determine whether the subject has selected the correct sequence, block 830. If the subject has not selected the correct sequence, this is recorded as an error, block 832. Next, the program checks to determine whether this is a second error, block 834. If not, the program jumps to block 838. If so, the results are printed and stored and the next routine is run, block 836. If the user did select the correct sequence, the program jumps from block 830 to block 838 where the number of numbers to be displayed on the screen is increased. Next, the program loops back to block 824, and the process is repeated.

3.) Accomoflex

The purpose of the Accomoflex Diagnostic routine is to test accommodative flexibility, i.e. focusing ability.

The subject wears a concave lens and a red filter over the right eye and a convex lens with a green filter over the left eye. After one minute the lenses are switched to the opposite eye. The colored filters remain unswitched.

Figure 12A:
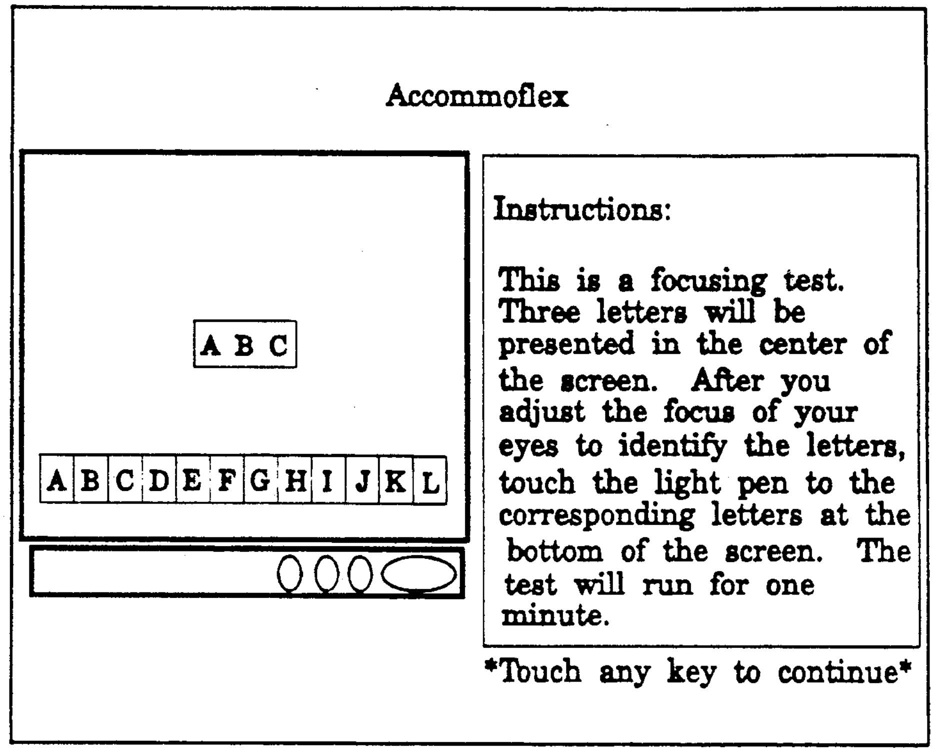
FIGS. 12a, 12b are displays provided by the vision training system of the present invention in connection with an Accomoflex diagnostic routine.
Figure 12B:
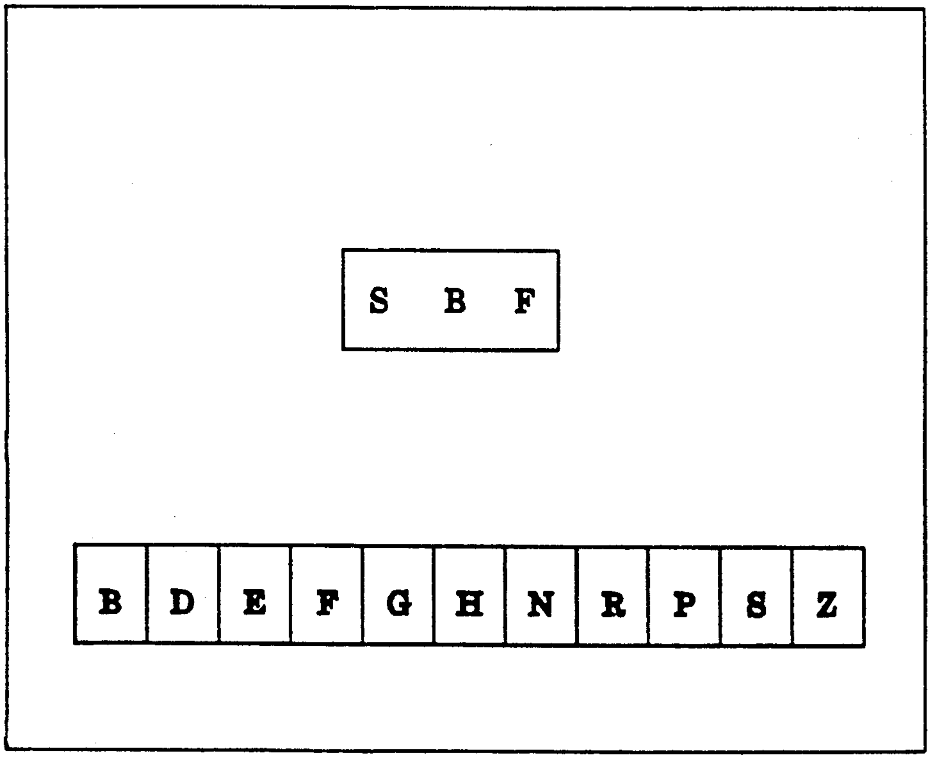

There are 11 letters constantly displayed at the bottom of the screen with three of those letters randomly chosen and displayed in the center of the screen. See FIGS. 12*a*, 12*b*. These are the targets. The letters should be selected on the basis of being moderately or markedly difficult to identify as Snellen optotypes. See *Clinical Refraction*, Borish.

The subject reads instructions (not shown) and touches the active light pen to the screen to continue. As a result of the colors used for the letters and background, combined with the red/green filters worn by the subject, the first set of letters presented are only visible to the right eye. The subject is instructed to attempt to clear the letters from the screen center by touching the corresponding letters at the bottom of the screen. As soon as three letters are touched, the three letters in the center of the screen change along with the color. Now the letters are visible only to the left eye.

The test runs for one minute, and then each lens is switched to the opposite eye and the test runs for another one minute. The output includes (i) the mean time per screen for each eye, and (ii) the total number of screens presented.

Figure 13A:
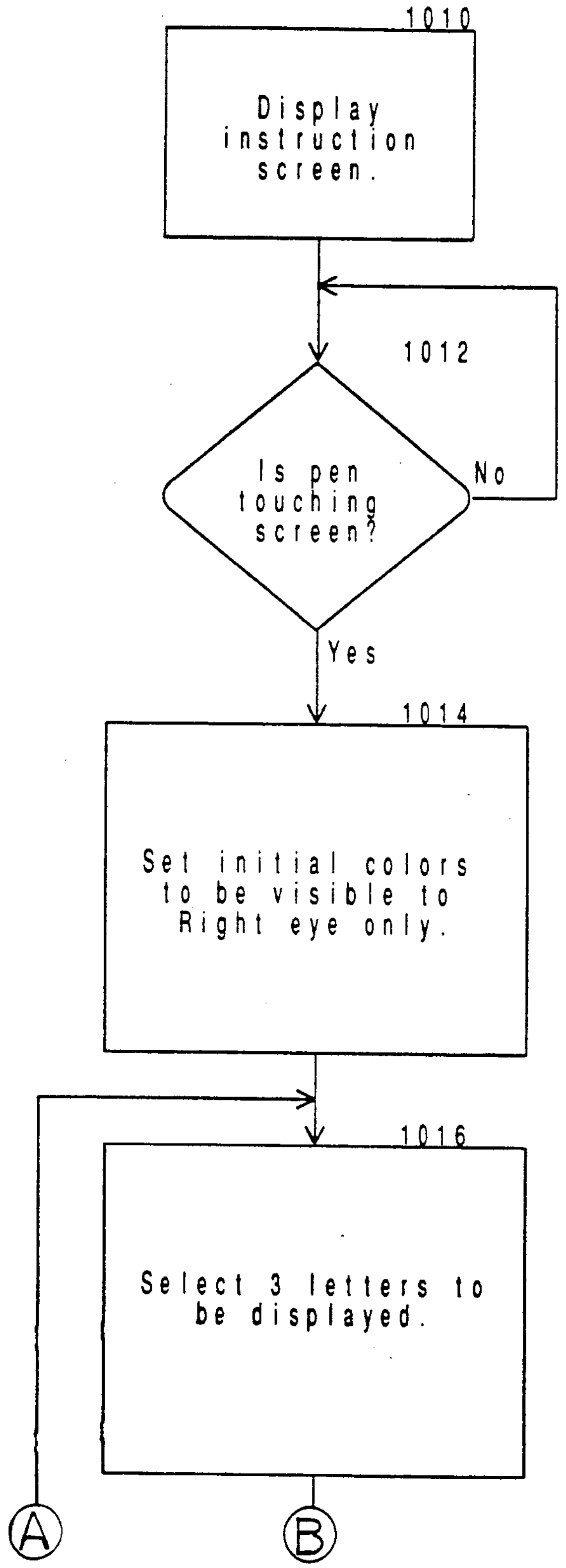
FIGS. 13a-13c are a flowchart illustrating an Accomoflex diagnostic routine.
Figure 13B:
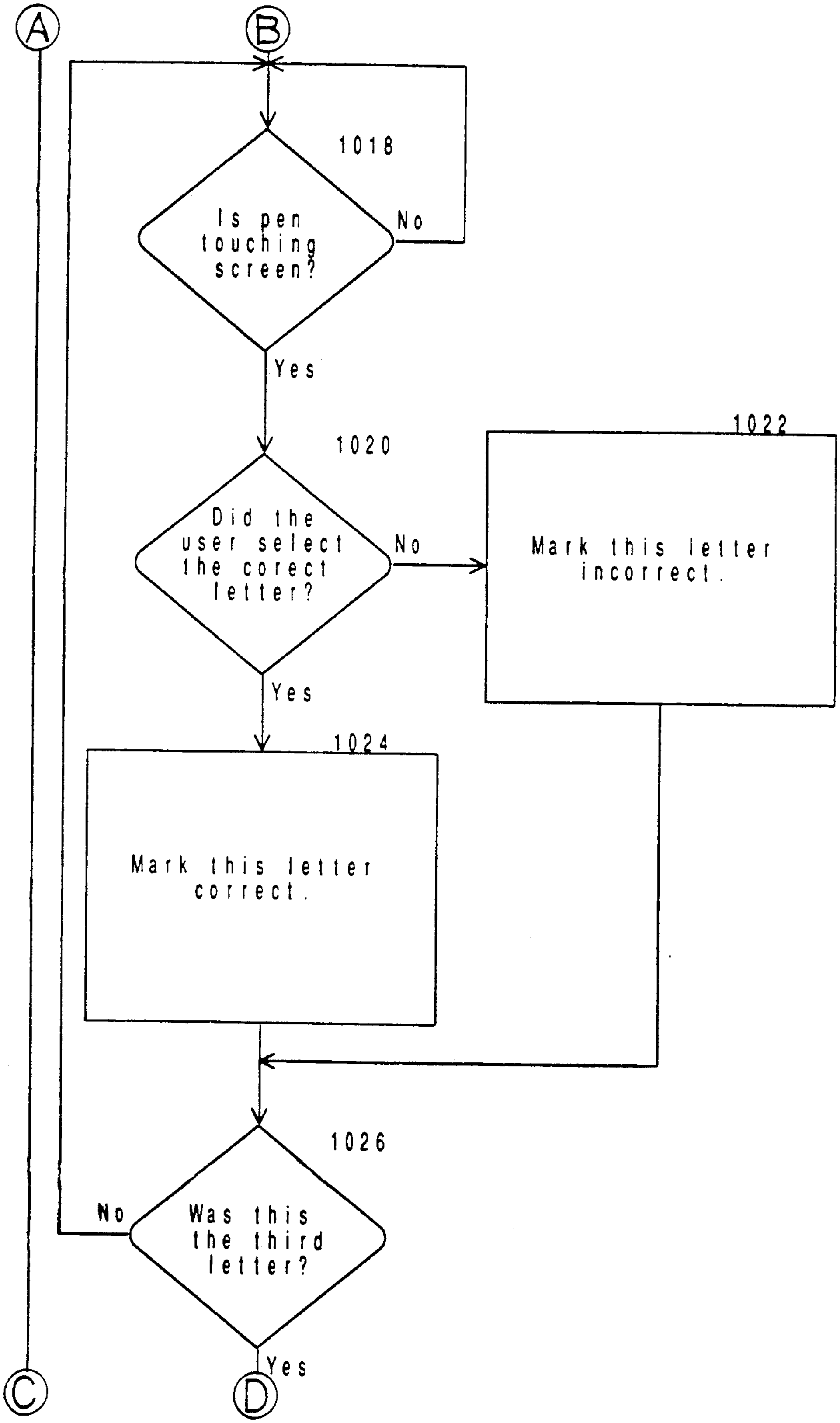
Figure 13C:
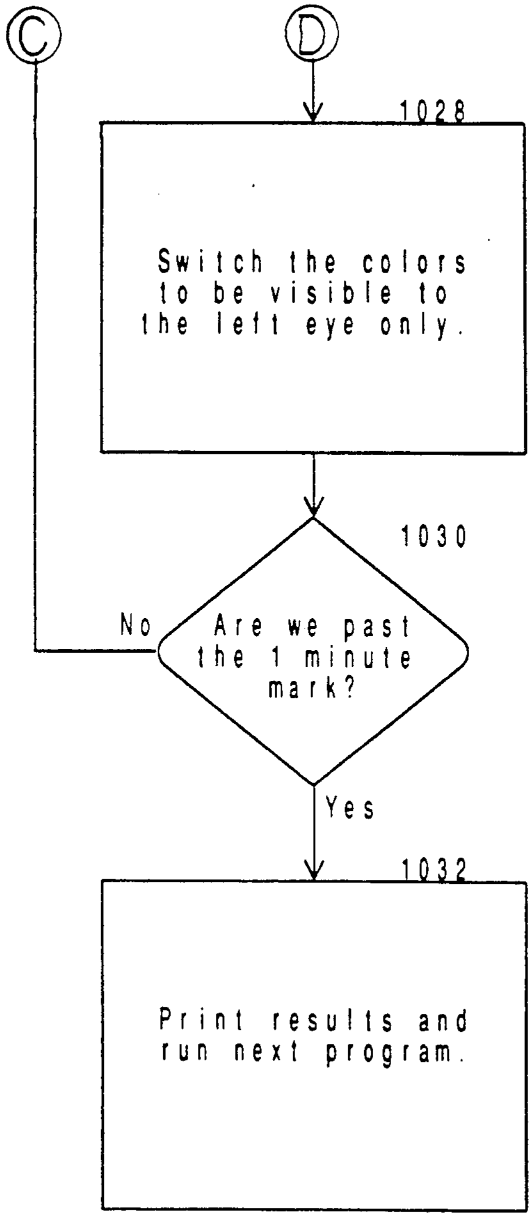
Figure 14A:
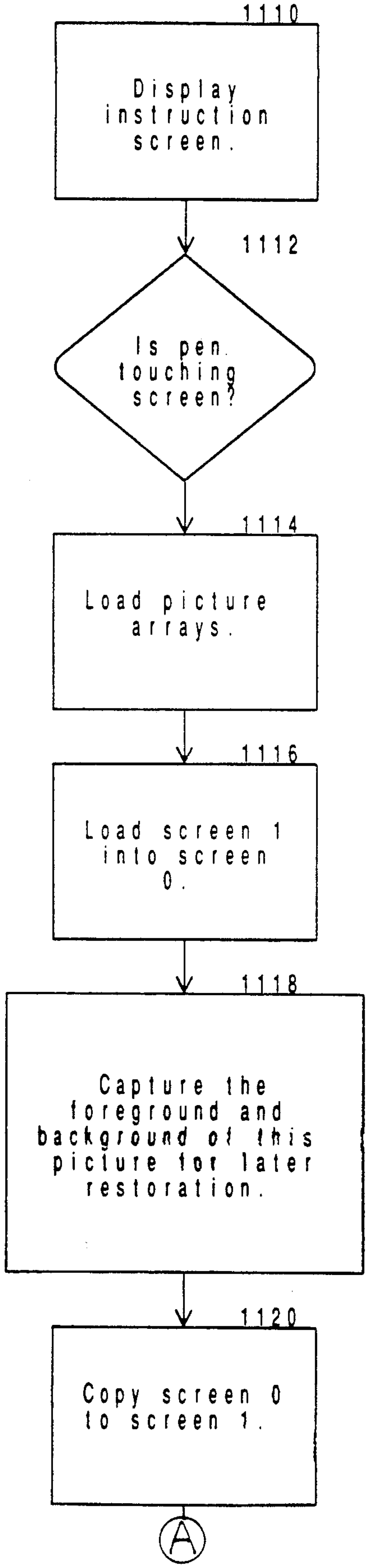
FIGS. 14a-14d are a flowchart illustrating a Fusion diagnostic routine.
Figure 14B:
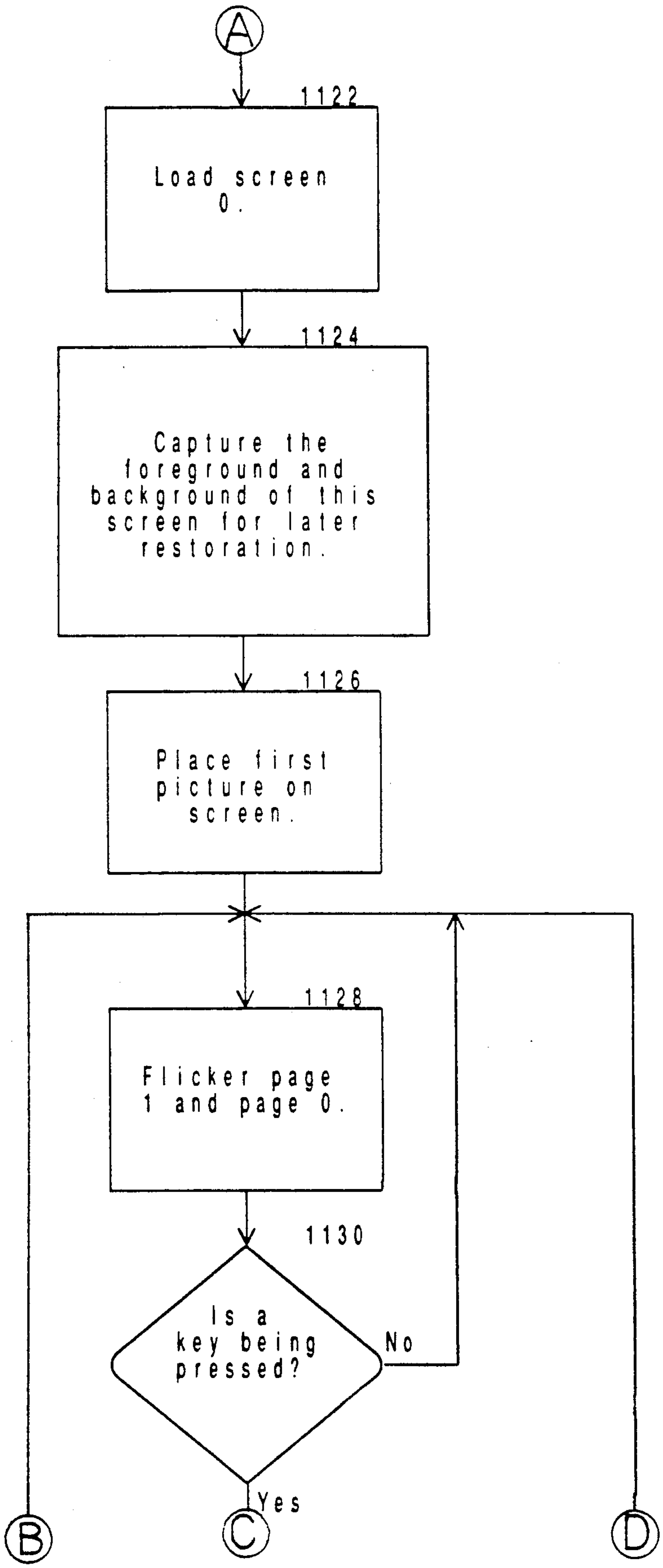
Figure 14C:
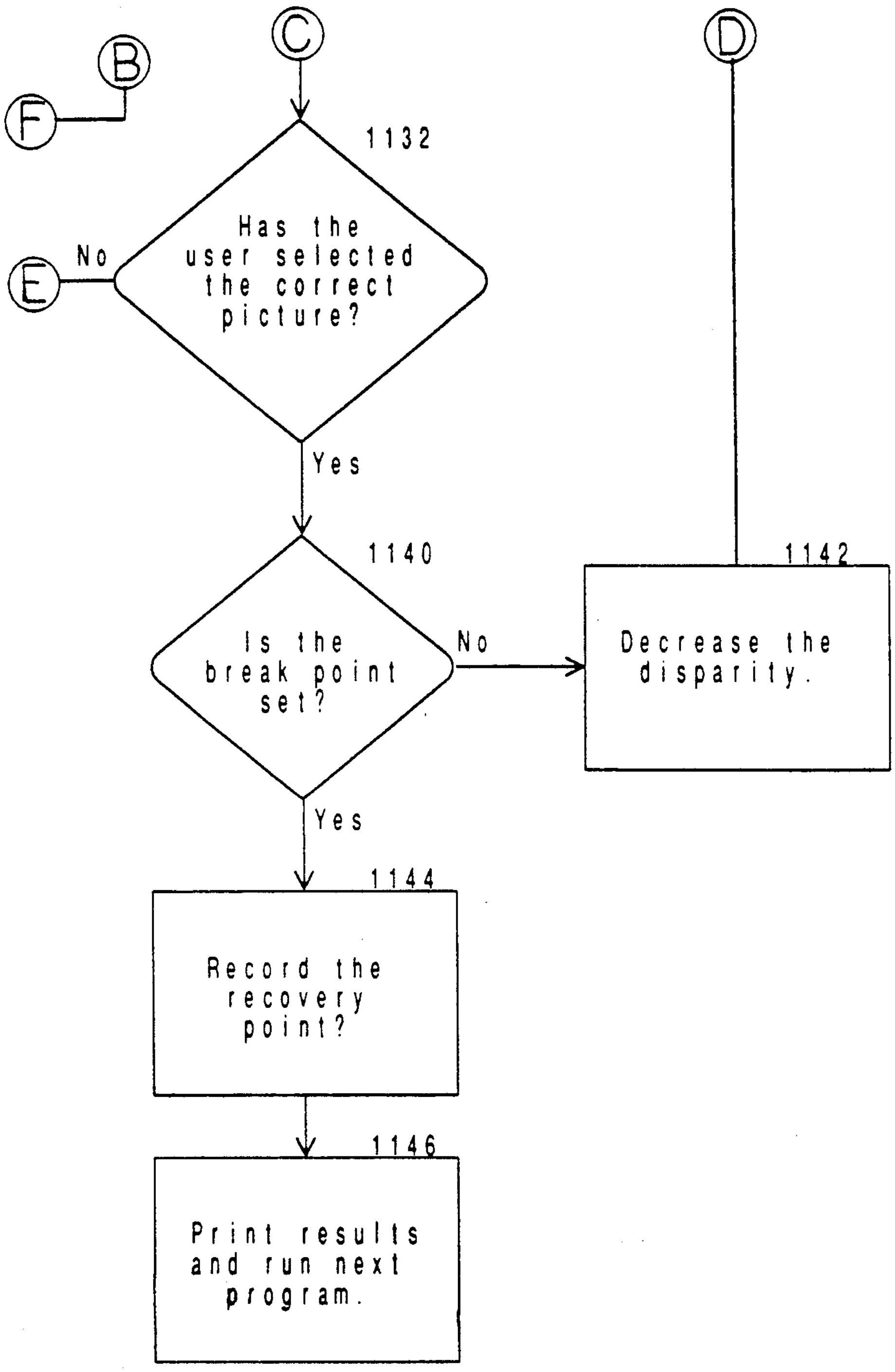
Figure 14D:
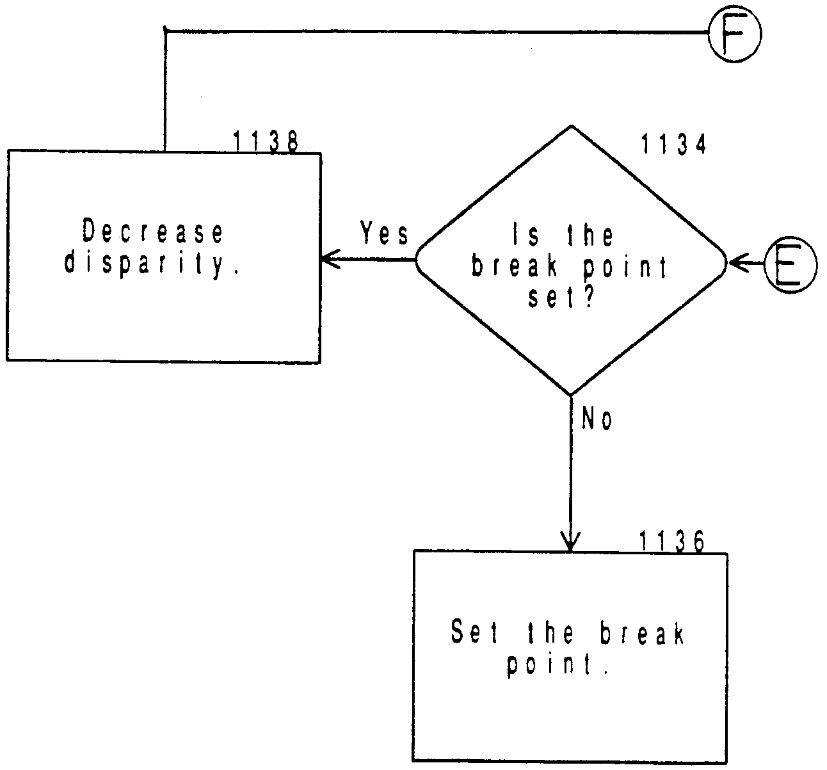

The following is a detailed description of the flowchart, shown in FIGS. 13*a, b,* and 13*c*, for the Accomoflex Diagnostic routine. First, a title screen (not shown) is displayed, block 1010. Next, the program waits for the active light pen to touch the screen, block 1012, before setting the initial colors to be visible to the right eye, block 1014. At block 1016, the three letters to be displayed are selected. At block 1018, the program waits for the light pen to touch the screen before continuing to block 1020 where a check is made to determine whether the user selected the correct letter. If the user did not select the correct letter, this letter is recorded as being incorrectly selected, block 1022, and the program jumps forward to block 1026. If the subject did select the correct letter, this letter is recorded as being correctly recorded, block 1024. Next, at block 1026, a check is made to determine whether this was the third letter selected. If not, the program loops back to block 1018. If so, the colors are switched so that the targets will be visible to the opposite eye, block 1028. Next, at block 1030, a check is made to determine whether the routine has passed the one-minute mark. If so, the results are printed and stored and the next program is run, block 1032. If the routine is not past the one-minute mark the program loops back to block 1016.

4.) Fusion

Figure 25A:
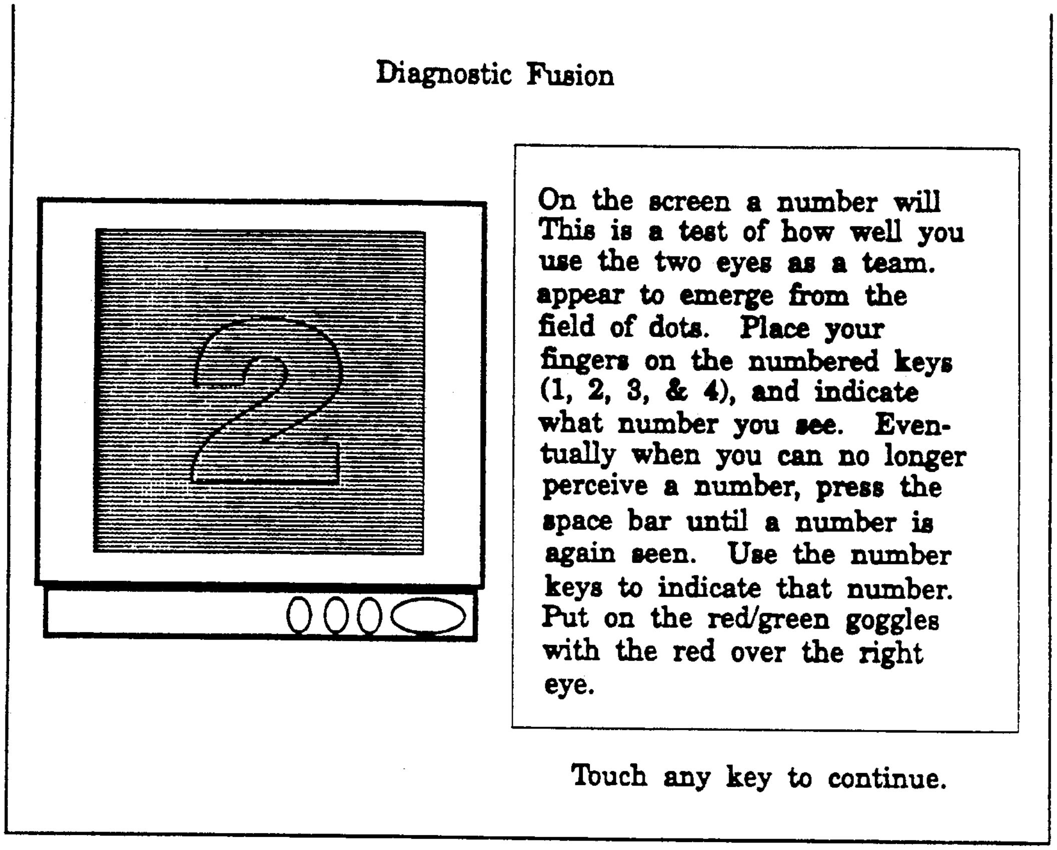
FIGS. 25a and 25b are displays provided by the vision training system of the present invention in connection with a Fusion diagnostic routine.
Figure 25B:
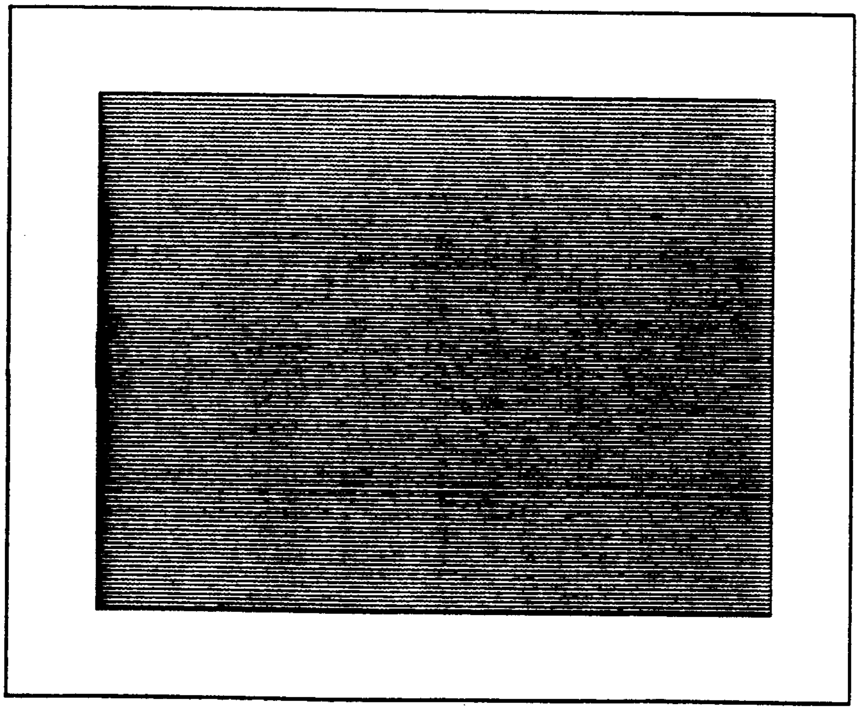
Figure 26A:
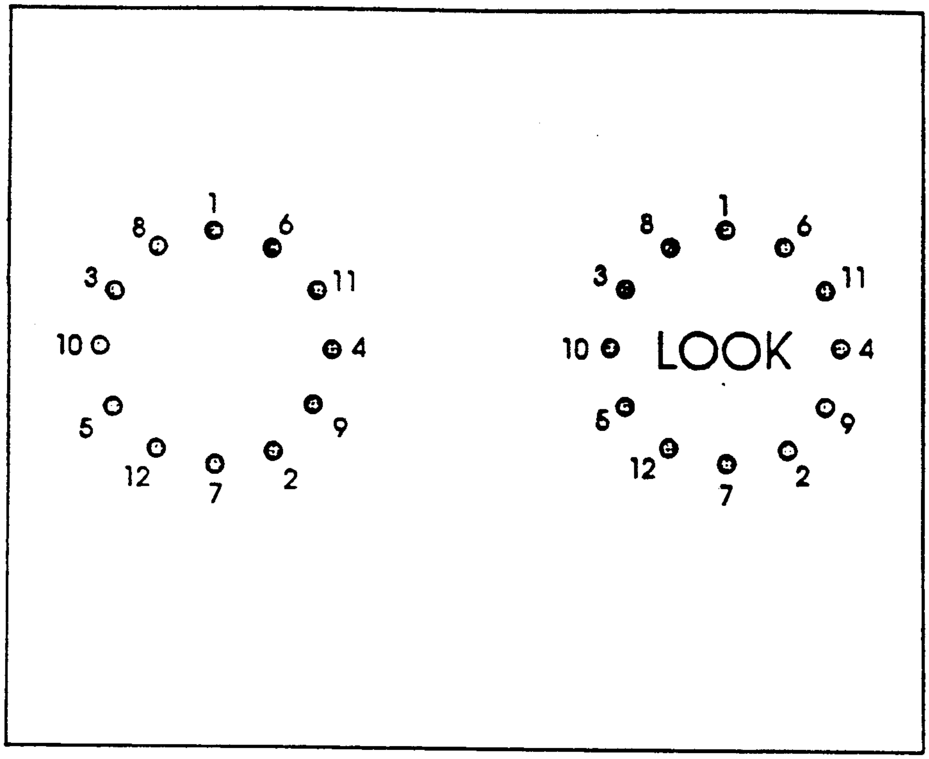
FIGS. 26a-26d are displays provided by the vision training system of the present invention in connection with a Fixations Level II therapeutic exercise routine.
Figure 26B:
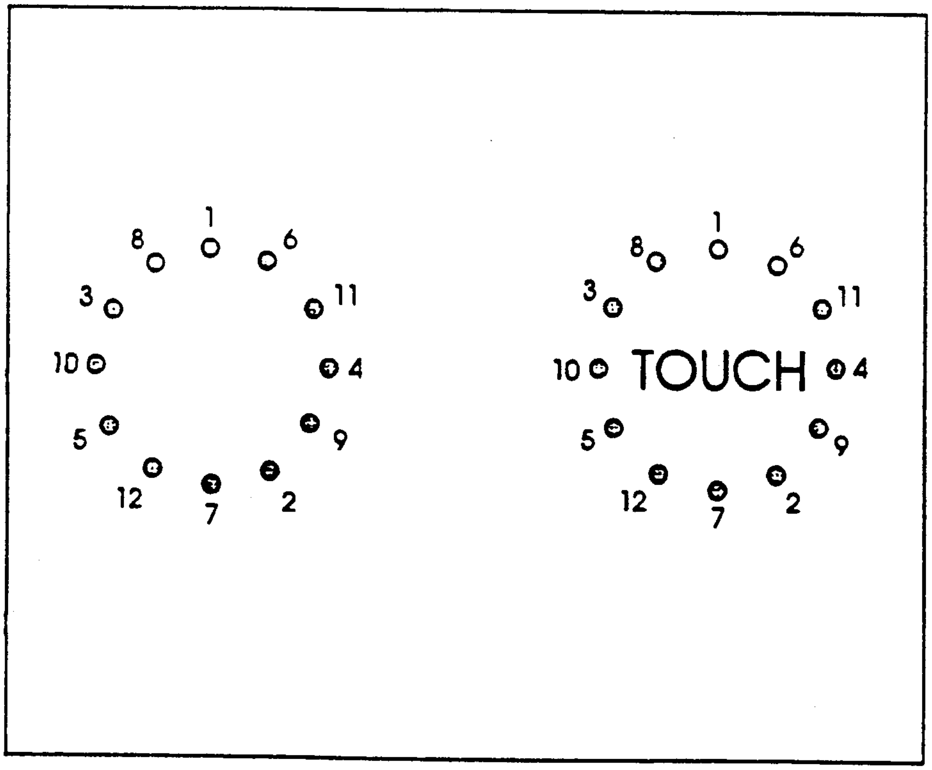
Figure 26C:
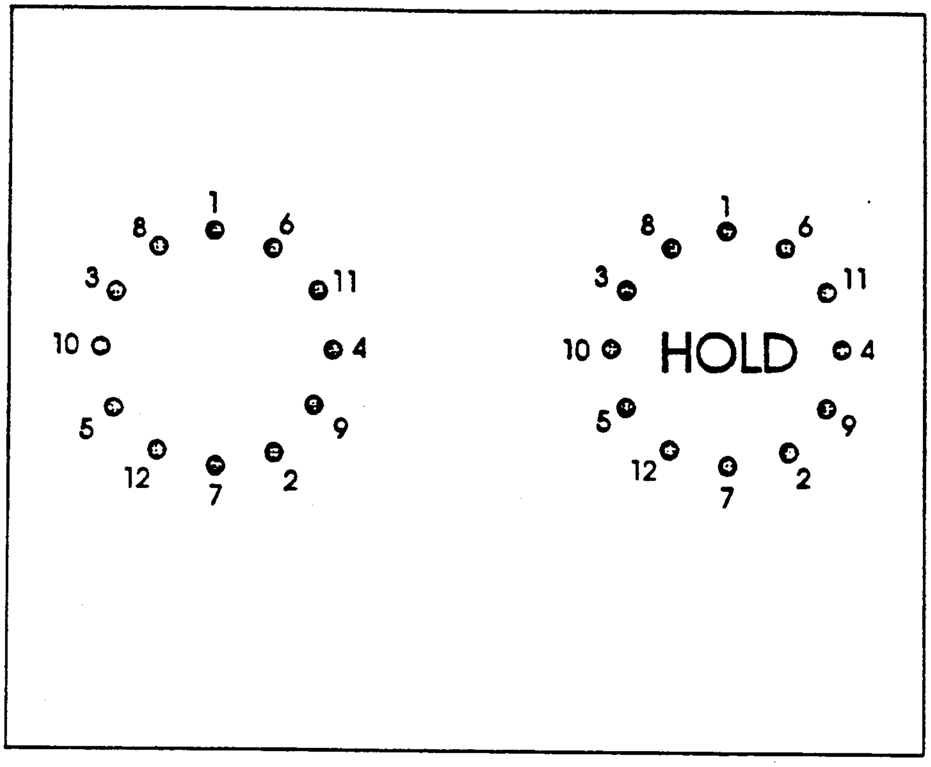
Figure 26D:
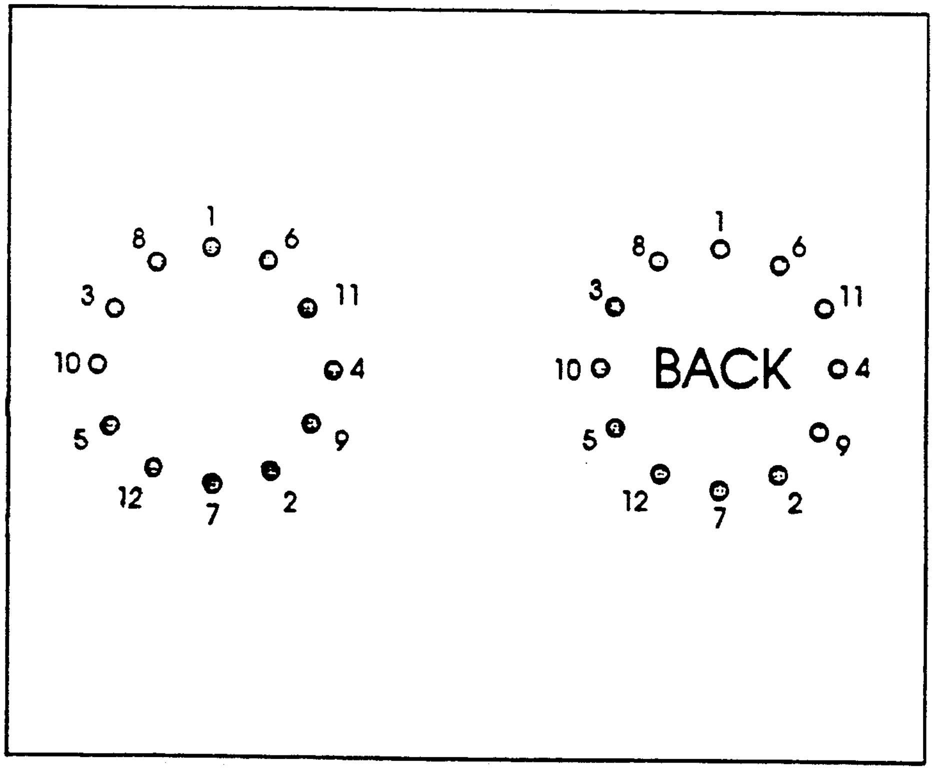
Figure 27A:
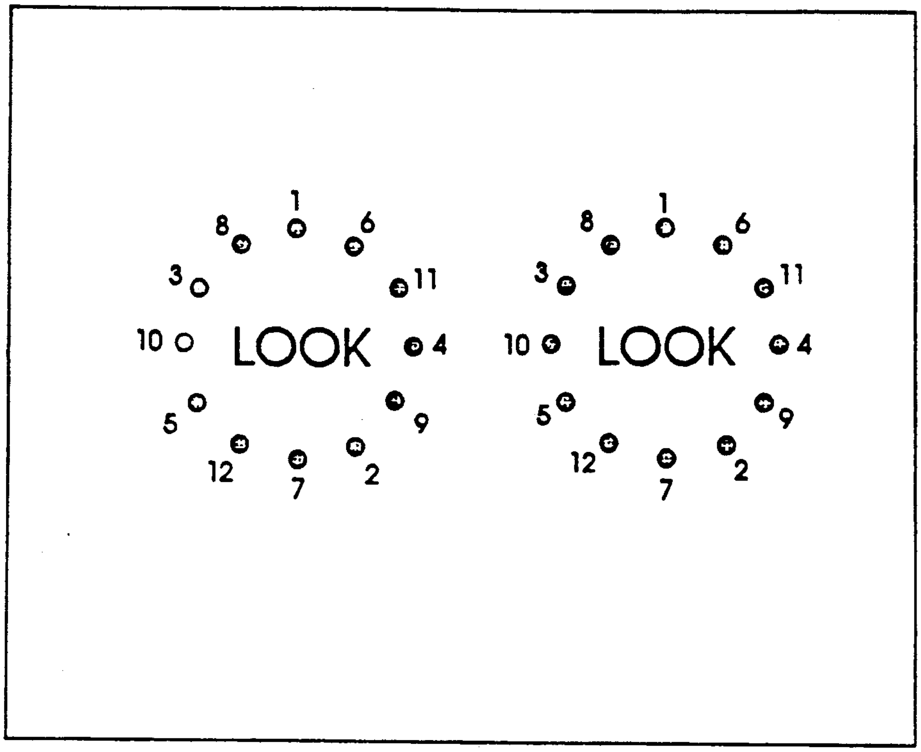
FIGS. 27a-27f are displays provided by the vision training system of the present invention in connection with a Fixations Level III therapeutic exercise routine.
Figure 27B:
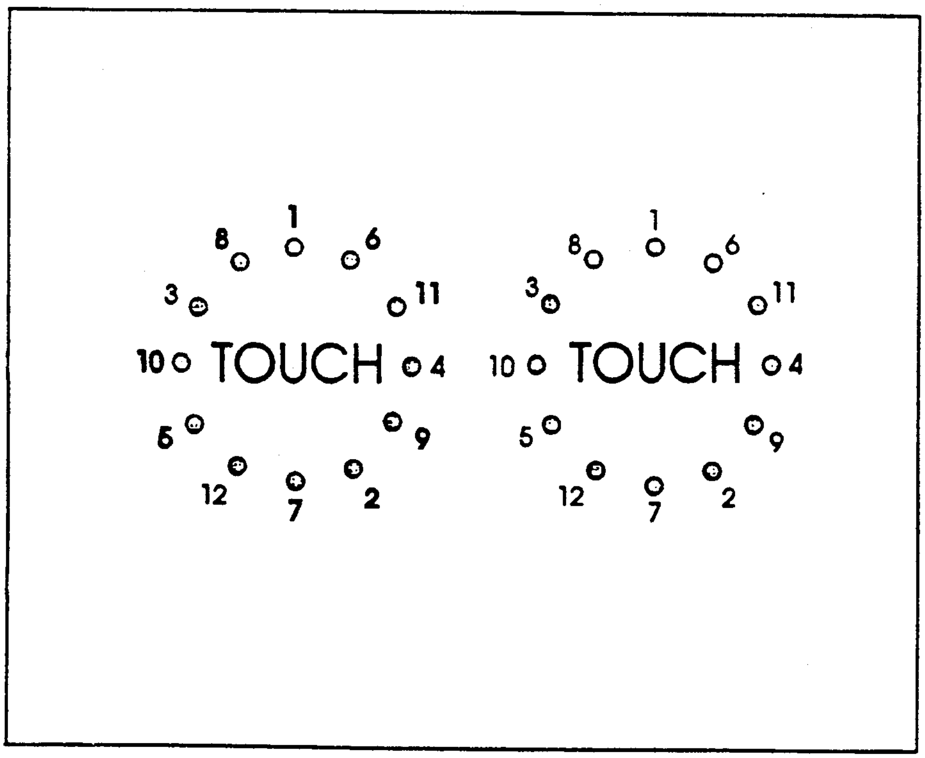
Figure 27C:
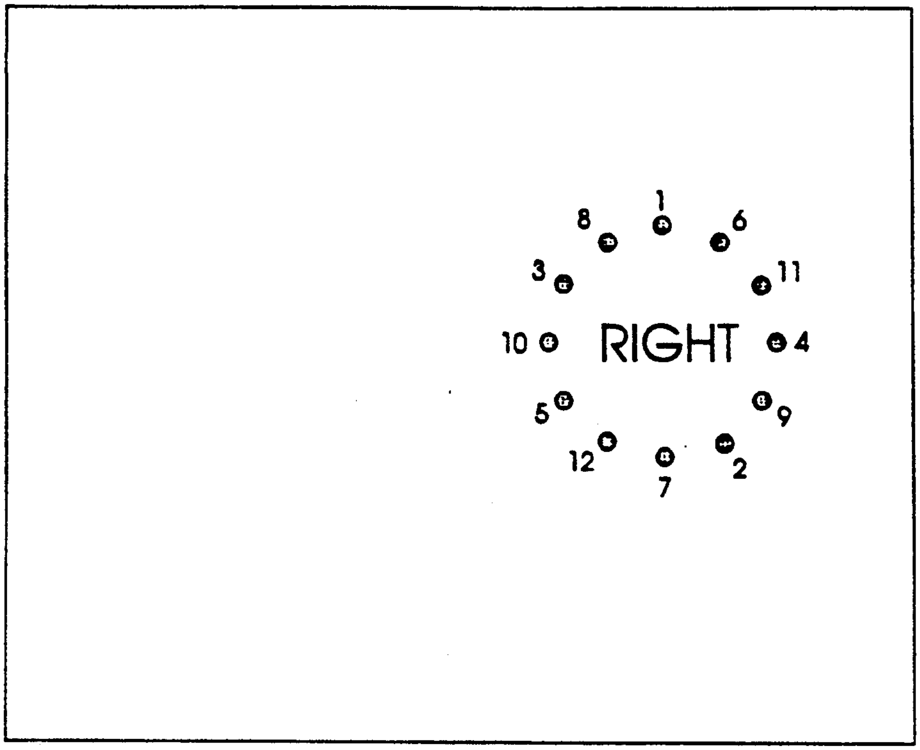
Figure 27D:
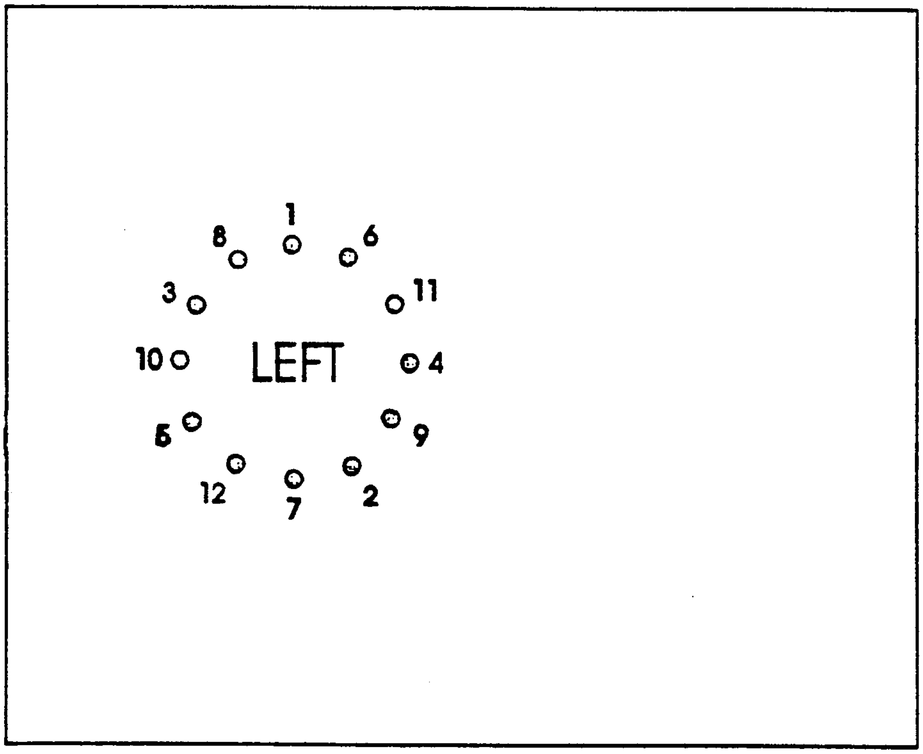
Figure 27E:
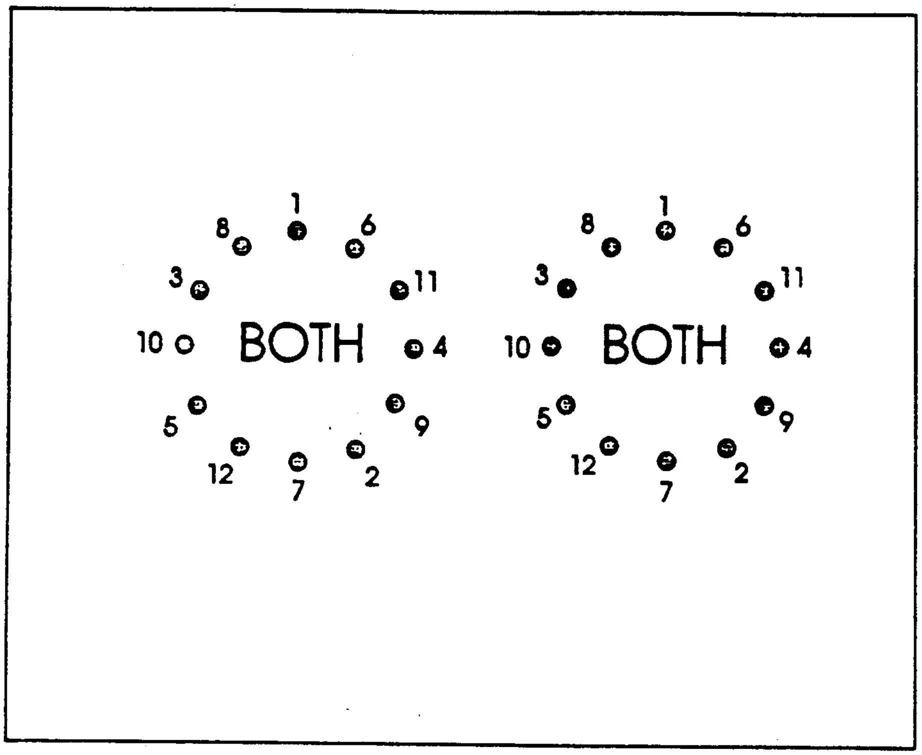
Figure 27F:
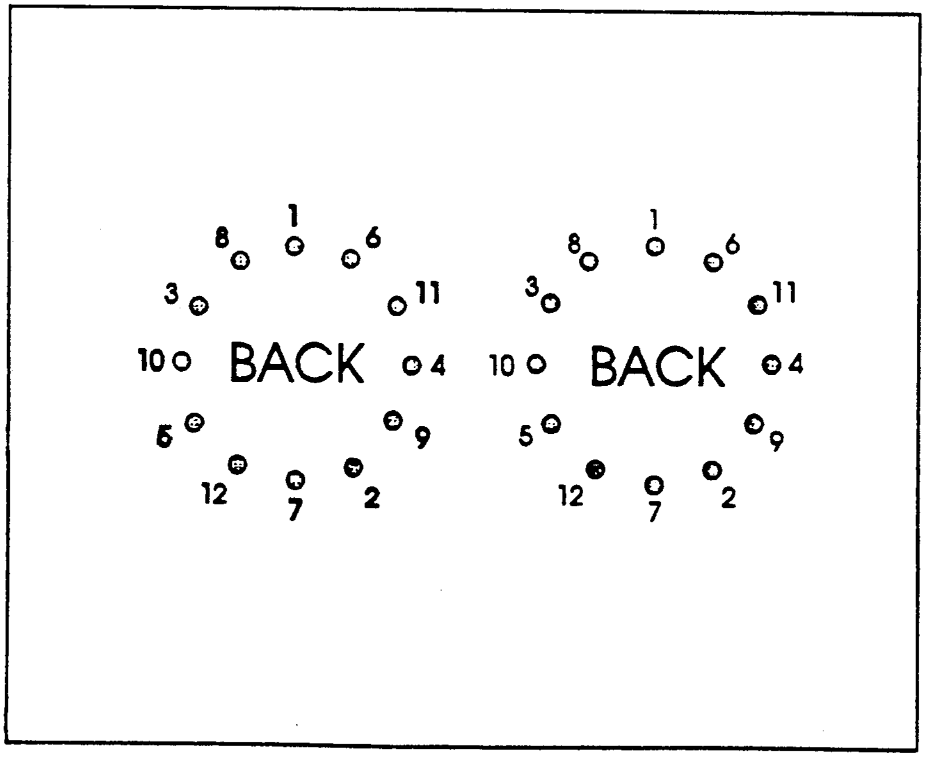

The purpose of the Fusion diagnostic routine is to test fusion ranges, that is, degrees of freedom within the binocularity system. The numerical keys 1, 2, 3 and 4 are used to input the subject's response. The subject wears red/green filters with red worn over the right eye. Using a so called random dot stereogram format (discussed herein), a number 1, 2, 3, or 4 is presented in a certain color within a field of randomly placed dots so that the number cannot be perceived unless the subject is (a) wearing anaglyph lenses (red/green), and (b) has central fusion ability see FIGS. 25*a* and 25*b*). A 16-inch viewing distance is preferred. The idea is to make the display appear three dimensional so that the number appears to have a depth effect relative to the background of the display. Techniques for achieving this, by means of a random dot stereogram described herein, are known.

The subject reads instructions (not shown) and touches the screen with the active light pen to continue. The subject is encouraged to maintain visual contact with the screen. A number 1, 2, 3, or 4, is chosen at random and is displayed with a depth effect until the subject strikes a key. If the corresponding key was pressed, the base-out demand increases, i.e. the right eye field moves left and the left eye field moves right, and a new number is presented. If an incorrect response is given, the number changes but the base-out demand remains unchanged. At some point the subject will no longer perceive a number and will strike the space bar until a another number is recognized. The base-out level at which the number disappeared is recorded as a "break point", i.e. the point at which fusion was lost. Striking the space bar causes the right and left eye fields to start coming back to zero base-out disparity, with the base-out level where a number is again perceived recorded as a "recovery point", i.e. the point at which fusion was regained. The presentation is then repeated with base-in demand, i.e., the right eye field moving right and the left eye field moving left. The output includes (i) the base-out break point, in prism dioptors, (ii) the base-out recovery point, in prism dioptors, (iii) the base-in break point in prism dioptors, and (iv) the base-in recovery point in prism dioptors.

The following is a detailed description of the flowchart, shown in FIGS. 14*a* through 14*d*, for the Fusion Diagnostic routine. First, an instruction screen (not shown) is displayed, block 1110. Next, the program waits for the active pen to touch the screen, block 1112, before continuing to block 1114 where the picture arrays are loaded (for the random dot stereogram) into Screens: 0 and 1 of the computer. Screens 0 and 1 contain the dots and image data for the random dot stereogram and for the target (the number). Next, Screen 1 is loaded into Screen 0, block 1116. Next, the foreground and background of this picture are captured for later restoration, block 1118. Next, Screen 0 is copied to Screen 1, block 1120. At block 1122, Screen 0 is loaded. At block 1124, the foreground and background of this screen are captured for later restoration. At block 1126, the first picture is placed on the screen. At block 1128, Page 0 and Page 1 are alternately flickered. At block 1130, a check is made to determine whether a key is being pressed. If not, the program loops back to block 1128. If so, a check is made to determine whether the subject has correctly identified the picture, block 1132. If not, a check is made to determine if the break point is set, block 1134. If the break point is not set, the break point is set at block 1136, the disparity between the dots comprising the random dot stereogram is decreased, block 1138, and the program loops back to block 1128. Changing the disparity alters the depth effect of the number displayed. If, at block 1134 it is determined that the break point is set, the program jumps to block 1138. If, at block 1132, it is determined that the subject has selected the correct picture, a check is made to determine whether the break point is set, block 1140. If not, the disparity (depth effect) is increased, block 1142 and the program loops back to block 1128. If the break point is set, a recovery point is recorded, block 1144, and the results are printed and stored, and the next routine run, block 1146.

5.) Phoria

The purpose of the Phoria Diagnostic routine is to test near horizontal and vertical muscle balance.

Figure 15A:
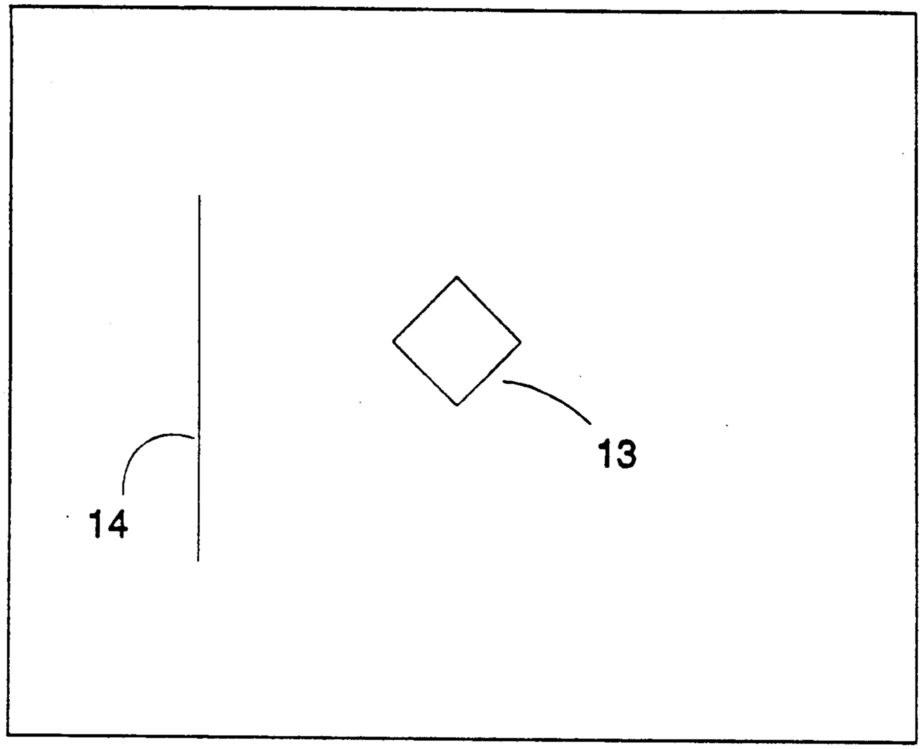
FIGS. 15a, 15b are displays provided by the vision training system of the present invention in connection with a Phoria diagnostic routine.
Figure 15B:
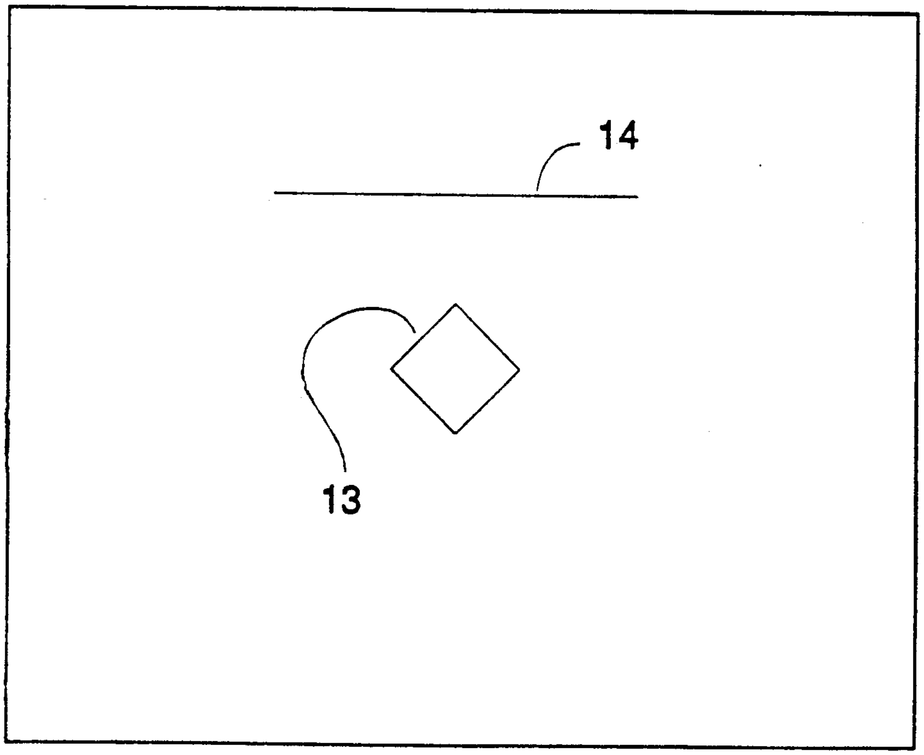

The subject wears red/green filters with red worn over the right eye. The space bar is used for inputting the subject's responses. A red diamond 13 centered in a black background with a blue line 14 is used as the target. See FIGS. 15*a*, 15*b*. For horizontal phoria, the blue line is in a vertical orientation, FIG. 15*b*, and preferably begins 53 millimeters to the left of the diamond. For vertical phoria, the blue line is in horizontal orientation, FIG. 15*a*, and begins 58 millimeters above the diamond. The subject reads instructions (not shown) and touches the active light pen to the screen to continue. The first test is of horizontal phoria. The subject views the vertical blue line with the left eye and red diamond with the right eye. Tapping the space bar once starts the blue line moving toward the diamond. The subject is instructed to tap the space bar again when the blue line appears to bisect the diamond. The position of the line relative to the diamond is recorded. The display automatically changes to the vertical phoria test with the blue line now horizontally oriented above the diamond. Again, the subject is instructed to tap the space bar to start the blue line moving, and is instructed to tap it again when the line appears to bisects the diamond. After the first run through the routine the horizontal and vertical phoria tests are automatically repeated. The output includes (i) the two horizontal phoria responses in prism dioptors, (ii) the two vertical phoria responses in prism dioptors, and (iii) the averages of the results of the horizontal and vertical phoria tests.

Figure 16A:
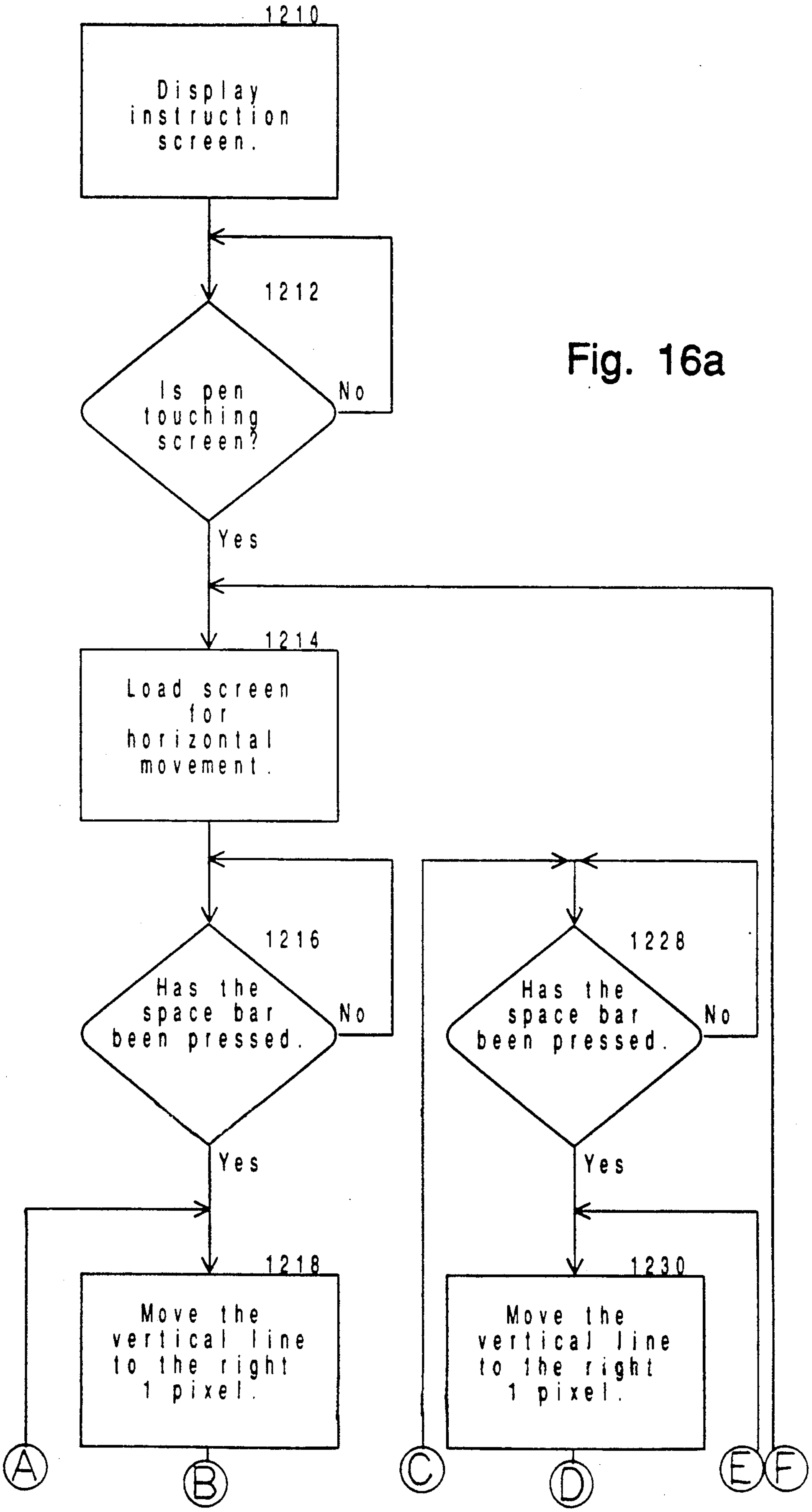
FIGS. 16a-16c are a flowchart illustrating a Phoria diagnostic routine.
Figure 16B:
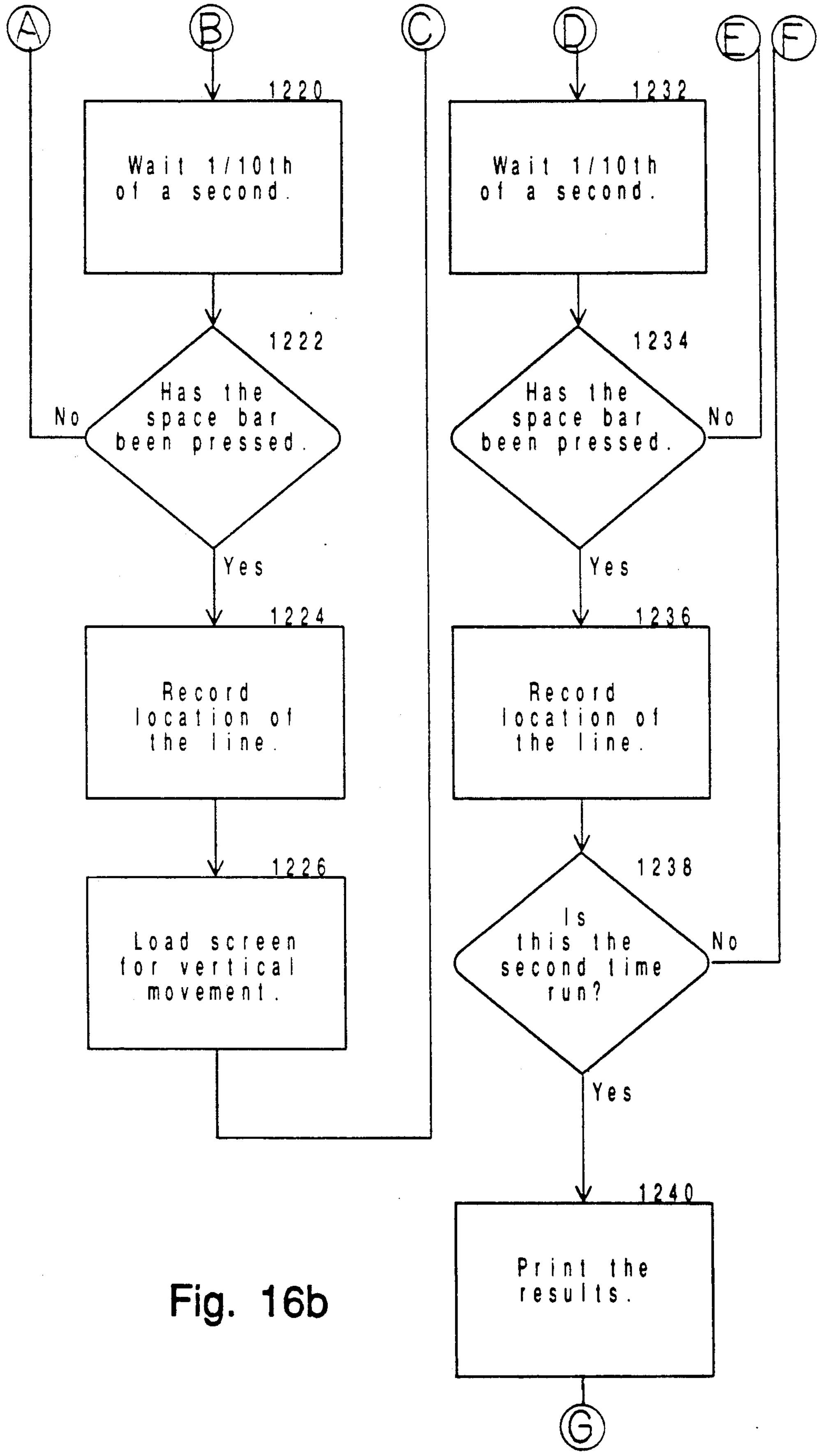
Figure 16C:
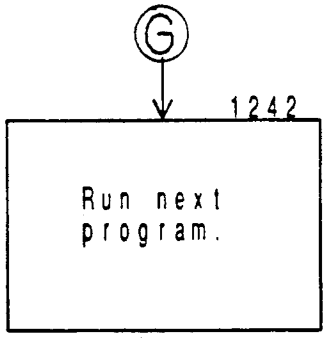
Figure 19A:
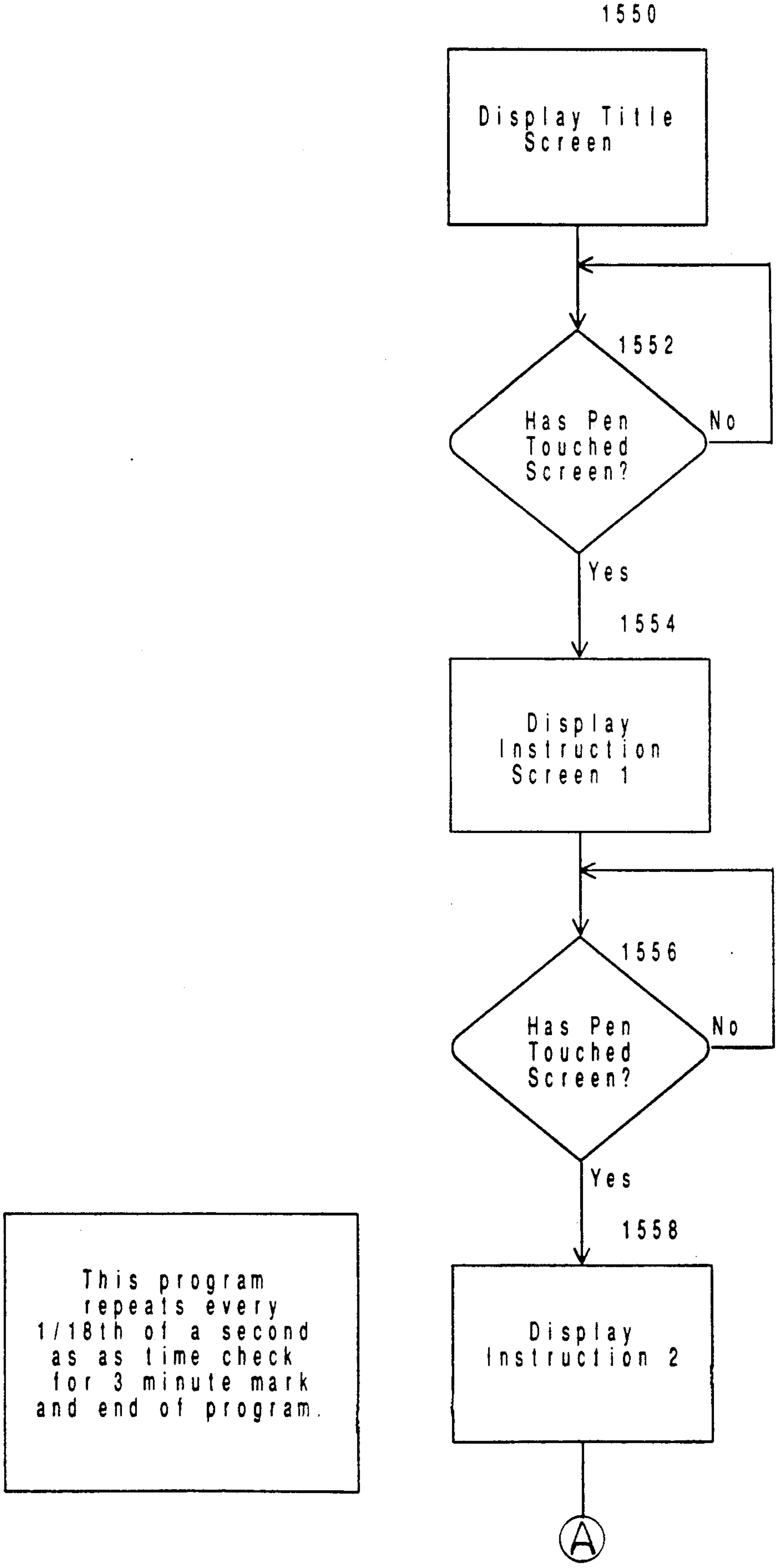
FIGS. 19a-19f are a flowchart illustrating Accomoflex Level I, II, III, and IV therapeutic exercise routines.
Figure 19B:
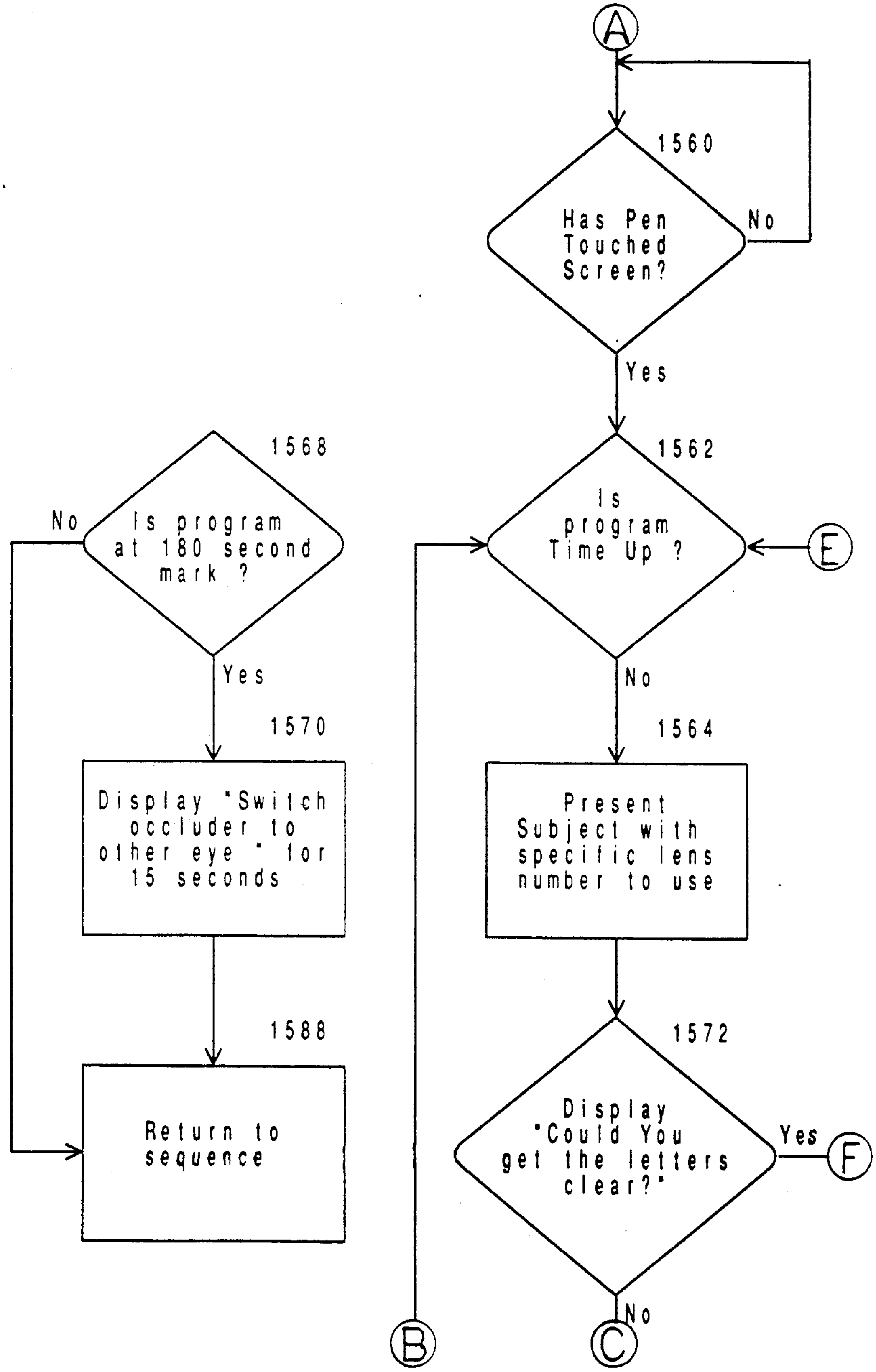
Figure 19C:
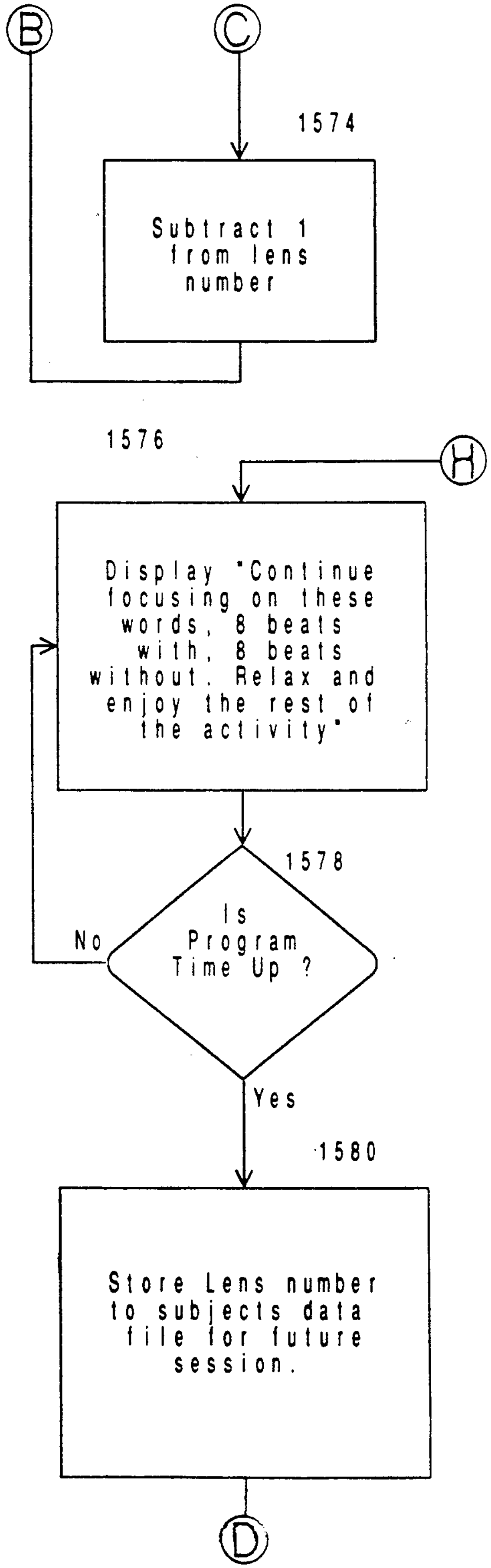
Figure 19D:
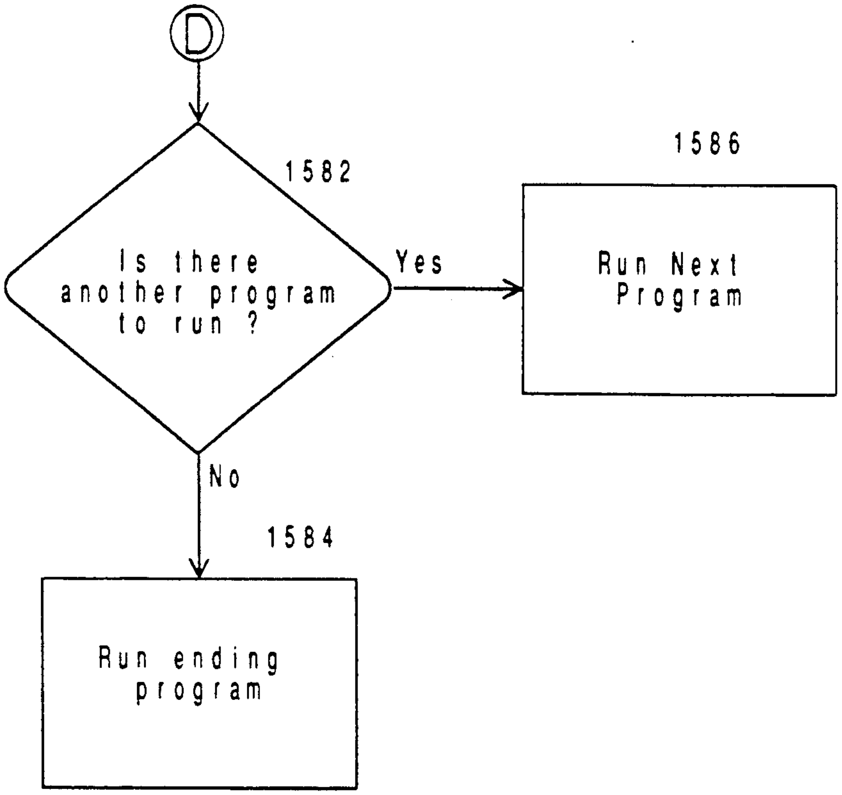
Figure 19E:
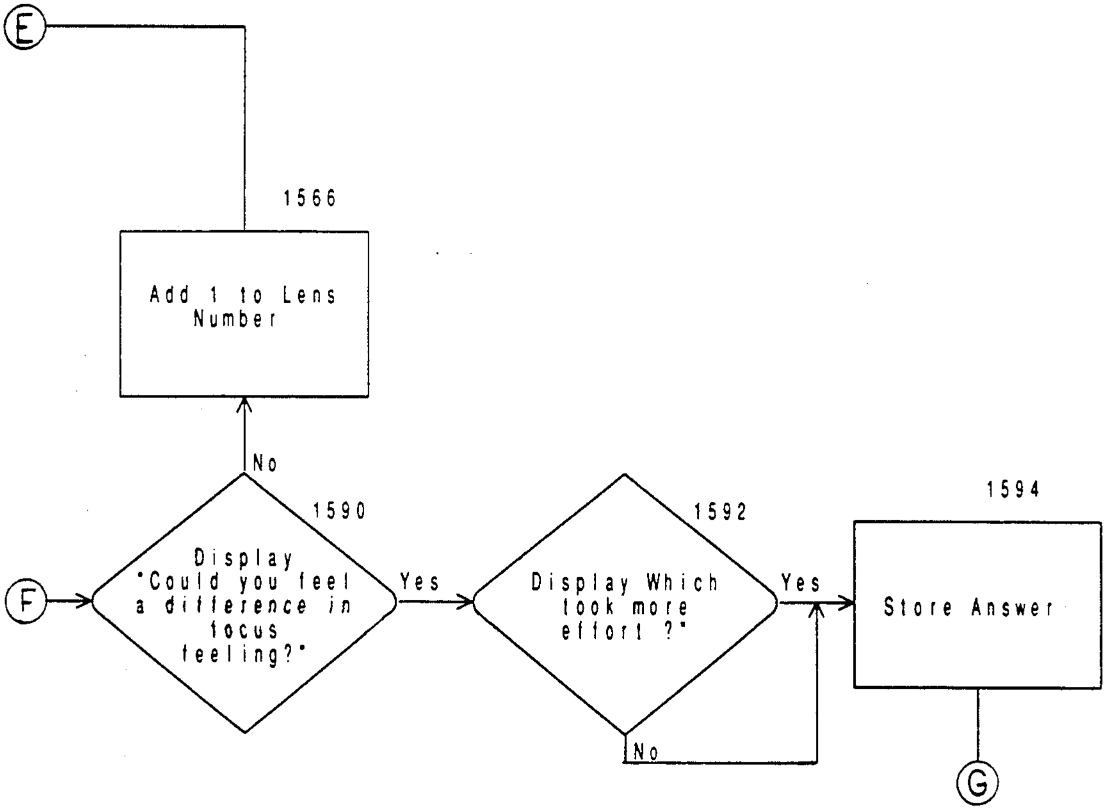
Figure 19F:
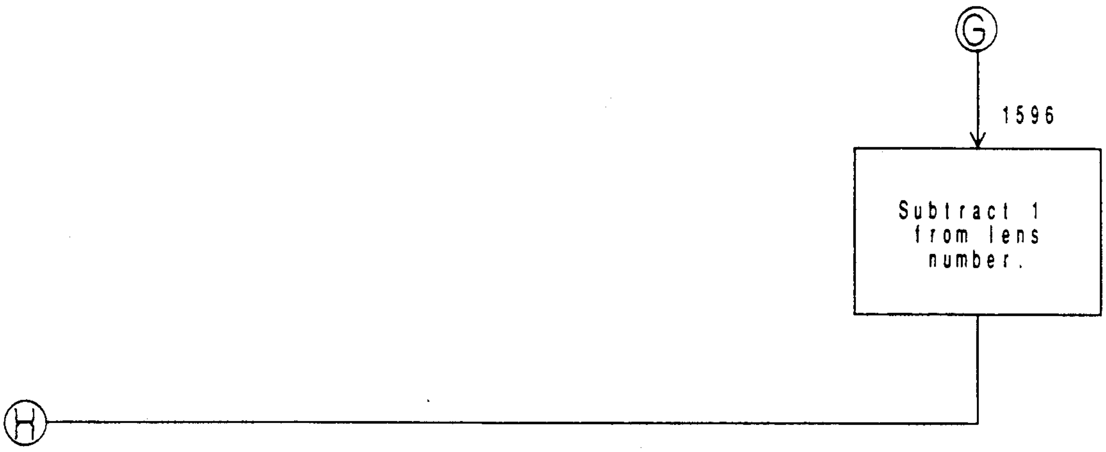

The following is a detailed description of the flowchart, shown in FIGS. 16*a*, *6*, and 16*c*, for the Phoria Diagnostic routine. First, an instruction screen (not shown) is displayed, block 1210. Next, the program waits for the active light pen to touch the screen, block 1212, before loading the screen for horizontal movement, block 1214. Next, the program waits for the space bar to be pressed, block 1216, before continuing to block 1218 where the vertical line is moved one pixel to the right. Next, at block 1220, the program waits for 1/10th of a second before continuing to block 1222 where a check is made to determine whether the space bar has been pressed. If the space bar has not been pressed, the program loops back to block 1218. If the space bar has been pressed, the location of the line is recorded, block 1224, and the screen is loaded for vertical movement, block 1226. Next, at block 1228, the program waits for the space bar to be pressed before continuing to block 1230 where the horizontal line is moved down one pixel. At block 1232, the program waits for 1/10th of a second before proceeding to block 1234 where the program checks to determine whether the space bar has been pressed. If the space bar has not been pressed, the program loops back to block 1230. If the space bar has been pressed, the location of the line is recorded, block 1236, and a check is made to determine whether this was the second time through the routine, block 1238. If not, the program loops back to block 1214. If so, the results are printed and stored, block 1240, and the next routine run, block 1242.

Based upon the data recorded from the diagnostic routines discussed above, a diagnostic file can be created and stored for each subject.

B. Therapeutic Exercise Routines

A therapeutic exercise program menu can be displayed on the CRT screen. FIG. 17. When therapeutics are selected, the name of the subject is requested for input to be matched to the diagnostic file already established. By entering the subject's name at each training session continuous data is collected in the appropriate file.

Figure 2A:
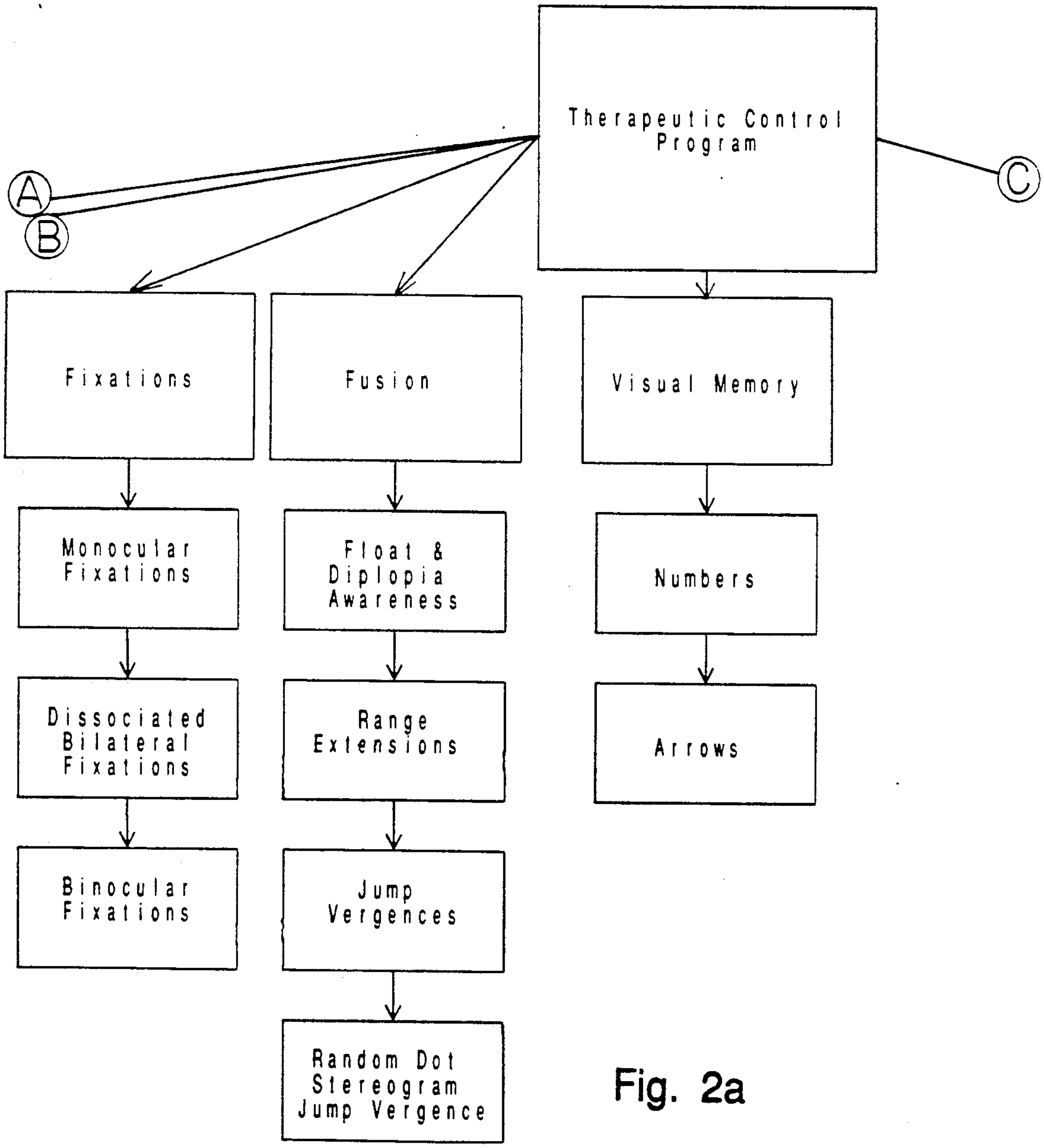
Figure 2B:
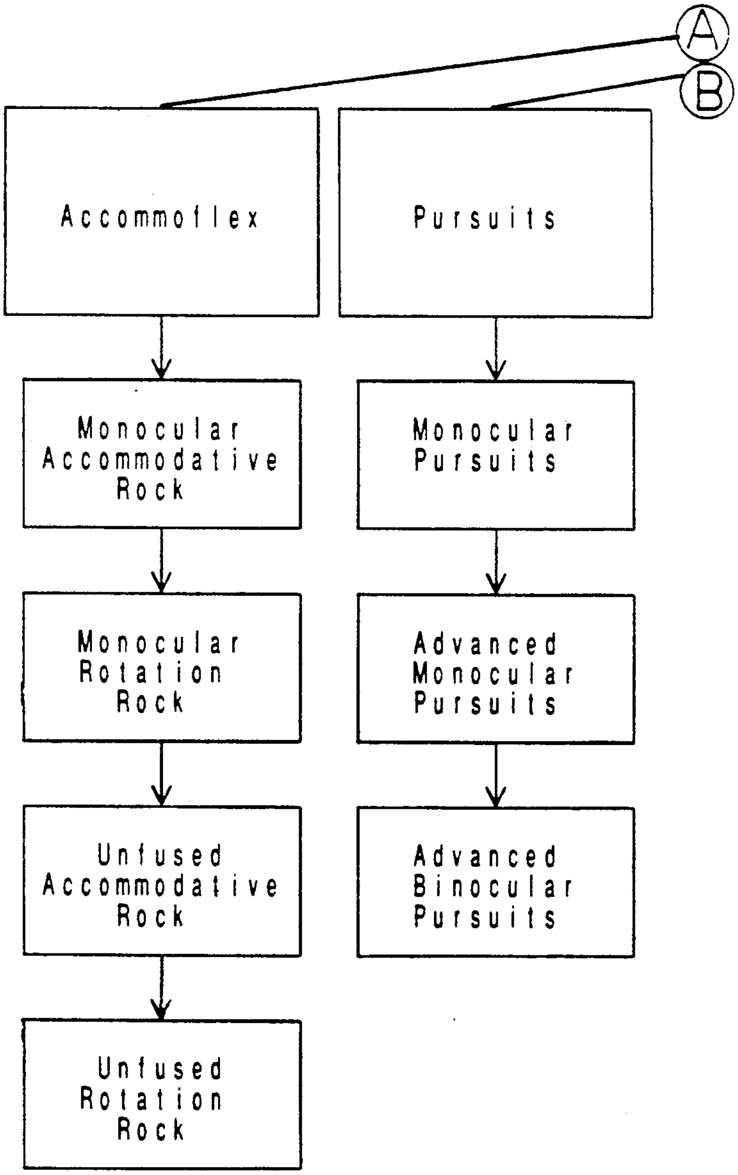

Eighteen activities are preferably organized into seven categories. See FIGS. 2*a*, *b*, and *c*. At each training session a subject will preferably participate in at least four activities, usually selected from different categories. The activities are listed in ascending order of difficulty within each category. Each activity preferably runs for six minutes.

1.) Description of Therapeutic Program Menus

The main therapeutic menu displays choices A through K, as well as the therapeutic activities selected. See FIG. 17. The following choices are available.

(A) Select new user.

(B) Display user settings. Displays configuration choices made on those activities that require them. See FIG. 18.

(C) Select programs. All training activities resident in the computer are displayed for selection. Up to eight activities can be chosen. Once selected, the activities are retained until performance criteria are met. They can be changed manually by the clinician or automatically by the self-directing program.

(D) Run therapeutics.

(E) Exit therapeutics.

(F) Fixations. Allows for selection of duration of visual prompts during fixation activities. This will be more fully described below.

(G) Visual Memory. Allows for selection of targets, flash duration and sequence length. This will be more fully described below.

(H) Accomoflex lens number. Allows for selection of lens power to be used for the Accomoflex exercise. This will be more fully described below.

(I) Fusion Level II. Allows for selection of the ratio of base-out to base-in trials. This will be more fully described below.

(J) Fusion Level III. Allows for selection of vergence jump degree. This will be more fully described below.

(K) Print result. Choice of "yes" or "no".

2.) Accomoflex Level I

The purpose of the exercise is to develop smooth focusing with conscious awareness of kinesthetic feedback under monocular conditions. Throughout the exercise a metronome programmed into the computer preferably beats at 120 beats per second. The subject is provided with a lens box containing loose ophthalmic lenses as follows:

Lens No. 1: −2.00 dioptors
Lens No. 2: −2.50 dioptors
Lens No. 3: −3.00 dioptors
Lens No. 4: −3.50 dioptors
Lens No. 5: −4.00 dioptors
Lens No. 6: −5.00 dioptors
Lens No. 7: −6.00 dioptors
Lens No. 8: −7.00 dioptors
Lens No. 9: −8.00 dioptors
Lens A: +1.00 dioptors The subject wears an occluder over the left eye for the first three minutes, and over the right eye for the final three minutes. After reading instructions (not shown), the subject continues by touching the screen with the active light pen. The program directs the subject to chose a specific lens from the set provided. The default lens is −4.00 dioptors, although the clinician can configure the activity with any lens. Three minutes into the activity the subject is instructed to change the occluder to the opposite eye. The subject's answers to questions are stored as well as the number of the final lens used. The configuration program automatically reduces the lens number by 1 for the subsequent session. The goal is to be aware of the kinesthetic feedback associated with focusing. Most subjects start with a −4.00 dioptor lens and work down to −2.00 dioptors in 0.50 diopter steps. Presbyopes may have to start with lower powers than −4.00 dioptors, and fully presbyopic subjects may skip the Accomoflex activities altogether. The output of the program includes the starting lens number, the finishing lens number, and the subject's responses to the questions presented, all of which are stored.

The following is a detailed description of the flowchart, shown in FIGS. 19*a* through 19*f*, for the Accomoflex Level I Exercise. At block 1550 a title screen (not shown) is displayed. At block 1552, the program waits for the subject to the touch the screen with the active light pen before continuing on to block 1554 where a first instruction screen (not shown) is displayed. At block 1556 the program again waits for the subject to touch the screen with the active light pen before displaying a second instruction screen (not shown) at block 1558. At block 1560, the program waits for the subject to touch the screen with the active light pen before proceeding to block 1562, where the program checks to see whether the time is up. If not, the program executes block 1564 where the subject is presented with a specific lens number to use. At block 1572 the program asks the subject whether the subject could see clearly through the lens. If the subject responds in the negative, the program, at block 1574 subtracts one from the lens number and loops back to block 1562. If the subject responds in the affirmative the program questions the subject whether the subject could feel a difference in the focusing effort, block 1590. A negative response by the subject causes the program to execute block 1566, where one is added to the lens number, and loops back to block 1562. An affirmative response by the subject causes the program to display the question "Which took more effort?", block 1592. The subject's answer is stored, block 1594, and at block 1596 the program subtracts one from the lens number and proceeds to block 1576 where the program instructs the subject to continue focusing on the words for eight metronome beats with the lens and eight metronome beats without the lens and reminds the subject to relax and enjoy the rest of the activity. At block 1578, the program checks to see whether the time is up. If not, the program loops back to block 1576. If so, the program proceeds to block 1580 where the lens number is added to the subject's stored data file for future sessions. At block 1582, the program checks to see whether there is another program to run. If not, the program ends, block 1584. If so, the program executes the next program in the chain, block 1586. As can be seen from the flowchart, 180 seconds into the exercise, block 1568, the program instructs the subject to switch the occluder to the other eye, block 1570, after which the program continues on in the sequence, block 1588.

3.) Accomoflex Level II

Figure 20:
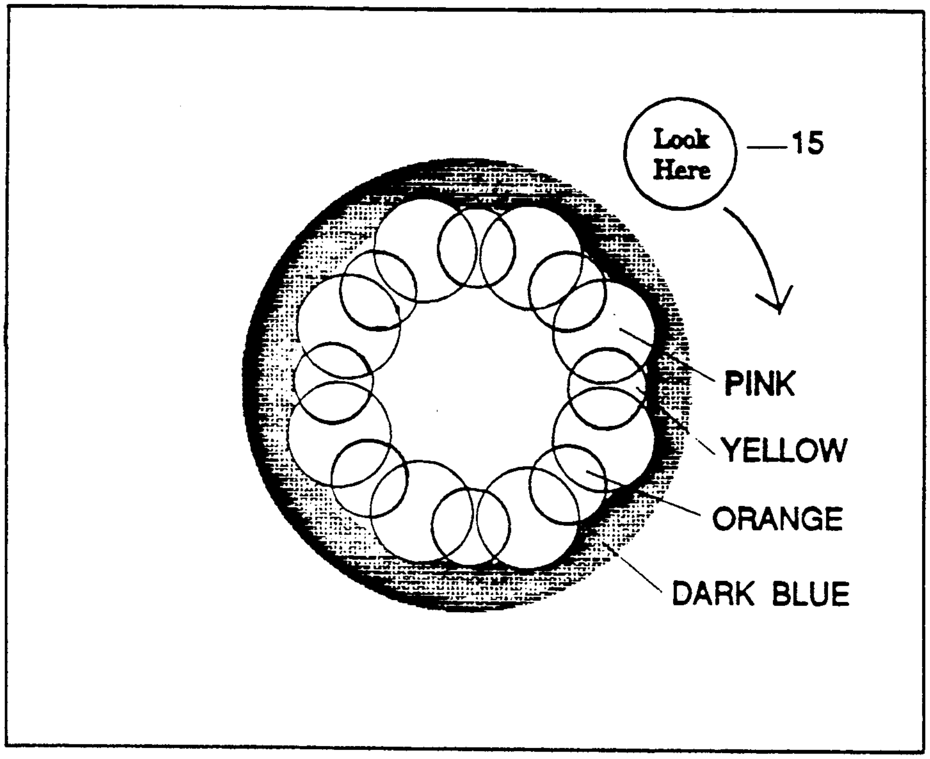
FIG. 20 is a display provided by the vision training system of the present invention in connection with an Accomoflex Level II therapeutic exercise routine.

The purpose of the Accomoflex Level II exercise is to develop smooth focus while tracking a moving target under monocular conditions. The subject holds the active light pen in either hand. The computer software metronome is set at 120 beats per second. The same lens set as in Accomoflex Level I is used. The subject wears an occluder over the left eye for the first three minutes and over the right eye for the final three minutes. after reading the instructions and the title screen (not shown), the subject continues by touching the screen with the active light pen. The program directs the subject to use a specific lens, the default being the same as in Accomoflex Level I. The subject is instructed to follow a circle 15 that moves around a pattern of colors; the circle moves for 60 seconds and contains the words "look here". See FIG. 20. The flowchart of FIGS. 19*a* through 19*f*, indicates the various loops that can be activated by the subject's responses. The subject focuses the target for eight metronome beats with the lens and eight metronome beats without the lens, and is instructed by the computer to switch the occluder to the opposite eye at the three minute mark.

The program for Accomoflex Level III is nearly identical to the program for Accomoflex Level I (FIGS. 19*a* through 19*f*) with the following two exceptions. After block 1564, the subject is directed to follow the moving circle for 60 seconds and then the circle moves around the pattern in the other direction for 60 seconds. Then control proceeds to block 1572. Also, at block 1578, if the program time has not expired, the subject is to continue focusing on the moving circle. The configuration program can automatically reduce the lens number by 1 for the subsequent session.

4.) Accomoflex Level III

The purpose of the Accomoflex Level III Exercise is to develop smooth focus with monocular targets in a binocular field. Again, as in Level II, the metronome is set at 120 beats per minute. The same lens set is used as in Accomoflex Level I.

Figure 21:
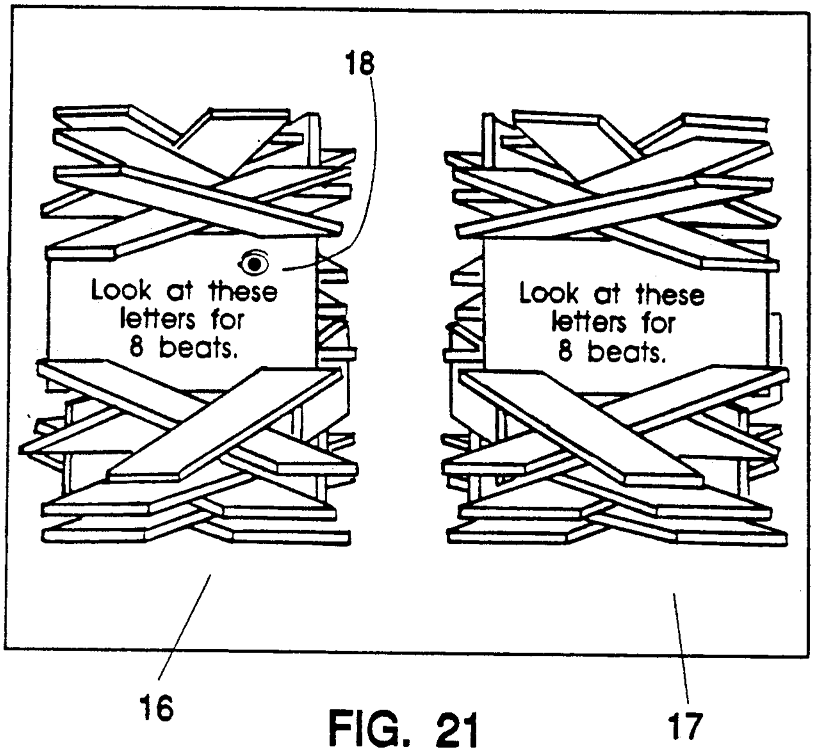
FIG. 21 is a display provided by the vision training system of the present invention in connection with an Accomoflex Level III therapeutic exercise routine.

After reading instructions (not shown), the subject touches the active light pen to the screen to continue. The subject wears a +1.00 dioptor lens over the left eye and a −4.00 diopter lens over the right eye. If glasses are usually worn, the training lenses are attached to the glasses with Halberg trial clips. Red/green filters are worn with the red filter over the right eye and the green filter over the left eye. The screen has mirror image pictures 16, 17 (FIG. 21) so that the left picture is visible only to the left eye and the right picture is visible only to the right eye. Every eight metronome beats, the icon next to the pictures alternates from one picture to the other to remind the subject to shift attention.

The program for Accomoflex Level III is nearly identical to the program for Accomoflex Level I (FIGS. 19*a* through 19*f*) with the following exceptions. After block 1564, the subject follows an icon (the eye 18 illustrated in FIG. 20) as it jumps from each image 16, 17 every eight beats. Then control passes to block 1572. Also, at block 1578, if the program time has not expired, the subject is to continue following the icon. Further, at block 1570, the subject is directed to switch lenses rather than the occluder to opposite eyes. The configuration program can automatically reduce the lens number by one for the subsequent session.

5.) Accomoflex Level IV

The purpose of the Accomoflex Level IV Exercise is to develop smooth focus with a moving monocular target in a binocular field.

Figure 22:
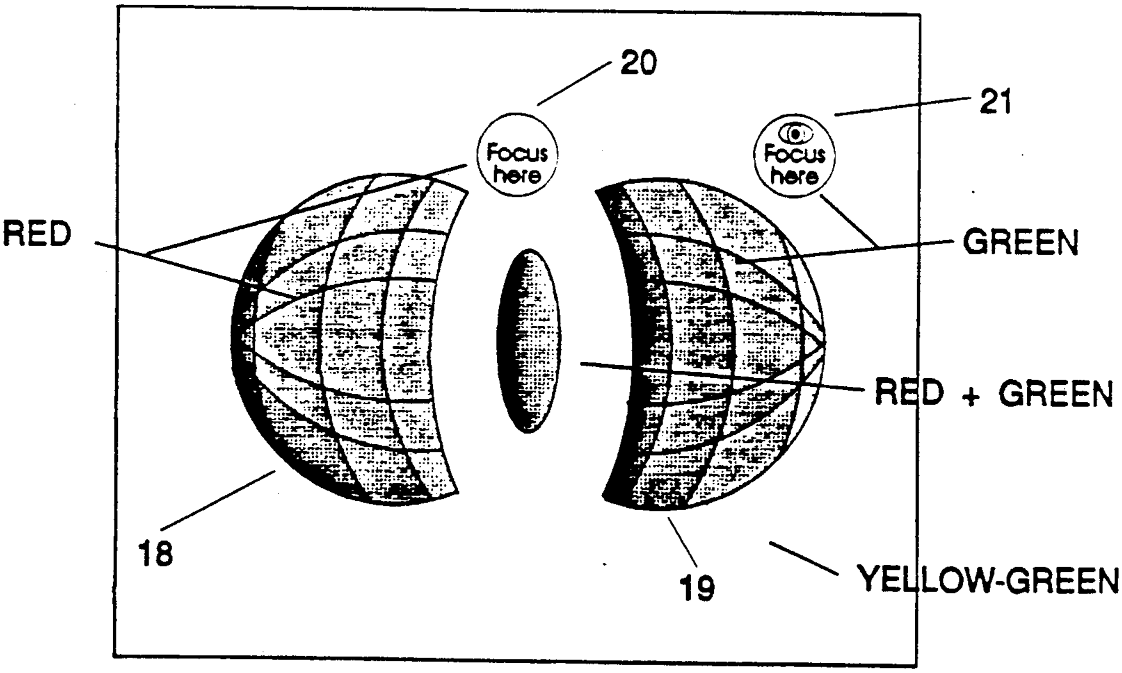
FIG. 22 is a display provided by the vision training system of the present invention in connection with an Accomoflex Level IV therapeutic exercise routine.

After reading instructions (not shown), the subject touches the screen with the active light pen to continue. The subject wears a +1.00 dioptor lens over the right eye and a −4.00 dioptor lens over the right eye. If glasses are usually worn by the subject, the training lenses are attached to the glasses with Halberg trial clips. Red/green filters are worn with the red filter over the right eye and the green filter over the left eye. The activity screen (FIG. 22) has mirror image pictures 18, 19 so that the left one is only visible to the left eye and the right one is only visible to the right eye. The subject does the same as in Level III except that two focus targets 20, 21 rotate about the images 18, 19 alternating between clockwise and counter-clockwise directions.

The program for Accomoflex IV is nearly identical to the program for Accomoflex I with the following exceptions. At block 1570, the subject is instructed to switch lenses to opposite eyes rather than the occluder. Also, after block 1564, the subject follows the moving targets for 60 seconds before control passes to block 1572. Further, at block 1578, if the program time has not expired, the subject continues to follow the moving targets. The configuration program can automatically reduce the lens number by 1 for the subsequent session.

6.) Fixations Level I

Figure 23A:
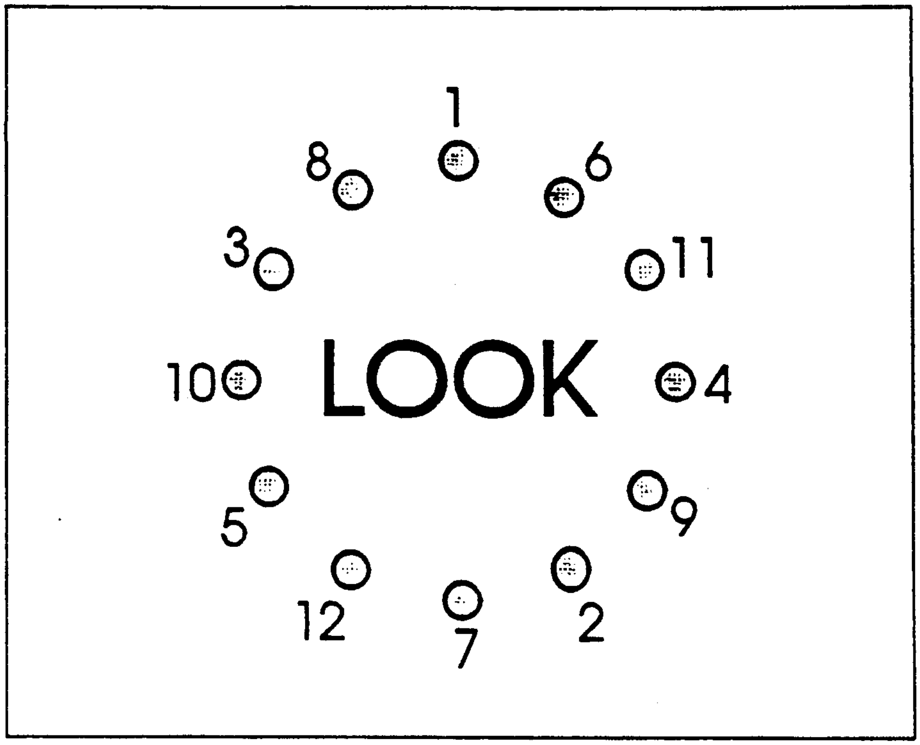
FIGS. 23a-23d are displays provided by the vision training system of the present invention in connection with a Fixations Level I therapeutic exercise routine.
Figure 23B:
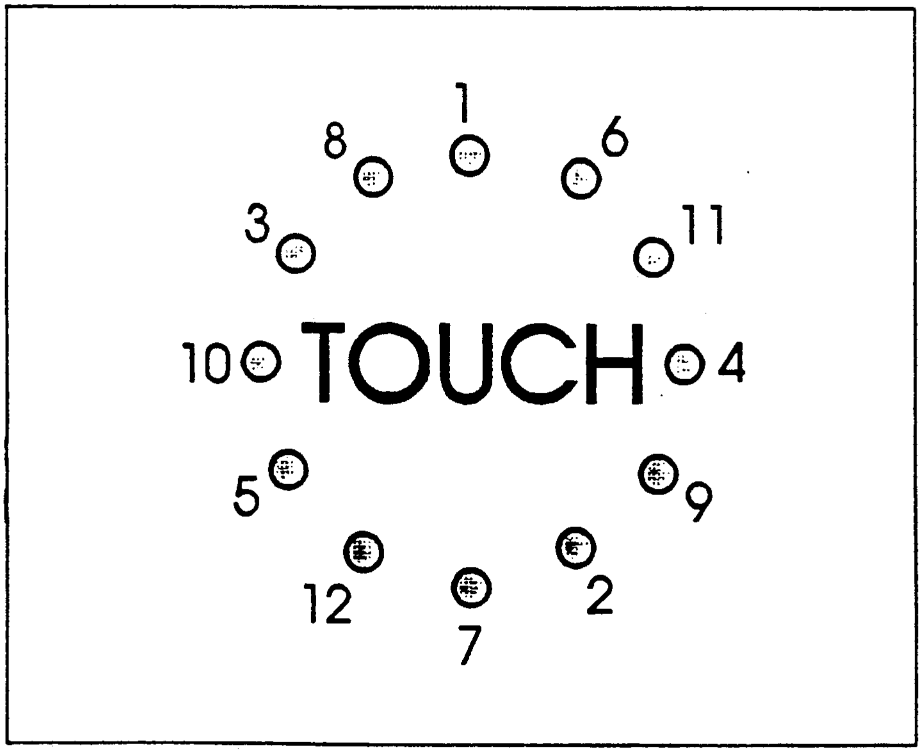
Figure 23C:
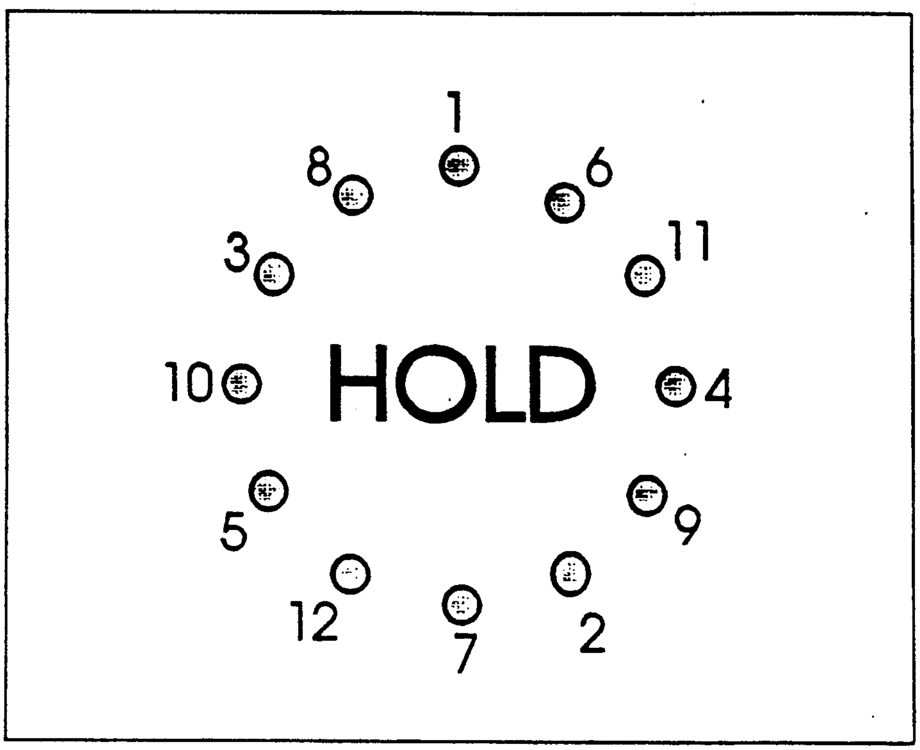
Figure 23D:
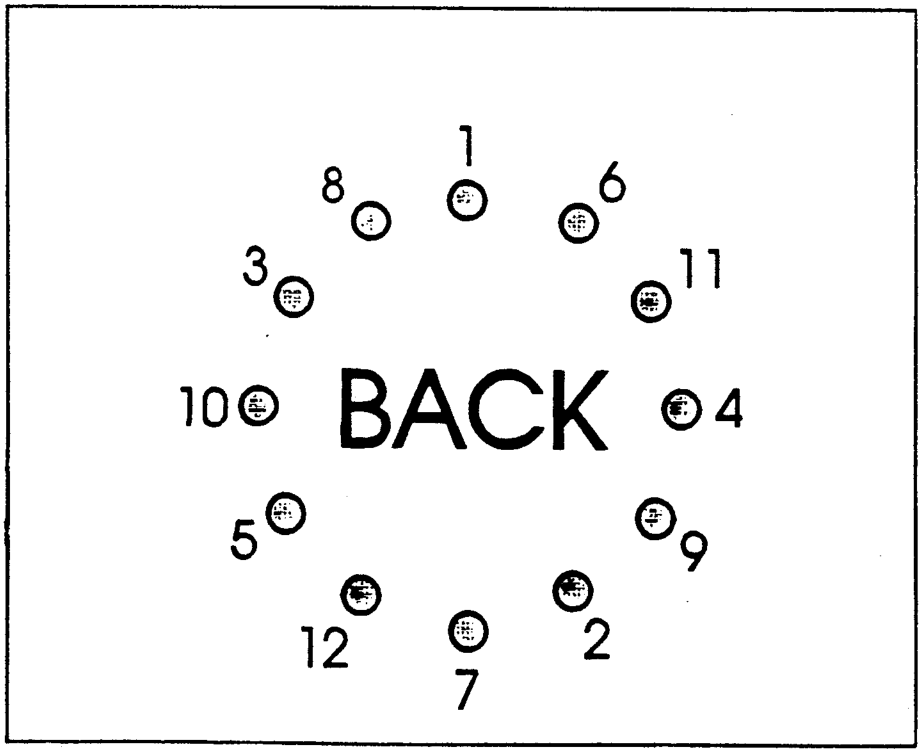
Figure 24A:
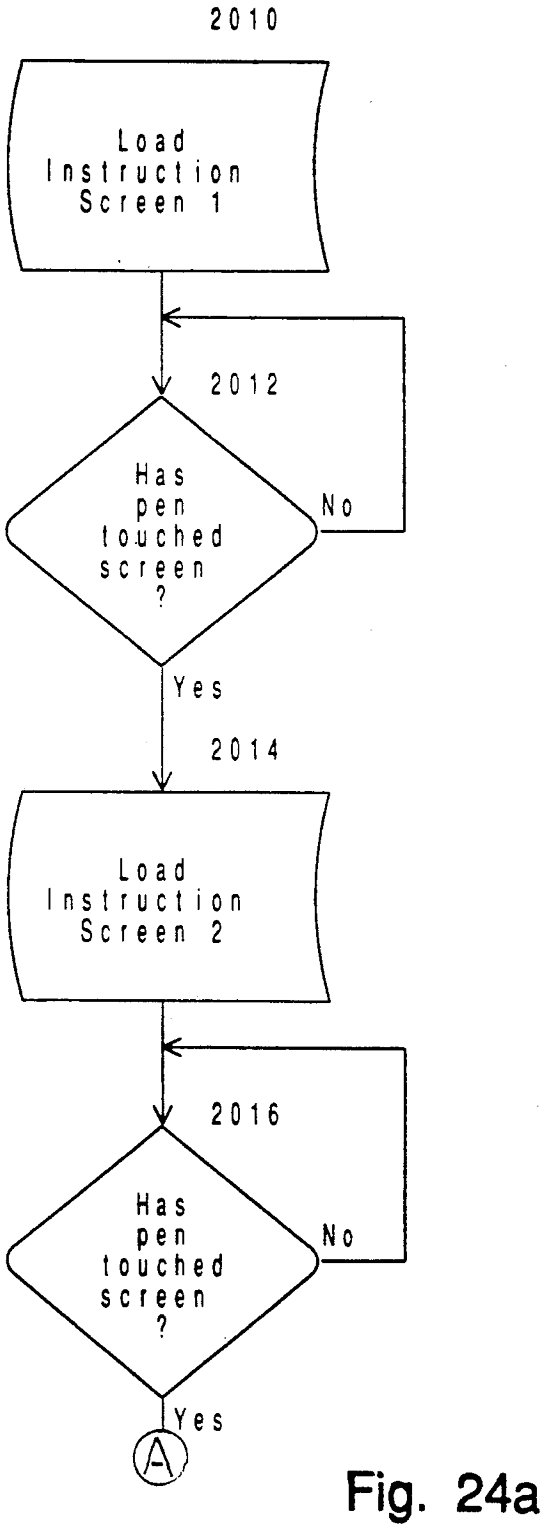
Figure 24C:
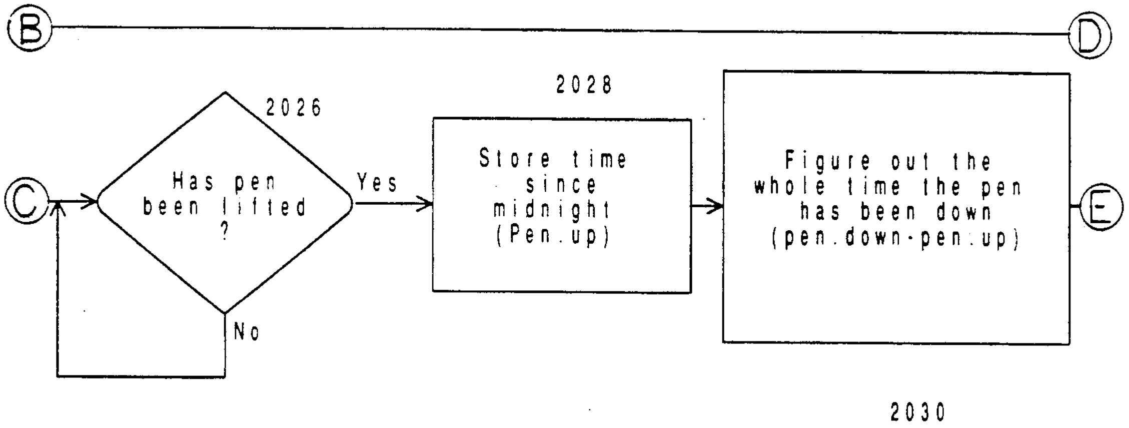
Figure 24D:
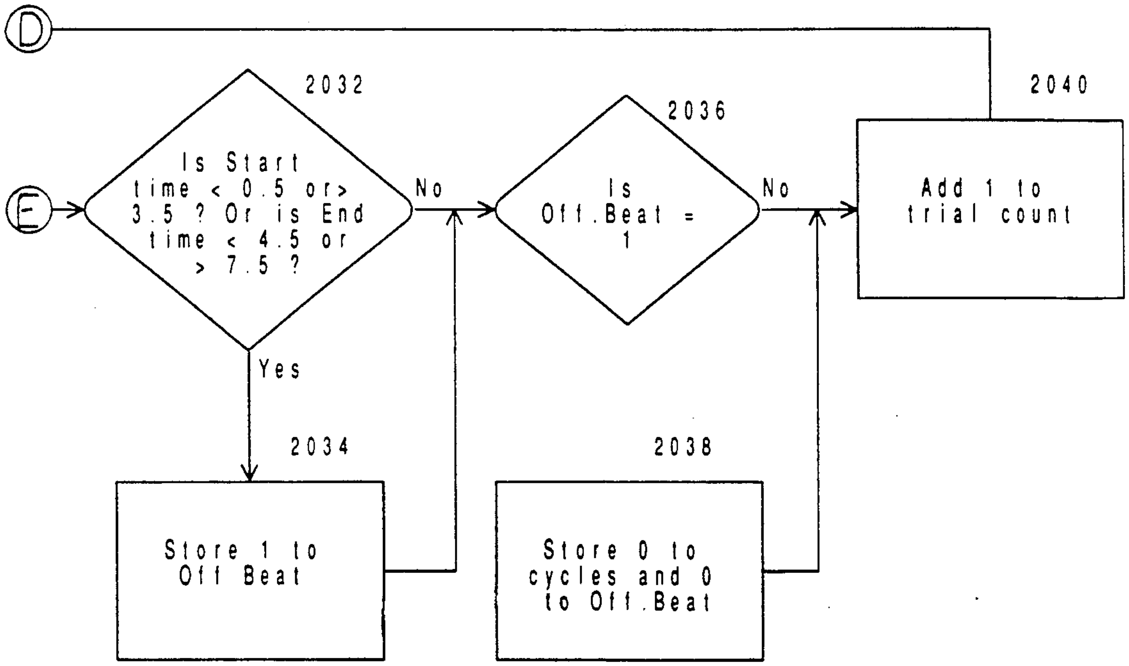
Figure 24E:
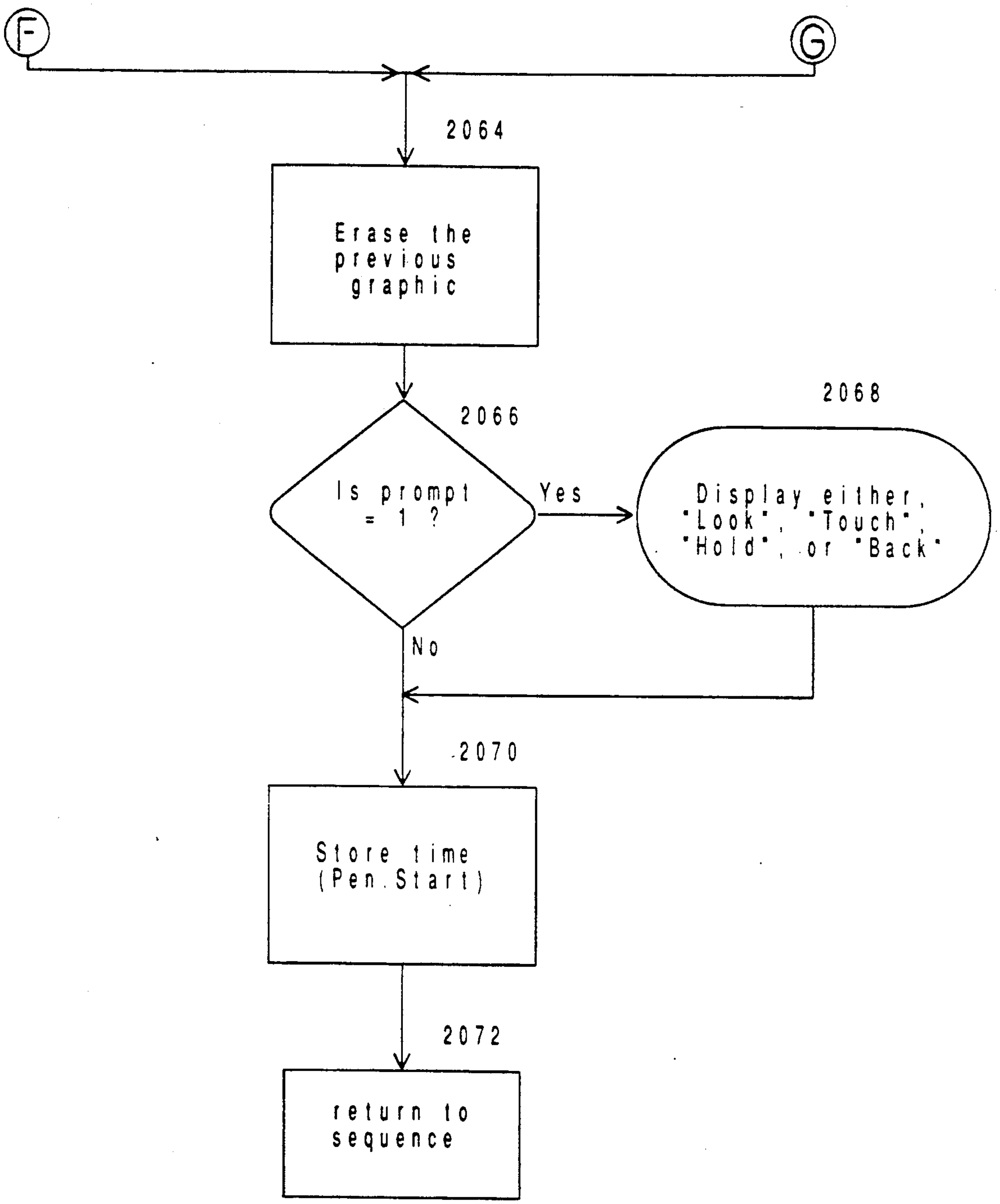
Figure 24F:
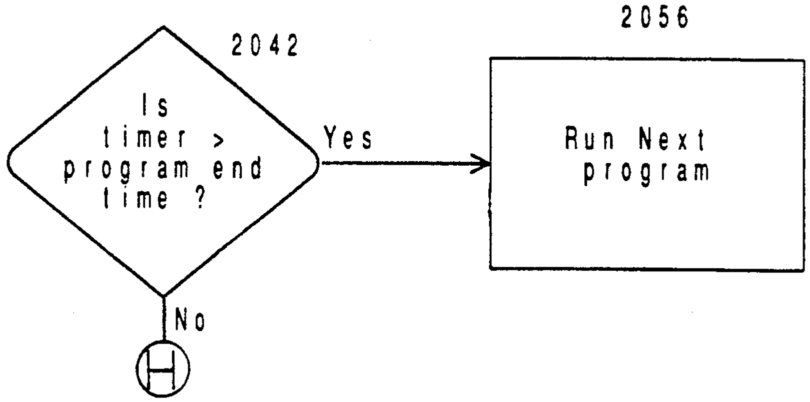
Figure 24G:
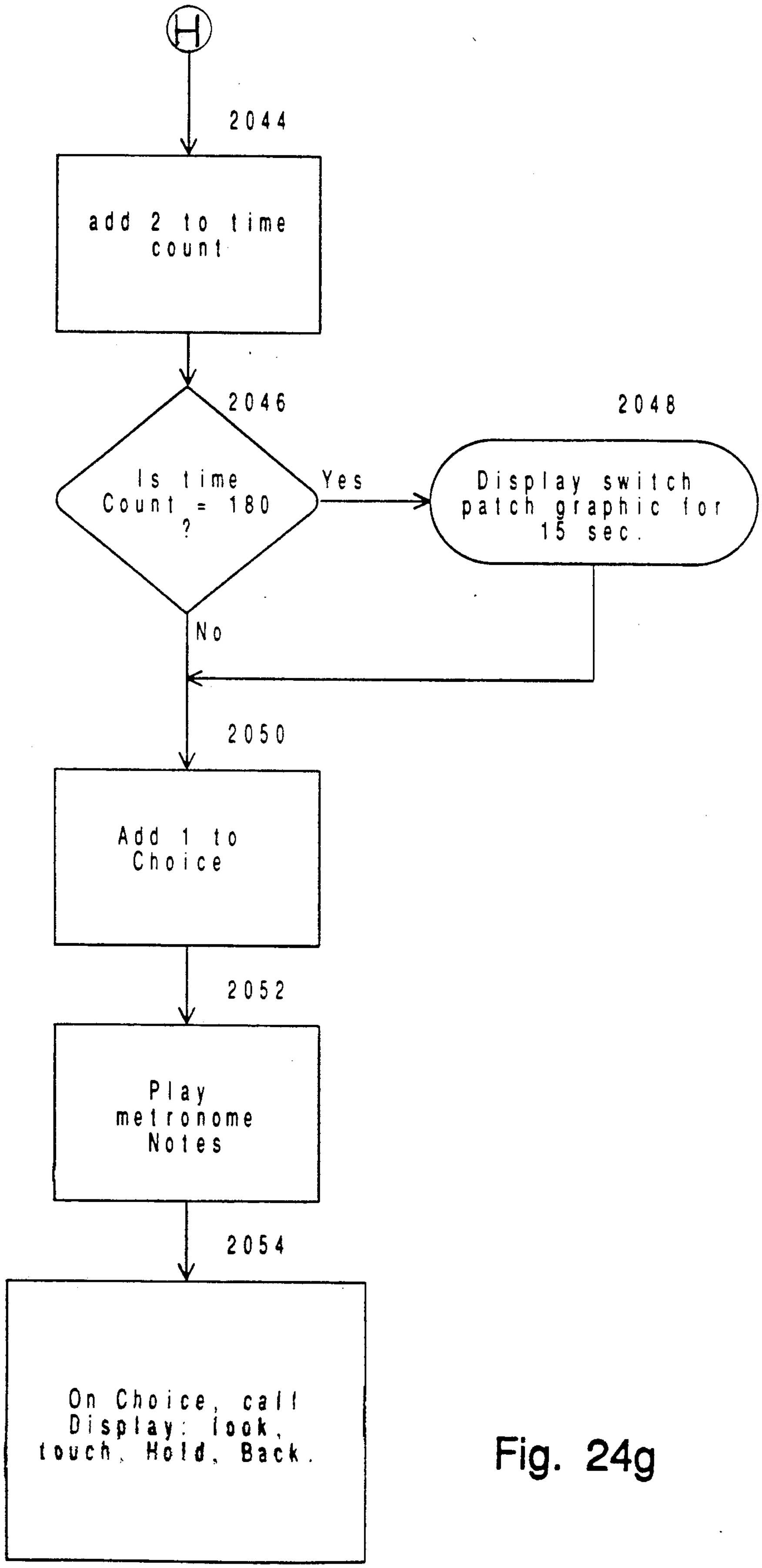

The purpose of the Fixations Level I Exercise is to develop accurate, effortless, saccadic eye movement with monocular presentation. After reading an instruction screen (not shown), the subject touches the screen with the active light pen to continue. In this exercise, the two lights pens are alternately and oppositely activated, i.e., only one light pen is active at a time, and the computer switches between the two. The left eye is occluded initially and a light pen is held in each hand, pen number 1 in one hand and pen number 2 in the other. When the word "look" appears on the screen, the subject focuses his attention on the number 1. See FIG. 23*a*. The metronome is again used. After four metronome beats, the word "touch" appears for four metronome beats, and the subject is instructed to touch the circle next to number 1 with the right-hand light pen. See FIG. 23*b*. While "hold" is displayed for four metronome beats, the right-hand light pen is to be held in contact with the circle. FIG. 23*c*. When "back" appears, the right-hand light pen is to be withdrawn. FIG. 23*d*. The same look, touch, hold, back sequence is followed throughout the activity as the subject points to each number in sequence, alternately using the right-and-left hand light pens, as directed by the computer. The visual prompts, look, touch, hold, and back, are programmed to disappear once the subject has sustained rhythm for a specific number of trials. The default is four trials. If rhythm is lost, the prompts reappear until the rhythm is re-established for a specified number of trials. As the subject develops skill, the prompts disappear more quickly and do not reappear. The length of presentation of the prompts may be automatically adjusted by the configuration program. The light pens are powered through the switch box 8 connected to the computer and switching is under software control. This way the computer knows which light pen is active. A small letter "R" appears in the top left corner of the screen when the right-hand light pen is active. After three minutes, the occluder is switched to the right eye and the process repeated. The letter "L" appears in the top left corner of the screen when the left-hand pen is active.

The output includes (i) a graph with time per trial on the y-axis, and trials on the x-axis, showing the light pen touch and release time, (ii) the total number of trials for each pen, (iii) the average start time and standard deviation for each light pen, and (iv) the average release time and standard deviation for each light pen, all of which are stored.

The following is a detailed description of the flowchart, shown in FIGS. 24*a* through 24*g*, for the Fixations Level I Exercise. First, instruction screen 1 (not shown) is loaded, block 2010. Next, the program waits for the subject to touch the screen with the active light pen, block 2012, before proceeding to block 2014 to load instruction screen 2 (not shown). The program then waits for the subject to touch the screen with the active light pen, block 2016, before loading a picture into memory, block 2018. The first graphic screen is set up at block 2020. The program then waits for the subject to touch the screen with the active light pen, block 2022, before proceeding to block 2024 where the time for the pen to touch the screen is stored. The program then waits until the pen has been lifted from the screen, block 2026. At block 2028, the time for the pen to be lifted from the screen is stored. At block 2030, the total time that the pen was "down" (not touching the screen) is calculated. At block 2032, a check is made to determine whether the start time at which the pen first touched the screen was less than 0.5 second or greater than 3.5 seconds, or the end time, that is the time at which the pen was lifted from the screen, is less than 4.5 or greater than 7.5 seconds. If any of these conditions are met, a one is stored to the variable "off.beat", block 2034. If none of these conditions are met, a check is made to determine whether "off.beat" equal to one, block 2036. If so, a zero is stored to the variable "cycles" and a zero is stored to "off.beat", block 2038. If not, a one is added to the "trial" count, block 2040, and the program loops back to block 2022.

Every two seconds, the above sequence will be interrupted with the routine beginning at block 2042 on the flowchart. First, a check is made to determine whether the program time is up, block 2042. If so, the program jumps to block 2056 where this program terminates and the next program in the chain is run. If the program time is not up, the program continues to block 2044 where two is added to the "time" count. Next, a check is made to determine whether the "time" count is equal to 180 seconds, block 2046. If so, the program displays a message to the subject to switch the occluder to the other eye. This message is displayed for 15 seconds, block 2048. If the "time" count is not equal to 180 seconds, a one is added to the variable "choice", block 2050. At block 2052, the metronome is activated. Next, the subroutine "Display" is called, block 2054. The subroutine Display shows the visual prompts "look", "touch", "hold", or "back" depending on the value of choice. Display begins at block 2058 where a check is made to determine whether the value of the variable "pen.num" is even or odd. If even, block 2060 is executed where pen number 1 is activated, one is added to the value of "pen.num", and one is stored to the variable "act.pen". If "pen.num" is not even, block 2062 is executed, where pen number 2 is activated, one is added to the value of "pen.num", and a zero is stored to "act.pen". Next the previous graphic is erased from the screen, block 2064. Next, a check is made to determine whether the value of the variable "prompt" is equal to one. If so, the graphic "look", "touch", "hold" or "back" is displayed depending on the value of "choice", block 2068. Next, the time is stored to the variable "pen.start", block 2070, and finally the program returns to the exercise at the point at which it was interrupted, block 2072. Results are stored to the user's file.

7.) Fixations Level II

The subject views a screen through a stereoscope preferably placed 13 inches from the screen. The lenses in the stereoscope, +3.00 dioptors with 9 prism dioptors base-out on each side, are adapted for the specified distance. A septum in the stereoscope blocks the view of the contralateral side of the screen. The subject holds two light pens, one in each hand. The metronome is set at 120 beats per second.

After reading instructions (not shown), the subject touches the screen with the active light pen to continue.

With a light pen held in each hand, the subject is instructed to look through the stereoscope. Again, the active light pen will be switched between pen number 1 and pen number 2. As in Fixations Level I, the prompting sequence is "look", "touch", "hold", "back", with four metronome beats between prompts. However, in Fixations Level II, there are two rings of numbers. The right ring is visible to the right eye and the left ring is visible to the left. eye. The prompts appear on the right ring first. See FIGS. 26*a* through 26*d*. The subject is instructed to use the right-hand light pen for the right picture and the left-hand light pen for the left picture. The light pen switch box insures that the correct pen is active when needed. Again, as in Fixations Level I, the visual prompts appear for the number of trials specified in the configuration program. The default is four trials. The output includes (i) the total number of trials per light pen, (ii) the average start time and standard deviation for each light pen, and (iii) the average release time and standard deviation for each light pen, all of which are stored to the user's file.

The program for the Fixations Level II exercise is substantially the same as the program for the Fixations Level I exercise, the only difference being that in the Fixations Level II exercise the subject performs the activity alternately with the right and left hand. Thus, at blocks 2054 and 2068 the choices available to the subroutine Display include not only "look", "touch", "hold" and "back", but also "left look", "left hold", and "left back".

8.) Fixations Level III

The purposes of the Fixations Level III exercise is to develop accurate, effortless, saccadic eye movements with binocular presentation.

The subject will view the screen through a stereoscope preferably placed 13 inches from the screen. After reading instructions (not shown), the subject touches the screen with the active light pen to continue. With a light pen held in each hand, the subject is instructed to look through the stereoscope. The rhythmic sequence of the activity is "look", "touch", "right", "left", "both", "back", with four metronome beats of the metronome per word. See FIGS. 27*a* through 27*f*. On "look", the subject finds the number. At this level, the two targets appear as one. Therefore, on "touch" the subject moves both pens simultaneously to the selected number, e.g., number 1 on the display. On "right" the left target disappears so that the subject can check the accuracy of the right-hand light pen, and then on "left" the right target disappears to allow the left-hand pen accuracy to be checked. On "both" the subject holds both pens accurately in position as they appear to be touching the same target. On "back" the pens are to be withdrawn. Although both pens are used simultaneously, they are alternately activated so the computer can read them through one port. As in the previous two levels, the number of trials for which visual prompts appear is set in the configuration program.

The output includes (i) the total number of trials per light pen, (ii) the average start time and standard deviation for each light pen, and (iii) the average release time and standard deviation for each light pen, all of which are stored to the user's file.

The program for the Fixations Level III exercise is substantially the same as the program for the Fixations Level I exercise with the following exception: at block 2054, depending on the value of the variable "choice", the subroutine Display is called to display the prompt "look", "touch", "right", "left", "both" or "back". This difference is also applicable to block 2068.

9.) Pursuits Level I

The purpose of the Pursuits Level I exercise is to develop smooth, effortless pursuit eye movements with monocular presentation.

Figure 28:
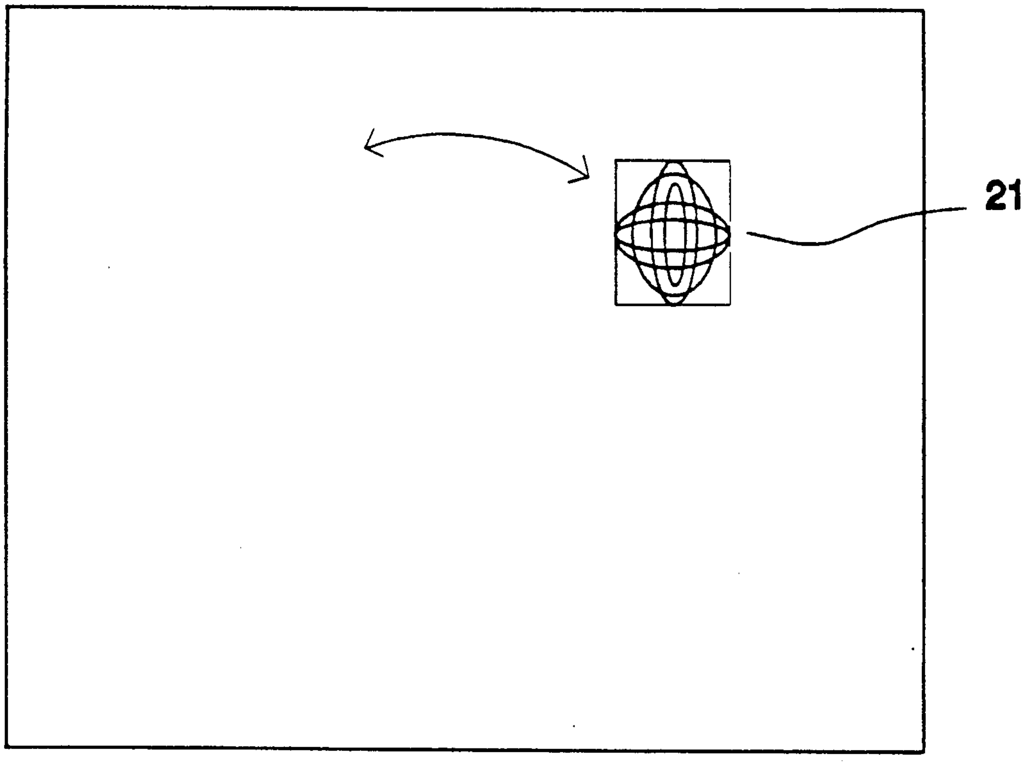
FIG. 28 is a display provided by the vision training system of the present invention in connection with a Pursuits Level I therapeutic exercise routine.
Figure 29A:
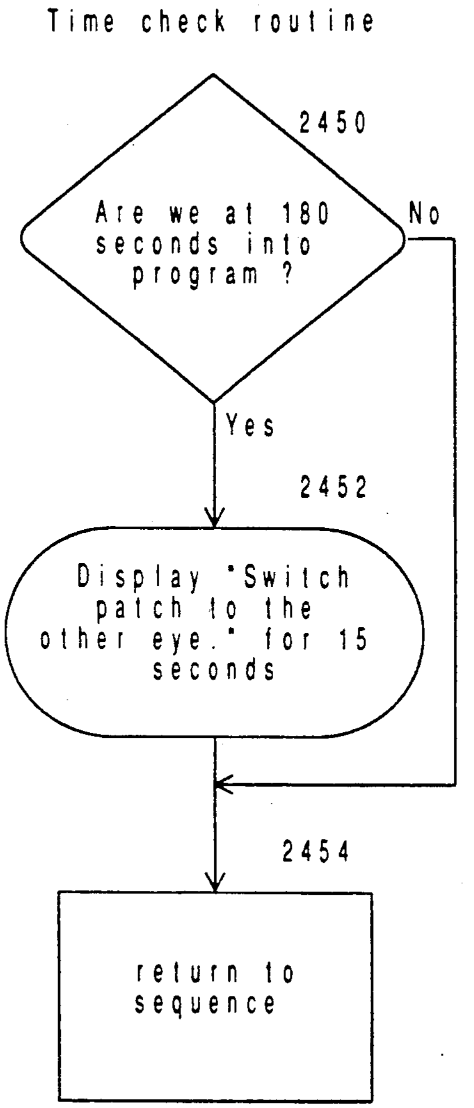
FIGS. 29a-29g are a flowchart illustrating a Pursuits Level I therapeutic exercise routine.
Figure 29B:
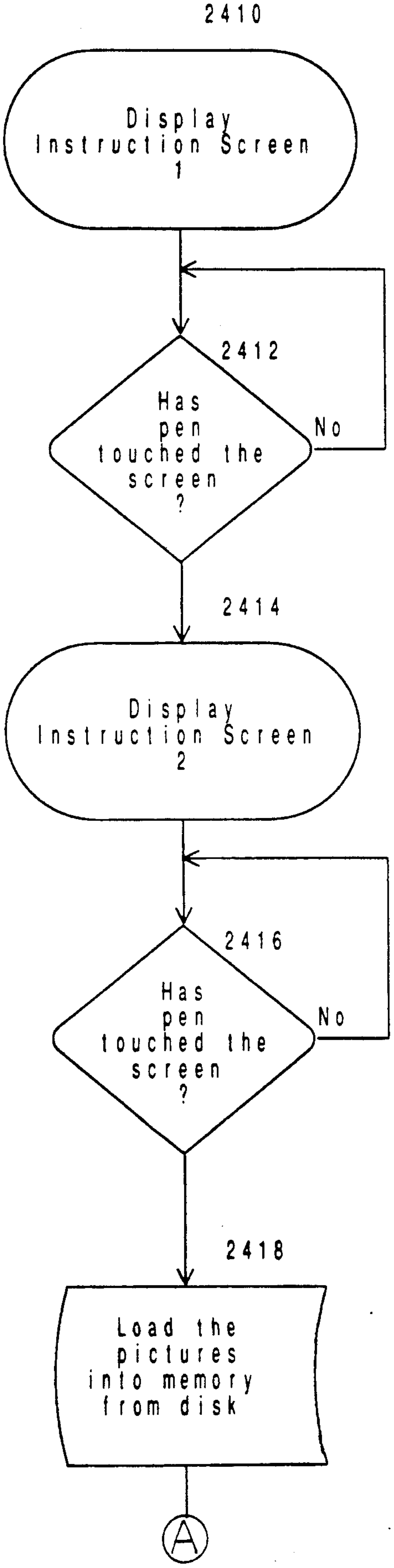
Figure 29C:
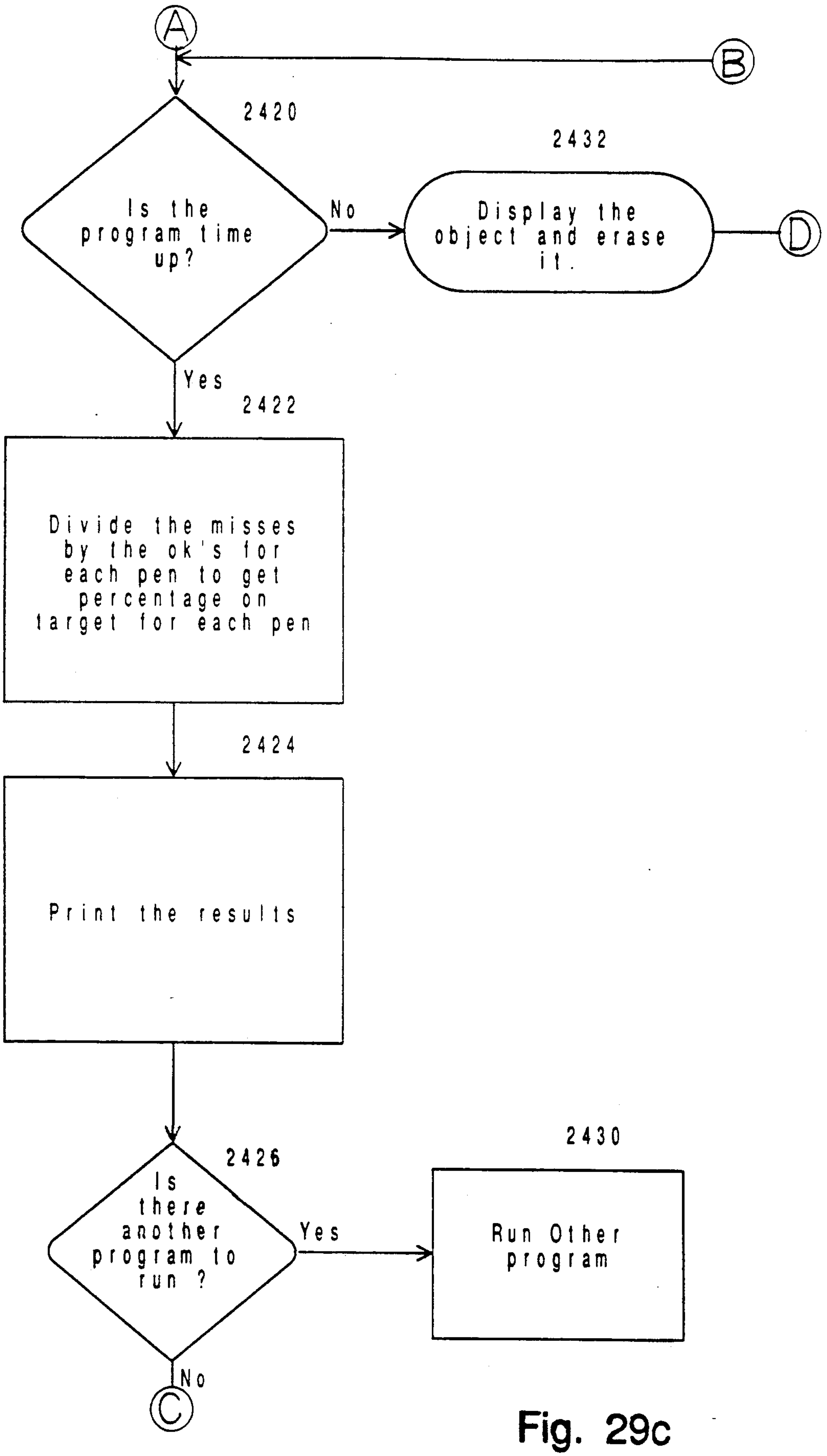
Figure 29D:
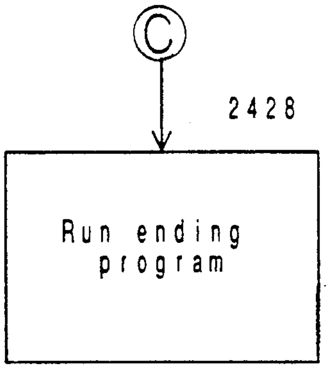
Figure 29E:
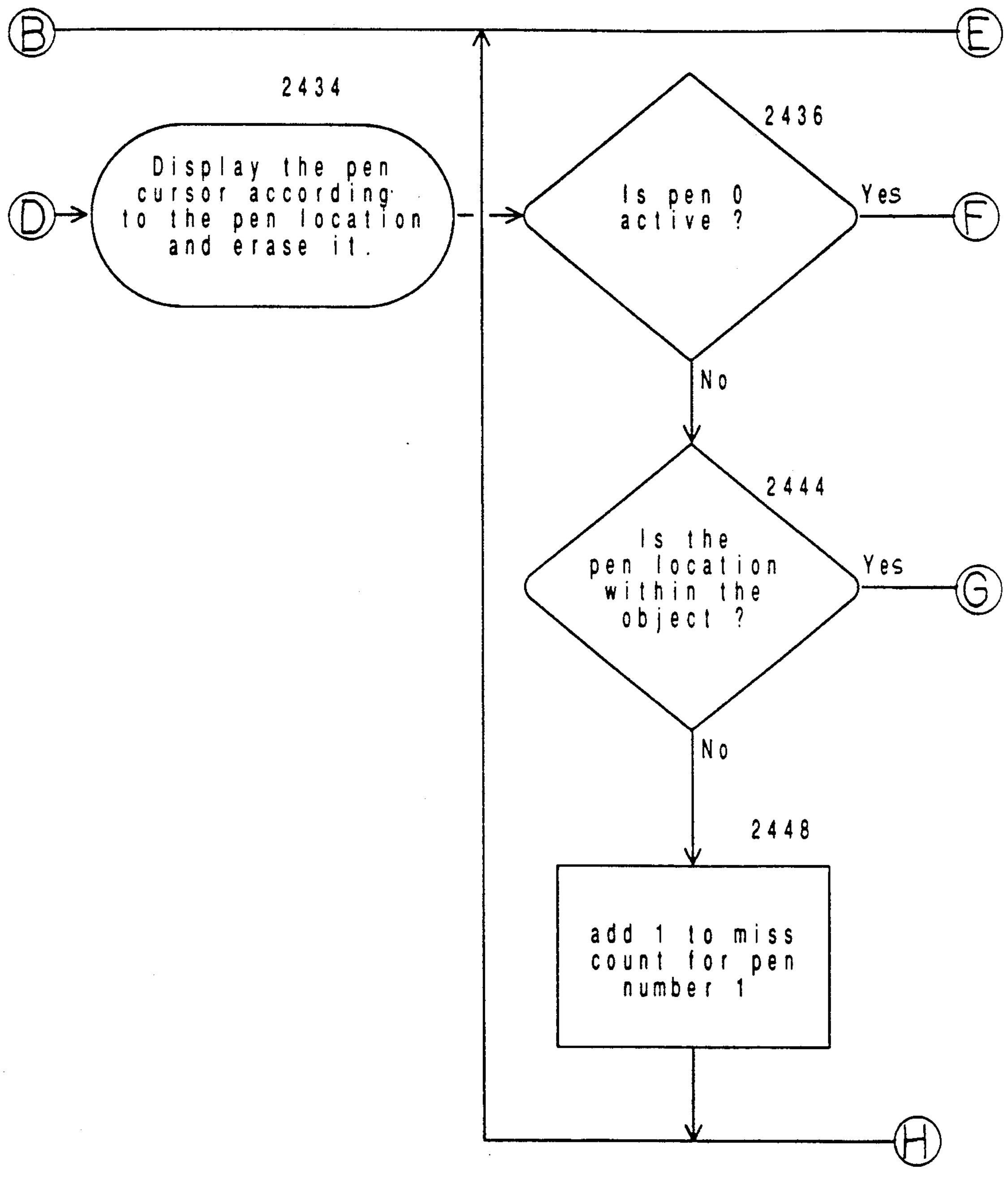
Figure 29F:
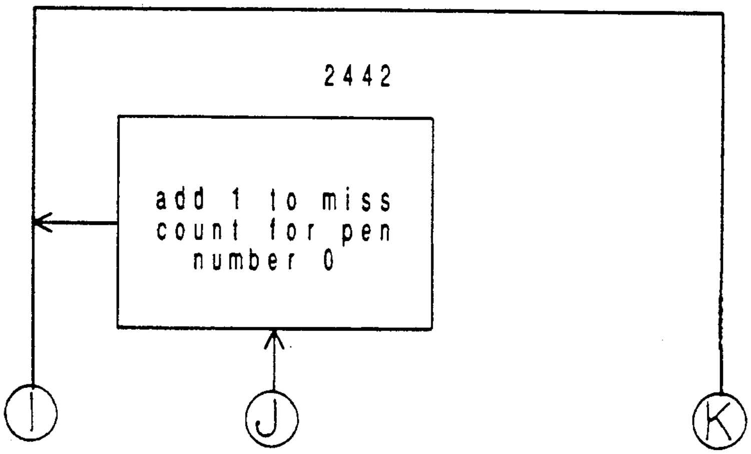
Figure 29G:
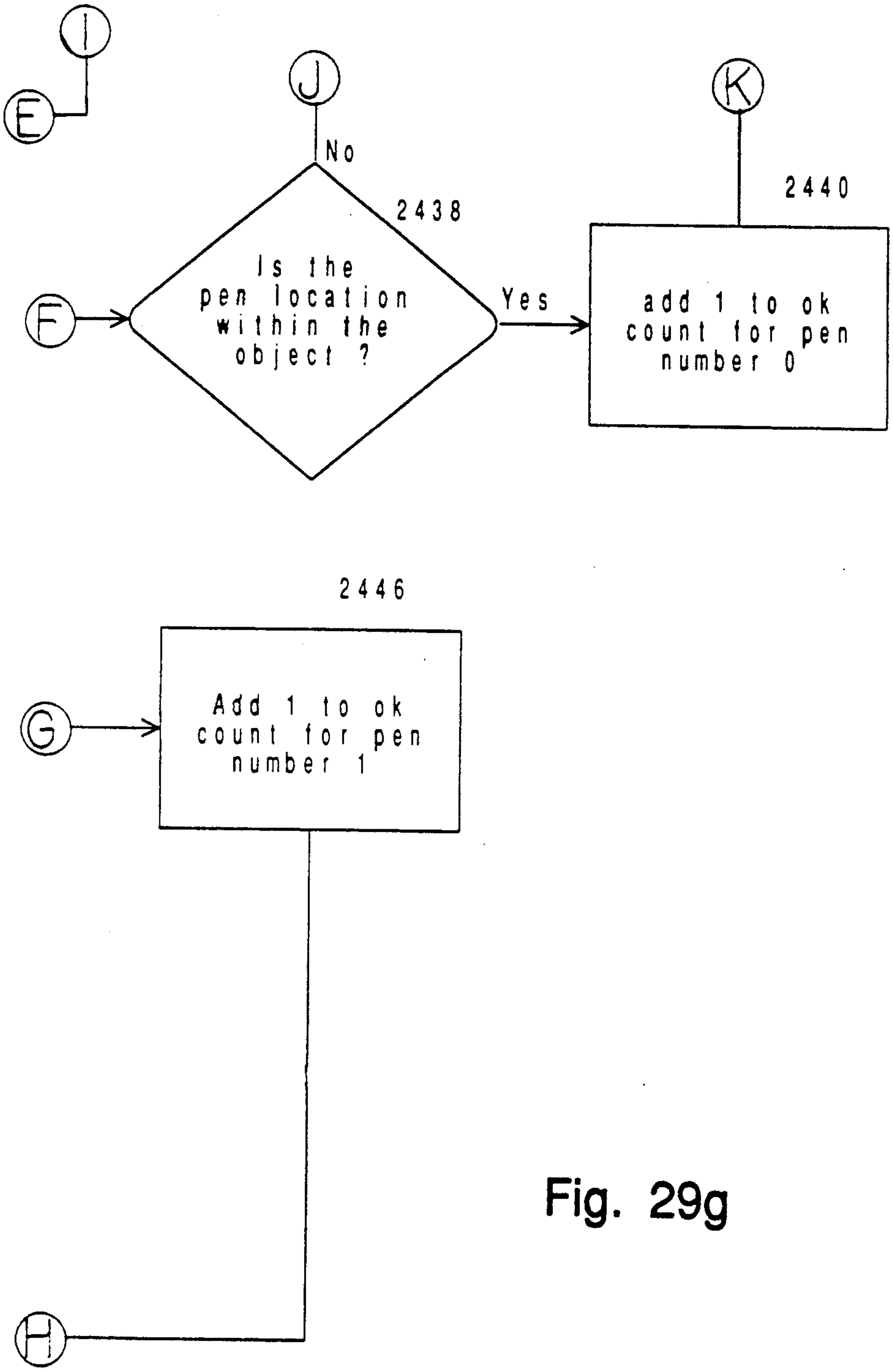

The subject reads instructions (not shown), and touches the screen with the active light pen to continue. A light pen is held in each hand, and an occluder is placed over the left eye. A one-inch square 21 follows a circular path around the screen, five seconds per revolution, changing from clockwise to counter-clockwise every minute. See FIG. 28. The subject is directed to hold the active light pen two to three inches from the screen and use the active light pen to keep a curser within the circling box. The active light pen is alternated every eight beats of the metronome. A small letter "R" is visible in the top left corner of the screen when the right light pen is on and vice versa. The occluder is put over the right eye after the three-minute mark, and the: routine repeated. The output includes the percent of time on the target for each light pen for each eye, which is stored to the user's file.

The following detailed description refers to the flowchart in FIGS. 29*a* through 29*g* for Pursuits Level I. First an instruction screen 1 (not shown) is displayed, block 2410. Next the program waits for the user to touch the screen with the active light pen, block 2412, before displaying instruction screen 2 (not shown), block 2414. Next, the program waits for the subject to touch the screen with the active light pen, block 2416, before continuing to block 2418 where the first picture is loaded into memory from disk. At block 2420, the program checks to see whether the program time is up. If the program time is up, block 2422 is executed where the on-target percentage is calculated for each pen. Results are then printed and stored, block 2424, and a check is made to see whether there is another program to run, block 2426. If not, the ending program is executed, block 2428. If so, the next program in the sequence is run, block 2430. If, at block 2420, the program time is not up, the target is displayed and erased, block 2432. Next, the pen curser is displayed in accordance with the active light pen location and erased, block 2434. Next, a check is made to see whether pen number 1 is active, block 2436. If so, block 2438 is executed where a check is made to determine whether the pen location is within the target. If not, one is added to the "miss" count for pen number 1, block 2442, and the program loops back to block 2420. If the pen location is within the object, one is added to the "ok" count for per number 1, block 2440, and the program loops back to block 2420. If, at block 2436, it is determined that pen number 1 is not active, a check is made to determine whether the pen location of pen number 2 is within the target, block 2444. If so, one is added to the "ok" count for pen number 2, block 2446, and the program loops back to block 2420. If not, one is added to the miss count for pen number 2, block 2448, and the program loops back to block 2420. The time check routine is indicated in blocks 50, 52 and 54. As shown in the flowchart, 180 seconds into the program the subject is instructed to switch the occluder to the other eye, and then repeat the activity. The "switch patch" message is displayed for 18 seconds, block 2452.

10.) Pursuits Level II

The purpose of the Pursuits Level II exercise is to develop smooth, effortless pursuit eye movements with monocular presentation in a binocular field.

Figure 30:
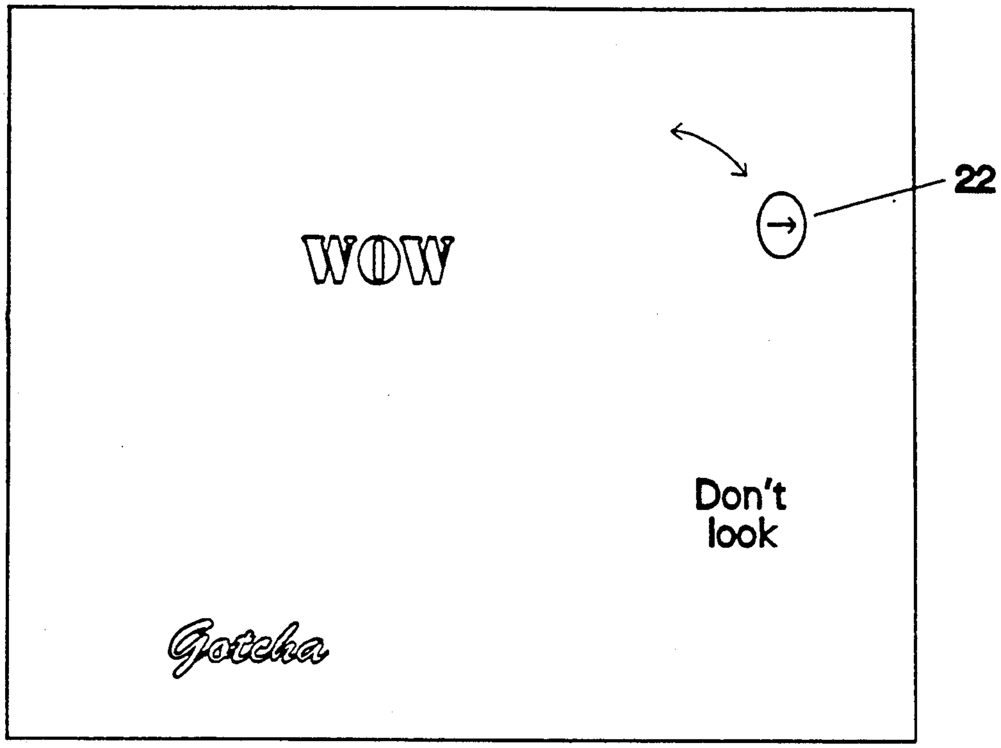
FIG. 30 is a display provided by the vision training system of the present invention in connection with a Pursuits Level II therapeutic exercise routine.

The subject reads instructions (not shown) and touches the screen with the active light pen to continue. A one-inch diameter circle 22 containing an arrow follows a circular path around the screen, five seconds per revolution. See FIG. 30. Every minute the circle reverses direction and the colors of the circle and arrow change together from red to green or green to red. The orientation of the arrow changes randomly every 2 to 8 seconds. The subject is instructed to input the arrow's direction using the keyboard arrow keys. As an additional level of difficulty, small word messages ("distraction targets") flash on and off and are randomly placed on the screen, e.g., "don't look", "wow", "boo", "gotcha". The goal is to maintain visual grasp of the circle and arrow in a relaxed way. The output includes the percentage of correct responses and the mean reaction time, which is stored to the subject's file.

The following detailed description refers to the flowchart in FIGS. 31*a* through 31*d* for Pursuits Level II. First instruction screen 1 (not shown) is displayed, block 2510. Next the program waits for the subject to touch the screen with the active light pen, block 2512, before displaying instruction screen 2 (not shown), block 2514. The program waits for the subject to touch the screen with the active light pen, block 2516, before loading the pictures into memory from disk, block 2518. At block 2520, a check is made to determine whether the program time is up. If the program time is up, the average response time for each object is calculated, block 2522. The correct percentage for each object is calculated, block 2524, and the results are printed, block 2526. At block 2528, a check is made to determine whether there is another program to run. If not, the ending program is run, block 2530. If so, the next program is run, block 2532. If the program time is not up, a check is made to determine whether a key has been pressed, block 2534. If a key has been pressed, a check is made to compare the key pressed against the object on the screen (i.e., for correspondence). Whether or not a correct key has been pressed is stored, as well as the subject's response time, block 2536. If a key has not been pressed, the target is displayed and erased, block 2538. One is added to the distraction target count, block 2540, and a check is made to determine whether the distraction target count is greater than 10, block 2542. If the distraction target count is greater than 10, a new distraction target location is calculated, block 2544, and the distraction target is displayed at the new location and erased, block 2546. If in block 2542, the distraction target count is not greater than 10, the program jumps to block 2546 where the distraction target is displayed and erased. After executing block 2546, the program loops back to block 2520. The time check routine is indicated by blocks 48, 50, and 52. As can be seen by blocks 48, 50 and 52, three minutes into the program the subject is instructed to switch the occluder to the other eye, this instruction is displayed for 15 seconds, after which the program repeats the exercise at the point at which it was interrupted.

11.) Pursuits Level III

The purpose of the Pursuits Level III exercise is to develop smooth, effortless pursuit eye movements with binocular awareness.

The subject wears red/green filters with the red filter worn over the right eye and vice versa. The presentation is the same as in Pursuits Level II (FIG. 30) except that the circle and arrow are different colors, one red and the other green. The goal is to not have either the circle or the arrow disappear as well as to keep the arrow centered in the circle. The output is the same as in Pursuits Level II.

The program for Pursuits Level III is nearly identical to the program for Pursuits Level II with the following exception. At block 2538, the target displayed consists of a circle and an arrow where the circle and the arrow are of different colors, i.e. opposite anaglyph colors. In Pursuits Level II, the circle and the arrow are the same color.

12.) Visual Memory

The purpose of the Visual Memory exercise is to enhance visual imagery, short-term Visual Memory and the ability to perceive more information with less effort.

Figure 32:
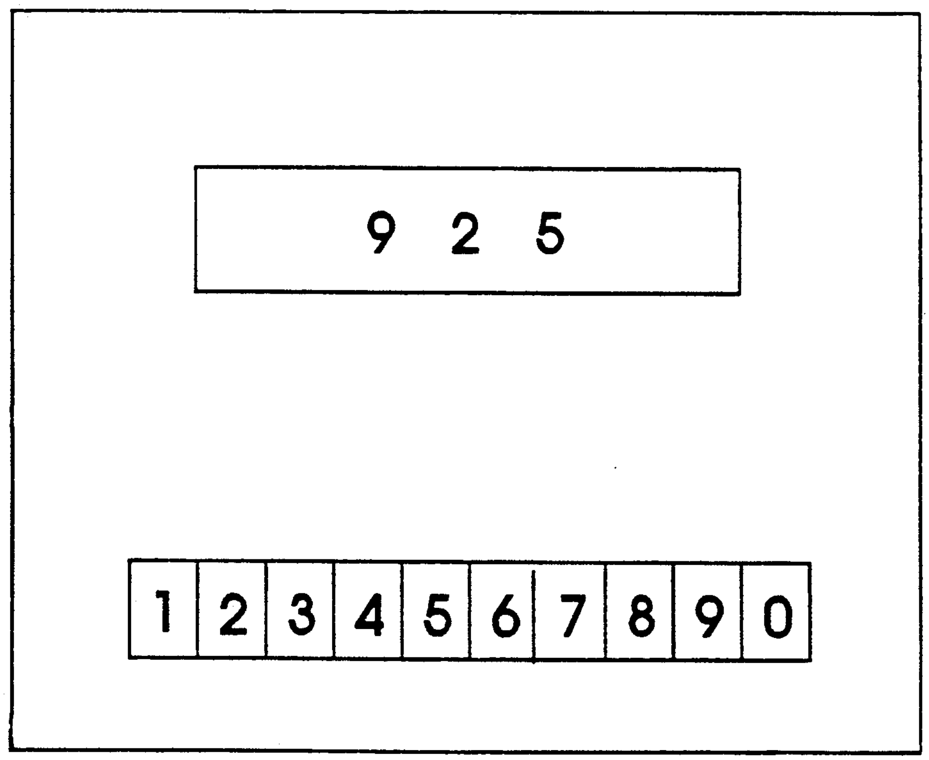
FIG. 32 is a display provided by the vision training system of the present invention in connection with a Visual Memory therapeutic exercise routine.
Figure 31A:
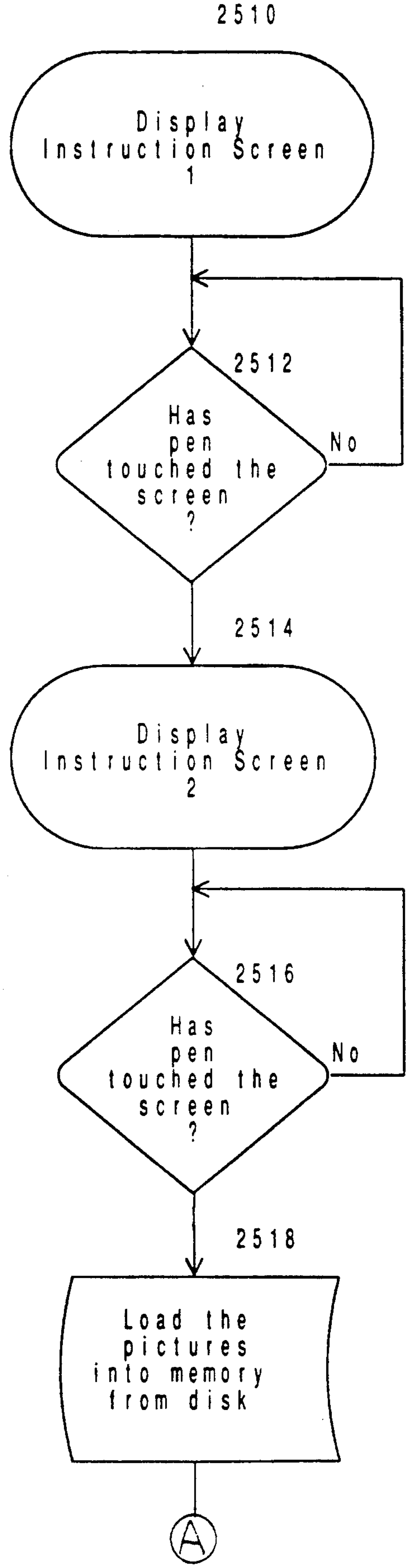
Figure 31B:
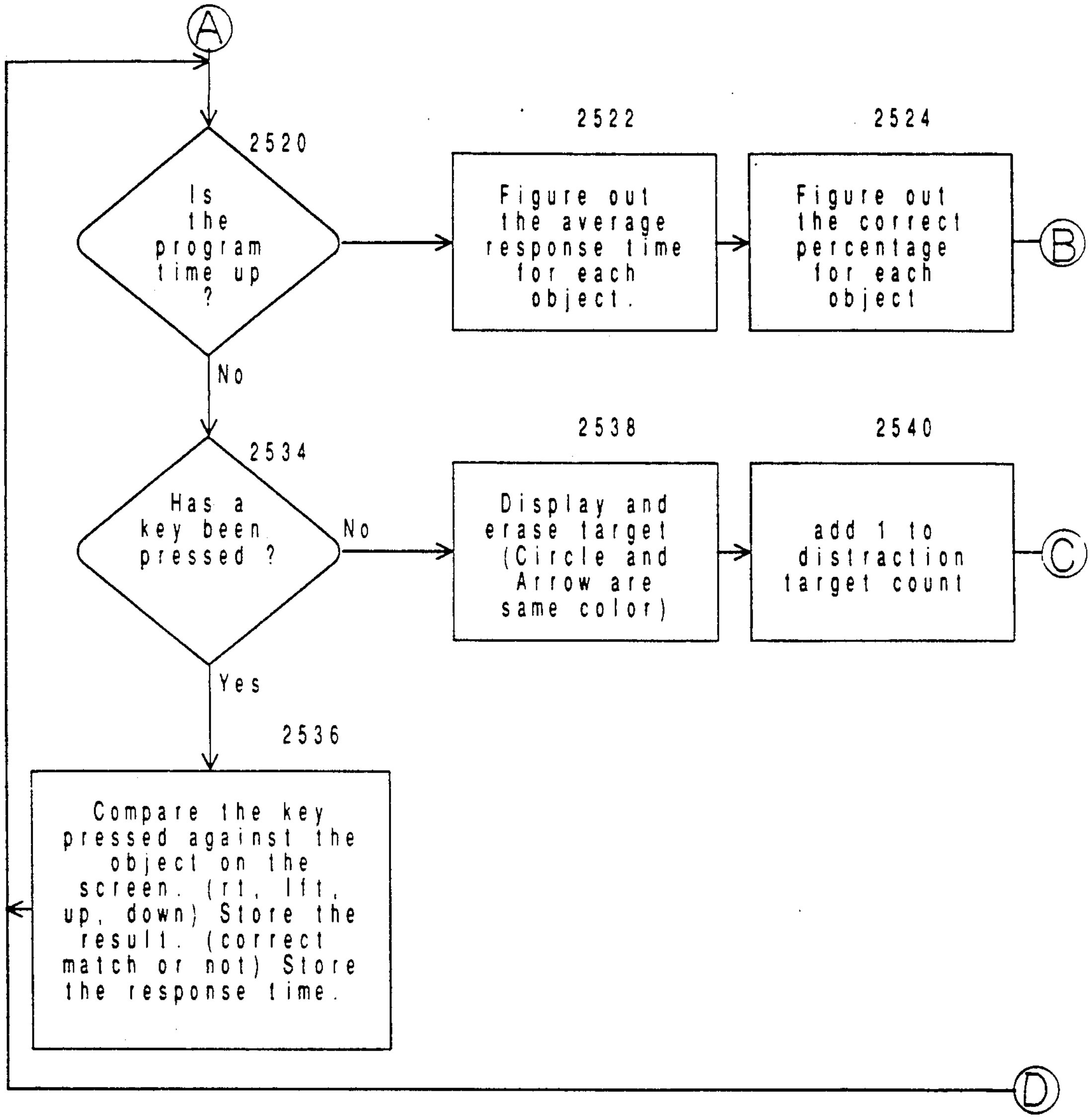
Figure 31D:
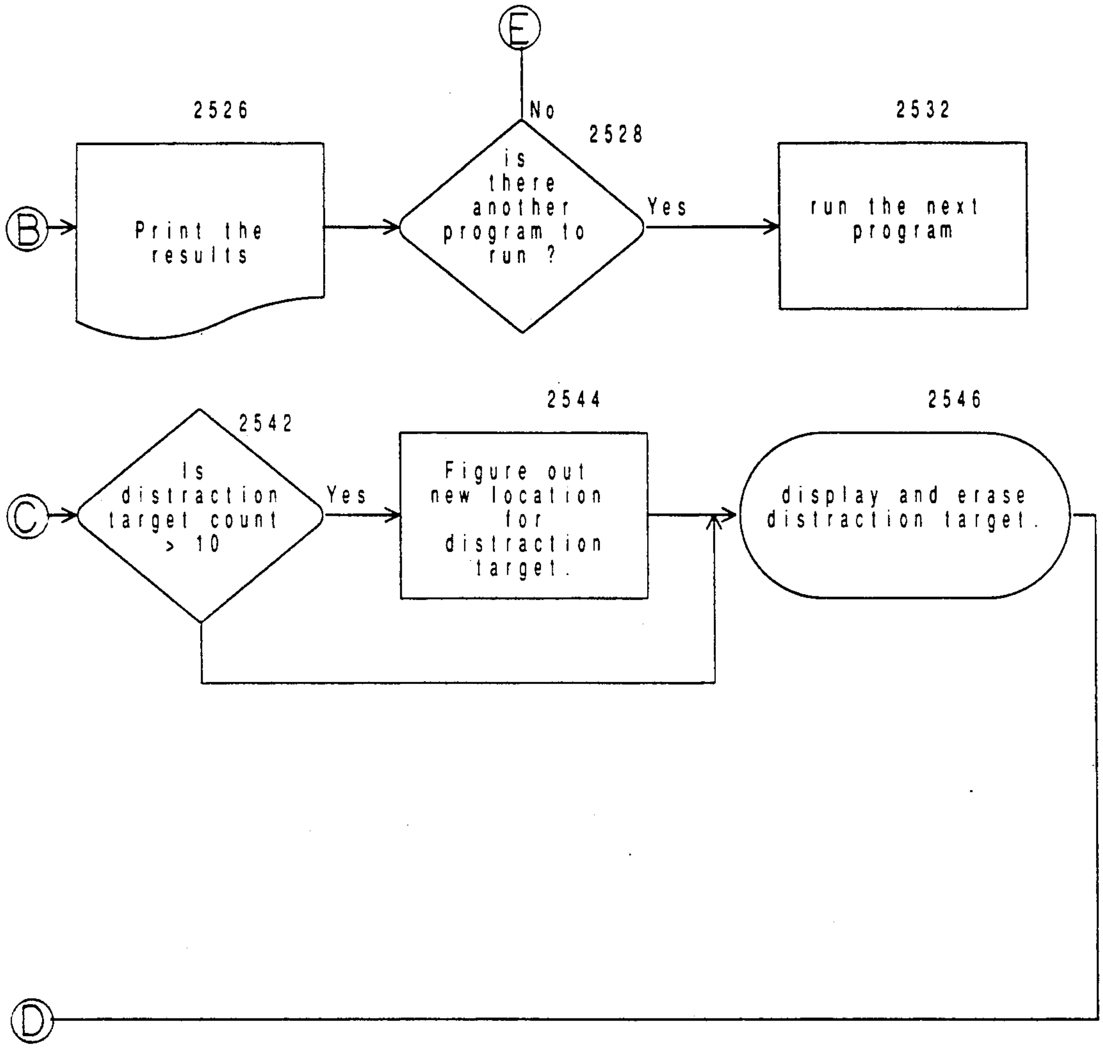
Figure 33A:
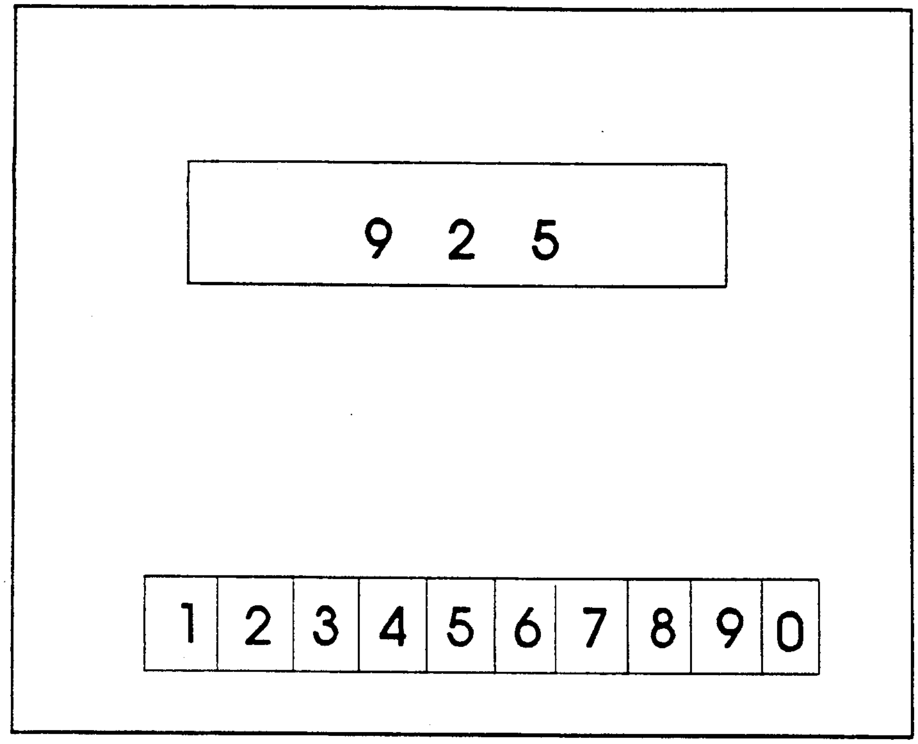
FIGS. 33a, 33b are displays provided by the vision training system of the present invention in connection with a Visual Memory therapeutic exercise routine.
Figure 33B:
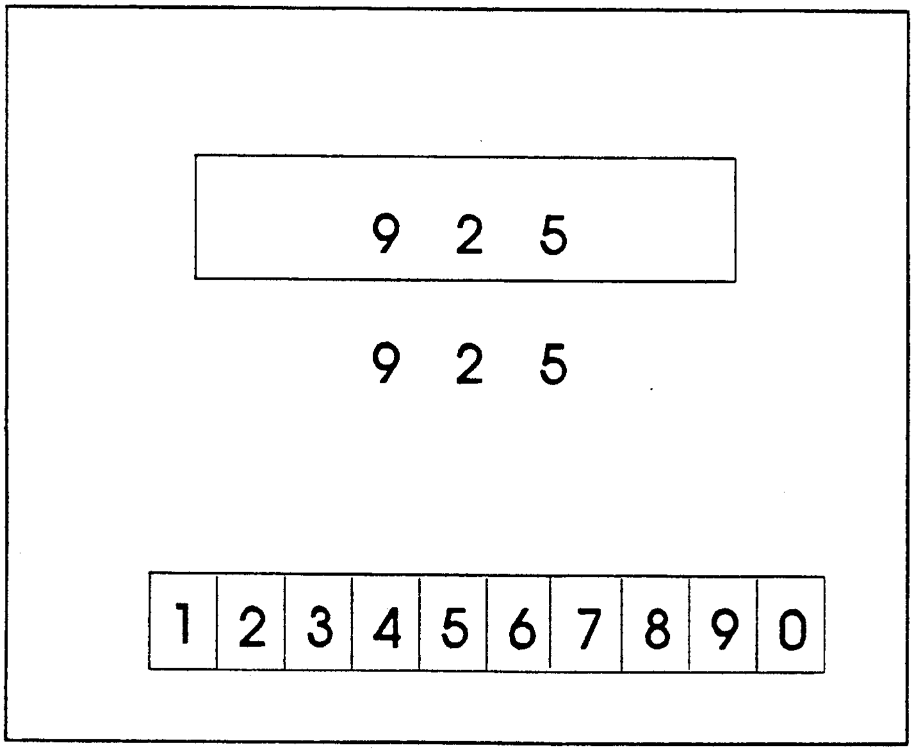
Figure 34A:
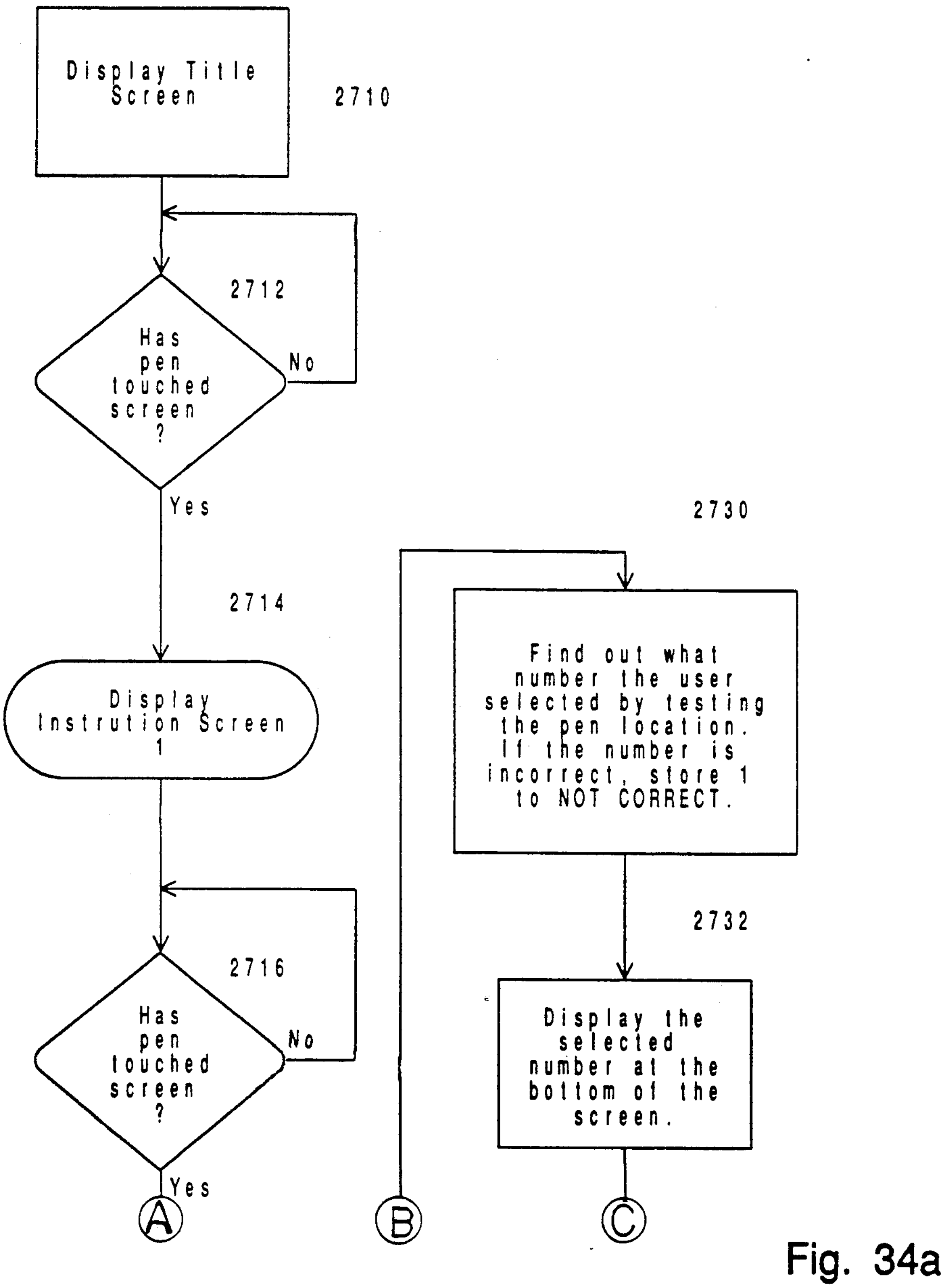
FIGS. 34a-34f are a flowchart illustrating a Visual Memory therapeutic exercise routine.
Figure 34B:
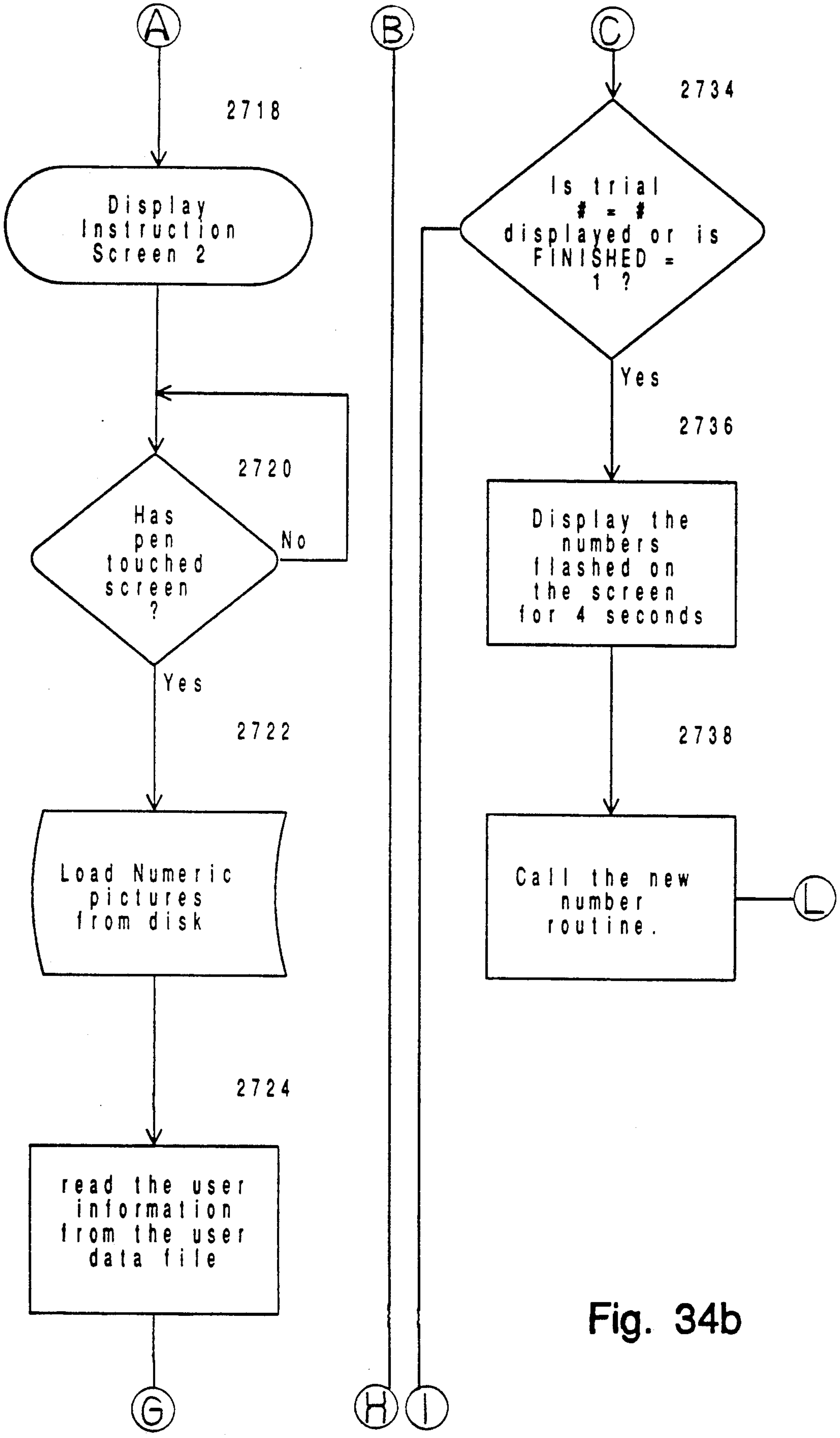
Figure 34C:
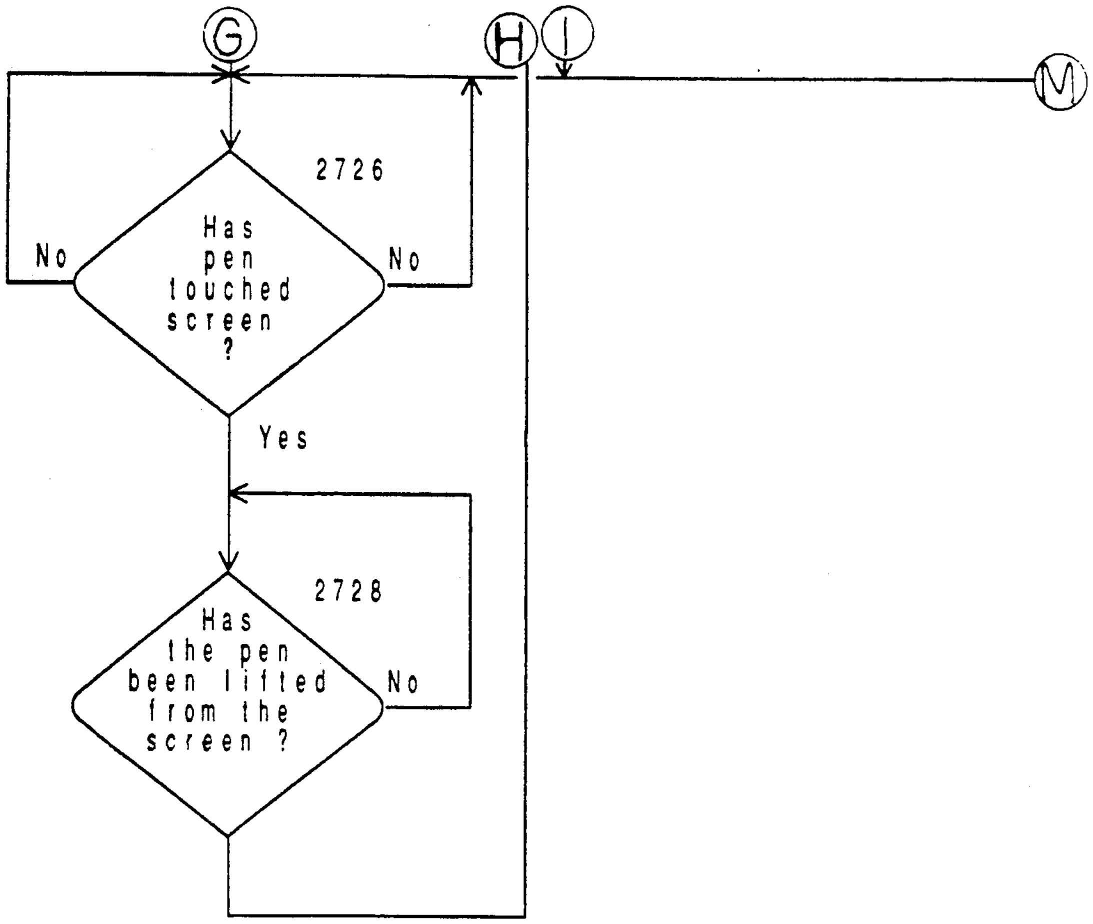
Figure 34D:
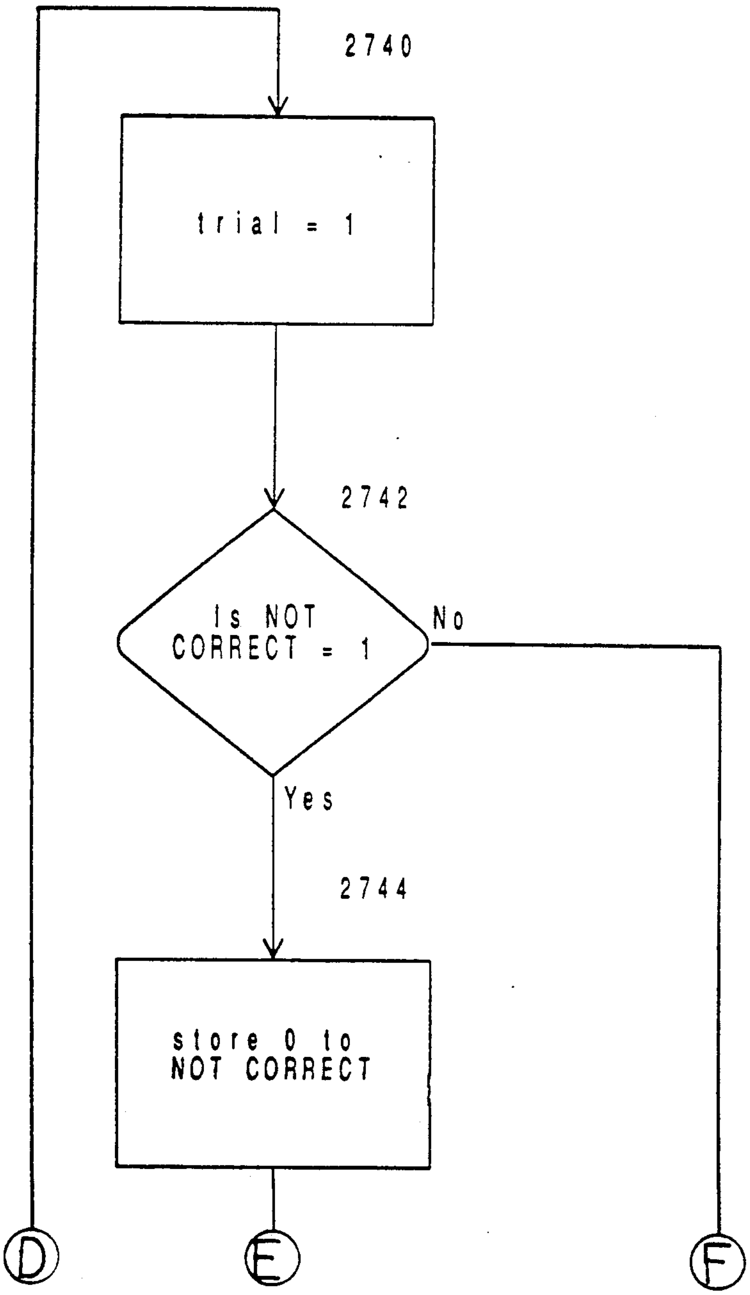
Figure 34E:
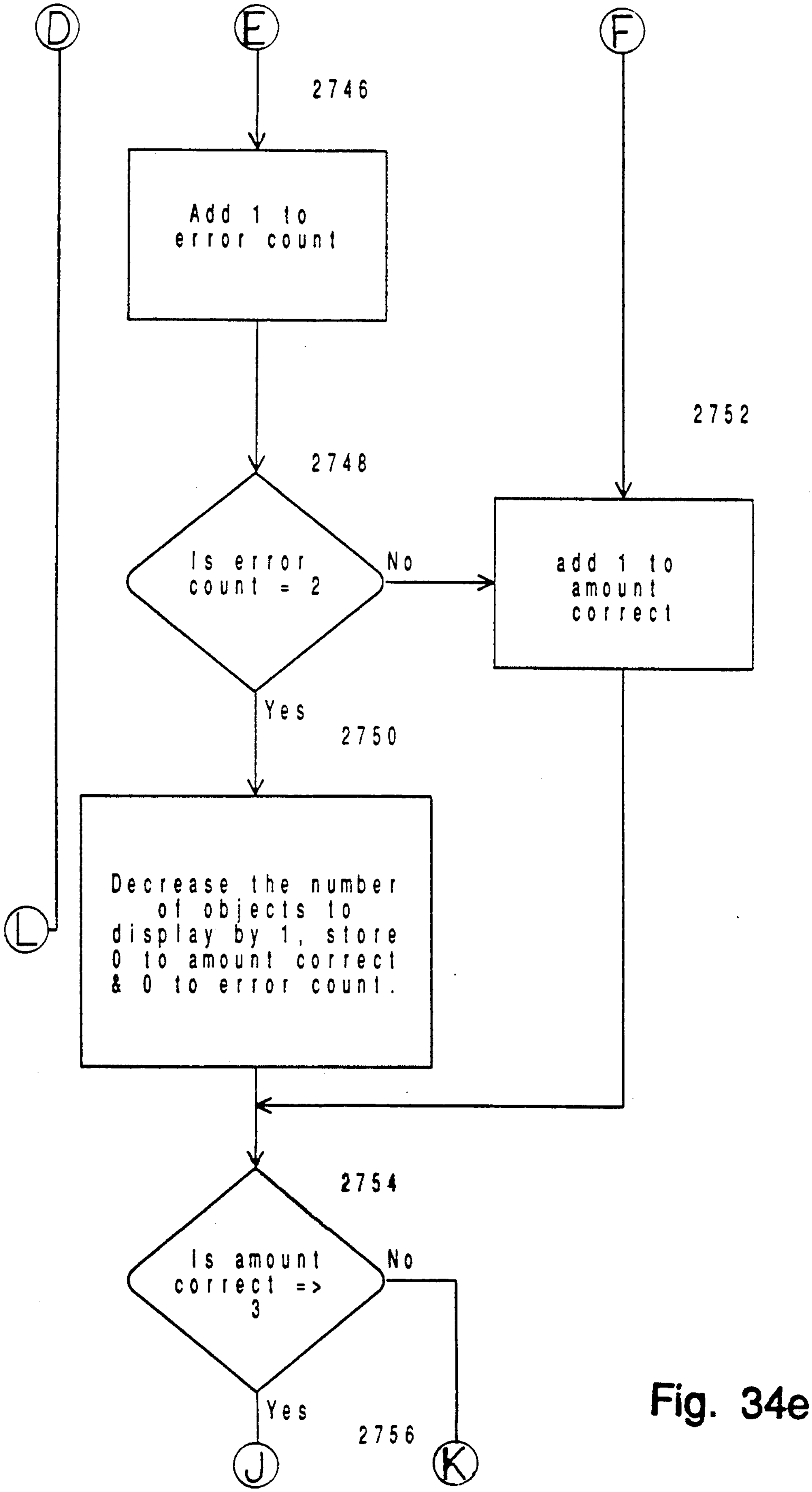
Figure 34F:
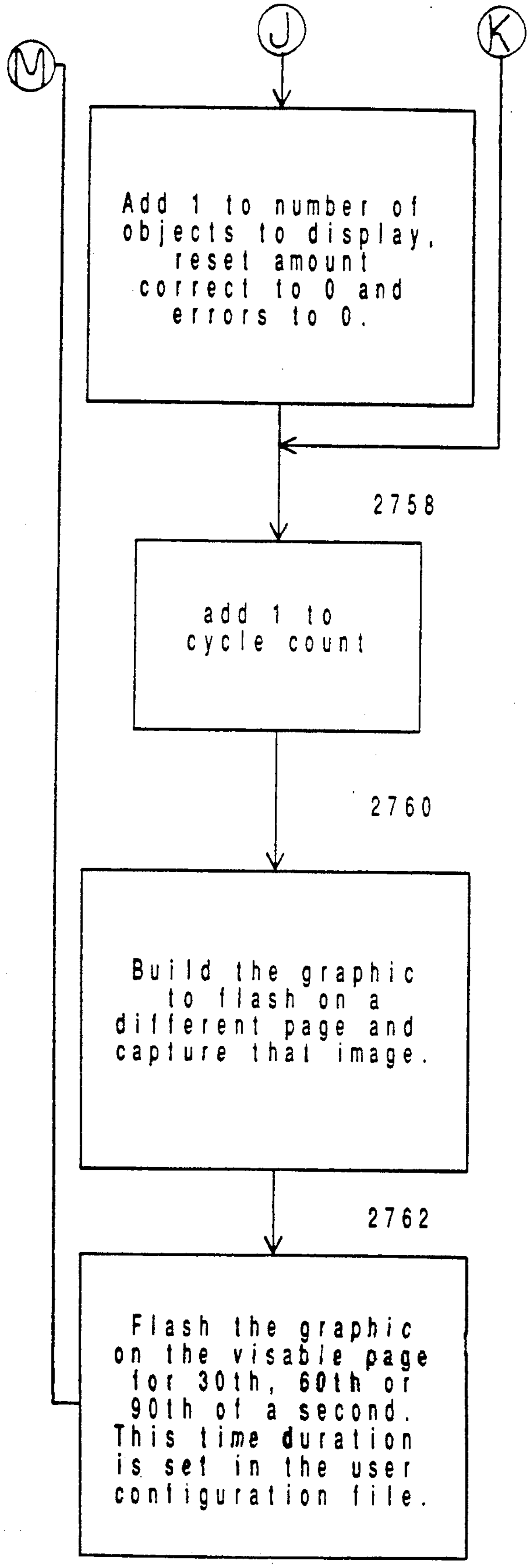

The configuration program offers the following options:

i) digits (FIG. 32) or arrows (FIGS. 33*a, b*) (up, down, left or right);

ii) flash duration equal to 1/30, 1/60, or 1/90 second;

iii) the number of arrows or digits initially presented;

The subject reads instructions (not shown) and touches the screen with the active light pen to continue. As the subject watches an empty rectangle (e.g., FIG. 32), two computer generated tones, one second apart, are followed by a flashed sequence of arrows (FIG. 33*a*) or digits (FIG. 32). Using the active light pen, the subject is instructed to enter a response by touching the numbers or arrows at the bottom of the screen in the same order as presented. The entered response is displayed as it is entered just below the rectangle (FIG. 32, 33*b*). After the response is completed, the original digit or arrow sequence appears in the rectangle for comparison. A response must be 100% to be considered correct. When correct responses occur in three consecutive trials of the same length sequence, the length of the sequence increases by one. When two consecutive errors occur, the length of the sequence decreases by one. Whenever the subject fails to enter a response within ten seconds of the flash, the trial terminates and a new one starts. After the response is completed, there is a five second delay before the next trial begins. At any time, if the subject needs rest, he can press the "escape" key for a 15 second delay before the next trial. During that period, the screen displays reminders to breath deeply and be visually aware of the space surrounding the computer. Usually numbers are utilized before arrows. The target presented and/or the length of the initial sequence and/or the duration of target presentation may be automatically controlled by the configuration program.

The output includes (i) the target used, arrows or numbers, (ii) a list of the total trials and total correct, grouped by sequence length, and (iii) the total percentage correct, all of which are stored to the subject's file.

The following detailed description refers to the flowchart in FIGS. 34*a* through 34*f* for the Visual Memory exercise routine. First a title screen (not shown) is displayed, block 2710. Next the program waits for the subject to touch the screen with the active light pen 2712 before displaying instruction screen 1, 2714. Next the program waits for the subject to touch the screen with the active light pen 2716 before displaying instruction screen 2, block 2718. Again, the program waits for the subject to touch the screen with the light pen 2720 before loading the numeric pictures from disk, block 2722. Next the subject's information is read from the subject's data file, block 2724. Next the program waits for the subject to touch the screen with the active light pen, block 2726, before continuing to block 2728, where a check is made to determine whether the pen has been lifted from the screen. If not, the program waits for the pen to be lifted. Once the pen has been lifted from the screen, the program continues to block 2730, where the program determines what number was selected by the subject by testing the pen location. If the number is incorrect, a one is stored to the variable "not correct". Next the number selected is displayed on the bottom of the screen, block 2732. Next a check is made to determine whether the trial number is equal to the number displayed or whether the variable "finished" is equal to one, block 2734. If either of these conditions is met the program displays the numbers flashed on the screen for four seconds, block 2736. If neither one of these conditions is met, the program jumps back to block 2726. Next, at block 2738, the new number routine is called. At block 2740, the variable "trial" is set equal to one. At block 2742 a check is made to determine whether "not correct" is equal to one. If so, a zero is stored to "not correct", block 2744, and one is added to the error count, block 2746. Next a check is made to determine whether the error count is equal to two, block 2748. If not, the program jumps to block 2752 where a one is added to the variable "amount correct". If, at block 2742, "not correct" is not equal to one, the program jumps to block 2752. If, at block 2748, the error count is equal to two, the program jumps to block 2750, where the number of objects to display is decreased by one, a zero is stored to "amount correct", and a zero is stored to the error count. At block 2754, a check is made to determine whether "amount correct" is greater than or equal to three. If not, the program jumps to block 2758. If so, the program executes block 2756, where one is added to the number of objects to display "amount correct" is reset to zero and the error count is reset to zero. Next, at block 2758, one is added to "cycle count". Next the graphic to be flashed is constructed and captured, block 2760. Next this graphic is flashed on the visible page for 1/30th, 1/60th, or 1/90th of a second, depending on the duration set in the configuration file, block 2762. The program then loops back to block 2726.

13.) Depth of Fusion Level I

Figure 35A:
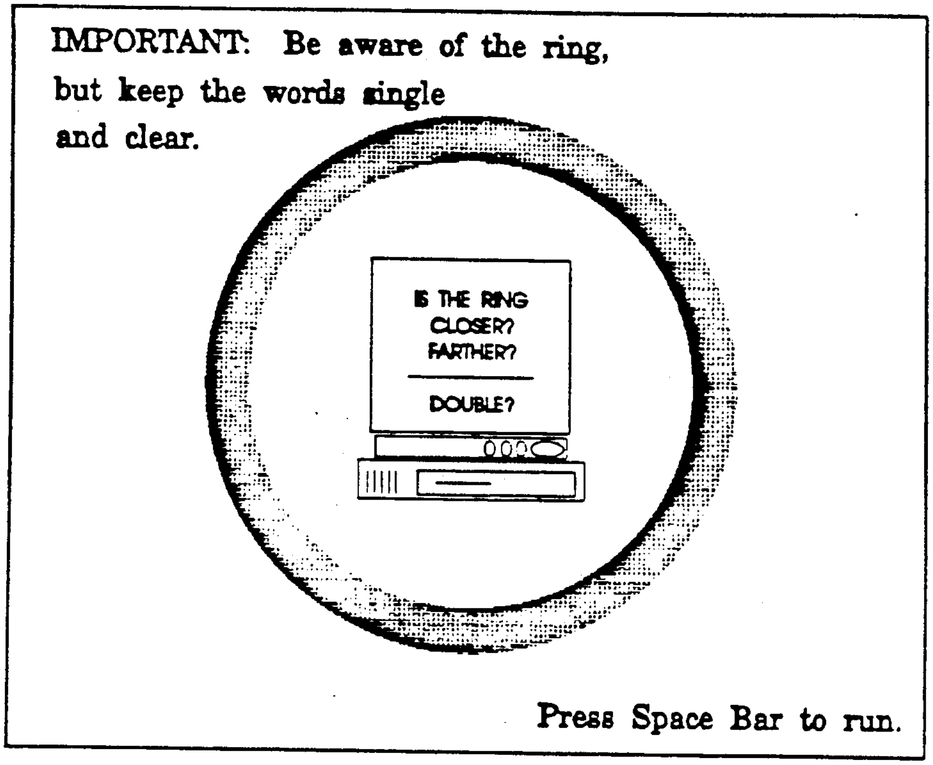
FIGS. 35a-35c are displays provided by the vision training system of the present invention in connection with a Depth of Fusion Level I therapeutic exercise routine.

The purpose of the Depth of Fusion Level I exercise is to enhance binocular integration by developing float awareness. The subject wears red and green filters, one over each eye. The subject reads instructions (not shown) and touches the screen with the active light pen to continue. The red filter is placed over the right eye and vice versa. The subject is instructed to center and focus on the picture of the computer as shown in FIG. 35*a* while maintaining peripheral awareness of the ring. The center picture is visible to both eyes. There are two superimposed rings of different (opposite) colors, one visible to the right eye and the other visible to the left eye.

Figure 35B:
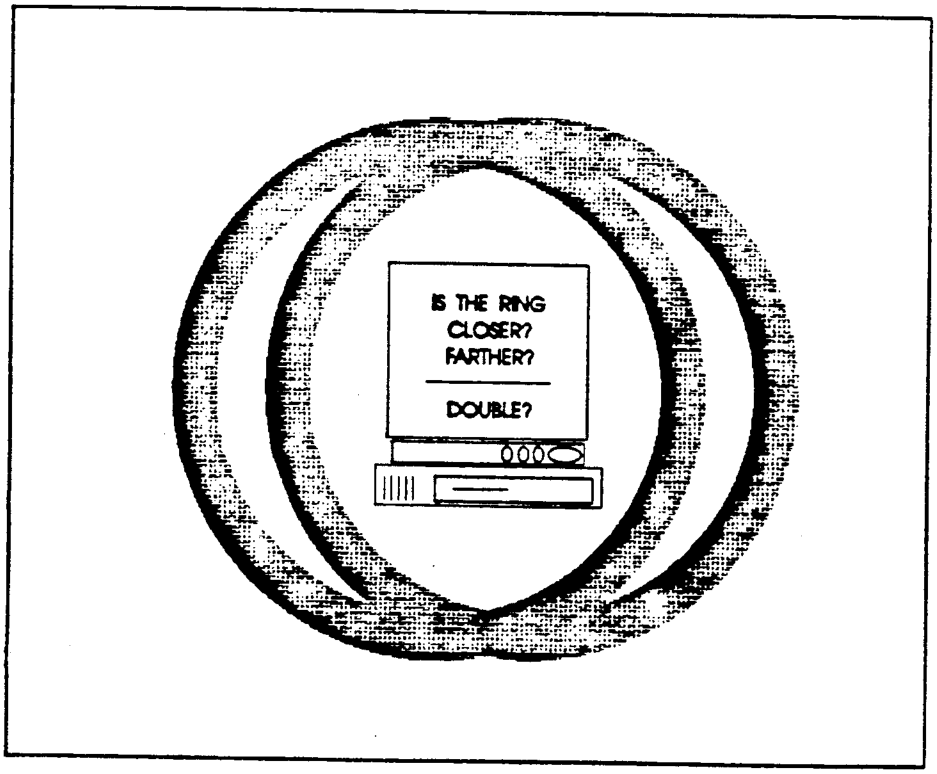
Figure 35C:
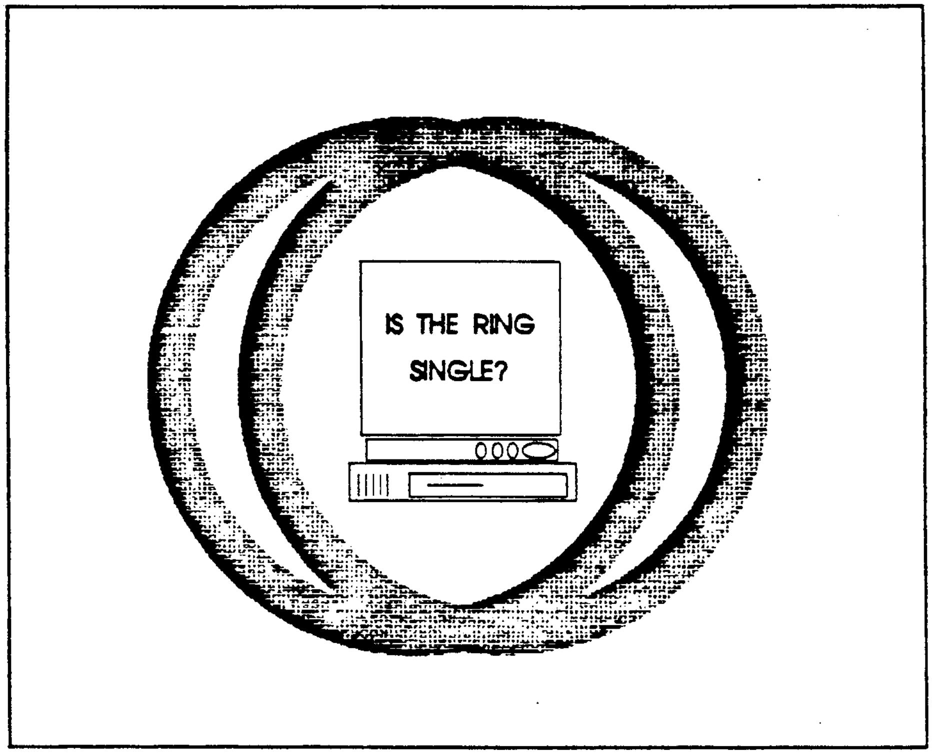
Figure 36A:
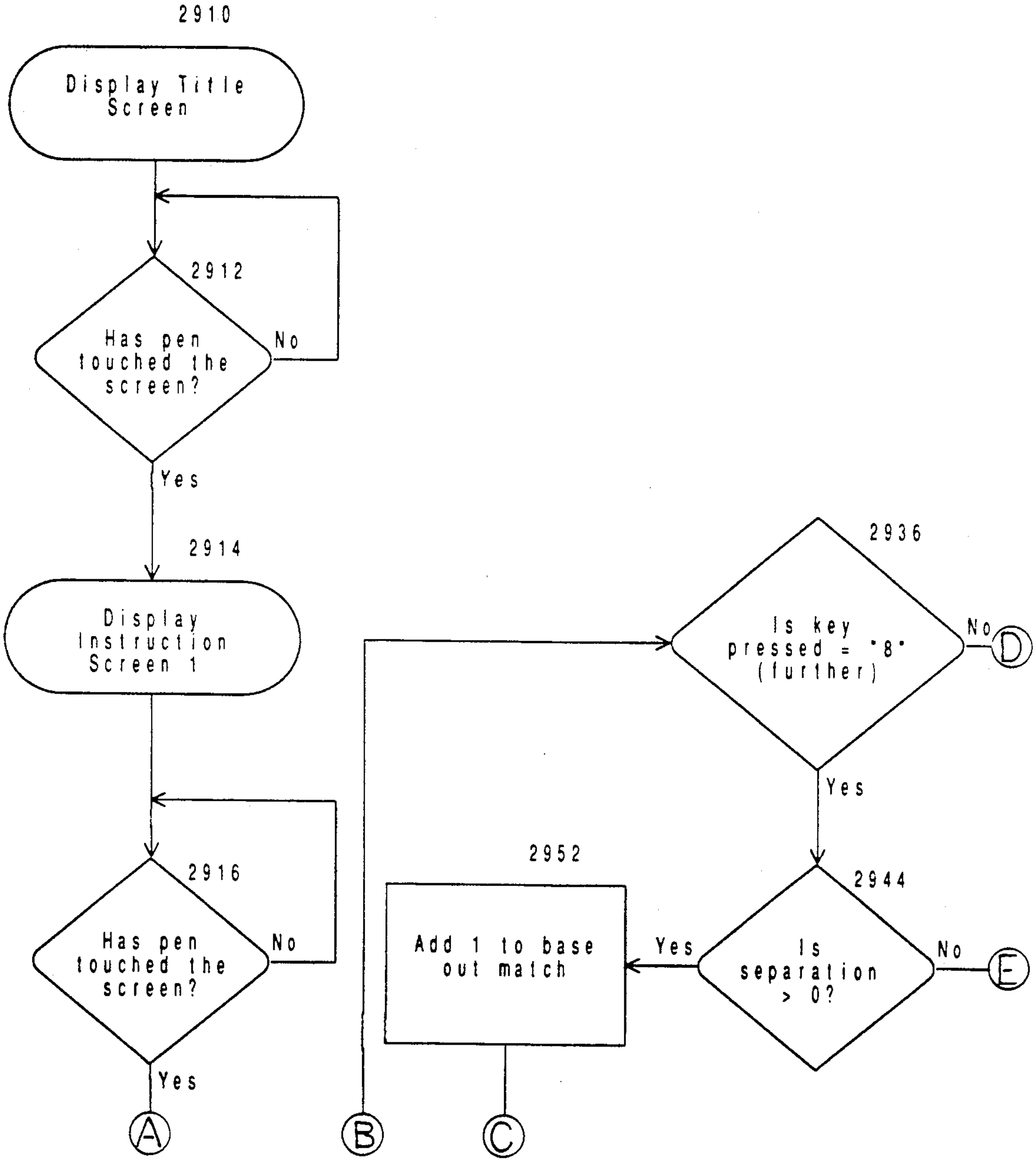
Figure 36B:
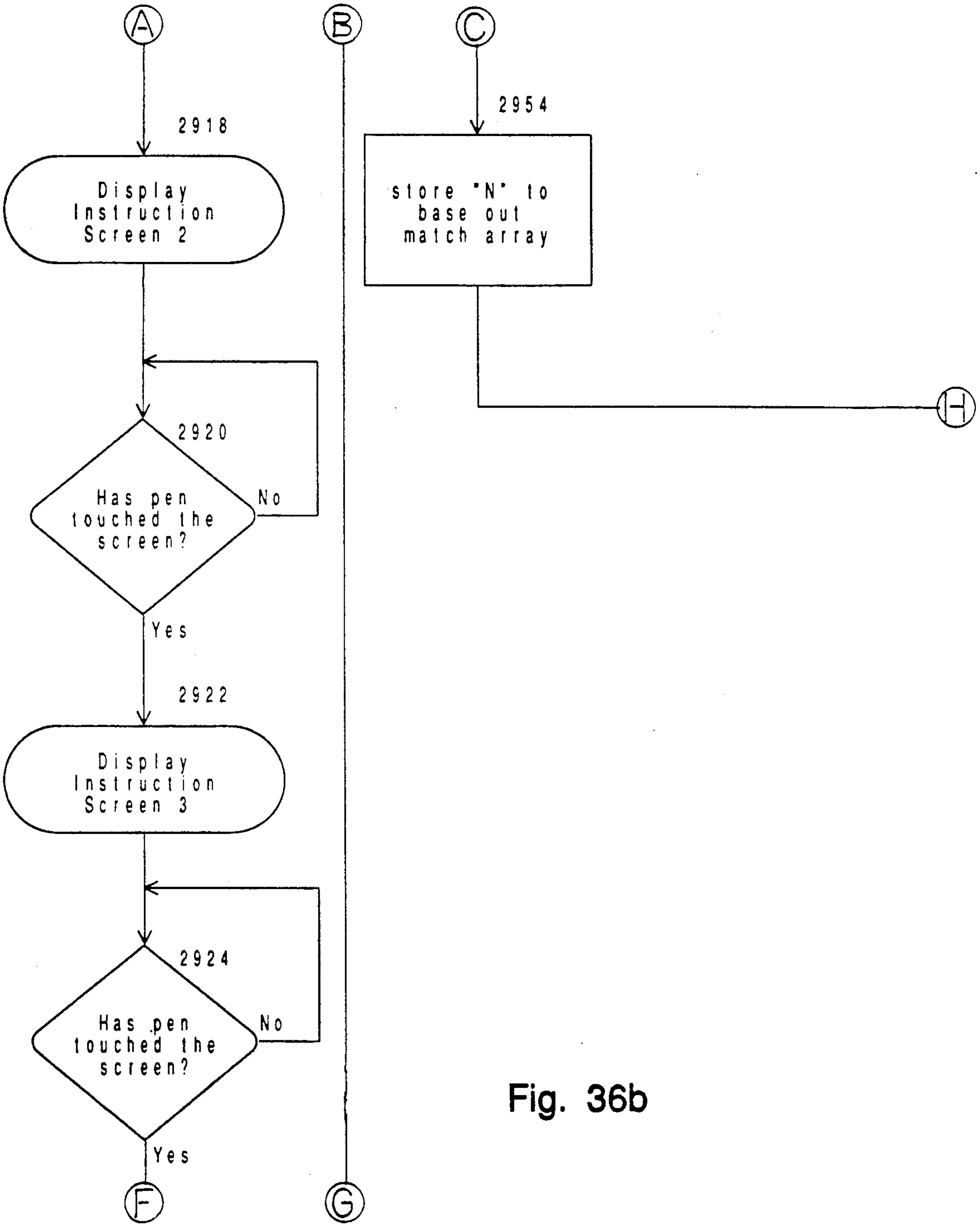
Figure 36C:
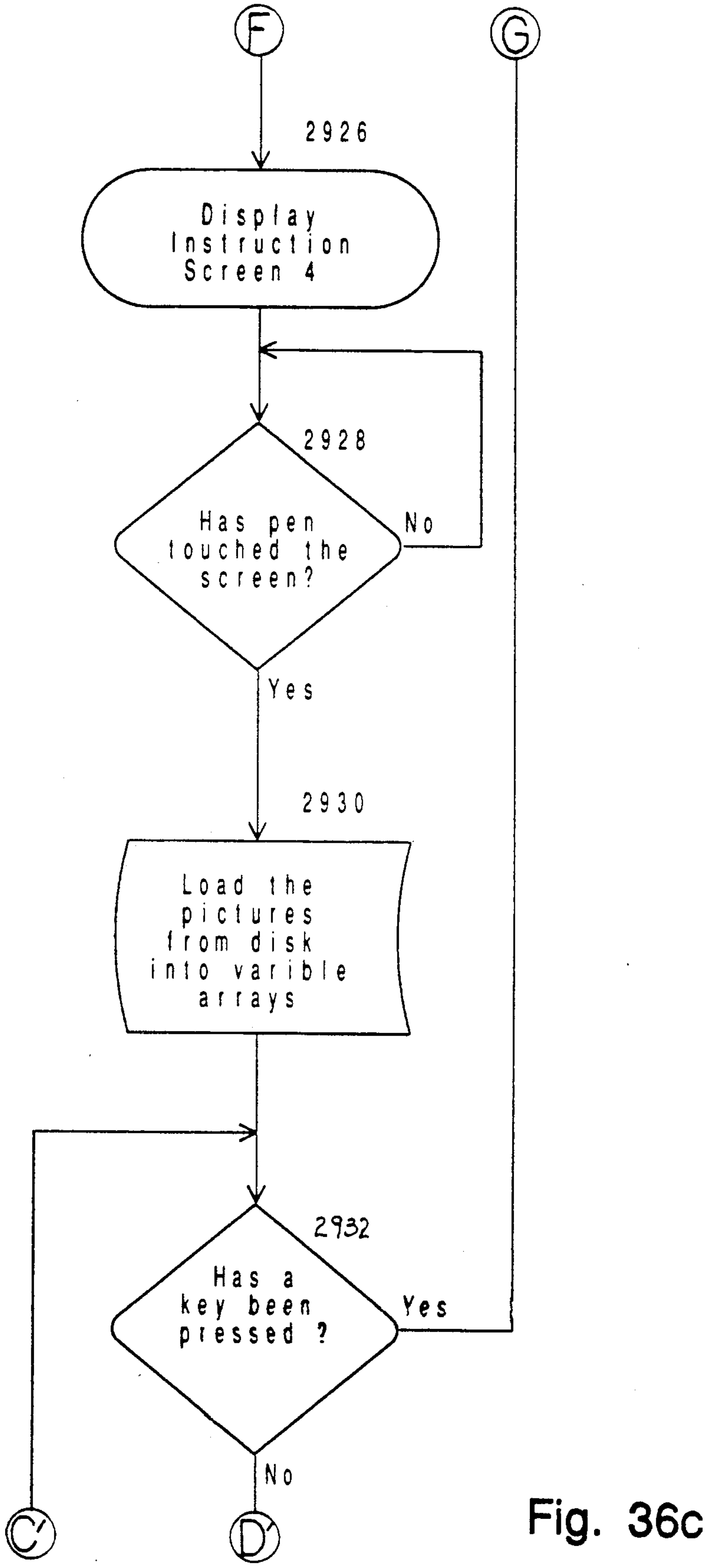
Figure 36D:
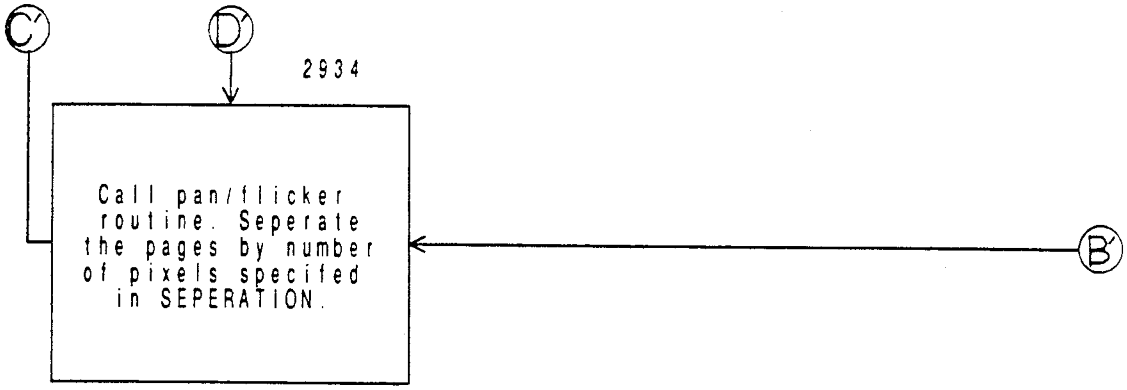
Figure 36E:
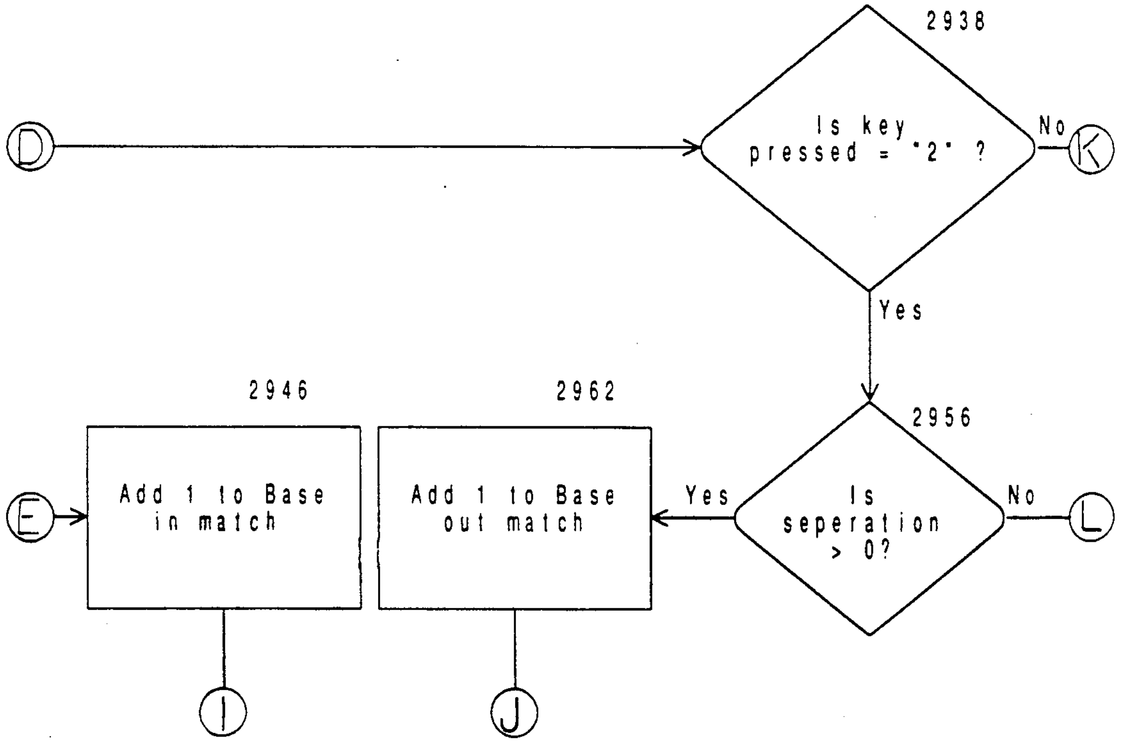
Figure 36F:
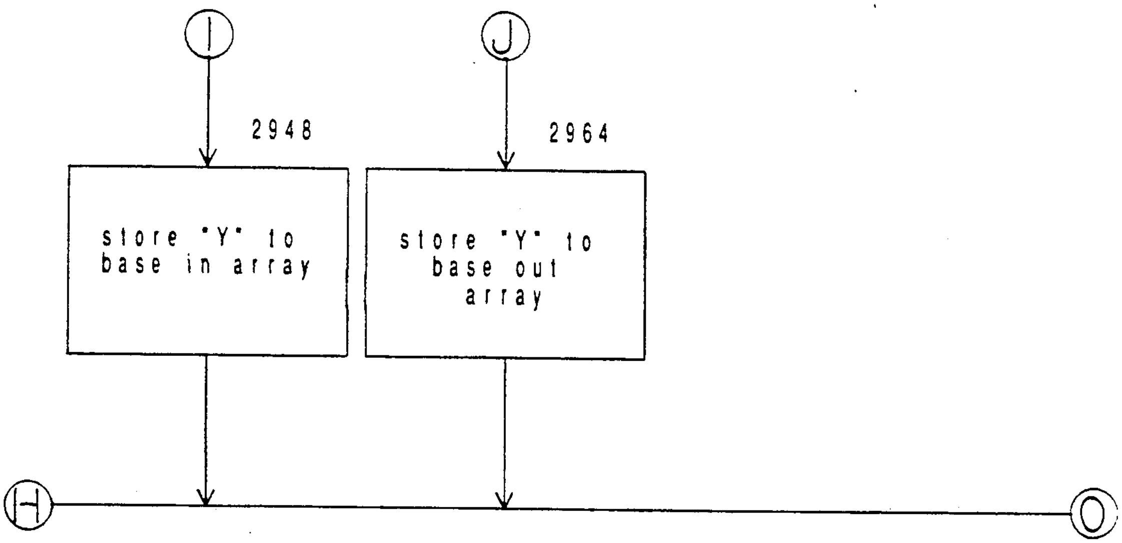
Figure 36G:
Figure 36H:
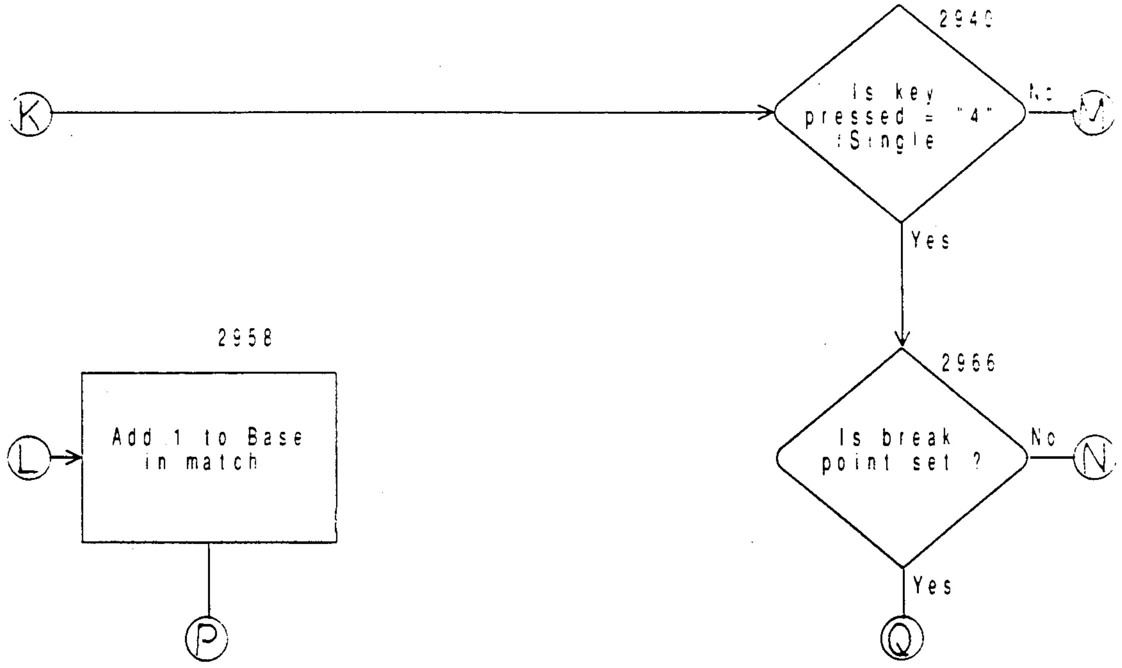
Figure 36I:
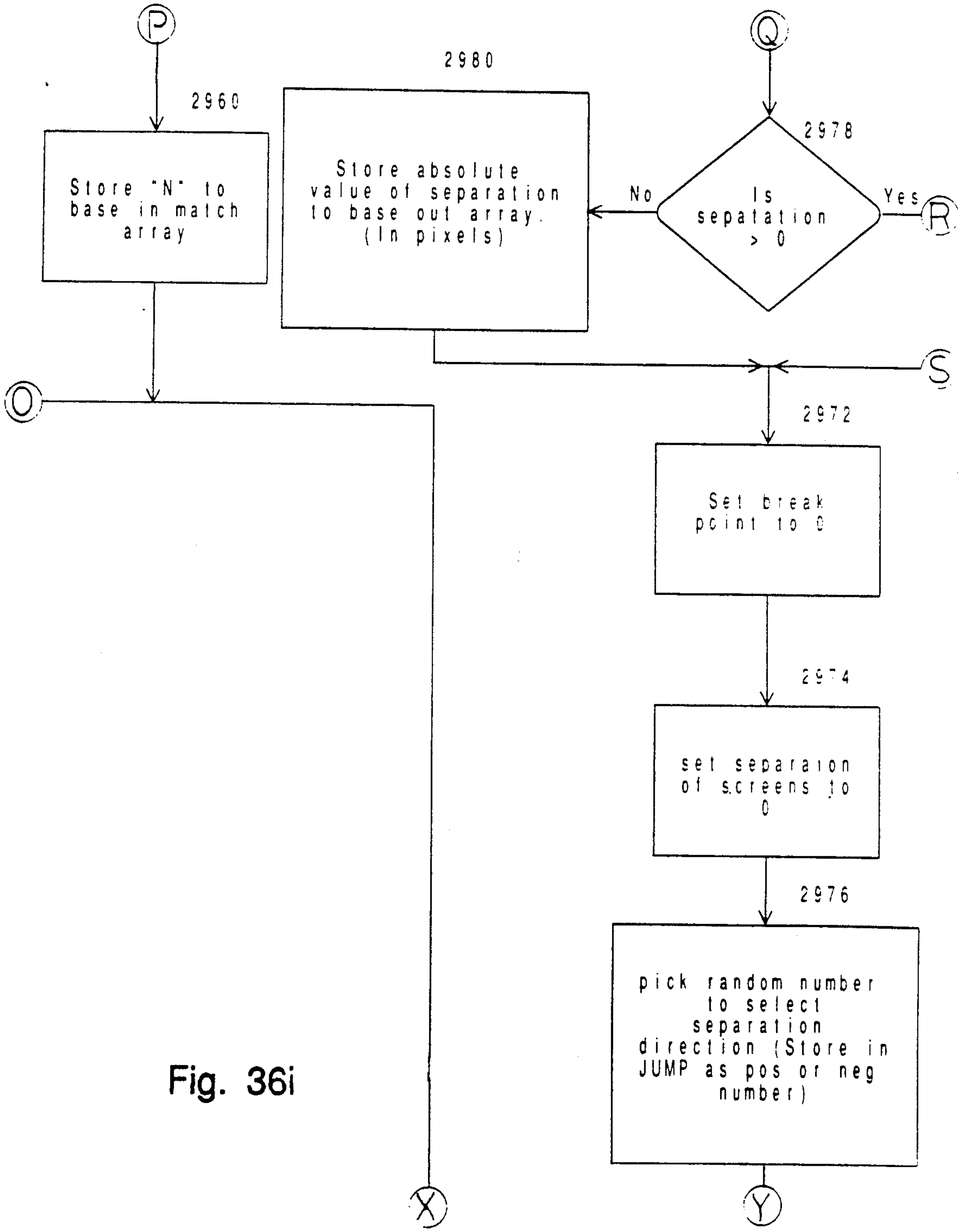
Figure 36J:
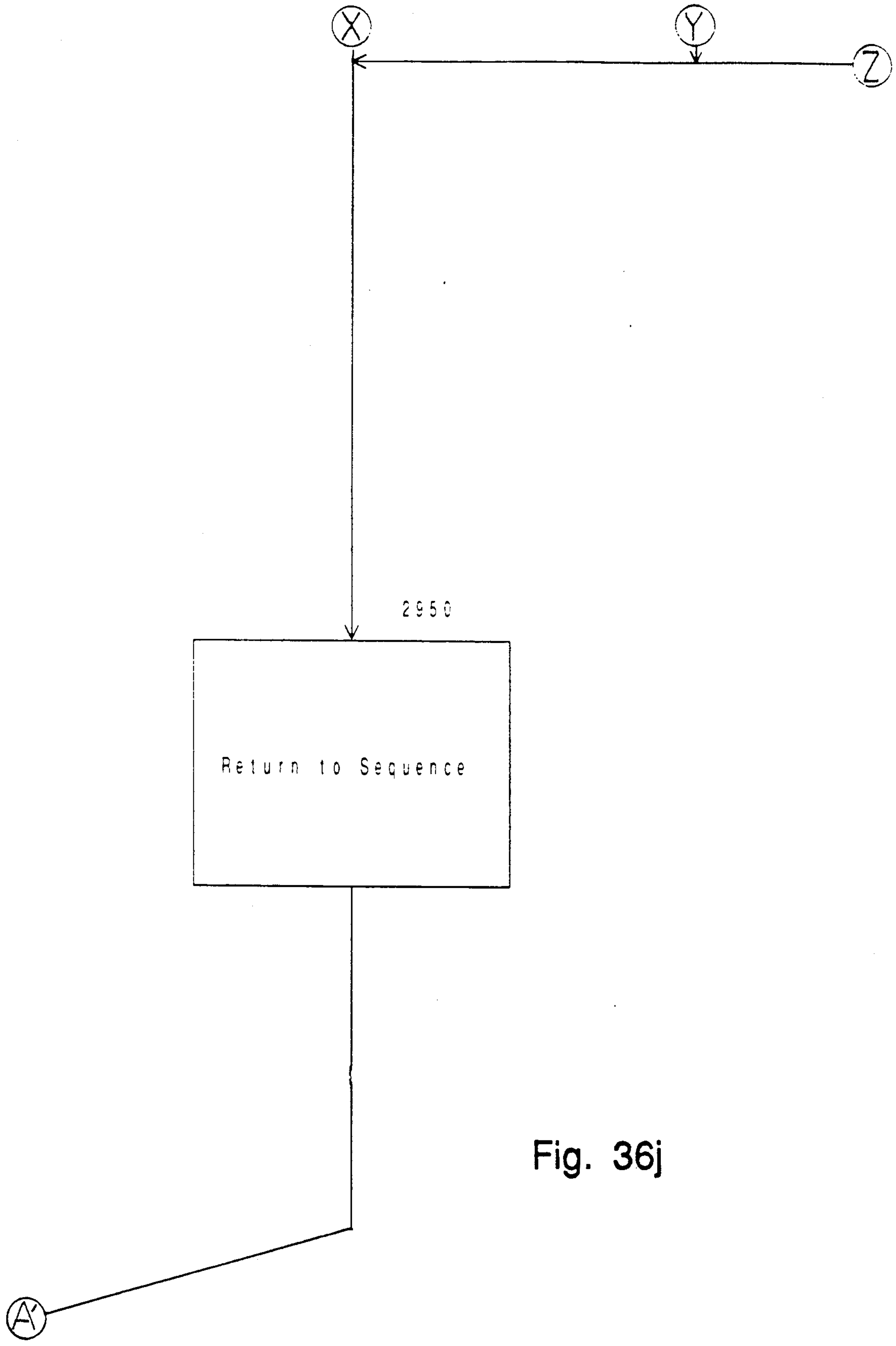
Figure 36K:
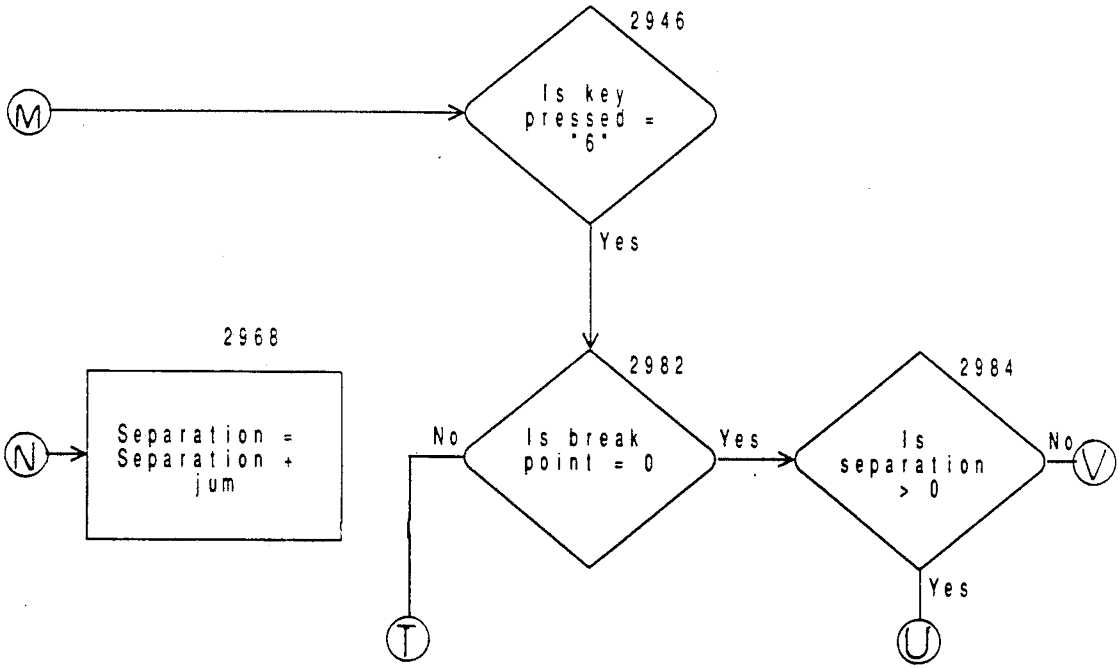
Figure 36I:
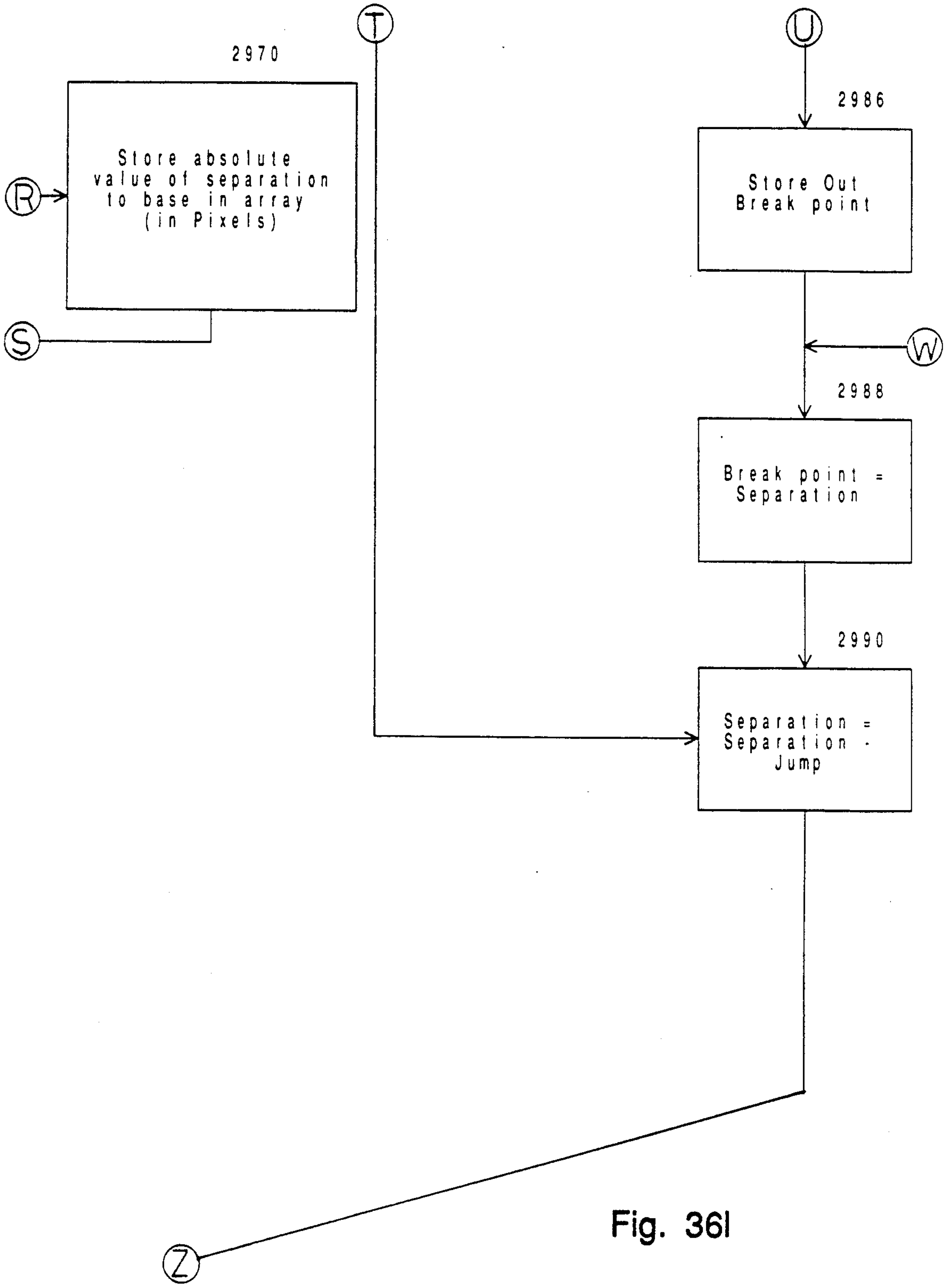
Figure 36M:
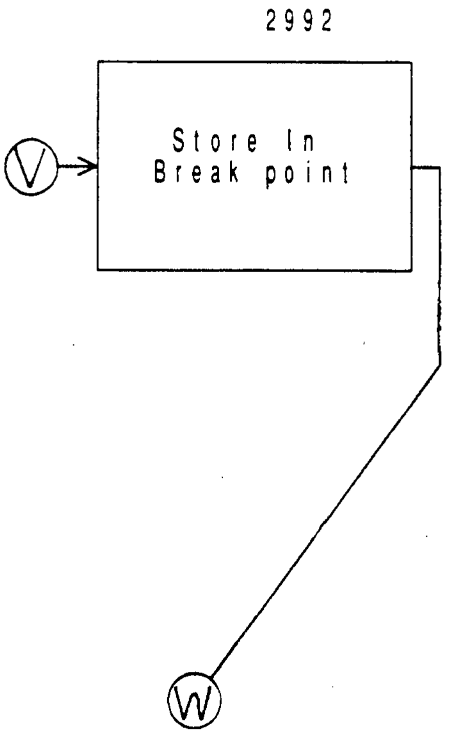

The subject is instructed to use the numerical key pad to direct the activity as follows. Press the "single" key, no. four, when only one ring is perceived. As this key is pressed, the rings separate laterally, base-out or base-in demand, as chosen by the computer, with 50% probability of one or the other. The key can be tapped for slow separation or held down for continuous separation. When the subject becomes aware of the two rings, the "double" key, no. six, is pressed. See FIG. 35*b*. This is recorded as a break point and the rings begin moving back toward each other. When the rings return to the appearance of being single, the "single" key is tapped. See FIG. 35*c*. This is recorded as a "recovery" point and the rings automatically reset to zero separation, and a new trial begin. During each trial, if the subject perceives the ring "floating" closer or farther from the center picture, he is instructed to tap the appropriate key, "closer", no. 2, or "farther", no. 8.

The output includes (i) the average break point, in prism dioptors, for base-in and base-out, and standard deviation, (ii) the average recovery point in prism dioptors for base-in and base-out, and standard deviation, (iii) the number of trials, grouped by base-out and base-in, and (iv) the closer/farther responses, all of which are stored to the subject's files.

The following detailed description refers to the flowchart in FIGS. 36*a* through 36*m* for the Fusion Level I routine. First a title screen (not shown) is displayed, block 2910. In block 2912, the program waits for the subject to touch the screen with the active light pen after which instruction screen 1 (not shown) is displayed, block 2914. After the user touches the screen with the active light pen again, block 2916, instruction screen 2 (not shown) is displayed, block 2918. In a similar manner, instructions screens 3 and 4 (not shown) are displayed in blocks 2922 and 2926, respectively. After waiting for the subject to touch the screen with the light pen in block 2928, pictures from the disk are loaded into variable arrays, block 2930. At block 2932, a check is made to determine whether a key has been pressed. If not, the "pen/flicker" routine is called whereby the computer's internal screen pages are separated by the number of pixels specified in the variable "separation", and the program loops back to block 2932. The "pen/-flicker" routine refers to two separate routines. The "pen/flicker" routine rapidly alternates between two other routines while waiting for some event to happen. These routines are as follows: (i) flicker routine—the flicker routine rapidly copies the contents of data memory into the display memory to rapidly alternate the presentation of Screen page 1 and Screen page 0 to create a transparency effect; (ii) light pen routine--the light pen routine checks three functions of the light pen. These functions are: X position of the pen; Y position of the pen; and, combination of the light pen switch and light pen status, i.e., whether the push switch on the light pen itself is on or off, and whether the light pen is sensing light or not sensing light. This status will be represented as one of the following: no light/switch off; no light/switch on; light/switch off; or, light/switch on.

If a key has been pressed, the program proceeds to block 2936. At block 2936, a check is made to determine whether the key pressed was the number eight. If not, the program proceeds to block 2938 where a check is made to determine whether the key pressed was the number two. If not, a check is made to determine whether the key pressed was the number four, block 2940. If not, a check is made to determine whether the key pressed was the number six, block 2946. If the key pressed was the number eight, the program proceeds to block 2944 where a check is made to determine whether the separation is greater than zero. If not, one is added to the variable "base-in match", block 2946, and a "Y" is stored to the base-in array, block 2948, after which the program loops back to block 2934. If, in block 2944, the separation is greater than zero, one is added to the variable "base-out match", block 2952, and an "N" is stored to the base-out match array, block 2954, after which the program loops back to block 2934. If the key pressed is the number two key, block 2956 is executed where a check is made to determine whether the separation is greater than zero. If not, one is added to "base-in match", block 2958, and an "N" is stored to the base-in match array, block 2960, and the program loops back to block 2934. If it is determined at block 2956 that "separation" is greater than zero, one is added to the "base-out match", block 2962, a "Y" is stored to the base-out array, block 2964, and the program loops back to block 2934. If the key pressed was the number four, a check is made at block 2966 to determine whether the break point has been set. If not, "separation" is incremented, block 2968, and the absolute value of "separation" is stored to the base-in array, block 2970. The break point is then set to zero, block 2972. Next, "separation" is set to zero, block 2974, and a new separation direction is selected based on a random number, block 2976. The program then loops back to block 2934. If, at block 2966, the break point is set, a check is made to determine whether "separation" is greater than zero, block 2978. If not, the absolute value of "separation" is stored to the base-out array, block 2980, and the program jumps to block 2972. If "separation" is greater than zero, the absolute value of "separation" is stored to the base-in array, block 2970, and the program jumps to block 2972. If the key pressed was not the number eight, number two or number four, the program reaches block 2941, where it continues on to block 2982 where a check is made to determine whether the break point is equal to zero. If the break point is equal to zero a check is made to determine whether "separation" is greater than zero, block 2984. If so, the "out break point" is stored, block 2986. Next, the break point is set equal to "separation", block 2988, and "separation" is reduced by the value of the variable "jump", block 2990, afterwhich the program loops back to block 2934. If, at block 2984, "separation" is not greater than zero, the "in break point" is stored, block 2992, and the program jumps to block 2988. If, at block 2982, the break point is not equal to zero, the program jumps to block 2990.

14.) Depth of Fusion Level II

The purpose of the Depth of Fusion Level II exercise is to develop ranges of freedom within the binocularity system.

Figure 37:
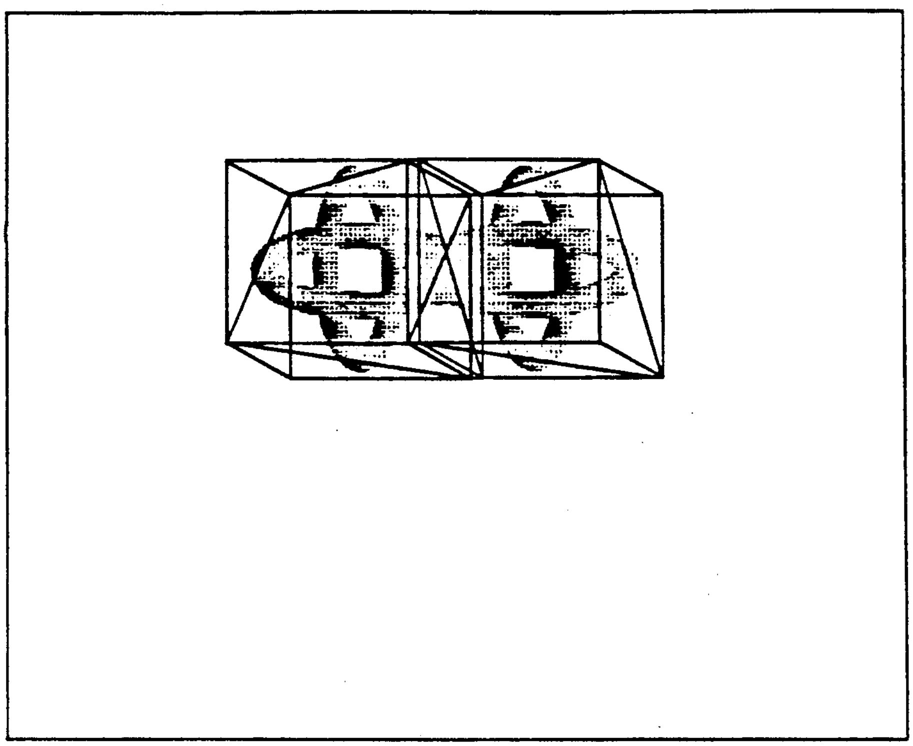
FIG. 37 is a display provided by the vision training system of the present invention in connection with a Depth of Fusion Level II therapeutic exercise routine.

The subject wears red and green filters with red worn over the right eye and vice versa. The subject reads instructions (not shown) and touches the screen with the active light pen to continue. In this activity, the entire picture is in anaglyph form. In the center of the picture are the letters "R", in a color visible only to the right eye, and the letter "L", in a color visible only to the left eye, to serve as suppression checks. See FIG. 37. The subject is encouraged to hold the picture single as long as possible by learning to recognize the feeling of looking closer and farther. The numerical key pad is used in the same way as in Depth of Fusion Level I. The configuration default would present base-out and base-in trials on a 50% basis. The clinician can choose any other ratio of base-out to base-in trials or the ratio of base-out to base-in trials may be automatically controlled by the configuration program. Until each trial starts however, it is not known what direction is set. The "single" key is pressed until the picture can no longer by fused, the break point is recorded, and the "double" key is pressed until fusion is regained and the "single" key is again pressed, and the recovery point is recorded. The closer/farther keys are pressed when the subject perceives a distance change.

The output includes (i) the average break point, in prism dioptors, for base-in and base-out, and the standard deviation, (ii) the average recovery point in prism dioptors for base-in and base-out, and the standard deviation, (iii) the number of trials grouped by base-out and base-in, and (iv) the closer/farther responses, all of which are stored in the subject's file.

The program flowchart for the Depth of Fusion Level II exercise is the same as the program flowchart for the Fusion Level I exercise.

15.) Depth of Fusion Level III

The purpose of the Depth of Fusion Level III exercise is to develop flexibility and higher levels of binocular control.

Figure 38:
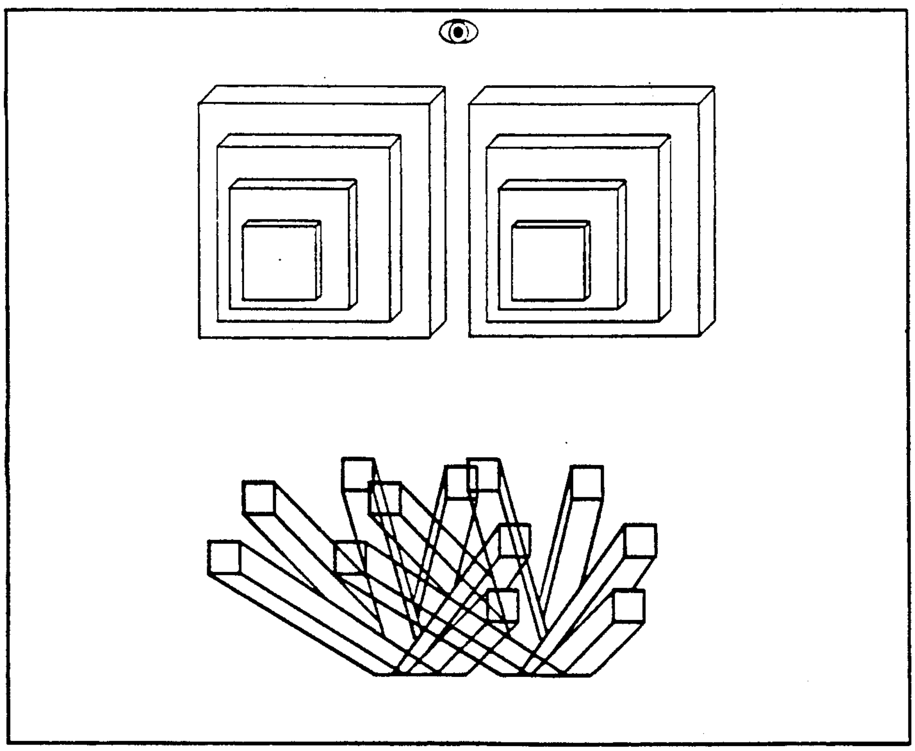
FIG. 38 is a display provided by the vision training system of the present invention in connection with a Depth of Fusion Level III therapeutic exercise routine.
Figure 39A:
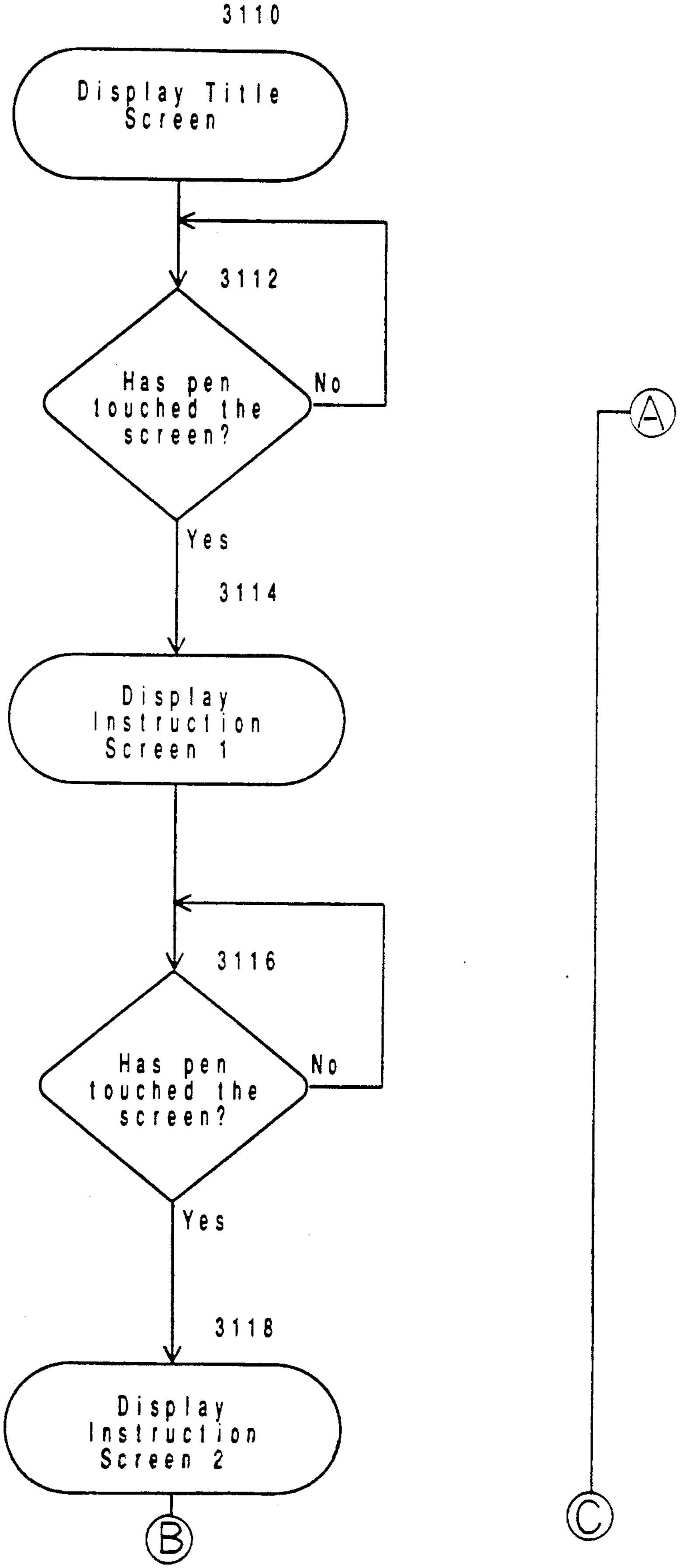
Figure 39B:
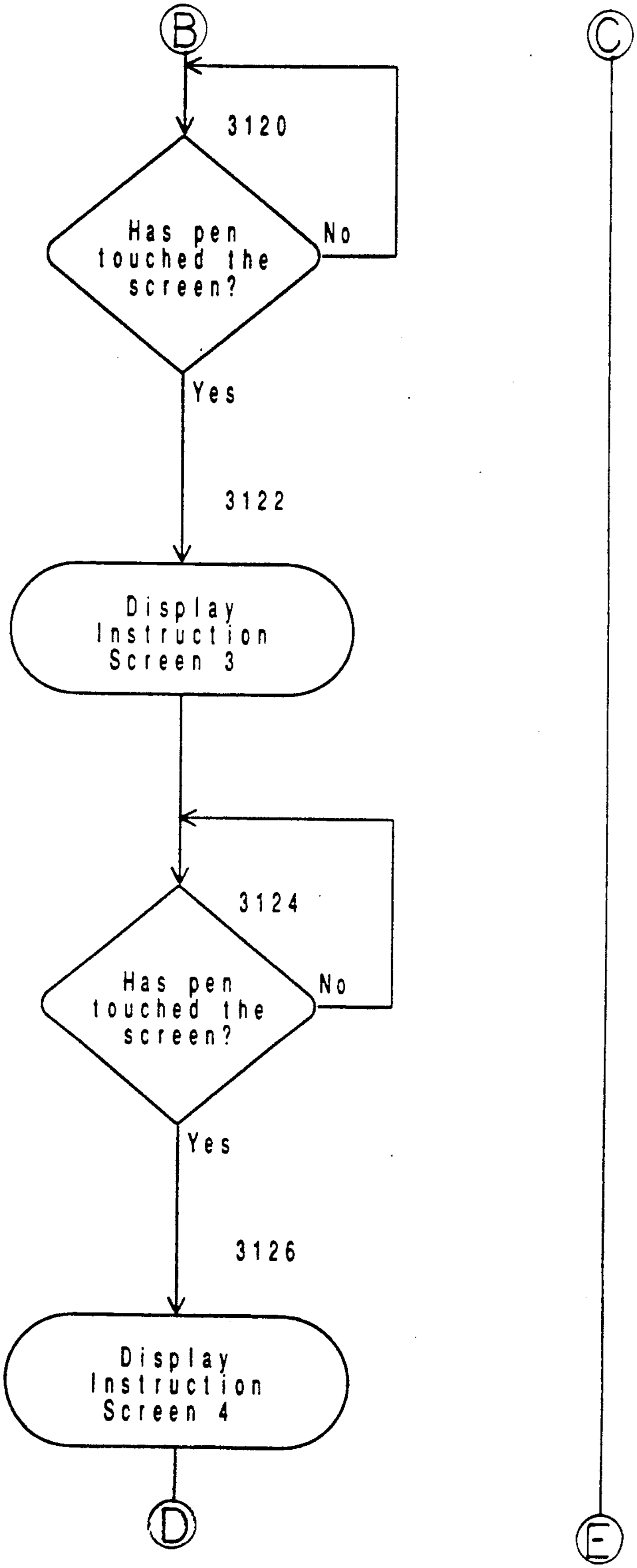
Figure 39C:
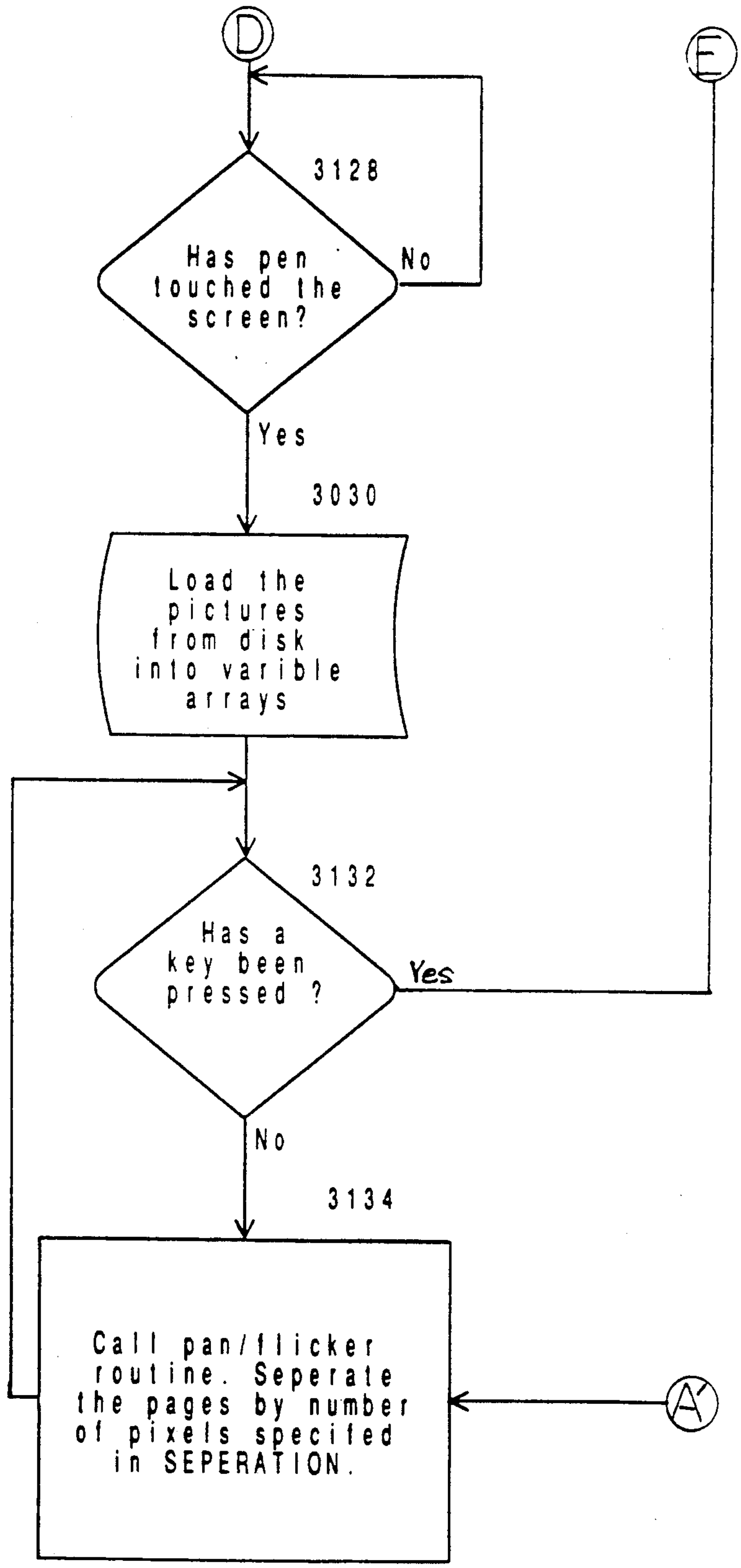
Figure 39D:
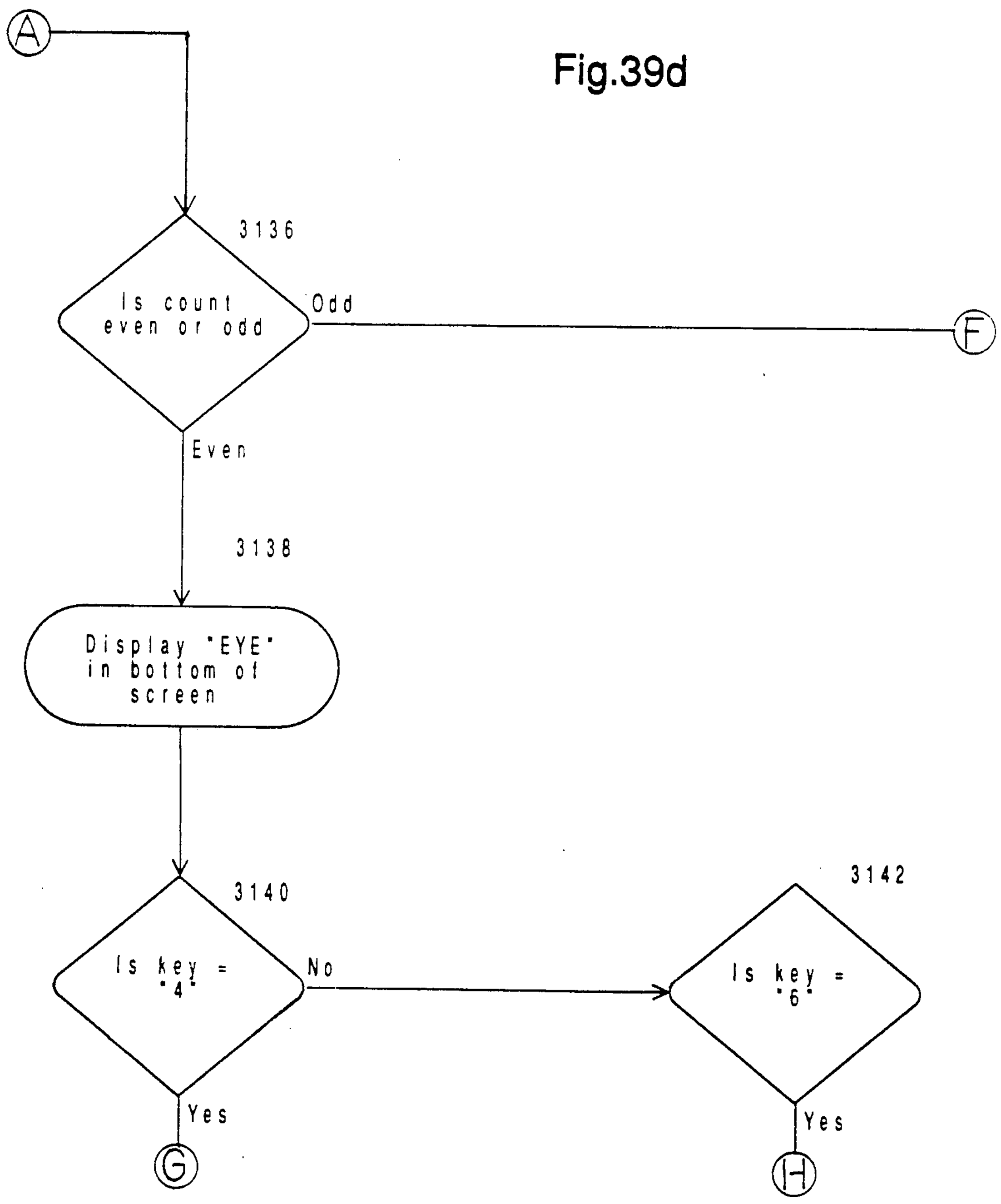
Figure 39E:
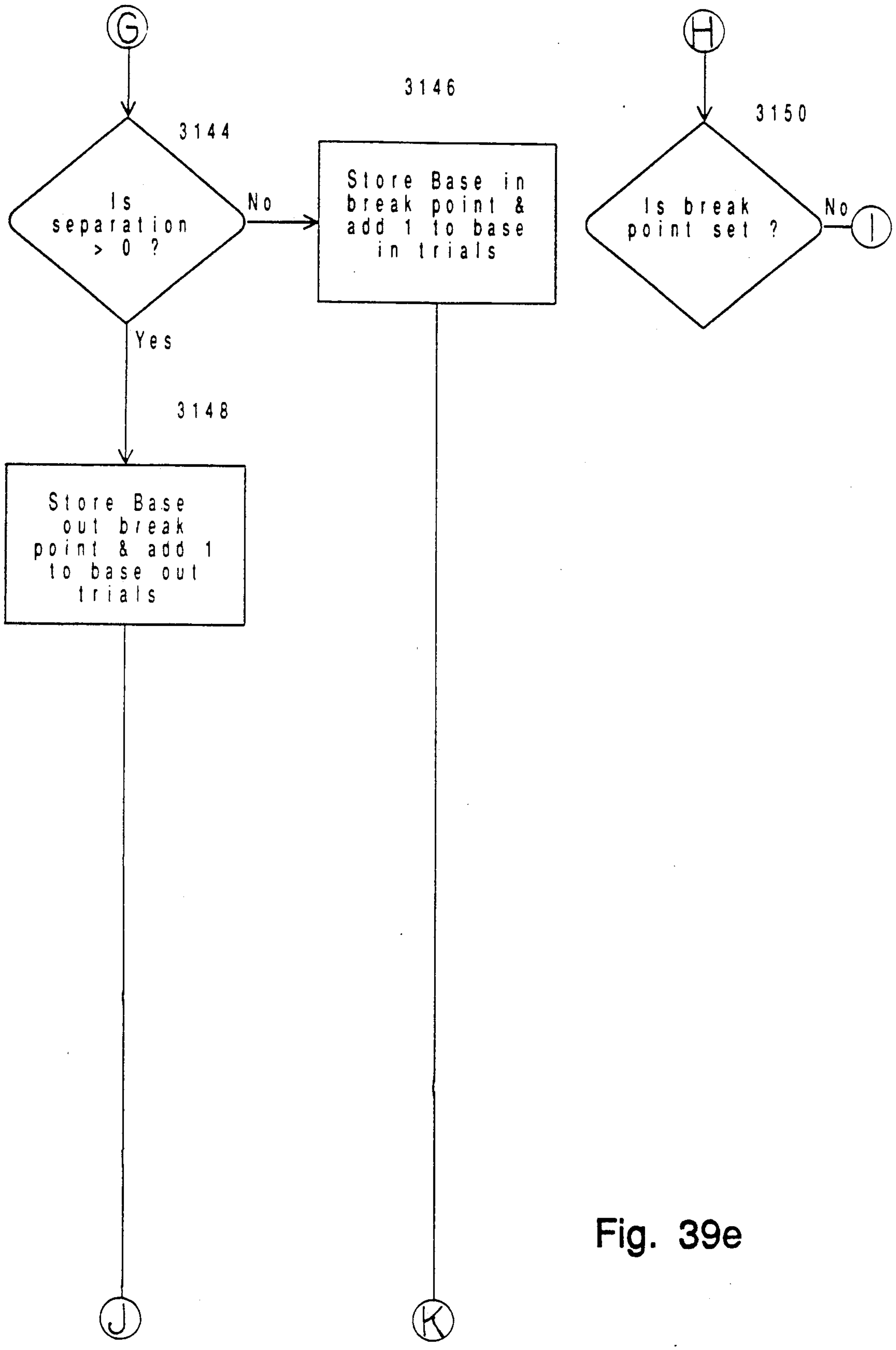
Figure 39F:
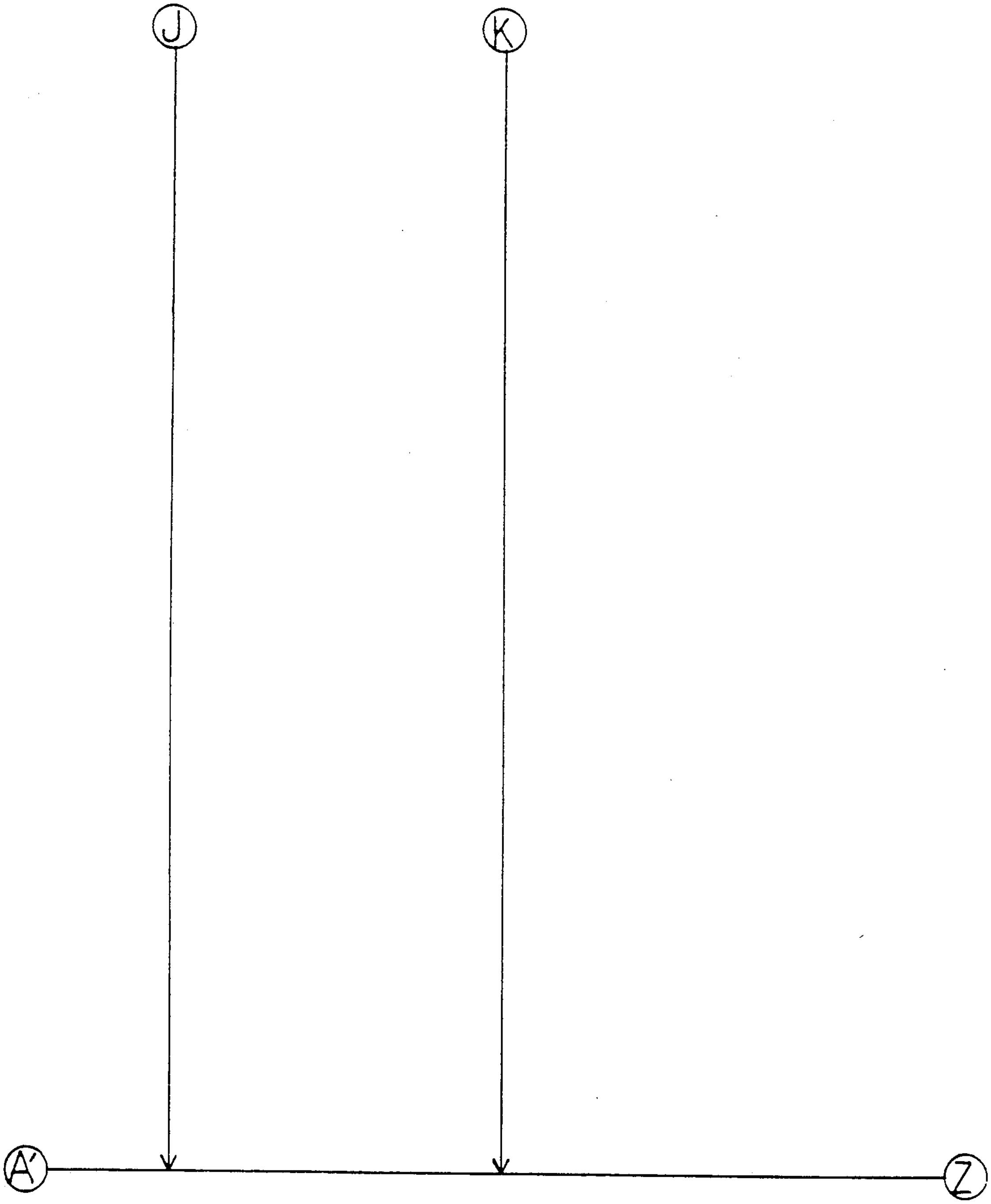
Figure 39G:
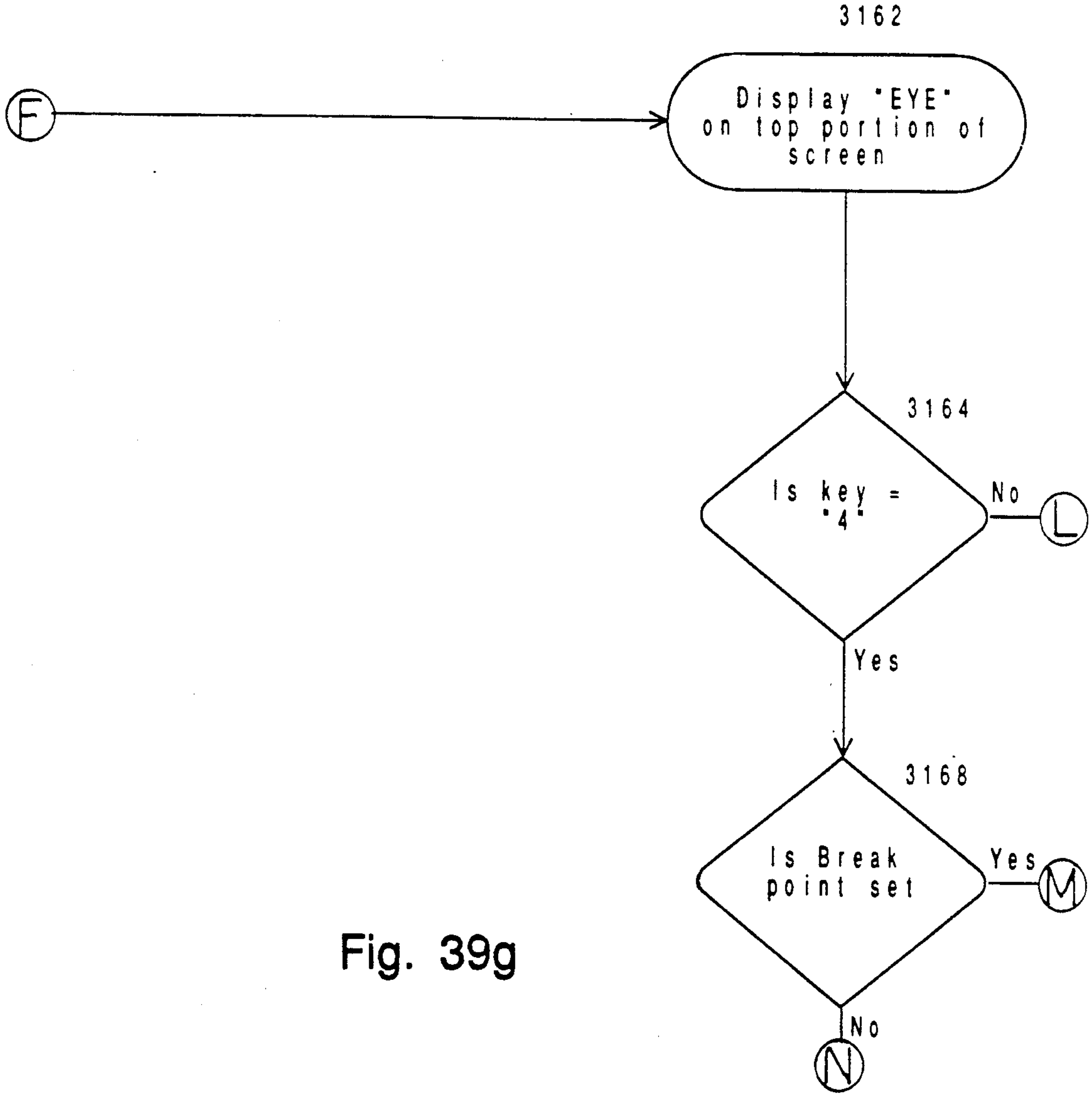
Figure 39H:
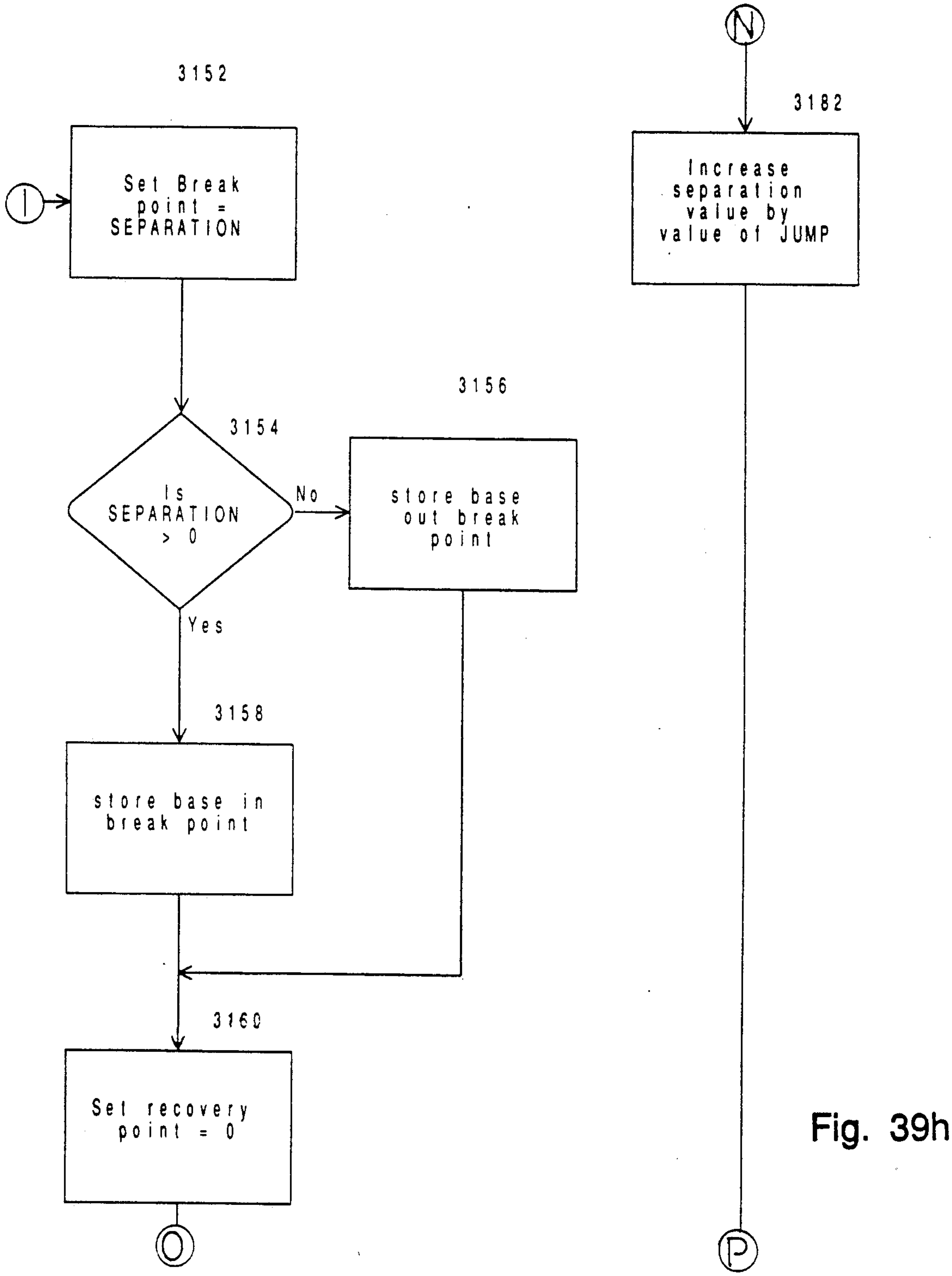
Figure 39I:
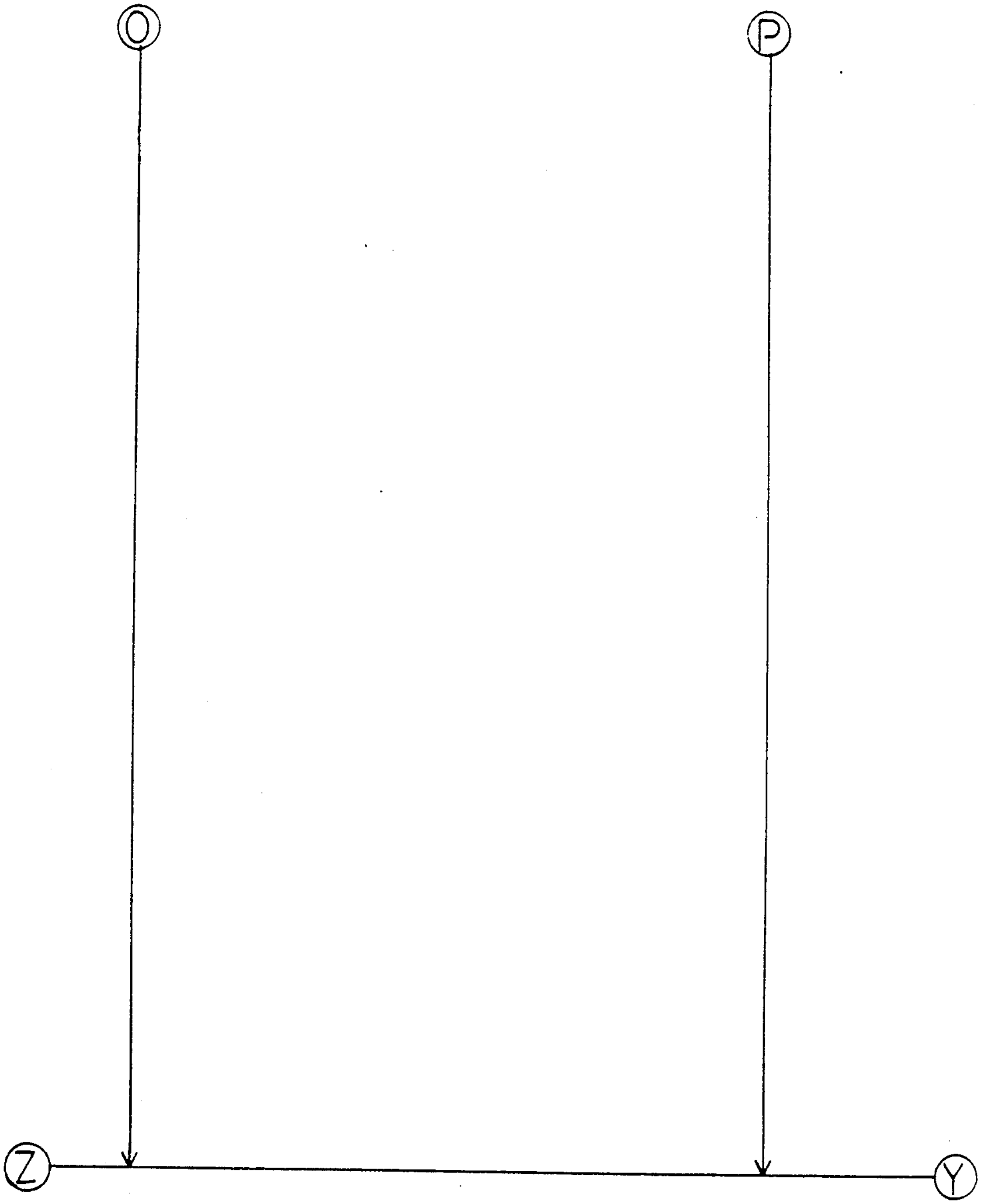
Figure 39J:
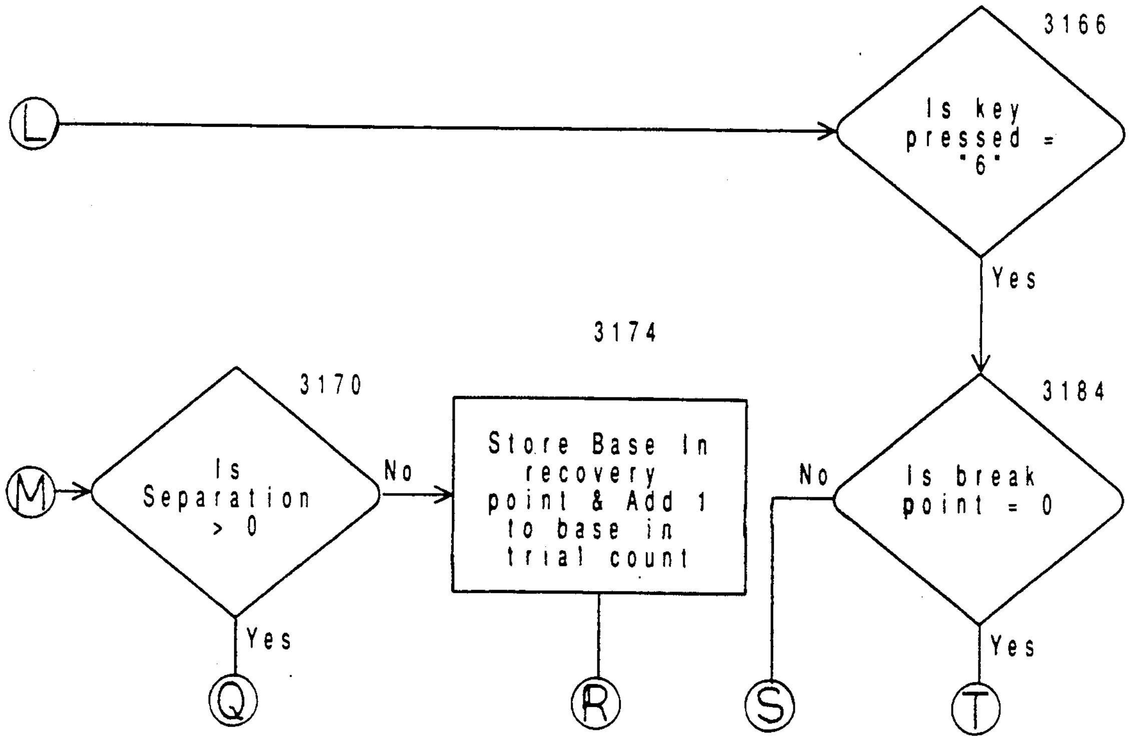
Figure 39K:
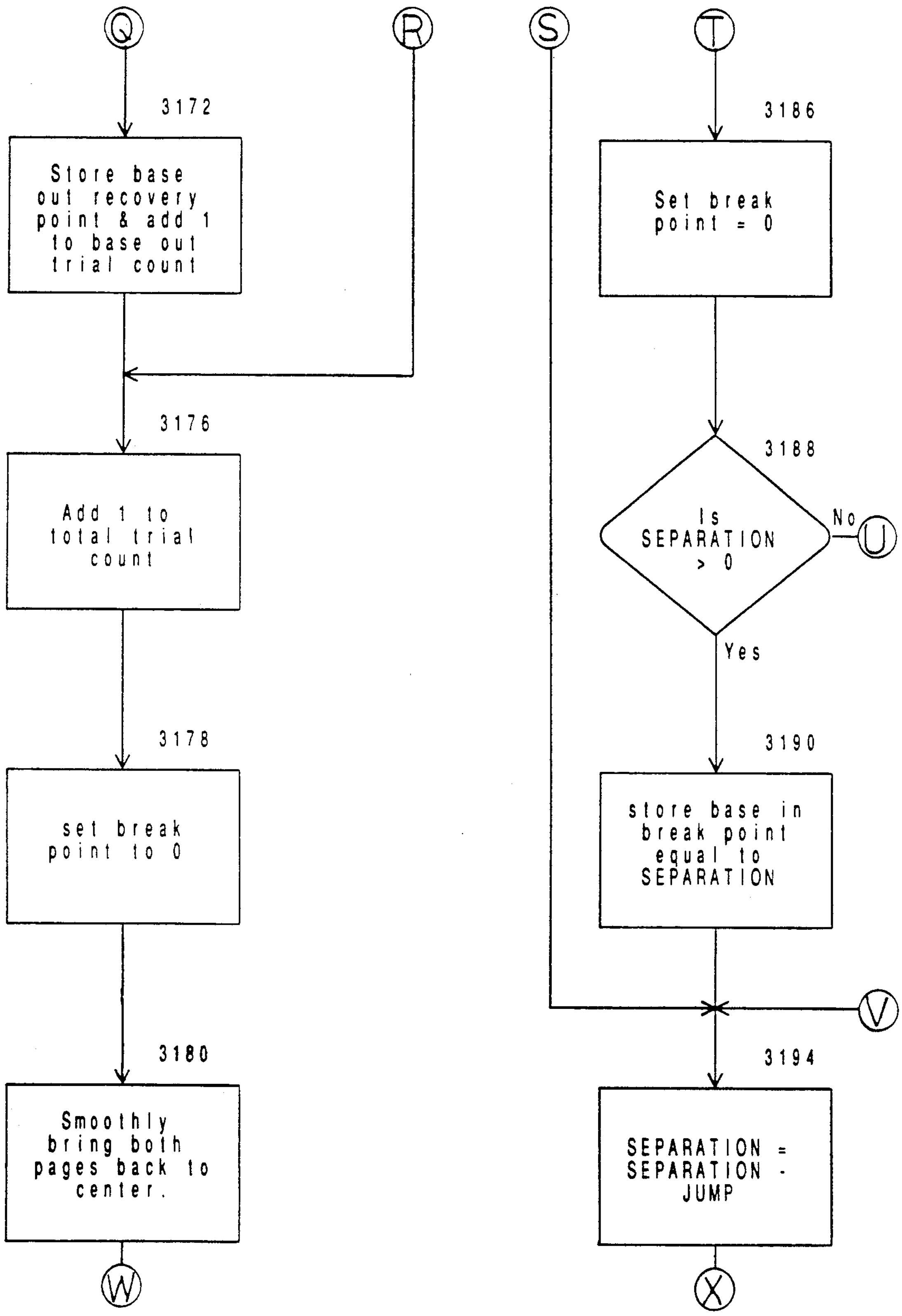
Figure 39I:
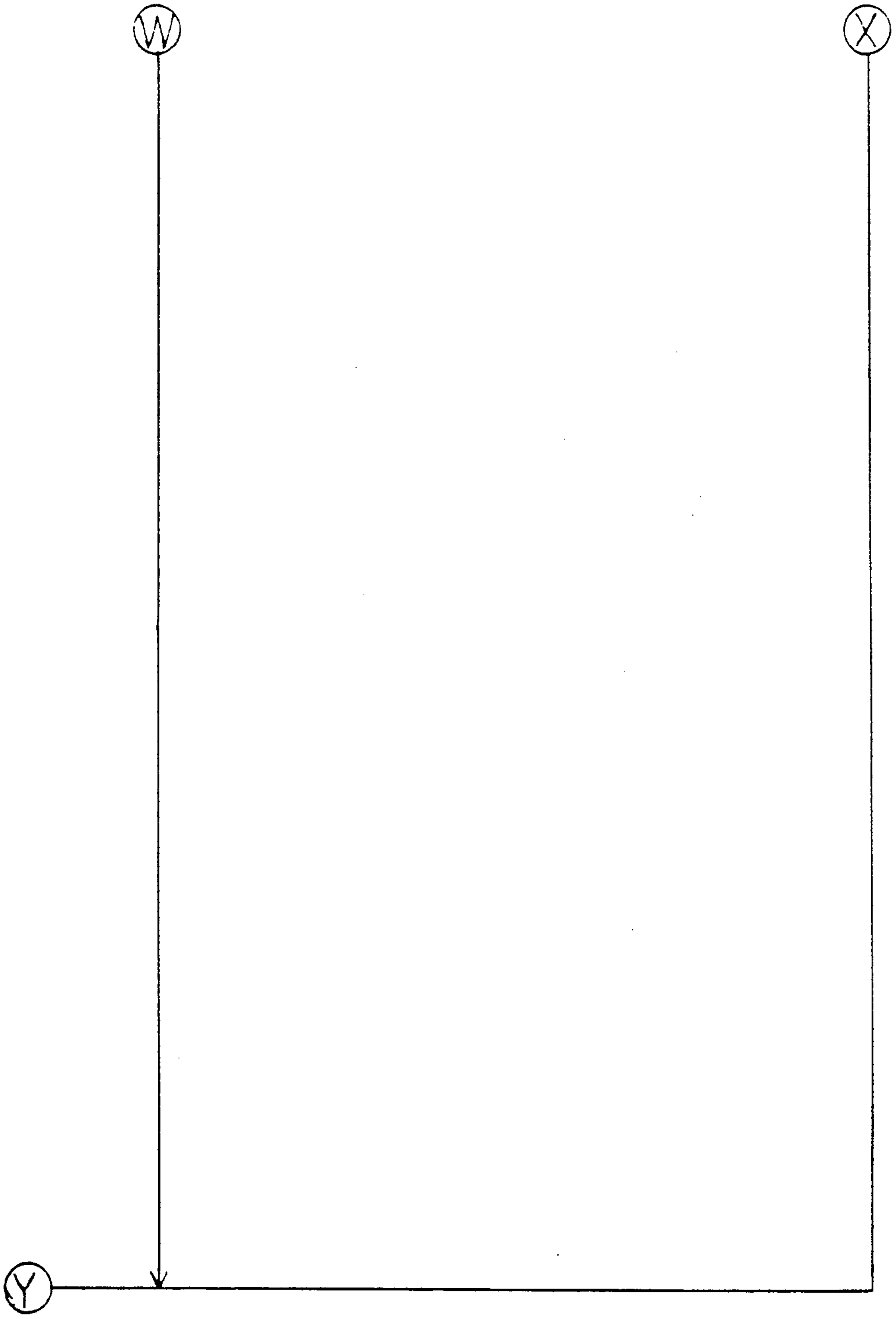
Figure 39M:
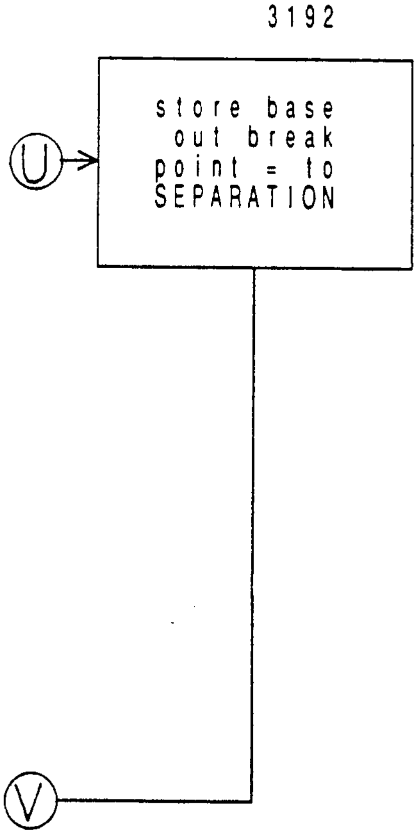

The subject reads instructions (not shown) and touches the screen with the active light pen to continue. The red/green filters are worn with the red over the right eye. There are two pictures simultaneously displayed. See FIG. 38. However, when one picture is base-out, the other is base-in. Which picture is base-out or base-in is chosen at random by the computer. The subject is instructed to focus on the picture accompanied by an icon of an eye 23 and to attempt to fuse the picture. Depending on the subject's ability to fuse the picture, the "single" or "double" key is pressed. The icon then jumps to the other picture where the subject again indicates single o double. Each time the "single" key is pressed, picture separation increases by an amount set in the configuration program. When the point is reached where a picture cannot be fused, the "double" key is pressed. This marks the break point and the picture separation will decrease by the configured rate until "single" is again pressed, which marks the recovery point. Meanwhile the other picture may still be separating if the break point has not been reached. If one picture has broken and recovered before the other picture breaks, the icon remains on the unbroken picture until the break and recovery are reached. The system then resets both pictures at zero separation to begin again. The jump increment from base-out to base-in may be controlled automatically by the configuration program. The output includes a list of the base-out and base-in trials for each picture, with breaks and recoveries in prism dioptors, all of which are stored to the subject's file.

The following detailed description refers to the flowchart in FIGS. 39a through 39m for Fusion Level III. First, a title screen (not shown) is displayed, block 3110. Next, the program waits for the active light pen to touch the screen, block 3112, before displaying instruction screen 1 (not shown), block 3114. Next, the program waits for the active light pen to touch the screen, block 3116, before displaying instruction screen 2 (not shown), block 3118. At block 3120 the program waits for the active light pen to touch the screen before displaying instruction screen 3 (not shown), block 3122. Again, at block 3124, the program waits for the active light pen to touch the screen before displaying instruction screen 4 (not shown) at block 3126. The program again waits for the active light pen to touch the screen at block 3128 before loading the pictures from disk into variable arrays, block 3130. At block 3132, the program checks to determine whether a key has been pressed. If a key has not been pressed, the pen/flicker routine is called. The pages are separated by the number of pixels specified in the variable "separation". If a key has been pressed, the program jumps to block 3136 where a check is made to determine whether the count is even or odd. If the count is even, the program executes the loop beginning at block 3138. If the count is odd, the program executes the loop beginning at block 3162. If the count is even, a picture of an eye is displayed at the bottom half of the screen. Next, a check is made to determine whether the "4" key was pressed, block 3140. If not, the loop beginning at block 3142 is executed. If so, the loop beginning at block 3144 is executed. At block 3142, a check is made to determine whether the key pressed was the number six key. If so, a check is made to determine whether the break point is set, block 3150. If not, the break point is set equal to "separation", block 3152. At block 3154, a check is made to determine whether "separation" is greater than zero. If not, the base-out break point is stored, block 3156, before the program jumps forward to block 3160, where the recovery point is set equal to zero, and the program loops back to block 3134. If, at block 3154 it is determined that "separation" is greater than zero, the program jumps forward to block 3158 where the base-in break point is stored. The program then continues on to block 3160. If, at block 3140, the program determines that the key pressed was the number four key, the program jumps to block 3144 where the program checks to determine whether "separation" is greater than zero. If not, the base-in break point is stored and one is added to "base-in trials", block 3146, and the program loops back to block 3134. If "separation" is greater than zero, the base-out break point is stored and a one is added to "base-out trials", block 3148, and the program loops back to block 3134. If, at block 3136, the program determines that the count is odd, the loop beginning at block 3162 is executed. At block 3162 a picture of an eye is displayed on the top portion of the screen. Next, at block 3164, a check is made to determine whether the number four key has been pressed. If not, the program executes the loop beginning at block 3166. If the number four key was pressed, the program executes the loop beginning at block 3168. At block 3166, a check is made to determine whether the key pressed was the number six key. At block 3184, a check is made to determine whether the break point is equal to zero. If not, the program jumps to block 3194 where the value of "separation" is reduced by the value of "jump" and the program loops back to block 3134. If, at block 3184, it is determined that the break point is equal to zero, the program continues on to block 3186 where the break point is set equal to zero. Next, at block 3188, a check is made to determine whether "separation" is greater than zero. If not, the program jumps to block 3192 where the base-out break point is set equal to "separation", and the program jumps forward to block 3194. If "separation" is greater than zero, the program continues to block 3190 where the base-in break point is set equal to "separation" and the program continues on the block 3194 where the value of "separation" is reduced by the value of "jump", and the program loops back to block 3134. If, at block 3164, it is determined that the key pressed was the number four key, the program executes the loop beginning at block 3168. At block 3168, a check is made to determine whether the break point is set. If so, a check is made to determine whether "separation" is greater than zero, block 3170. If not, the program stores the base-in recovery point and adds one to the base-in trial count, block 3174, before jumping to block 3176. If "separation" is greater than zero, the base-out recovery point is stored and one is added to the base-out trial count, block 3172, before continuing to block 3176 where one is added to the total trial count. At block 3178 the break point is set to zero and at block 3180 both pages are smoothly brought back to center. The program then loops back to block 3134. If, at block 3168 it is determined that the break point is not set, the program jumps to block 3182 where the value of "separation" is increased by the value of "jump", after which the program loops back to block 3134.

16.) Depth of Fusion Level IV

The purpose of the Fusion Level IV exercise is to increase awareness and subtlety of binocular integration. The subject wears red/green goggles with red over the right eye and vice versa. The duration of the exercise is preferably six minutes. Targets include a variety of familiar objects recognizable by their outline and are presented one at a time in the form of a "random dot stereogram". On the previous Fusion activities, the target would be seen as single or double. In this activity the target is either perceived or it is not. The subject is instructed to indicate with one of two keys that the form is seen or not. With two other keys the subject can indicate awareness of the target being closer or farther.

The output includes the break and recovery points in prism diopters for base-out and base-in disparity. If enough trials are completed, averages are computed. Also the closer/farther responses are printed out. All data is stored to the subject's file. The forms used as targets, the base-in to base-out jump increments, and the ratio of base-out to base-in presentations can be selected and set in the configuration file.

A random dot stereogram is used to create a three-dimensional ("depth effect") illusion by varying disparity levels between two pictures. To create the random dot stereogram using two pages of graphic memory, the following steps are performed:

a. A large box of random green dots is generated on screen page zero.
b. The same box of dots is copied onto screen page 1 and offset by eight pixels to the left.
c. The green dots on page 1 are changed to red dots.
d. An object composed of random dots is generated as follows:
   1. Draw the object in one color, for example blue.
   2. Scan the picture of the object and turn all blue dots into either green dots or the color of the background.
   3. Save the picture from step 2 above.
   4. Save the background.
   5. Scan the picture again, turning all dots from step 2 to red.
   6. Save the red dot picture.
e. There are now three arrays, red, green, and background.

f. The region of dots that the picture of object will occupy on the screen is selected. This section of dots is needed to correct any disruption that occurs when the picture of objects is placed on the screen. If it is planned to put more than one picture of an object on the screen at one sitting, this must be placed over the area to clean it up before placing the next picture there. Otherwise, both pictures will be seen at the same time.
g. The green picture of the object is placed on the green page of random dots.
h. The red picture of the object is placed to the right on the red page of the random dots.
i. The two pages are rapidly switched back and forth, creating a transparency effect.
j. The difference in disparity of the background dots and the difference in disparity of the picture of the object will make the picture of the objects appear to separate from each other. Also, by moving the pages apart, the picture of object will appear to come forward or fall backward depending on which side the red and green glasses are on. The distance between the object and the background will remain constant. This distance is calculated when the program is written.

Figure 40A:
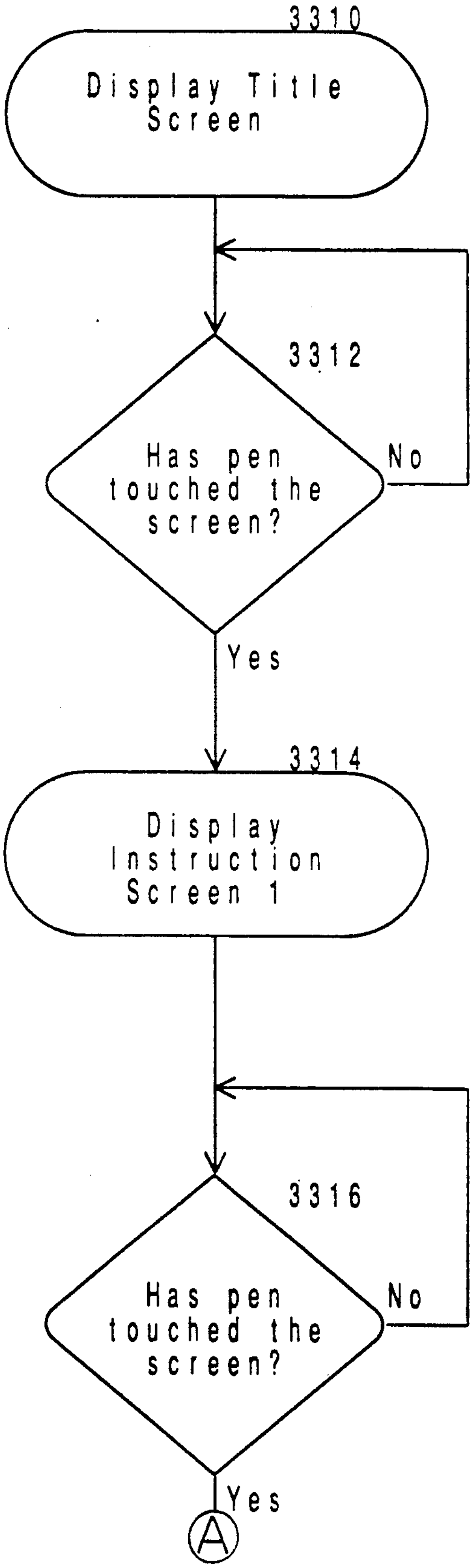
FIGS. 40a-40t are a flowchart illustrating a Depth of Fusion Level IV therapeutic exercise routine.
Figure 40B:
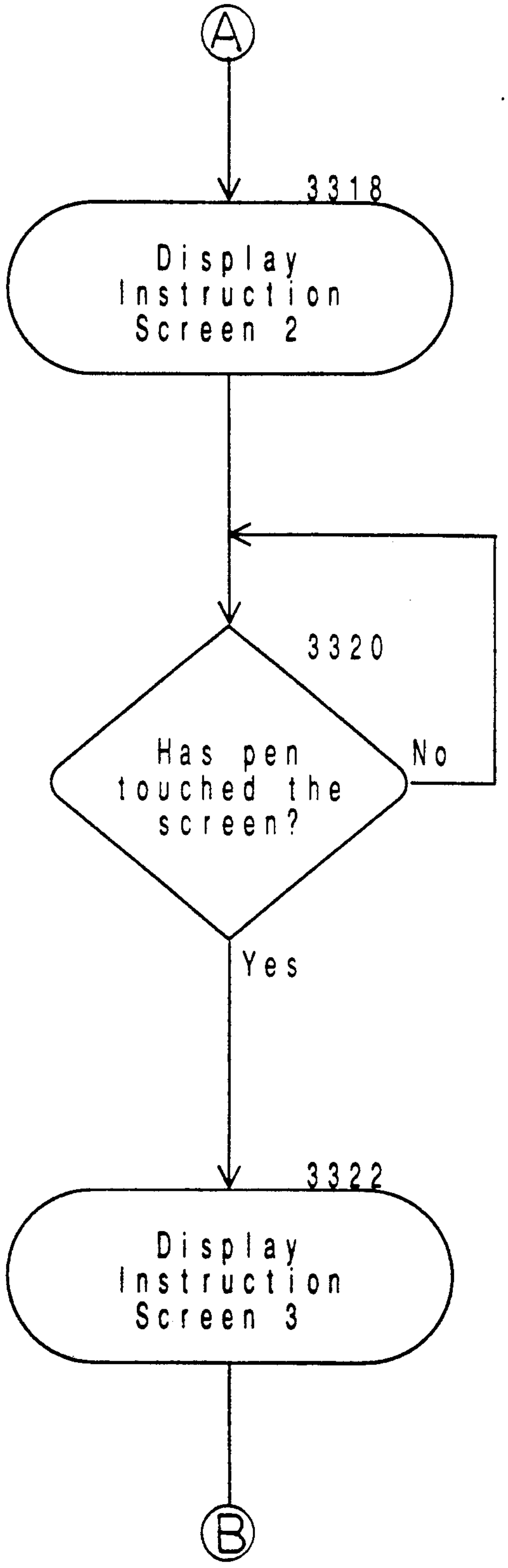
Figure 40C:
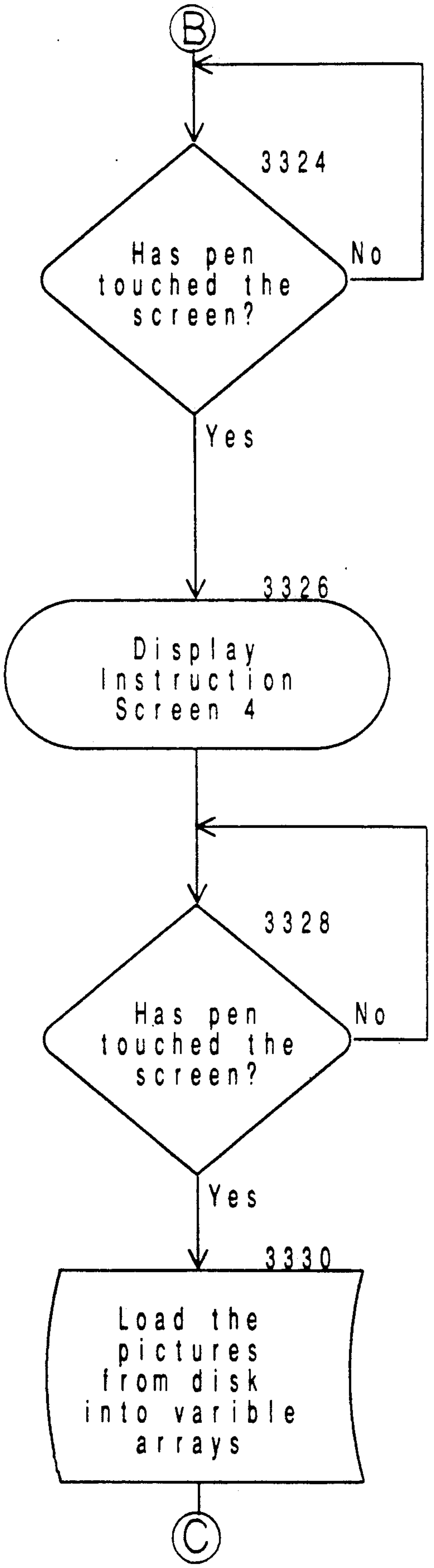
Figure 40D:
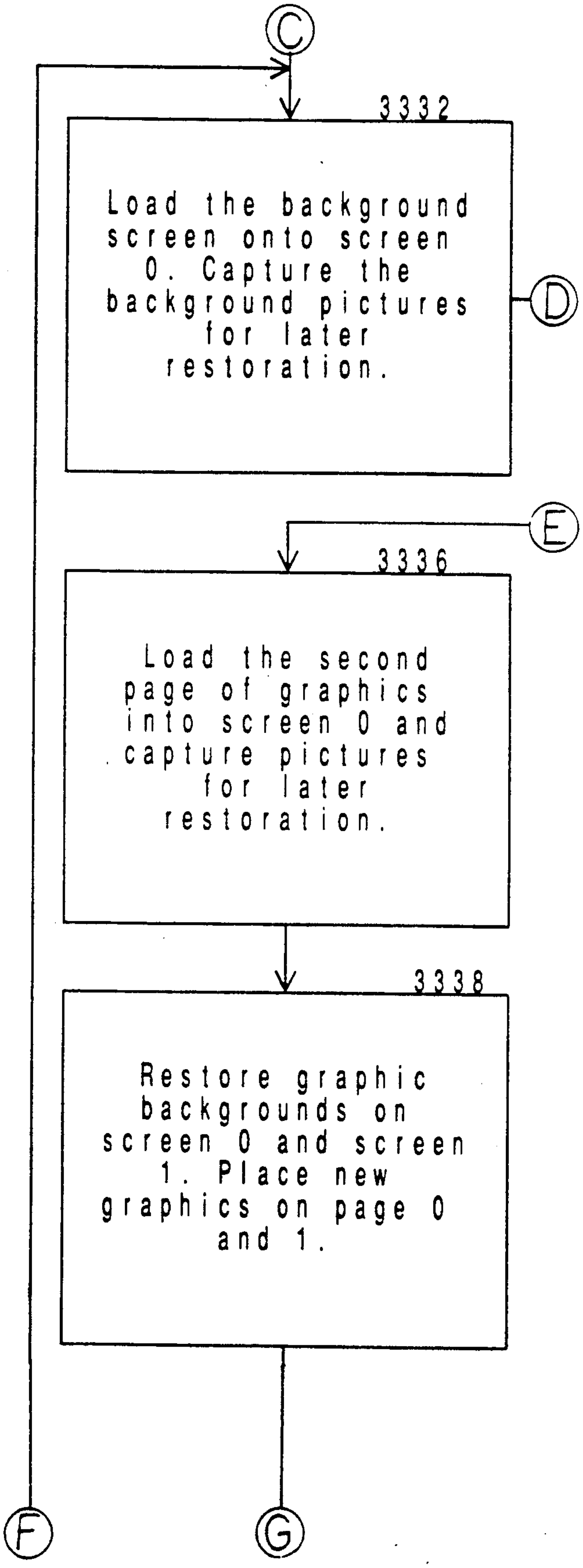
Figure 40E:
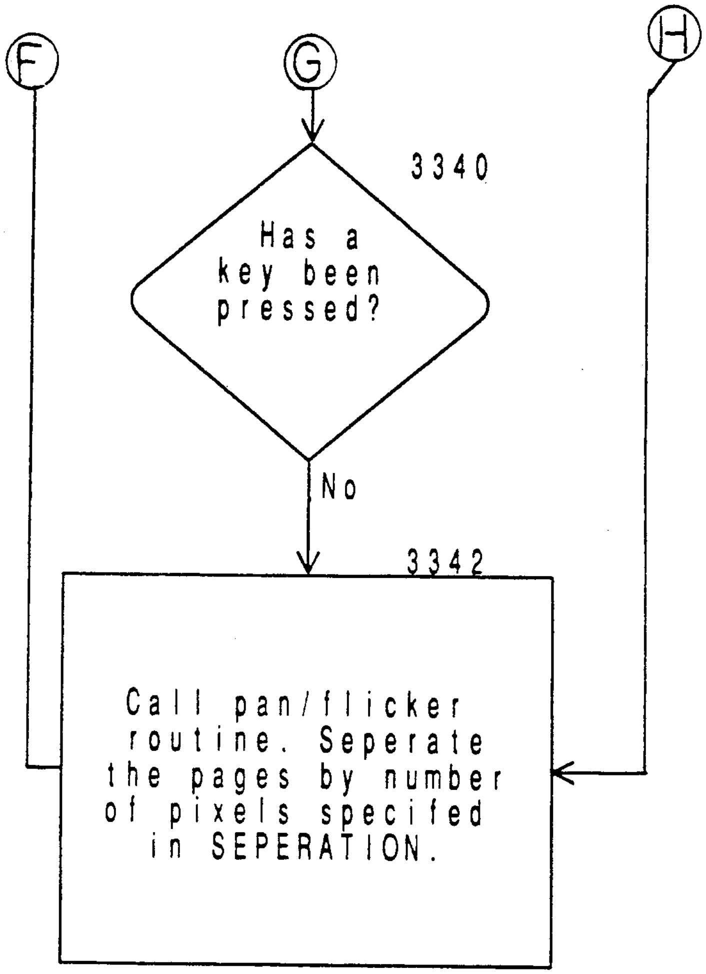
Figure 40F:
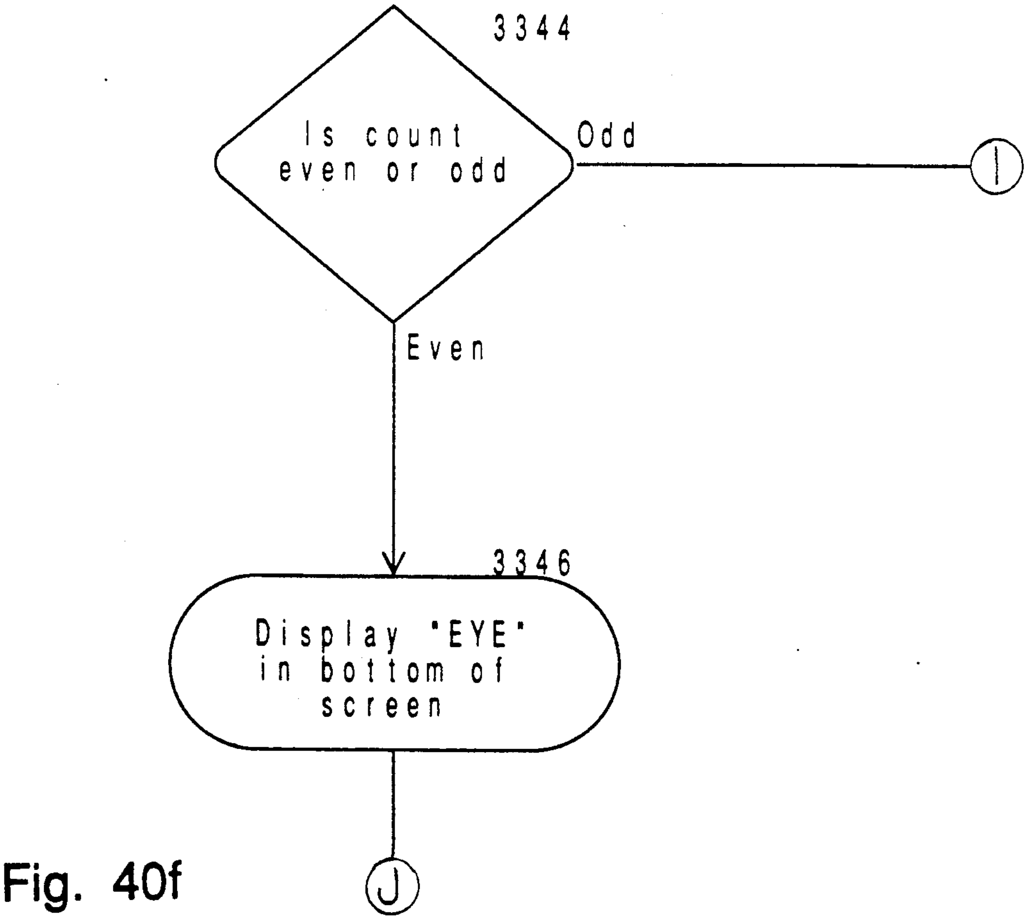
Figure 40G:
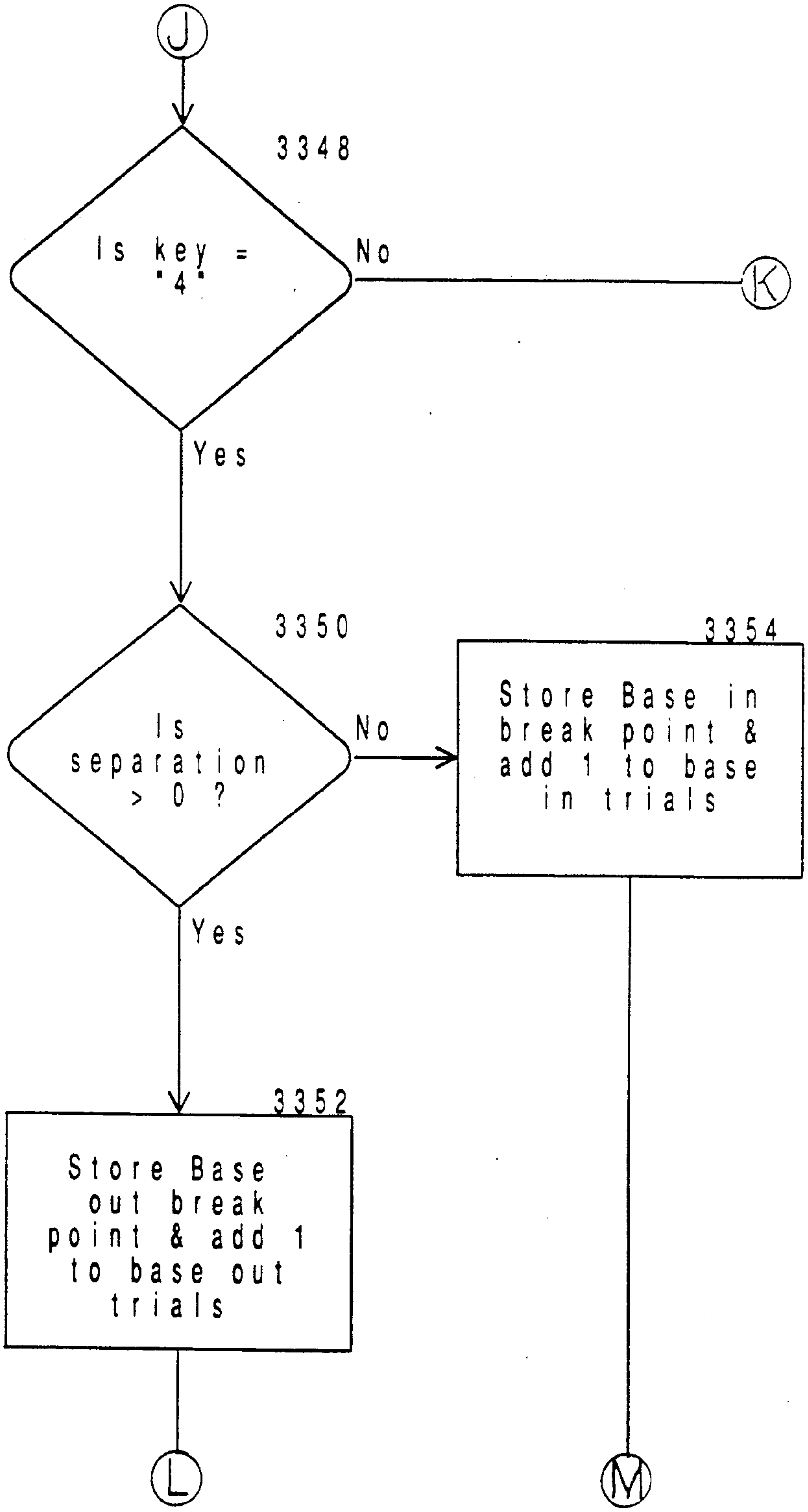
Figure 40H:
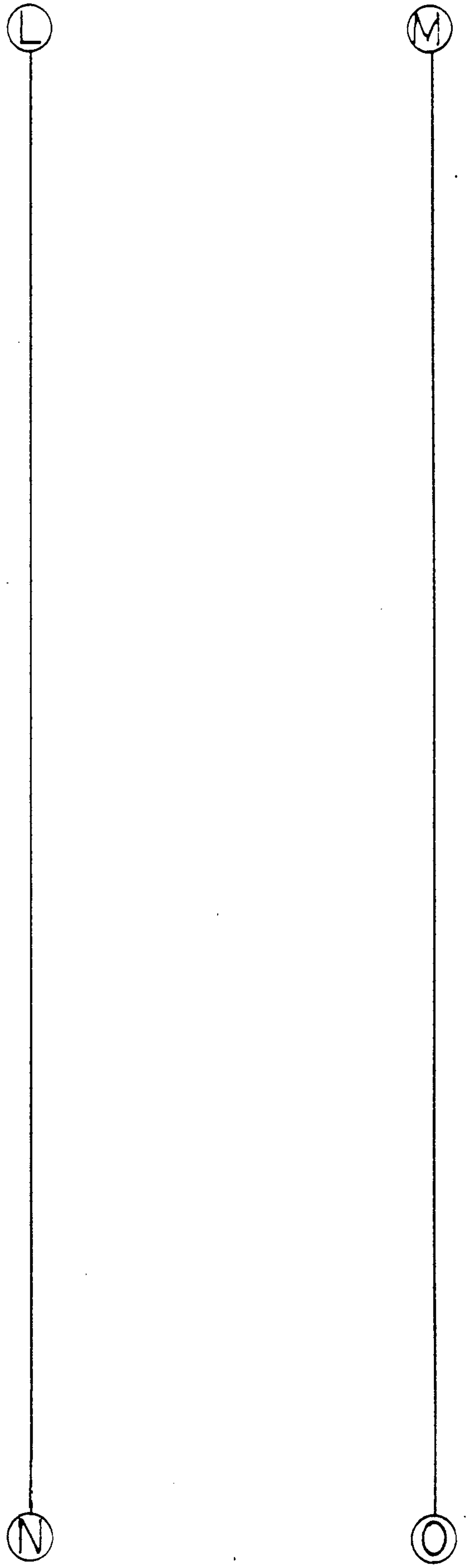
Figure 40I:
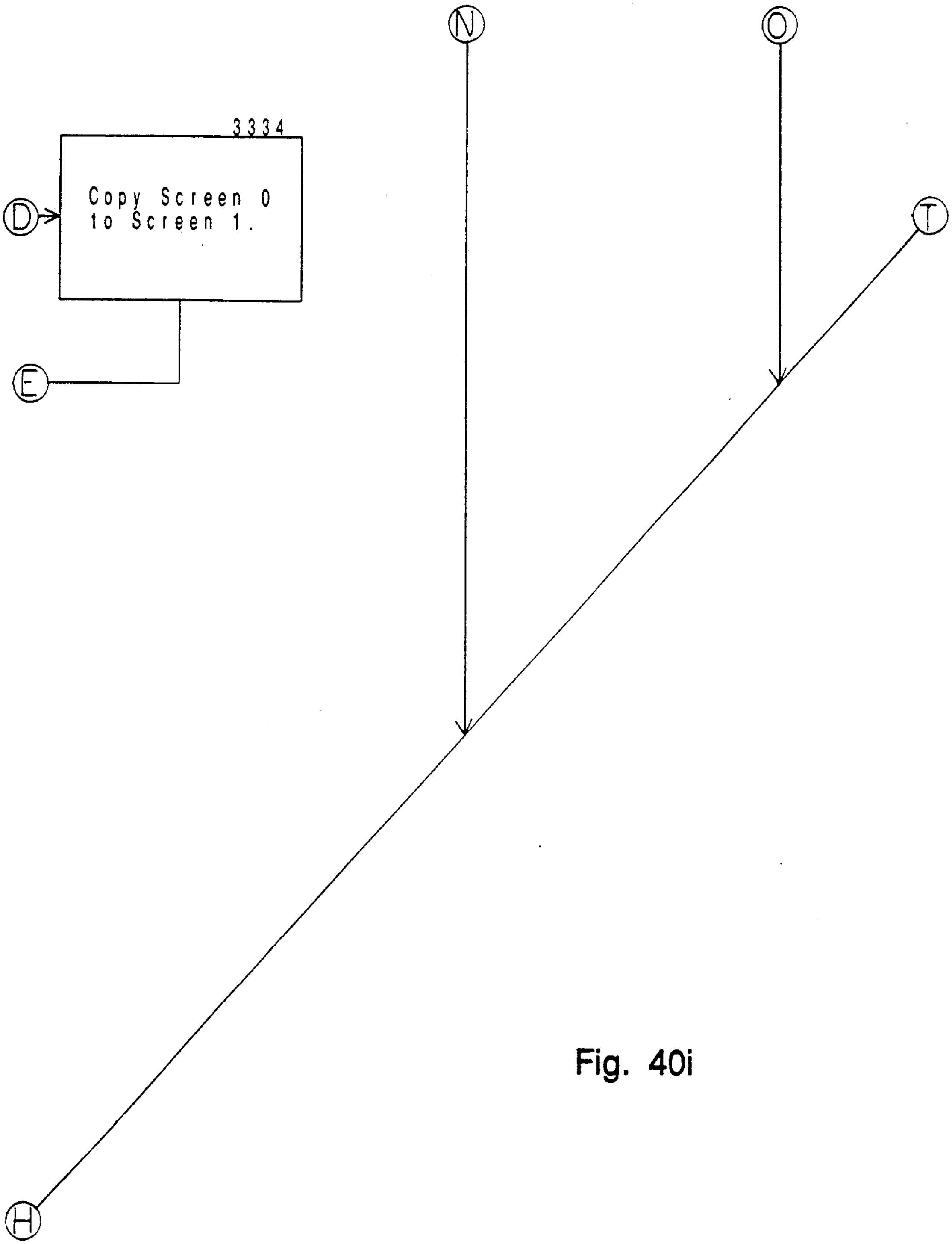
Figure 40J:
Figure 40K:
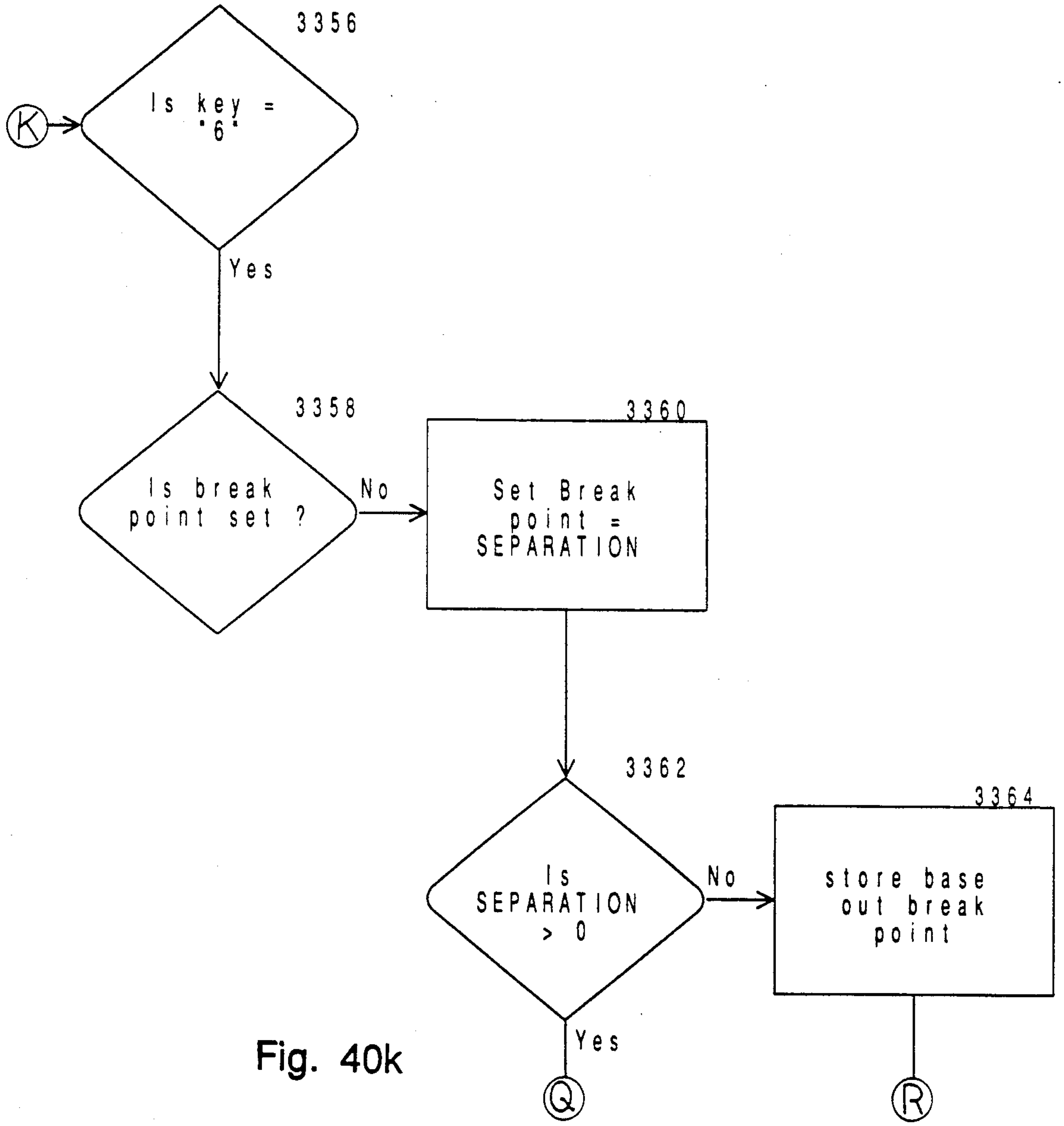
Figure 40L:
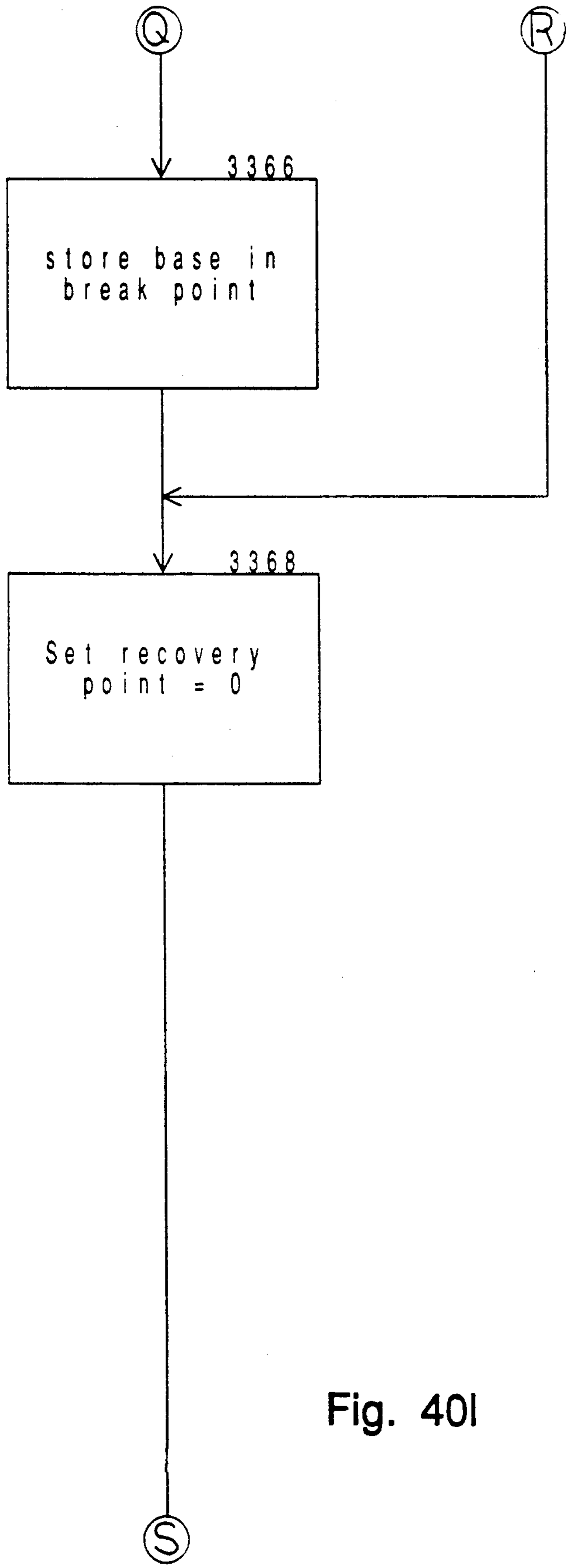
Figure 40M:
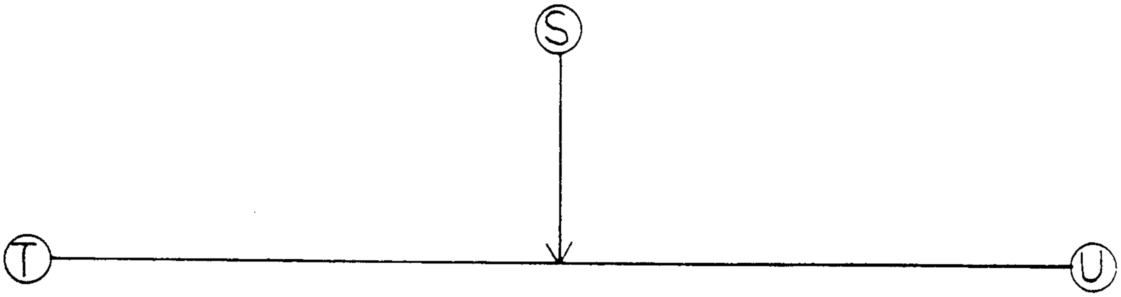
Figure 40N:
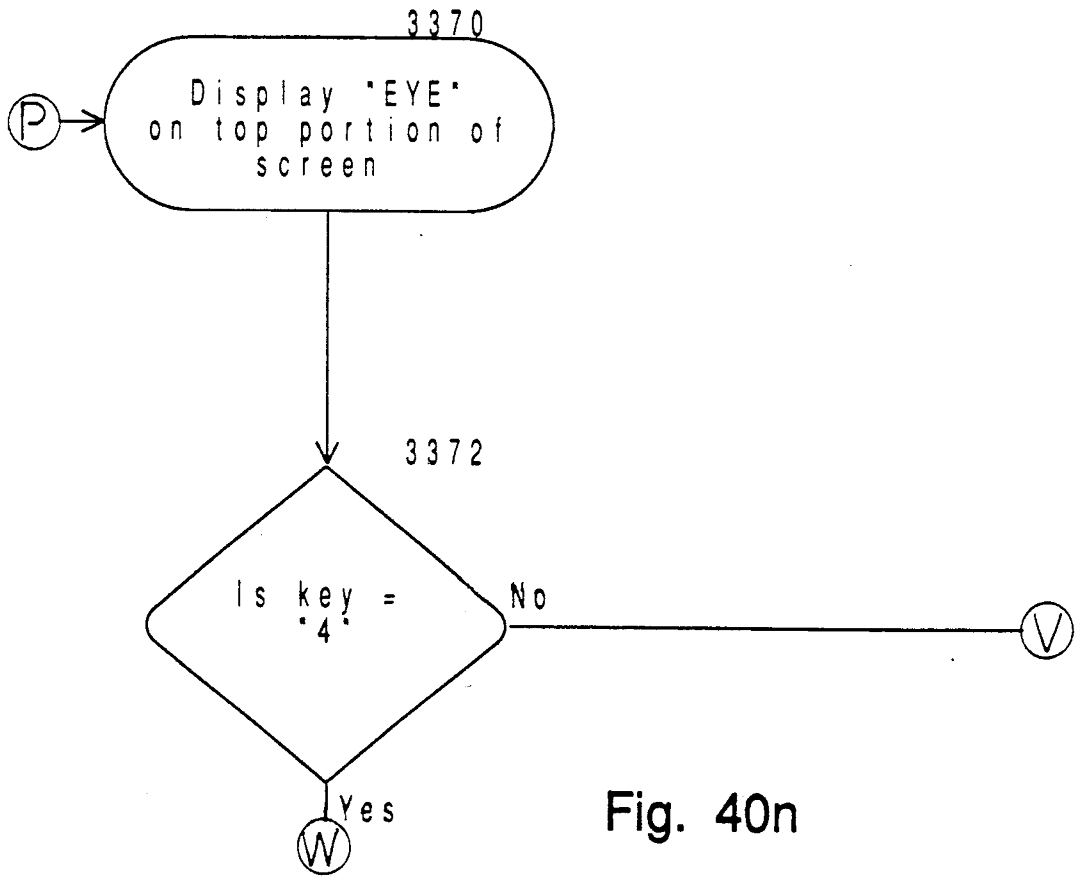
Figure 40O:
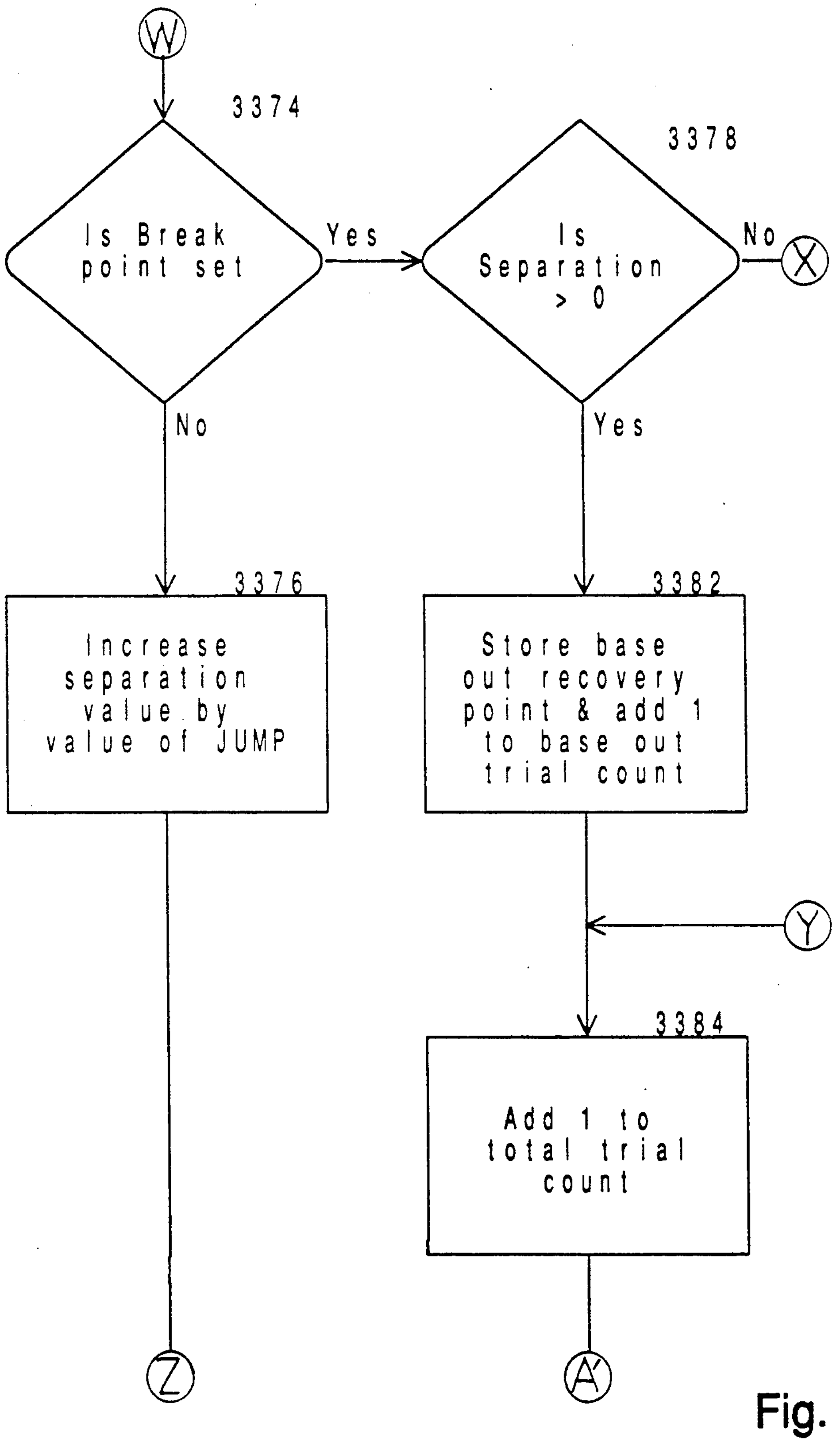
Figure 40P:
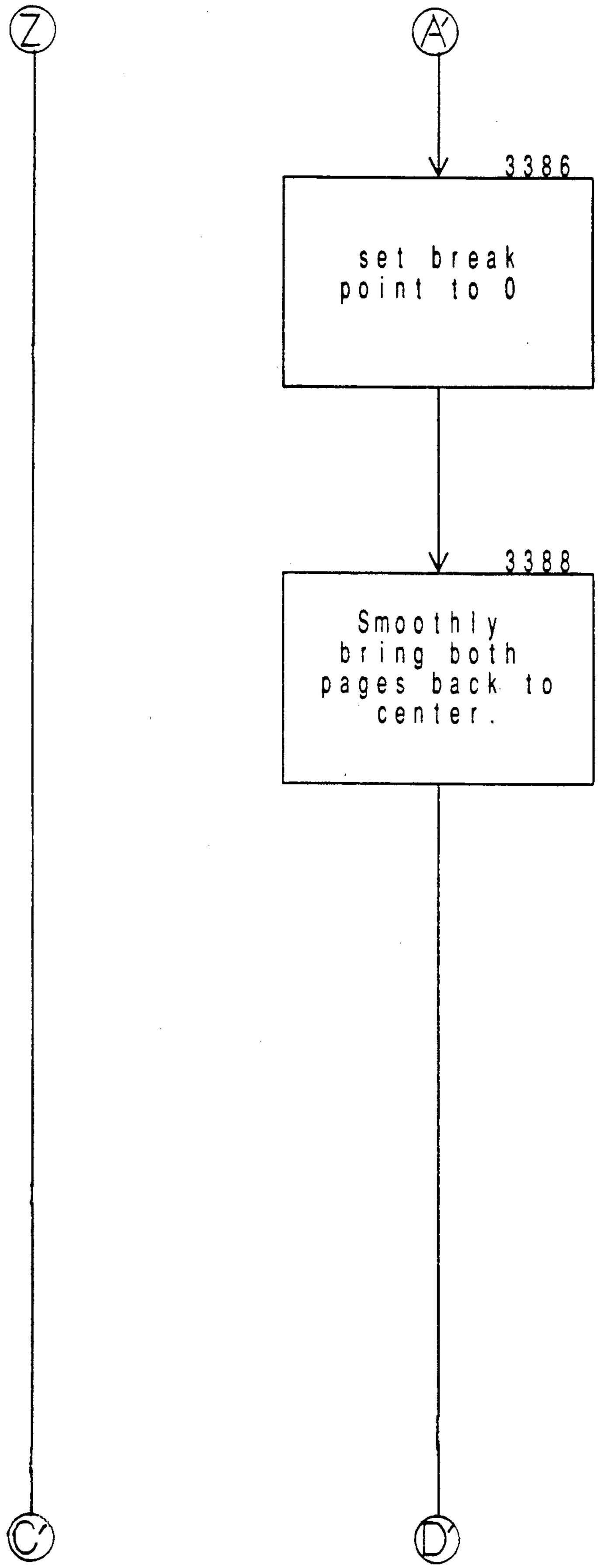
Figure 40Q:
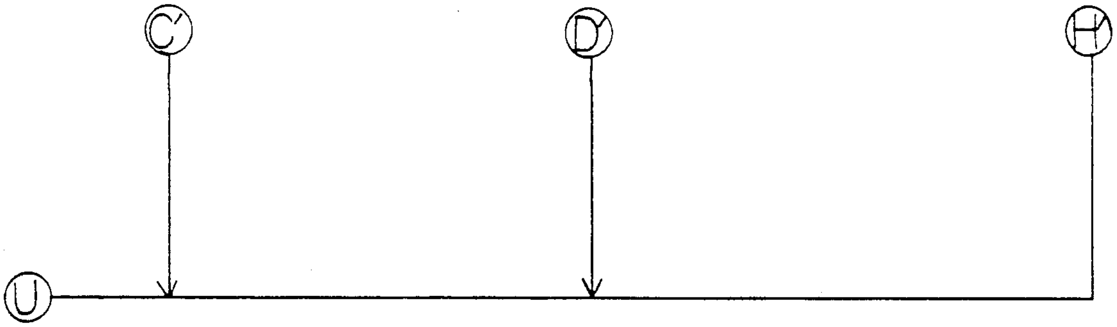
Figure 40R:
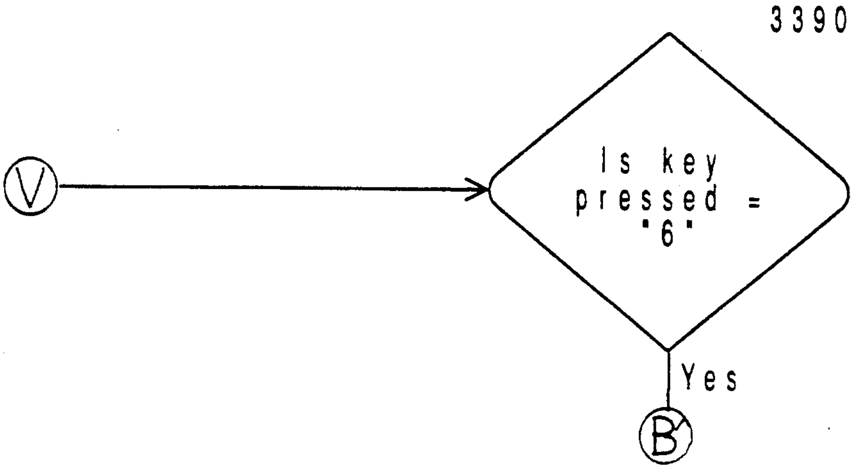
Figure 40S:
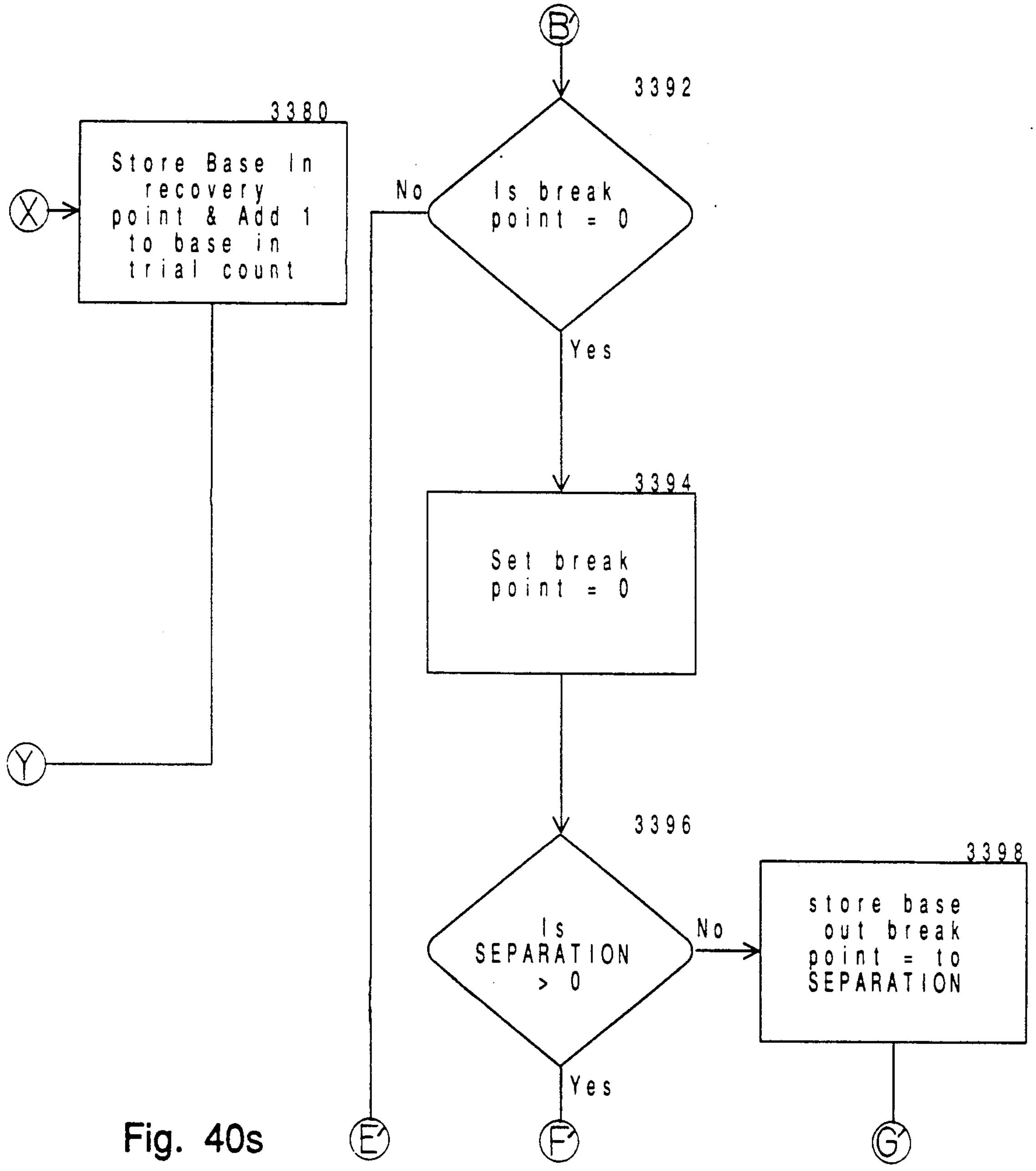
Figure 40T:
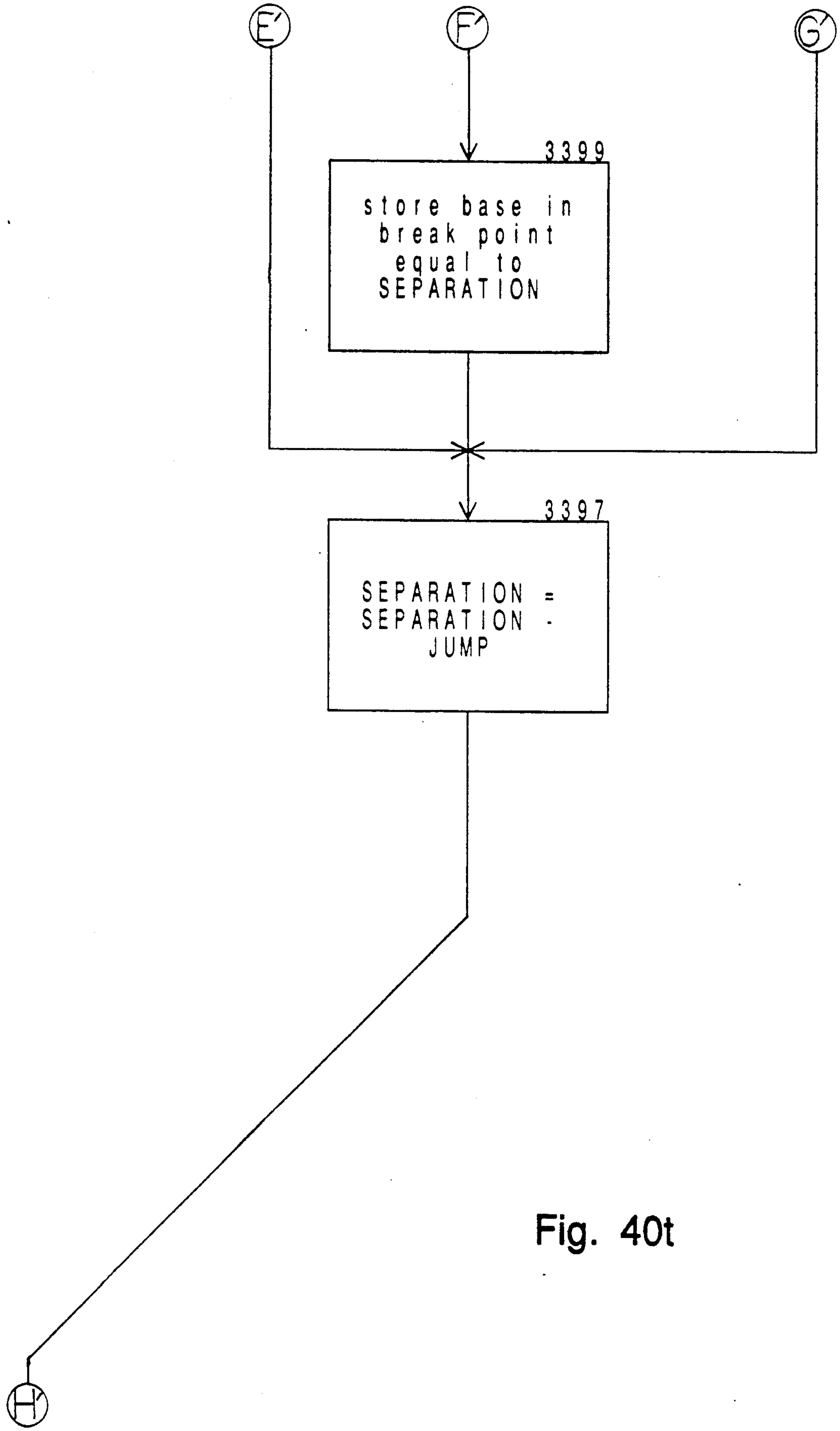

The following description refers to the flow charts in FIGS. 40*a* through 40*t* for Fusion Level IV. First a title screen (not shown) is displayed, block 3310. Next, the program waits for the subject to touch the screen with the active light pen, block 3312, before displaying instruction screen 1 (not shown), 3314. Next, the program waits for the subject to touch the screen with the active light pen, block 3316, before displaying instruction screen 2 (not shown), block 3318. Again, the program waits for the subject to touch the screen with the active light pen, block 3320, before displayinq instruction screen 3 (not shown), block 3322. At block 3324, the program waits for the subject to touch the screen with the active light pen before displaying instruction screen 4 (not shown), block 3326. At block 3328, the program waits for the subject to touch the screen with the active light pen before continuing to block 3330, where the pictures are loaded from disk into variable arrays. Next the background screen is loaded into page zero. Background pictures are then captured for later restoration, block 3332. Next, page zero is copied to page 1, 3334. Next the second page of graphics is loaded into page zero and captured for later restoration, block 3336. Next the graphic backgrounds are restored on page zero and page 1. The new graphics are stored in page zero and page 1, block 3338. Next the program checks to determine whether a key has been pressed, 3340. If not, the "pen/flicker" routine is called, block 3342, and the program loops back to block 3340. If a key has been pressed, the program continues to block 3344. At block 3344, a check is made to determine whether "count" is even or odd. If even, the loop beginning at block 3346 is executed. If odd, the loop beginning at block 3370 is executed. At block 3346, an icon of an "eye" is displayed in the bottom portion of the screen. Next a check is made to determine whether the number four key was pressed, block 3348. If so, a check is made to determine whether "separation" is greater than zero, block 3350. If so, the base-out break point is stored and 1 is added to the base-out trial count, block 3352. If "separation" is not greater than zero, the program jumps to block 3354, where the base in break point is stored and 1 is added to the base-in trial count. Following the execution of block 3352 and block 3354, the program loops back to block 3342. If, at block 3348 the number four key was not pressed, the program jumps to block 3356, where a check is made to determine whether the number six key was pressed. Next, at block 3358, a check is made to determine whether the break point has been set. If not, the break point is set equal to "separation", block 3360. Next a check is made to determine whether "separation" is greater than zero, 3362. If not, the base-out break point is stored, 3364, and the program jumps to block 3368. If "separation" is greater than zero the base-in break point is stored, block 3366, and the program jumps to block 3368 where the "recovery point" is set equal to zero. Next the program loops back to block 3342. At block 3370, an icon of an eye is displayed on the top portion of the screen. Next a check is made to determine whether the "four" key was pressed, 3372. If so, a check is made to determine whether the break point is set, 3374. If not, "separation" is increased by the value of "jump", 3376, and the program loops back to block 3342. If, at block 3374, it is determined that the break point was not set, the program jumps to block 3378, where a check is made to determine whether "separation" is greater than zero. If not, the base-in recovery point is stored and a one is added to the base-in trial count, block 3380, and the program jumps to block 3384. If "separation" is greater than zero, the base-out recovery point is stored and a one is added to the base-out trial count, block 3382. Next, at block 3384, one is added to the total trial count. Next the break point is set to zero, 3386, and both pages are smoothly brought back to center, 3388. Next the program loops back to block 3342. If, at block 3372, it is determined that the "four" key was not pressed, the program jumps to block 3390, where a check is made to determine whether the key pressed was the "six" key. Next a check is made to determine whether the break point is equal to zero, 3392. If so, the break point is set to zero, 3394, and a check is made to determine whether "separation" is greater than zero, 3396. If not, the base-out break point is set equal to "separation" and stored, block 3398. Next the program jumps to block 3397. If, at block 3396, it is determined that "separation" is greater than zero, the base-in break point is set equal to "separation" and stored, block 3399. The program then jumps to block 3397, where "separation" is reduced by the value of "jump". The program then loops back to block 3342.

17.) Z Axis Binocularity (Binocular Shaft)

Figure 41A:
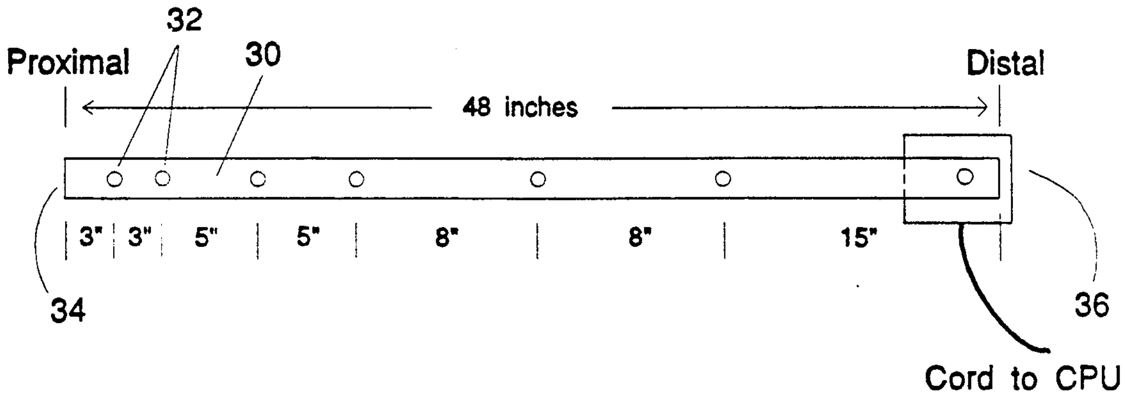
FIGS. 41a, 41b illustrate a binocular shaft provided according to the practice of the present invention.
Figure 41B:
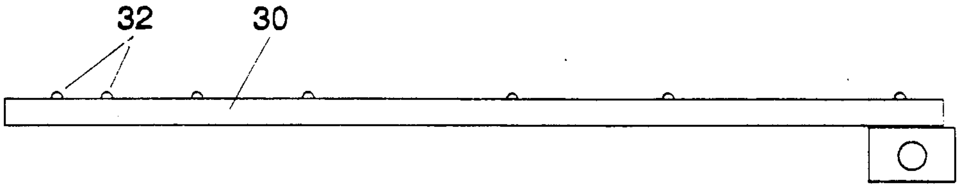
Figure 42A:
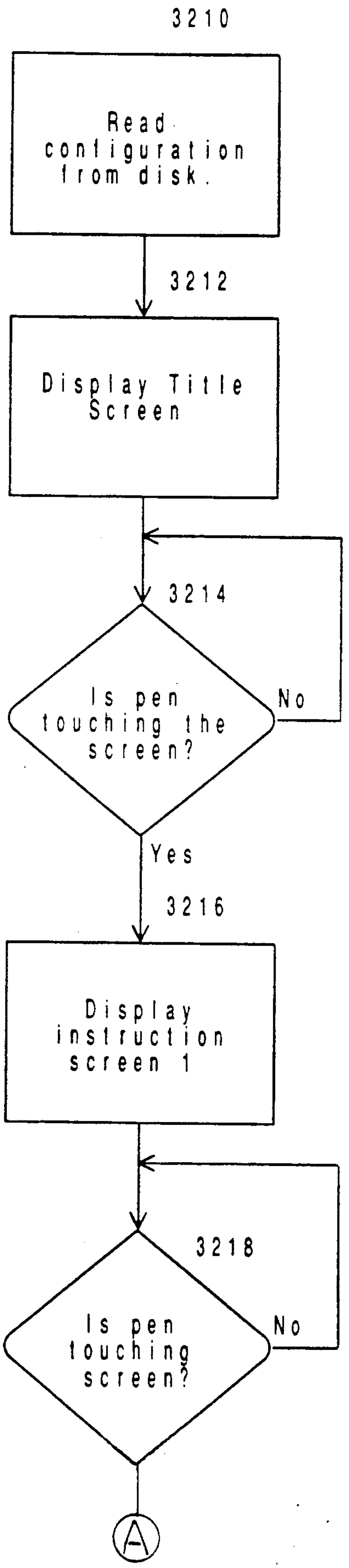
Figure 42B:
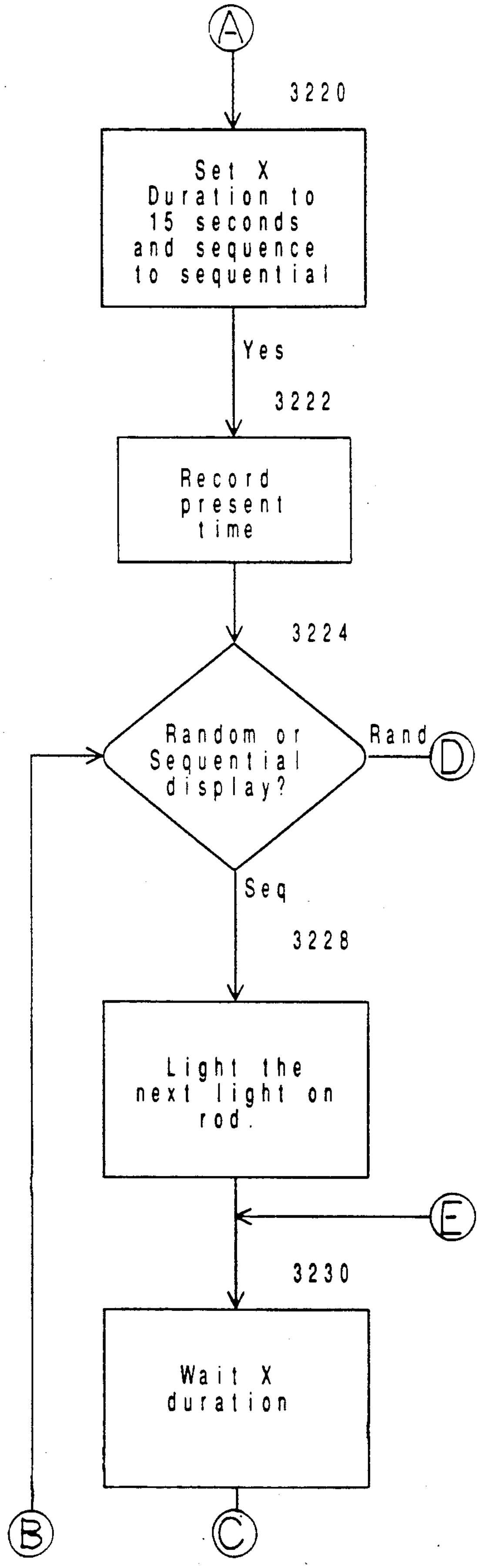
Figure 42C:
Figure 42D:
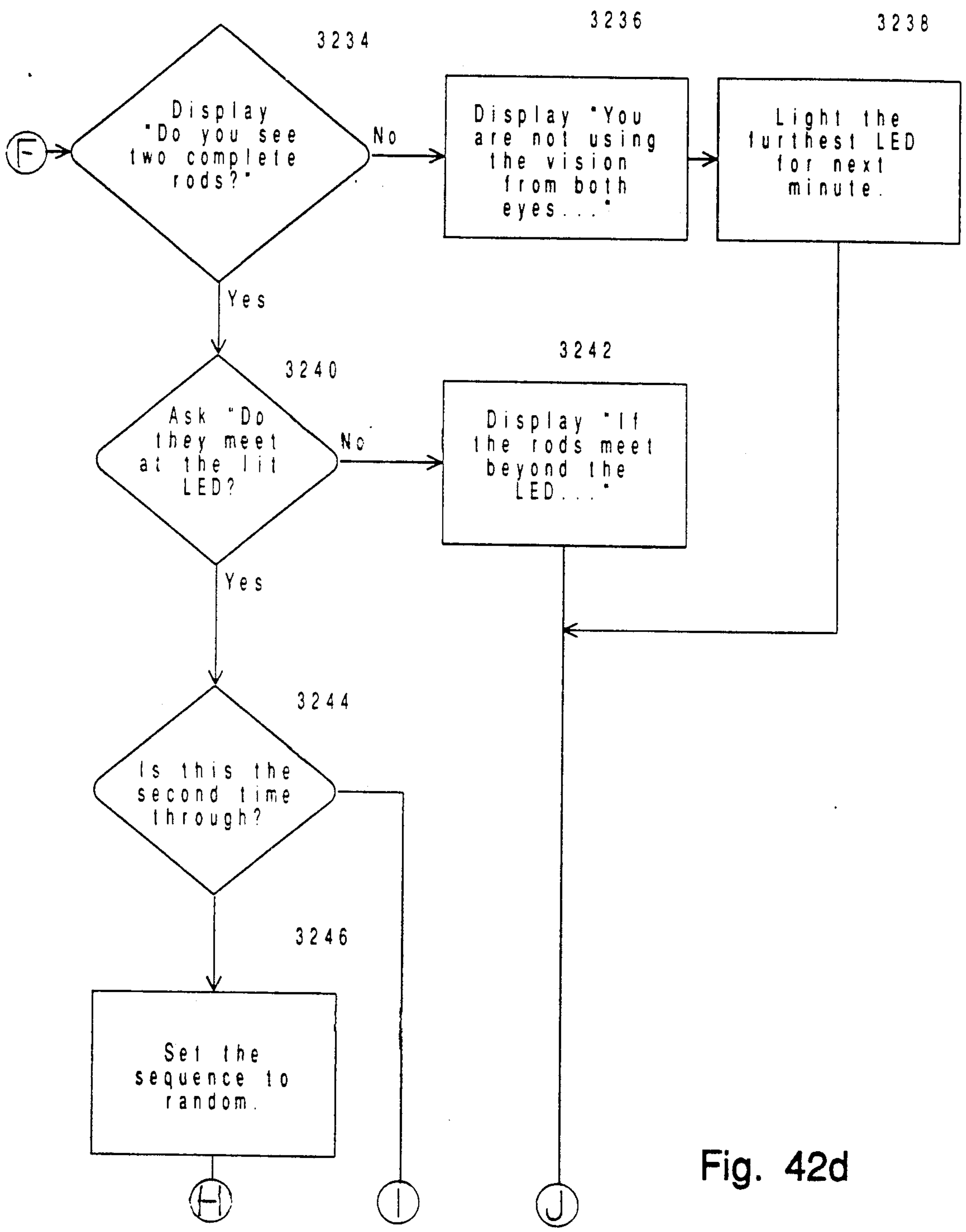
Figure 42E:
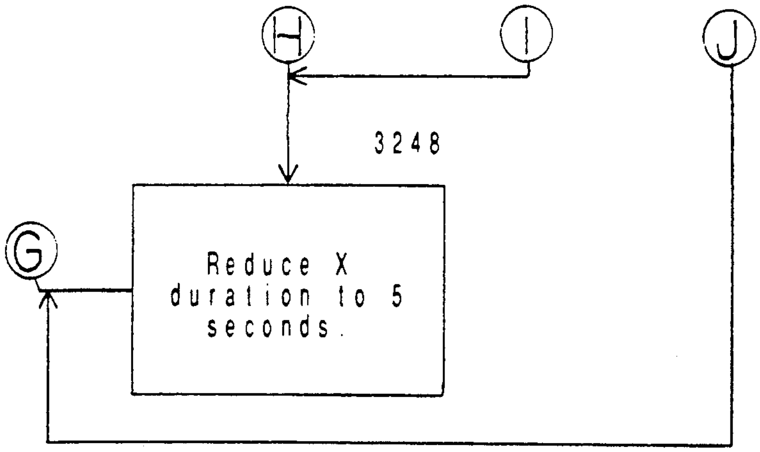

The purpose of the binocular shaft exercise is to develop smooth, accurate binocular convergence and divergence. The "shaft" is a 36-inch long shaft 30 wired with LED's 32 every 3 to 6 inches, FIGS. 41*a* , b, and the software drives the LED's in the configured patterns. The configuration program offers the following options:

1.)
(a) sequential illumination of LED's,
(b) random illumination of LED's; and
2.) the duration that each LED remains lit may also be selected.

The subject reads instructions (not shown) and touches the screen with the active light pen to continue. The shaft is positioned perpendicular to the subject's face with one end (the proximal end 34) of the shaft adjacent the nose. As the subject looks down the shaft, he should see two shafts that converge to one at the point of ocular fixation. The goal is to seek two solid shafts that are level with the convergence point easily achieved at the "on" LED. Missing segments indicate a suppression of visual input. Postorial distortion results in one rod appearing higher than the other. Each minute the CRT monitor displays questions to determine the subject's level of skill. Based on the subject's input, the LED presentation can change from sequential to random and the duration of illumination can change.

Initially, only the LED at the end of the shaft farthest from the subject (distal end 36) is illuminated. The LEDs initially remain illuminated for 15 seconds each. Each 15 seconds, one LED extinguishes and the next closer LED to the subject illuminates. After one minute, an auditory tone draws the subject's attention to the CRT monitor. The question "Do you see two complete shafts?" is displayed on the monitor. A "yes" response with the active light pen calls up the question "Did the two shafts meet at all lit LEDs?". A "yes" response reduces the duration of illumination each LED to 5 seconds. After one minute, if the subject responds "yes" to the questions, the illumination sequence changes to random. Continued "yes" responses causes the illumination duration to be reduced by one second per minute with 2 seconds as a minimum.

An answer of "no" to the question "Do you see 2 complete shafts?" calls up the message "You are tuning out vision from an eye when part or all of the shaft is missing. Close or cover one eye at a time to become aware of the input from each eye. You can also try blinking your eyes rapidly while looking down the shaft." For the next minute, the LEDs each remain illuminated for 15 seconds as they illuminate in sequential order starting at the farthest. Any further answers of "no" call up the message "As you look at the light, be aware of the full length of both shafts and the space around you. Also remember to breathe slowly and deeply."

An answer of "no" to the question "did the 2 shafts meet at all lit LEDs?" calls up the message "If the shafts meet beyond the LED, you are looking too far. If they meet closer than the LED, you are looking too close. Adjust the way you are looking to get a more accurate match." For the next minute, the LEDs again remain illuminated for 15 seconds each as they illuminate in sequential order starting at the farthest." Any further answers of "no" call up "As you look at the light be aware of the full length of both shafts in the space around you, also remember to breathe slowly and deeply."

The output includes a printout of the responses of the subject's responses to the questions, which may also be stored to the subject's file.

The following description refers to the flowchart in FIGS. 42*a* through 42*f*, which describes the binocular shaft exercise. First, the configuration file is read from disk, 3210. Next, a title screen (not shown) is displayed, 3212. Next, the program waits for the subject to touch the screen with the active light pen 3214, before displaying instruction screen 1 (not shown), 3216. Next, the program waits for the subject to touch the screen with the active light pen, 3218. The duration for which each of the LEDs will remain illuminated is set to 15 seconds and the LED illumination sequence is set to sequential, 3220. Next, the present time is recorded, 3222. Next, the program checks to determine whether the sequence is random or sequential 3224. If random, one LED is illuminated, 3226. If sequential, the next LED on the rod is illuminated, 3228. Next, the program waits for the LED duration to expire, 3230, before checking to determine whether one minute has passed from the recorded time, 3232. If not, the program loops back to block 3224. If so, the question "do you see 2 complete rods?" is displayed, 3234. If the subject's response is "no", the message "you are not using the vision from both eyes . . . " is displayed, block 3236. Next, at block 3238 the farthest LED is illuminated for one minute. Next, the program loops back to block 3224. If the subject's response to the question "do you see 2 complete rods?" was "yes" the program executes block 3240 where the question "do they meet at the lit LED" is displayed. If the subject responds in the negative, the message "if the rods meet beyond the LED . . . " is displayed, block 3242 and the program loops back to block 3224. If the subject responds in the affirmative, the program checks to determine whether this was the second through, block 3244. If not, the program jumps to block 3248. If so, the sequence is set to random, block 3246. Next, at block 3248, the duration is reduced to 5 seconds and the program loops back to block 3224.

A fully automated, self directing, self advancing, vision diagnostic and therapeutic exercise system has been disclosed. The invention may be embodied in other specific forms without departing from the spirit or essential attributes thereof and, accordingly, reference should be made to the appended claims, rather than the foregoing specifications, as indicating the scope of the invention.

We claim:

1. Method of treating near point visual stress comprising the steps of:

(A) automatically and interactively, on a computer, directing a subject in performance of:
   (i) a plurality of self advancing, self directing diagnostic tests each relating to a visual function of the the subject; and,
   (ii) a plurality of self advancing, self directing therapeutic exercises each relating to a visual function of the subject; said plurality of diagnostic tests and therapeutic exercises employing computer generated displays that are provided on a CRT coupled to the computer and employing input means coupled to the computer for registering a response of the subject;

(B) automatically creating a performance profile for the subject based upon the subject's responses;

(C) automatically recording the performance profile and data representing the subject's performance in a memory associated with the computer;

(D) automatically retrieving the data stored in step (C) on demand.

2. Method according to claim 1 wherein the diagnostic tests are for characterizing at least two of the following visual functions:

(A) saccadics;
(B) visual memory;
(C) accommodative flexibility;
(D) fusion ranges; and,
(E) phorias.

3. Method according to claim 1 wherein the therapeutic exercises are directed to at improving at least two of:

(A) accommodative focusing;
(B) saccadics;
(C) pursuits;
(D) visual memory;

(E) fusion;

(F) binocularity.

4. Method according to claim 1 wherein the subject is directed to touch a light pen to a portion of the screen displaying a particular pattern, the computer responding in a first preprogrammed manner if the light pen is touched to the portion of the screen displaying the particular pattern and in a second preprogrammed manner if the light pen is touched to a different portion of the screen.

5. Method according to claim 4 wherein two light pens are provided and are alternately and oppositely activated under computer control, and the subject is directed to hold one light pen in each hand and touch only the activated light pen to the portion of the screen displaying the particular pattern.

6. Method according to claim 1 wherein at least one of said diagnostic tests and therapeutic exercises employs a display having a depth effect.

7. Method of claim 1 further comprising the step of automatically varying parameters of the therapeutic exercises in accordance with a past performance of the subject and in accordance with a pre-programmed set of performance objectives so as to automatically adapt to a current performance level of the subject.

8. Method according to claim 1 further comprising the steps of:

(A) providing a series of targets that appear to be spaced along an axis that extends away from subject's face;

(B) directing the subject to view a specified one of the targets with both eyes until the subject can focus on the specified target with both eyes and maintain focus upon the specied target for a period of time;

(C) directing the subject to repeat step (B) for a different one of the targets.

9. Method according to claim 8 wherein the series of targets comprise a series of LEDs spaced along a rod having distal and proximal ends, and the subject is directed to place his nose adjacent the proximal end thereof to view the LEDs.

10. Method according to claim 9 wherein the LEDs are operatively coupled to the computer and illuminated under control of a computer program in response to an input to the computer provided by the subject.

11. Vision training apparatus comprising:

a) computer means programmed for automatically and interactively directing a subject in performance of both:

(i) a plurality of self advancing, self directing diagnostic tests each relating to a visual function of the subject; and, (ii) a plurality of self advancing, self directing therapeutic exercises each for improving functional aspects of vision and including at least one hand-eye coordination exercise, each therapeutic exercise relating to a visual function of the subject, said plurality of diagnostic tests and therapeutic exercises employing computer generated visual displays;

b) display means associated with the computer means for displaying the computer generated visual displays;

c) input means associated with the computer means for registering a response of the subject to the plurality of diagnostic and therapeutic exercises, the computer means automatically creating a performance profile for the subject based upon the subject's responses; and, d) storage means associated with the computer means for recording the performance profile and data representing the subject's performance, the computer means automatically retrieving the data stored in the storage means on demand.

12. Apparatus according to claim 11 further comprising a light pen operatively coupled to the computer for entering a response of the subject to a display on the CRT.

13. Apparatus according to claim 12 comprising two light pens operatively coupled to the computer, the light pens being alternately and oppositely activated under computer control.

14. Apparatus according to claim 11 further comprising means for providing a display having a depth effect.

15. Apparatus according to claim 11 further comprising means for providing a series of targets that appear to be spaced along an axis that extends away from subject's face.

16. Apparatus according to claim 15 wherein the series of targets comprise a series of LEDs spaced along a rod and the LEDs are operatively coupled to the computer and illuminated under control of a computer program in response to an input to the computer provided by the subject.

* * * * *